United States Patent
Brough et al.

(10) Patent No.: US 10,570,157 B2
(45) Date of Patent: Feb. 25, 2020

(54) CYCLIC DIARYLBORON DERIVATIVES AS NLRP3 INFLAMMASOME INHIBITORS

(71) Applicant: The University of Manchester, Manchester (GB)

(72) Inventors: David Brough, Manchester (GB); Stuart McRae Allan, Manchester (GB); Sally Freeman, Manchester (GB); Alex George Baldwin, Manchester (GB)

(73) Assignee: THE UNIVERSITY OF MANCHESTER, Manchester (GB)

( * ) Notice: Subject to any disclaimer, the term of this patent is extended or adjusted under 35 U.S.C. 154(b) by 0 days.

(21) Appl. No.: 15/748,557

(22) PCT Filed: Jul. 28, 2016

(86) PCT No.: PCT/GB2016/052332
§ 371 (c)(1),
(2) Date: Jan. 29, 2018

(87) PCT Pub. No.: WO2017/017469
PCT Pub. Date: Feb. 2, 2017

(65) Prior Publication Data
US 2018/0215772 A1 Aug. 2, 2018

(30) Foreign Application Priority Data
Jul. 30, 2015 (GB) .................................. 1513481.0

(51) Int. Cl.
*C07F 5/02* (2006.01)
(52) U.S. Cl.
CPC ...................................... *C07F 5/02* (2013.01)
(58) Field of Classification Search
CPC ........................................................ C07F 5/02
See application file for complete search history.

(56) References Cited

FOREIGN PATENT DOCUMENTS

WO        03/059916 A2    7/2003
WO     2006/048679 A2    5/2006

OTHER PUBLICATIONS

Dorokhov et al. CAS Accession No. 1989:57087.*

Bally et al., "Heterocyclic Organoboron Compounds-XVI: Chelated Compounds with α,β-Unsaturated β-Aminoketones," *Tetrahedron* 29:3185-3187, 1973.
Boese et al., "The Colour of Chelates of Boron. An X-Ray Structural Investigation of Bis(4-methylphenyl)boryl and 9-Borabicyclo[3.3.1]nonyl Acetylacetonates," *Chem. Ber.* 118:670-675, 1985.
Coll et al., "A small-molecule inhibitor of the NLRP3 inflammasome for the treatment of inflammatory diseases," *Nat. Med.* 21(3):248-255, 2015. (10 pages).
Dorokhov et al., "Alkyl 3-amino-5-aryl-2-benzoyl-5-oxo-2-pentenoates as new chelating ligands and reagents of heterocyclic synthesis," *Russ. Chem. Bull. Intl. Ed.* 52(9):2057-2062, 2003.
Dorokhov et al., "Synthesis of 3-acetyl-2-amino-4-pyridone," *Russ. Chem. Bull.* 45(1):168-170, 1996.
Dorokhov et al., "Structures of boron chelates of mono- and diacylketene aminals," *Russ. Chem. Bull.* 45(10):2411-2416, 1996.
Dorokhov et al., "Chelate synthesis of 3-ethoxycarbonyl-4-hydroxy-2-trifluoromethylpyridine from ethyl acetoacetate and trifluoroacetonitrile," *Russ. Chem. Bull.* 44(7):1283-1285, 1995.
Rettig et al., "Structural studies of organoboron compounds. XII. Crystal and molecular structures of (acetylacetonato)diphenylboron and (tropolonato)diphenylboron," *Can. J. Chem.* 60:2957-2964, 1982.
Tikhonov et al., "Photoelectron Spectra and Electronic Structure of Boron Acetylacetonates with Organic Substituents," *Russ. J. Phys. Chem. B* 8(5):626-633, 2014.
Vasil'ev et al., "Boron Chelates with 5,5,5-Trifluoro- and 5,5,5-Trichloro-4-Aminopent-3-En-2-Ones," *Russ. Chem. Bull.* 41(11):2104-2107, 1992.
Vasil'ev et al., "Synthesis of 4-hydroxy- and 3-acyl-4-amino-2-trifluoromethylpyridines," *Russ. Chem. Bull.* 45(11):2574-2577, 1996.
Vasil'ev et al., "Synthesis of derivatives of 4-amino-2-trifluoromethylnicotinic acid," *Russ. Chem. Bull. Intl. Ed.* 53(10):2319-2321, 2004.
Vasil'ev et al., "Trifluoromethyl-substituted 1,6-naphthyridines and pyrido[4,3-d]pyrimidines," *Russ. Chem. Bull. Intl. Ed.* 62(5):1255-1261, 2013.
Voronkova et al., "Diaminomethylidene derivatives of β-oxo sulfones as potential reagents in heterocyclic synthesis and chelating ligands," *Russ. Chem. Bull. Intl. Ed.* 59(10):1937-1945, 2010.
Dewar et al., "A Novel Disproportionation of Arylboronic Acids," *Tetrahedron Letters* 16:907-911, 1964.
European Examination Report, dated Jul. 3, 2019, in corresponding EP Application No. 1674586.2, 5 pages.
International Search Report and Written Opinion, dated Sep. 30, 2016, in corresponding International Application No. PCT/GB2016/052332, 13 pages.

* cited by examiner

*Primary Examiner* — Joseph R Kosack
(74) *Attorney, Agent, or Firm* — Seed IP Law Group LLP

(57) ABSTRACT

Inhibitor compounds are disclosed. The compounds are effective in the treatment of diseases or conditions in which interleukin 1 β activity is implicated. Methods of synthesis of the compounds, as well as pharmaceutical compositions comprising the compounds are also disclosed.

25 Claims, 5 Drawing Sheets

US 10,570,157 B2

CYCLIC DIARYLBORON DERIVATIVES AS NLRP3 INFLAMMASOME INHIBITORS

INTRODUCTION

The present invention relates to novel inhibitor compounds, as well as to the use of the novel inhibitor compounds in the treatment of diseases or conditions in which interleukin 1β activity is implicated. The present invention also relates to processes for the preparation of the novel inhibitor compounds, as well as pharmaceutical compositions comprising the novel inhibitor compounds.

BACKGROUND OF THE INVENTION

Inflammation is an early and important response to tissue injury and infection. In the absence of pathogens, it is considered sterile and exacerbates the pathology of major non-communicable diseases (e.g. stroke, myocardial infarction, Alzheimer's, atherosclerosis, diabetes, cancer)[1,2]. Inflammatory cytokines associated with sterile inflammation are members of the interleukin-1 (IL-1) family, namely IL-1α and IL-1β[1]. On-going research is establishing the NLRP3-inflammasome complex as one of the most important regulators of inflammation. The NLRP3 inflammasome forms a molecular platform inside macrophages and microglial cells, catalysing the activation of the protease caspase-1. Caspase-1 is responsible for converting the potent pro-inflammatory cytokine interleukin-1 beta (IL-1β) from an inactive to an active secreted form. The NLRP3 inflammasome represents an important new target for the development of novel therapeutics. We have developed novel small molecule inhibitors of the NLRP3 inflammasome and have characterised their potency in vitro.

IL-1β is produced as a pro-IL-1β precursor. This precursor is expressed in response to pathogen associated molecular patterns (PAMPs) or damage associated molecular patterns (DAMPs) that bind to pattern recognition receptors (PRRs) on macrophages to upregulate pro-inflammatory gene expression[3,4]. PAMPs are motifs carried by pathogens, such as bacterial endotoxin (or lipopolysaccharide (LPS)), and DAMPs are commonly endogenous molecules released by necrosis. Pro-IL-1β is inactive and remains intracellular until a further PAMP or DAMP stimulation activates cytosolic PRRs, often of the NLR family, to form large multi-protein complexes called inflammasomes[5]. These complexes consist of the PRR, pro-caspase-1, and, depending upon the PRR, an adaptor protein called ASC (apoptosis-associated speck-like protein containing a caspase recruitment domain), that interact via CARD and pyrin homology binding domains[5]. When the PRR senses PAMPs or DAMPs it recruits ASC, which in turn recruits caspase-1 causing its activation (FIG. 1). Caspase-1 then processes pro-IL-1β to a mature form that is rapidly secreted from the cell[5]. Although the closely related pro-IL-1α is not a substrate for caspase-1, the activation of inflammasomes can also drive IL-1α release[6]. The activation of caspase-1 itself can also cause cell death directly[7].

A number of inflammasome forming PRRs have been identified including NLRP1, NLRP3, NLRP6, NLRP7, NLRP12, NLRC4, AIM2, IFI16, and RIG-1[5]. Of these inflammasomes identified to-date, the best characterised, and most strongly associated with sterile inflammation is formed by NLRP3.

There are many endogenous ('sterile') activators of NLRP3 including molecules such as ATP[8], sphingosine[9], crystals of monosodium urate (MSU)[10], cholesterol[11], and Aβ fibrils[12]. There is limited evidence supporting a direct interaction between DAMP and NLRP3 and additional host cellular signals such as K+ efflux[13], lysosomal destabilisation and cathepsin activity[14], ROS production and/or mitochondrial dysfunction[15], post-translational modification such as deubiquitination of inflammasome components[16-16], are suggested to be important.

Anti-IL-1β therapies (such as Anakinra) are remarkably safe, with far fewer incidences of opportunistic infections compared with anti-TNF therapies[19]. Furthermore, selectively targeting the NLRP3 inflammasome will avoid major anti-microbial inflammasomes such as NLRC4 or AIM2[20] and are thus even less likely to cause immunosuppressive effects.

The present invention was devised with the foregoing in mind.

SUMMARY OF THE INVENTION

According to one aspect of the present invention, there is provided a compound for use in the treatment of diseases or conditions in which interleukin 1β activity is implicated, said compound, or a pharmaceutically acceptable salt or solvate thereof, having the structural formula I defined herein.

According to another aspect of the present invention, there is provided a compound having the structural formula I defined herein, or a pharmaceutically acceptable salt or solvate thereof.

According to another aspect of the present invention, there is provided a pharmaceutical composition which comprises a compound of formula I defined herein, or a pharmaceutically acceptable salt or solvate thereof, and one or more pharmaceutically acceptable excipients.

According to another aspect of the present invention, there is provided a compound of formula I defined herein, or a pharmaceutically acceptable salt or solvate thereof, for use as a medicament.

According to another aspect of the present invention, there is provided a compound of formula I defined herein, or a pharmaceutically acceptable salt or solvate thereof, for use in the production of an inflammasome inhibitory effect.

According to another aspect of the present invention, there is provided a compound of formula I defined herein, or a pharmaceutically acceptable salt or solvate thereof, for use in the production of an anti-inflammatory effect.

According to another aspect of the present invention, there is provided a method of inhibiting inflammasome activity in vitro or in vivo, said method comprising contacting a cell with an effective amount of a compound of formula I defined herein, or a pharmaceutically acceptable salt or solvate thereof According to another aspect of the present invention, there is provided a method of treating a disease or condition in which interleukin 1β activity is implicated, said method comprising administering to a patient in need of such treatment a therapeutically effective amount of a compound of formula I defined herein, or a pharmaceutically acceptable salt or solvate thereof, or a pharmaceutical composition as defined herein.

According to another aspect of the present invention, there is provided a method of synthesising a compound of formula I defined herein, or a pharmaceutically acceptable salt or solvate thereof.

According to another aspect of the present invention, there is provided a compound of formula I defined herein, or a pharmaceutically acceptable salt or solvate thereof, obtainable by, or obtained by, or directly obtained by a method of synthesis as defined herein.

DETAILED DESCRIPTION OF THE INVENTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl. A similar convention applies to other radicals, for example "phenyl(1-6C)alkyl" includes phenyl(1-4C)alkyl, benzyl, 1-phenylethyl and 2-phenylethyl.

The term "(m-nC)" or "(m-nC) group" used alone or as a prefix, refers to any group having m to n carbon atoms.

"(3-10C)cycloalkyl" means a hydrocarbon ring containing from 3 to 10 carbon atoms, for example, cyclopropyl, cyclobutyl, cyclopentyl, cyclohexyl, cycloheptyl or bicycle [2.2.2]octane, bicycle[2.1.1]hexane, bicycle[1.1.1]pentane, adamantane and bicyclo[2.2.1]heptyl.

The term "halo" refers to fluoro, chloro, bromo and iodo.

The term "fluoroalkyl" is used herein to refer to an alkyl group in which one or more hydrogen atoms have been replaced by fluorine atoms. Examples of fluoroalkyl groups include —$CHF_2$, —$CH_2CF_3$, or perfluoroalkyl groups such as —$CF_3$ or —$CF_2CF_3$. An analogous definition applies to the term "haloalkyl".

The term "heterocyclyl", "heterocyclic" or "heterocycle" means a non-aromatic saturated or partially saturated monocyclic, fused, bridged, or spiro bicyclic heterocyclic ring system(s). Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

The term "Heterocyclyl(m-nC)alkyl" means a heterocyclyl group covalently attached to a (m-nC)alkylene group, both of which are defined herein.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from:
a) a benzene ring fused to a 5- or 6-membered ring containing 1, 2 or 3 ring heteroatoms;
b) a pyridine ring fused to a 5- or 6-membered ring containing 1, 2 or 3 ring heteroatoms;
c) a pyrimidine ring fused to a 5- or 6-membered ring containing 1 or 2 ring heteroatoms;
d) a pyrrole ring fused to a 5- or 6-membered ring containing 1, 2 or 3 ring heteroatoms;
e) a pyrazole ring fused to a 5- or 6-membered ring containing 1 or 2 ring heteroatoms;
f) a pyrazine ring fused to a 5- or 6-membered ring containing 1 or 2 ring heteroatoms;
g) an imidazole ring fused to a 5- or 6-membered ring containing 1 or 2 ring heteroatoms;
h) an oxazole ring fused to a 5- or 6-membered ring containing 1 or 2 ring heteroatoms;
i) an isoxazole ring fused to a 5- or 6-membered ring containing 1 or 2 ring heteroatoms;
j) a thiazole ring fused to a 5- or 6-membered ring containing 1 or 2 ring heteroatoms;
k) an isothiazole ring fused to a 5- or 6-membered ring containing 1 or 2 ring heteroatoms;
l) a thiophene ring fused to a 5- or 6-membered ring containing 1, 2 or 3 ring heteroatoms;
m) a furan ring fused to a 5- or 6-membered ring containing 1, 2 or 3 ring heteroatoms;
n) a cyclohexyl ring fused to a 5- or 6-membered heteroaromatic ring containing 1, 2 or 3 ring heteroatoms; and
o) a cyclopentyl ring fused to a 5- or 6-membered heteroaromatic ring containing 1, 2 or 3 ring heteroatoms.

Particular examples of bicyclic heteroaryl groups containing a six membered ring fused to a five membered ring include but are not limited to benzofuranyl, benzothiophenyl, benzimidazolyl, benzoxazolyl, benzisoxazolyl, benzothiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl, pyrrolopyridine, and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

"Heteroaryl(m-nC)alkyl" means a heteroaryl group covalently attached to a (m-nC)alkylene group, both of which are defined herein. Examples of heteroaralkyl groups include pyridin-3-ylmethyl, 3-(benzofuran-2-yl)propyl, and the like.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In particular embodiment, an aryl is phenyl.

The term "aryl(m-nC)alkyl" means an aryl group covalently attached to a (m-nC)alkylene group, both of which are defined herein. Examples of aryl-(m-nC)alkyl groups include benzyl, phenylethyl, and the like.

This specification also makes use of several composite terms to describe groups comprising more than one functionality. Such terms will be understood by a person skilled in the art. For example heterocyclyl(m-nC)alkyl comprises (m-nC)alkyl substituted by heterocyclyl.

The term "optionally substituted" refers to either groups, structures, or molecules that are substituted and those that are not substituted.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

Compounds of the Invention

As discussed hereinbefore, according to one aspect of the present invention, there is provided a compound of formula I shown below:

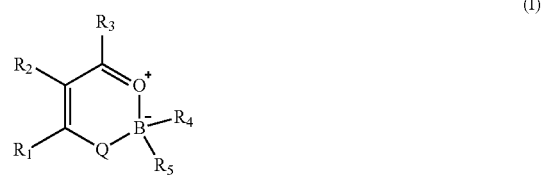

(I)

wherein

Q is O or $NR_a$, wherein $R_a$ is H or (1-4C)alkyl;

$R_1$ is halo, (1-4C)alkyl, (1-4C)haloalkyl, S-(1-4C)alkyl, aryl, heteroaryl or a (1-6C)α,β-unsaturated aldehyde or ketone;

$R_2$ is selected from hydrogen, halo, amino, cyano, nitro, hydroxyl, or a group -$L^1$-$X^1$—$R_b$ wherein $L^1$ is absent or (1-2C)alkylene $X^1$ is absent or selected from —O—, —C(O)—, —C(X)O—, —OC(X)—, —CH($OR_c$)—, —N($R_c$)—, —N($R_c$)—C(X)—, —N($R_c$)—C(X)O—, —C(X)—N($R_c$)—, —N($R_d$)C(X)N($R_c$)—, —S—, —SO—, —$SO_2$—, —$S(O)_2N(R_c)$—, or —N(R$_c$)SO$_2$— wherein X is O or NR$_x$; R$_x$ is hydrogen or (1-3C)alkyl; and R$_c$ and R$_d$ are each independently selected from hydrogen or (1-6C)alkyl; and R$_b$ is hydrogen, (1-6C)alkyl, (2-6C)alkenyl, (2-6C)alkynyl, cyano, aryl, aryl(1-2C)alkyl, (3-6C)cycloalkyl, heteroaryl, heterocyclyl or a sugar or amino acid, each of which is optionally substituted by one or more substituent groups independently selected from oxo, halo, cyano, nitro, hydroxy, carboxy, phosphate, NR$^e$R$^f$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, aryl, aryloxy, heterocyclyl, heterocyclyloxy, heterocyclyl-(1-2C)alkyl, heteroaryl, heteroaryloxy, heteroaryl-(1-2C)alkyl, C(O)NR$^e$R$^f$, NR$^e$C(O)R$^f$, NR$^e$S(O)$_2$R$^f$ and S(O)$_2$NR$^e$R$^f$;

wherein R$^e$ and R$^f$ are each independently selected from hydrogen, (1-4C)alkyl or (3-6C)cycloalkyl or (3-6C)cycloalkyl(1-2C)alkyl;

or R$^e$ and R$^f$ can be linked such that, together with the nitrogen atom to which they are attached, they form a heterocyclic ring which is optionally substituted by oxo, halo, cyano, nitro, hydroxy, carboxy, NR$^g$R$^h$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, C(O)NR$^g$R$^h$, NR$^g$C(O)R$^h$, NR$^g$S(O)$_2$R$^h$ and S(O)$_2$NR$^g$R$^h$, wherein R$^g$ and R$^h$ are each independently selected from hydrogen, (1-4C)alkyl, (3-6C)cycloalkyl or (3-6C)cycloalkyl(1-2C)alkyl;

or R$_b$ and R$_c$ are linked such that, together with the nitrogen atom to which they are attached, they form a heterocyclic ring which is optionally substituted by oxo, halo, cyano, nitro, hydroxy, carboxy, NR$^i$R$^j$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, C(O)NR$^i$R$^j$, NR$^i$C(O)R$^j$, NR$^i$S(O)$_2$R$^j$ and S(O)$_2$NR$^i$R$^j$, wherein R$^i$ and R$^j$ are each independently selected from hydrogen, (1-4C)alkyl, (3-6C)cycloalkyl or (3-6C)cycloalkyl(1-2C)alkyl;

R$_3$ is selected from methyl, OR$^p$, C(O)OR$^p$, C(O)NR$^p$R$^q$ or NR$^k$R$^l$, wherein R$^k$ and R$^l$ are each independently selected from hydrogen, (1-6C)alkyl, (3-10C)cycloalkyl, (3-10C)cycloalkyl(1-2C)alkyl, (2-6C)alkenyl, (2-6C)alkynyl, aryl, aryl(1-2C)alkyl, heteroaryl, heteroaryl(1-2C)alkyl, S(O)R$^o$, S(O)$_2$R$^o$ or a sugar or amino acid residue;

R$^o$ is selected from (1-4C)alkyl, (2-4C)alkenyl, (2-4C)alkynyl or an aryl or heteroaryl group, each of which may be optionally substituted with one or more substituents selected from halo, OH, (1-4C)alkyl, (1-4C)hydroxyalkyl, (2-4C)alkenyl and (2-4C)alkynyl;

R$^p$ and R$^q$ are independently selected from hydrogen, (1-6C)alkyl, (3-10C)cycloalkyl, (3-10C)cycloalkyl(1-2C)alkyl, (2-6C)alkenyl, (2-6C)alkynyl, aryl, aryl(1-2C)alkyl, heteroaryl or heteroaryl(1-2C)alkyl;

R$_4$ and R$_5$ are each independently aryl or heteroaryl ring, each of which is optionally substituted by halo, cyano, nitro, hydroxy, carboxy, NR$^m$R$^n$, (1-2C)alkoxy, (1-4C)alkyl, (1-4C)haloalkyl, (3-4C)cycloalkyl, (3-4C)cycloalkyl-(1-2C)alkyl, aryl, aryl(1-2C)alkyl, (1-2C)alkanoyl, (1-2C)alkylsulphonyl, SR$^m$, SOR$^m$, C(O)NR$^m$R$^n$, NR$^m$C(O)R$^n$, NR$^m$S(O)R$^n$ and S(O)$_2$NR$^m$R$^n$, wherein R$^m$ and R$^n$ are each independently selected from hydrogen, (1-2C)alkyl;

or R$_4$ and R$_5$ are linked to one another by a bond, an alkylene linker optionally comprising one or more heteroatoms, or a fused cycloalkyl, aryl, heteroaryl or heterocyclic ring;

or a pharmaceutically acceptable salt thereof, with the proviso that the compound is not one of the following:

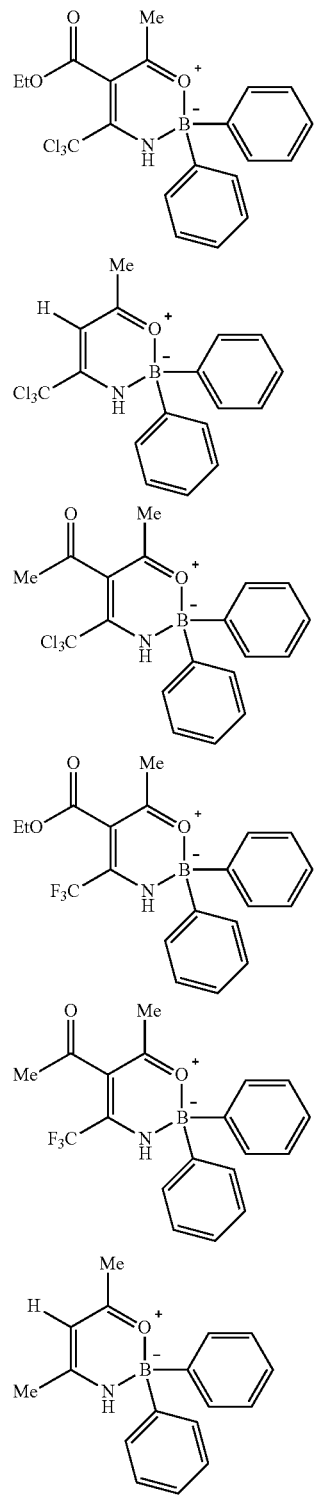

-continued

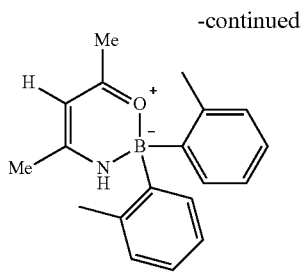

Particular compounds of the invention include, for example, compounds of the formula I, or pharmaceutically acceptable salts or solvates thereof, wherein, unless otherwise stated, each of Q, $R_a$, $R_1$, $R_2$, $L^1$, $X^1$, X, $R_x$, $R_b$, $R_c$, $R_d$, $R^e$, $R^f$, $R^g$, $R^h$, $R^i$, $R^j$, $R_3$, $R^k$, $R^l$, $R_4$, $R_5$, $R^m$, $R^n$, $R^p$, $R^q$ and $R^o$ has any of the meanings defined hereinbefore or in any one of paragraphs (1) to (84) hereinafter:

(1) Q is $NR_a$ and $R_a$ is optionally as defined in any one of paragraphs (2) to (4) below;
(2) $R_a$ is H or (1-4C)alkyl;
(3) $R_a$ is H, methyl or ethyl;
(4) $R_a$ is H;
(5) $R_1$ is halo, (1-4C)alkyl, (1-4C)haloalkyl, S-(1-4C)alkyl, phenyl or a (1-6C)α,β-unsaturated aldehyde or ketone;
(6) $R_1$ is halo, (1-4C)alkyl, (1-4C)haloalkyl or a (1-6C) α,β-unsaturated aldehyde or ketone;
(7) $R_1$ is halo, (1-4C)alkyl, (1-4C)haloalkyl, S-(1-4C)alkyl or phenyl;
(8) $R_1$ is (1-4C)alkyl or (1-4C)haloalkyl;
(9) $R_1$ is (1-4C)haloalkyl;
(10) $R_1$ is (1-2C)haloalkyl;
(11) $R_1$ is methyl, di-halomethyl or per-halo methyl;
(12) $R_1$ is per-halo methyl;
(13) $R_1$ is dichloromethyl, trichloromethyl or triflurom-ethyl;
(14) $R_1$ is $CCl_3$;
(15) $R_2$ is selected from hydrogen, halo, amino, cyano, nitro, hydroxyl, or a group -$L^1$-$X^1$—$R_b$;
(16) $R_2$ is selected from hydrogen or a group -$L^1$-$X^1$—$R_b$;
(17) $R_2$ is selected from hydrogen, cyano, $C(O)R^{2a}$, $C(O)OR^{2a}$ or $C(O)NR^{2b}R^{2c}$, wherein $R^{2a}$ is (1-4C)alkyl and $R^{2b}R^{2c}$ are independently selected from hydrogen or (1-4C)alkyl;
(18) $R_2$ is selected from cyano, $C(O)R^{2a}$, $C(O)OR^{2a}$ or $C(O)NR^{2b}R^{2c}$, wherein $R^{2a}$ is (1-4C)alkyl and $R^{2b}R^{2c}$ are independently selected from hydrogen or (1-4C)alkyl;
(19) $L^1$ is absent or (1-2C)alkylene;
(20) $L^1$ is absent;
(21) $X^1$ is absent or selected from —O—, —C(O)—, —C(X)O—, —OC(X)—, —CH(OR$_c$)—, —N(R$_c$)—, —N(R$_c$)—C(X)—, —N(R$_c$)—C(X)O—, —C(X)—N(R$_c$)—, —N(R$_d$)C(X)N(R$_c$)—, —S—, —SO—, —SO$_2$—, —S(O)$_2$N(R$_c$)—, or —N(R$_c$)SO$_2$—;
(22) $X^1$ is absent or selected from —O—, —C(O)—, —C(X)O—, —OC(X)—, —CH(OR$_c$)—, —N(R$_c$)—C(X)O—, —C(X)—N(R$_c$)—, —S—, —SO—, —SO$_2$—, —S(O)$_2$N(R$_c$)—, or —N(R$_c$)SO$_2$—;
(23) $X^1$ is absent or selected from —O—, —C(O)—, —C(X)O—, —OC(X)—, —CH(OR$_c$)—, —N(R$_c$)—C(X)O— or —C(X)—N(R$_c$)—;
(24) $X^1$ is absent or selected from —C(O)—, —C(X)O— or —C(X)—N(R$_c$)—;

(25) In any one of paragraphs (21) to (24) above, X is O or $NR_x$;
(26) In any one of paragraphs (21) to (24) above, X is O;
(27) $R_x$ is hydrogen or methyl;
(28) $R_b$ is hydrogen, (1-6C)alkyl, (2-6C)alkenyl, (2-6C)alkynyl, cyano, aryl, aryl(1-2C)alkyl, (3-6C)cycloalkyl, heteroaryl, heterocyclyl or a sugar or amino acid, each of which is optionally substituted by one or more substituent groups independently selected from oxo, halo, cyano, nitro, hydroxy, carboxy, phosphate, $NR^eR^f$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, aryl, aryloxy, heterocyclyl, heterocyclyloxy, heterocyclyl-(1-2C)alkyl, heteroaryl, heteroaryloxy, heteroaryl-(1-2C)alkyl, $C(O)NR^eR^f$, $NR^eC(O)R^f$, $NR^eS(O)_2R^f$ and $S(O)_2NR^eR^f$;
(29) $R_b$ is (1-6C)alkyl, (2-6C)alkenyl, (2-6C)alkynyl, cyano, aryl, aryl(1-2C)alkyl, (3-6C)cycloalkyl, heteroaryl, heterocyclyl or a sugar or amino acid, each of which is optionally substituted by one or more substituent groups independently selected from oxo, halo, cyano, nitro, hydroxy, carboxy, phosphate, $NR^eR^f$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, aryl, aryloxy, heterocyclyl, heterocyclyloxy, heterocyclyl-(1-2C)alkyl, heteroaryl, heteroaryloxy, heteroaryl-(1-2C)alkyl, $C(O)NR^eR^f$, $NR^eC(O)R^f$, $NR^eS(O)_2R^f$ and $S(O)_2NR^eR^f$;
(30) $R_b$ is hydrogen, (1-6C)alkyl, (2-6C)alkenyl, (2-6C)alkynyl, cyano, aryl, aryl(1-2C)alkyl, (3-6C)cycloalkyl, heteroaryl or heterocyclyl, each of which is optionally substituted by one or more substituent groups independently selected from oxo, halo, hydroxy, carboxy, $NR^eR^f$, (1-4C)alkoxy, (1-4C)alkyl, (3-8C)cycloalkyl, (3-8C)cycloalkyl-(1-3C)alkyl, aryl, heterocyclyl, heterocyclyloxy, heterocyclyl-(1-2C)alkyl, heteroaryl, heteroaryloxy, heteroaryl-(1-2C)alkyl, $C(O)NR^eR^f$, $NR^eC(O)R^f$, $NR^eS(O)_2R^f$ and $S(O)_2NR^eR^f$;
(31) $R_b$ is (1-6C)alkyl, (2-6C)alkenyl, (2-6C)alkynyl, cyano, aryl, aryl(1-2C)alkyl, (3-6C)cycloalkyl, heteroaryl or heterocyclyl, each of which is optionally substituted by one or more substituent groups independently selected from oxo, halo, hydroxy, carboxy, $NR^eR^f$, (1-4C)alkoxy, (1-4C)alkyl, (3-8C)cycloalkyl, (3-8C)cycloalkyl-(1-3C)alkyl, aryl, heterocyclyl, heterocyclyloxy, heterocyclyl-(1-2C)alkyl, heteroaryl, heteroaryloxy, heteroaryl-(1-2C)alkyl, $C(O)NR^eR^f$, $NR^eC(O)R^f$, $NR^eS(O)_2R^f$ and $S(O)_2NR^eR^f$;
(32) $R_b$ is hydrogen, (1-6C)alkyl, (2-4C)alkenyl, (2-4C)alkynyl, cyano, aryl, aryl(1-2C)alkyl, (3-6C)cycloalkyl, heteroaryl or heterocyclyl, each of which is optionally substituted by one or more substituent groups independently selected from oxo, halo, hydroxy, carboxy, $NR^eR^f$, (1-4C)alkoxy, (1-4C)alkyl, (3-6C)cycloalkyl, (3-6C)cycloalkyl-(1-3C)alkyl, aryl, heterocyclyl, heterocyclyloxy, heterocyclyl-(1-2C)alkyl, heteroaryl, heteroaryloxy and heteroaryl-(1-2C)alkyl;
(33) $R_b$ is (1-6C)alkyl, (2-4C)alkenyl, (2-4C)alkynyl, cyano, aryl, aryl(1-2C)alkyl, (3-6C)cycloalkyl, heteroaryl or heterocyclyl, each of which is optionally substituted by one or more substituent groups independently selected from oxo, halo, hydroxy, carboxy, $NR^eR^f$, (1-4C)alkoxy, (1-4C)alkyl, (3-6C)cycloalkyl, (3-6C)cycloalkyl-(1-3C)alkyl, aryl, heterocyclyl, heterocyclyloxy, heterocyclyl-(1-2C)alkyl, heteroaryl, heteroaryloxy and heteroaryl-(1-2C)alkyl;

(34) $R_b$ is hydrogen, (1-6C)alkyl, (2-4C)alkenyl, (2-4C)alkynyl, cyano, aryl, aryl(1-2C)alkyl, (3-6C)cycloalkyl, heteroaryl or heterocyclyl, each of which is optionally substituted by one or more substituent groups independently selected from oxo, halo, hydroxy, carboxy, $NR^eR^f$, (1-4C)alkoxy and (1-4C)alkyl;

(35) $R_b$ is (1-6C)alkyl, (2-4C)alkenyl, (2-4C)alkynyl, cyano, aryl, aryl(1-2C)alkyl, (3-6C)cycloalkyl, heteroaryl or heterocyclyl, each of which is optionally substituted by one or more substituent groups independently selected from oxo, halo, hydroxy, carboxy, $NR^eR^f$, (1-4C)alkoxy and (1-4C)alkyl;

(36) $R_b$ is hydrogen, (1-4C)alkyl, cyano, aryl, (3-6C)cycloalkyl, heteroaryl or heterocyclyl, each of which is optionally substituted by one or more substituent groups independently selected from oxo, halo, hydroxy, carboxy, $NR^eR^f$, (1-4C)alkoxy and (1-4C)alkyl;

(37) $R_b$ is (1-4C)alkyl, cyano, aryl, (3-6C)cycloalkyl, heteroaryl or heterocyclyl, each of which is optionally substituted by one or more substituent groups independently selected from oxo, halo, hydroxy, carboxy, $NR^eR^f$, (1-4C)alkoxy and (1-4C)alkyl;

(38) $R_b$ is hydrogen, (1-4C)alkyl or cyano;
(39) $R_b$ is (1-4C)alkyl or cyano;
(40) $R_b$ is hydrogen, methyl or cyano;
(41) $R_b$ is methyl or cyano;
(42) $R_c$ and $R_d$ are each independently selected from hydrogen or (1-6C)alkyl;
(43) $R_c$ and $R_d$ are each independently selected from hydrogen or (1-4C)alkyl;
(44) $R_c$ and $R_d$ are each independently selected from hydrogen, methyl or ethyl;
(45) $R_b$ and $R_c$ are linked such that, together with the nitrogen atom to which they are attached, they form a heterocyclic ring which is optionally substituted by oxo, halo, cyano, nitro, hydroxy, carboxy, $NR^iR^j$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, $C(O)NR^iR^j$, $NR^iC(O)R^j$, $NR^iS(O)_2R^j$ and $S(O)_2NR^iR^j$;
(46) $R_b$ and $R_c$ are linked such that, together with the nitrogen atom to which they are attached, they form a 5-6 membered heterocyclic ring which is optionally substituted by oxo, halo, hydroxy, carboxy, $NR^iR^j$, (1-4C)alkoxy, (1-4C)alkyl, (3-8C)cycloalkyl;
(47) $R^e$ and $R^f$ are each independently selected from hydrogen, (1-4C)alkyl or (3-6C)cycloalkyl or (3-6C)cycloalkyl(1-2C)alkyl;
(48) $R^e$ and $R^f$ are each independently selected from hydrogen or (1-4C)alkyl;
(49) $R^e$ and $R^f$ are linked such that, together with the nitrogen atom to which they are attached, they form a heterocyclic ring which is optionally substituted by oxo, halo, cyano, nitro, hydroxy, carboxy, $NR^gR^h$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, $C(O)NR^gR^h$, $NR^gC(O)R^h$, $NR^gS(O)_2R^h$ and $S(O)_2NR^gR^h$;
(50) $R^e$ and $R^f$ are linked such that, together with the nitrogen atom to which they are attached, they form a 5-6 membered heterocyclic ring which is optionally substituted by oxo, halo, hydroxy, carboxy, $NR^gR^h$, (1-4C)alkoxy, (1-4C)alkyl, (3-8C)cycloalkyl;
(51) $R^g$ and $R^h$ are each independently selected from hydrogen, (1-4C)alkyl, (3-6C)cycloalkyl or (3-6C)cycloalkyl(1-2C)alkyl;
(52) $R^g$ and $R^h$ are each independently selected from hydrogen or (1-4C)alkyl;
(53) $R^i$ and $R^j$ are each independently selected from hydrogen, (1-4C)alkyl, (3-6C)cycloalkyl or (3-6C)cycloalkyl(1-2C)alkyl;
(54) $R^i$ and $R^j$ are each independently selected from hydrogen or (1-4C)alkyl;
(55) $R_3$ is selected from methyl, $OR^p$ or $NR^kR^l$;
(56) $R_3$ is selected from methyl or $NR^kR^l$;
(57) $R_3$ is selected from $OR^p$ or $NR^kR^l$;
(58) $R_3$ is $NR^kR^l$;
(59) In any one of paragraphs (56) to (58) above, $R^k$ and $R^l$ are each independently selected from hydrogen, (1-6C)alkyl, (3-10C)cycloalkyl, (3-100C)cycloalkyl(1-2C)alkyl, (2-6C)alkenyl, (2-6C)alkynyl, aryl, aryl(1-2C)alkyl, heteroaryl, heteroaryl(1-2C)alkyl, $S(O)R^o$, $S(O)_2R^o$ or a sugar or amino acid residue;
(60) In any one of paragraphs (56) to (58) above, $R^k$ and $R^l$ are each independently selected from hydrogen, (1-6C)alkyl, (3-10C)cycloalkyl, (3-10C)cycloalkyl(1-2C)alkyl, (2-6C)alkenyl, (2-6C)alkynyl, aryl, aryl(1-2C)alkyl, heteroaryl, heteroaryl(1-2C)alkyl $S(O)R^o$, $S(O)_2R^o$;
(61) In any one of paragraphs (56) to (58) above, $R^k$ and $R^l$ are each independently selected from hydrogen, (1-4C)alkyl, (5-10C)cycloalkyl, (5-10C)cycloalkyl(1-2C)alkyl, (2-4C)alkenyl, (2-4C)alkynyl, phenyl, phenyl(1-2C)alkyl, 5-6 membered heteroaryl (e.g. pyridyl, imidazolyl, thiazolyl, thiadiazolyl or furanyl), 5-6 membered heteroaryl(1-2C)alkyl, $S(O)R^o$, $S(O)_2R^o$;
(62) In any one of paragraphs (56) to (58) above, $R^k$ and $R^l$ are each independently selected from hydrogen, (1-4C)alkyl, (5-10C)cycloalkyl, (2-4C)alkenyl, (2-4C)alkynyl, phenyl, phenyl(1-2C)alkyl or 5-6 membered heteroaryl (e.g. pyridyl, imidazolyl, thiazolyl, thiadiazolyl or furanyl);
(63) In any one of paragraphs (56) to (58) above, $R^k$ and $R^l$ are each independently selected from hydrogen, (1-4C)alkyl, (5-10C)cycloalkyl, (2-4C)alkenyl, (2-4C)alkynyl, aryl or aryl(1-2C)alkyl;
(64) In any one of paragraphs (56) to (58) above, $R^k$ and $R^l$ are each independently selected from hydrogen, (1-4C)alkyl, (6-10C)cycloalkyl, (2-4C)alkynyl, phenyl, 6 membered heteroaryl or aryl(1-2C)alkyl;
(65) In any one of paragraphs (56) to (58) above, $R^k$ and $R^l$ are each independently selected from hydrogen, (1-4C)alkyl, (6-10C)cycloalkyl, (2-4C)alkynyl, phenyl or aryl(1-2C)alkyl;
(66) In any one of paragraphs (56) to (58) above, $R^k$ and $R^l$ are each independently selected from hydrogen, (1-4C)alkyl, cyclohexyl, adamantyl, (2-4C)alkynyl, phenyl, pyridinyl or aryl(1-2C)alkyl;
(67) In any one of paragraphs (56) to (58) above, $R^k$ and $R^l$ are each independently selected from hydrogen, (1-4C)alkyl, cyclohexyl, adamantyl, (2-4C)alkynyl, phenyl or aryl(1-2C)alkyl;
(68) $R^p$ and $R^q$ are independently selected from hydrogen, (1-6C)alkyl, (3-10C)cycloalkyl, (2-6C)alkenyl, (2-6C)alkynyl, aryl or heteroaryl;
(69) $R^p$ and $R^q$ are independently selected from hydrogen, (1-6C)alkyl or (3-10C)cycloalkyl;
(70) $R^p$ and $R^q$ are independently selected from hydrogen or (1-6C)alkyl;
(71) $R^p$ is (1-4C)alkyl;
(72) $R^q$ is selected from hydrogen or (1-4C)alkyl;
(73) $R_4$ and $R_5$ are each independently aryl or heteroaryl ring, each of which is optionally substituted by halo, cyano, nitro, hydroxy, carboxy, NR'''R'', (1-2C)alkoxy, (1-4C)alkyl, (1-4C)haloalkyl, (3-4C)cycloalkyl, (3-4C)cycloalkyl-(1-2C)alkyl, aryl, aryl(1-2C)alkyl, (1-2C)alkanoyl, (1-2C)alkylsulphonyl, SR''', SOR''', C(O)NR'''R'', NR'''C(O)R'', NR'''S(O)R'' and S(O)$_2$NR'''R'';

(74) $R_4$ and $R_5$ are each independently phenyl or 5-6 membered heteroaryl ring, each of which is optionally substituted by halo, cyano, nitro, hydroxy, carboxy, NR'''R'', (1-2C)alkoxy, (1-4C)alkyl, (1-4C)haloalkyl, (3-4C)cycloalkyl, (3-4C)cycloalkyl-(1-2C)alkyl, aryl, aryl(1-2C)alkyl, (1-2C)alkanoyl, (1-2C)alkylsulphonyl, SR''', SOR''', C(O)NR'''R'', NR'''C(O)R'', NR'''S(O)R'' and S(O)$_2$NR'''R'';

(75) $R_4$ and $R_5$ are each independently phenyl or 5-6 membered heteroaryl ring (e.g. pyridyl, furanyl, thiophenyl or imidazolyl), each of which is optionally substituted by halo, hydroxy, carboxy, NR'''R'', (1-2C)alkoxy, phenyl, phenyl(1-2C)alkyl (1-4C)alkyl or (1-4C)haloalkyl;

(76) $R_4$ and $R_5$ are each phenyl, each of which is optionally substituted by halo, hydroxy, carboxy, NR'''R'', (1-2C)alkoxy or (1-2C)alkyl;

(77) $R_4$ and $R_5$ are each phenyl or para-tolyl;

(78) $R_4$ and $R_5$ are each phenyl;

(79) $R_4$ and $R_5$ are linked to one another by a bond, an alkylene linker optionally comprising one or more heteroatoms, or a fused cycloalkyl, aryl, heteroaryl or heterocyclic ring;

(80) $R'''$ and $R''$ are each independently selected from hydrogen, (1-2C)alkyl (81) $R'''$ and $R''$ are each independently selected from hydrogen or methyl;

(82) $R^o$ is selected from (1-4C)alkyl, (2-4C)alkenyl, (2-4C)alkynyl or an aryl or heteroaryl group optionally substituted with one or more substituents selected from halo, OH, (1-4C)alkyl, (1-4C)hydroxyalkyl, (2-4C)alkenyl and (2-4C)alkynyl;

(83) $R^o$ is selected from (1-4C)alkyl, or an aryl or heteroaryl group (e.g. furanyl) optionally substituted with one or more substituents selected from halo, OH, (1-4C)alkyl, (1-4C)hydroxyalkyl, (2-4C)alkenyl and (2-4C)alkynyl;

(84) $R^o$ is selected from (1-4C)alkyl, or an aryl or 5-6 membered heteroaryl group optionally substituted with one or more substituents selected from halo, (1-4C)alkyl, (1-4C)hydroxyalkyl, (2-4C)alkenyl and (2-4C)alkynyl.

Suitably, a heteroaryl or heterocyclyl group as defined herein is a monocyclic heteroaryl or heterocyclyl group comprising one, two or three heteroatoms selected from N, O or S.

Suitably, a heteroaryl is a 5- or 6-membered heteroaryl ring comprising one, two or three heteroatoms selected from N, O or S.

Suitably, a heterocyclyl group is a 4-, 5- or 6-membered heterocyclyl ring comprising one, two or three heteroatoms selected from N, O or S. Most suitably, a heterocyclyl group is a 5-, 6- or 7-membered ring comprising one, two or three heteroatoms selected from N, O or S [e.g. morpholinyl (e.g. 4-morpholinyl), pyridinyl, piperazinyl, homopiperazinyl or pyrrolidinonyl].

Suitably an aryl group is phenyl.

In one embodiment, the compound has a structure according to formula (I), wherein Q is $NR_a$, wherein $R_a$ is H or (1-4C)alkyl;

$R_4$ and $R_5$ are as defined in any of numbered paragraphs (75) to (79) above; and $R_1$, $R_2$, $L^1$, $X^1$, X, $R_x$, $R_b$, $R_c$, $R_d$, $R^e$, $R^f$, $R^g$, $R^h$, $R^i$, $R^j$, $R_3$, $R^k$, $R^l$, $R^m$, $R^n$, $R^p$, $R^q$ and $R^o$ have any of the definitions appearing in numbered paragraphs (2) to (84) above.

In another embodiment, the compound has a structure according to formula (I), wherein Q is $NR_a$, wherein $R_a$ is H or (1-4C)alkyl;

$R_4$ and $R_5$ are as defined in any of numbered paragraphs (75) to (79) above;

$R_1$ is as defined in any of numbered paragraphs (10) to (14) above; and $R_2$, $L^1$, $X^1$, X, $R_x$, $R_b$, $R_c$, $R_d$, $R^e$, $R^f$, $R^g$, $R^h$, $R^i$, $R^j$, $R_3$, $R^k$, $R^l$, $R^m$, $R^n$, $R^p$, $R^q$ and $R^o$ have any of the definitions appearing in numbered paragraphs (2) to (84) above.

In another embodiment, the compound has a structure according to formula (I), wherein Q is $NR_a$, wherein $R_a$ is H or (1-4C)alkyl;

$R_4$ and $R_5$ are as defined in any of numbered paragraphs (74) to (78) above;

$R_1$ is as defined in any of numbered paragraphs (7) to (14) above;

$R_2$ is as defined in numbered paragraph (16) above; and $L^1$, $X^1$, X, $R_x$, $R_b$, $R_c$, $R_d$, $R^e$, $R^f$, $R^g$, $R^h$, $R^i$, $R^j$, $R_3$, $R^k$, $R^l$, $R^m$, $R^n$, $R^p$, $R^q$ and $R^o$ have any of the definitions appearing in numbered paragraphs (2) to (84) above.

In another embodiment, the compound has a structure according to formula (I), wherein Q is $NR_a$, wherein $R_a$ is H or (1-4C)alkyl;

$R_4$ and $R_5$ are as defined in any of numbered paragraphs (75) to (79) above;

$R_1$ is as defined in any of numbered paragraphs (7) to (14) above;

$R_2$ is as defined in numbered paragraph (16) above;

$L^1$ is as defined in either of numbered paragraphs (19) or (20) above;

$X^1$ is as defined in either of numbered paragraphs (21) or (26) above; and

X, $R_x$, $R_b$, $R_c$, $R^e$, $R^f$, $R^g$, $R^h$, $R^i$, $R^j$, $R_3$, $R^k$, $R^l$, $R^m$, $R^n$, $R^p$, $R^q$ and $R^o$ have any of the definitions appearing in numbered paragraphs (2) to (84) above.

In another embodiment, the compound has a structure according to formula (I), wherein Q is $NR_a$, wherein $R_a$ is H or (1-4C)alkyl;

$R_4$ and $R_5$ are as defined in any of numbered paragraphs (75) to (79) above;

$R_1$ is as defined in any of numbered paragraphs (7) to (14) above;

$R_2$ is as defined in numbered paragraph (16) above;

$L^1$ is as defined in either of numbered paragraphs (19) or (20) above;

$X^1$ is as defined in either of numbered paragraphs (21) or (24) above;

$R_b$ is as defined in any of numbered paragraphs (34) to (41) above;

$R_c$ is as defined in any of numbered paragraphs (42) to (43) above;

or $R_b$ and $R_c$ are as defined in numbered paragraph (46) above; and

X, $R_x$, $R^e$, $R^f$, $R^g$, $R^h$, $R_3$, $R^k$, $R^l$, $R^m$, $R^n$, $R^p$, $R^q$ and $R^o$ have any of the definitions appearing in numbered paragraphs (2) to (84) above.

In another embodiment, the compound has a structure according to formula (I), wherein Q is $NR_a$, wherein $R_a$ is H or (1-4C)alkyl;

$R_4$ and $R_5$ are as defined in any of numbered paragraphs (75) to (79) above;

$R_1$ is as defined in any of numbered paragraphs (7) to (14) above;

$R_2$ is as defined in numbered paragraph (16) above;

$L^1$ is as defined in either of numbered paragraphs (19) or (20) above;

$X^1$ is as defined in either of numbered paragraphs (23) or (24) above;

$R_b$ is as defined in any of numbered paragraphs (34) to (41) above;

$R_c$ is as defined in any of numbered paragraphs (42) to (44) above;

or $R_b$ and $R_c$ are as defined in numbered paragraph (46) above;

$R^e$ and $R^f$ are as defined in either of numbered paragraphs (47) or (48) above;

$R^3$ is as defined in any of numbered paragraphs (55) to (58) above;

$R^k$ and $R^l$ are as defined in any of numbered paragraphs (61) to (67) above;

$R^p$ and $R^q$ are as defined in any one of numbered paragraphs (68) to (72) above;

$R^i$ and $R^j$ are as defined in numbered paragraph (54) above; and

X, $R_x$, $R_3$, $R^m$, $R^n$, $R^p$, $R^q$ and $R^o$ have any of the definitions appearing in numbered paragraphs (2) to (84) above.

In another embodiment, the compound has a structure according to formula (I), wherein Q is $NR_a$, wherein $R_a$ is H or (1-4C)alkyl;

$R_4$ and $R_5$ are as defined in any of numbered paragraphs (75) to (79) above;

$R_1$ is as defined in any of numbered paragraphs (8) to (14) above;

$R_2$ is as defined in numbered paragraph (16) above;

$L^1$ is as defined in either of numbered paragraphs (19) or (20) above;

$X^1$ is as defined in either of numbered paragraphs (23) or (24) above;

$R_b$ is as defined in any of numbered paragraphs (34) to (41) above;

$R_c$ is as defined in any of numbered paragraphs (42) to (44) above;

or $R_b$ and $R_c$ are as defined in numbered paragraph (46) above;

$R^e$ and $R^f$ are as defined in either of numbered paragraphs (47) or (48) above;

$R^k$ and $R^l$ are as defined in any of numbered paragraphs (61) to (67) above;

$R^i$ and $R^j$ are as defined in numbered paragraph (54) above; and

X, $R_x$, $R_3$, $R^m$, $R^n$, $R^p$, $R^q$ and $R^o$ have any of the definitions appearing in numbered paragraphs (2) to (84) above.

In another embodiment, the compound has a structure according to formula (I), wherein Q is $NR_a$, wherein $R_a$ is H or (1-4C)alkyl;

$R_4$ and $R_5$ are as defined in any of numbered paragraphs (75) to (79) above;

$R_1$ is as defined in any of numbered paragraphs (8) to (18) above;

$R_2$ is as defined in numbered paragraph (16) above;

$L^1$ is as defined in either of numbered paragraphs (19) or (20) above;

$X^1$ is as defined in either of numbered paragraphs (23) or (24) above;

$R_b$ is as defined in any of numbered paragraphs (34) to (41) above;

$R_c$ is as defined in any of numbered paragraphs (42) to (44) above;

$R^e$ and $R^f$ are as defined in either of numbered paragraphs (47) or (48) above;

$R^3$ is as defined in any of numbered paragraphs (55) to (58) above;

$R^k$ and $R^l$ are as defined in any of numbered paragraphs (61) to (67) above;

$R^p$ and $R^q$ are as defined in any one of numbered paragraphs (68) to (72) above; and X, $R_x$, $R_3$, $R^m$, $R^n$, $R^p$ and $R^q$ have any of the definitions appearing in numbered paragraphs (2) to (84) above.

In another embodiment, the compound has a structure according to formula (I), wherein Q is $NR_a$, wherein $R_a$ is H or (1-4C)alkyl;

$R_4$ and $R_5$ are as defined in any of numbered paragraphs (75) to (79) above;

$R_1$ is as defined in any of numbered paragraphs (9) to (14) above;

$R_2$ is as defined in numbered paragraph (16) above;

$L^1$ is as defined in either of numbered paragraphs (19) or (20) above;

$X^1$ is as defined in either of numbered paragraphs (23) or (24) above;

$R_b$ is as defined in any of numbered paragraphs (34) to (41) above;

$R_c$ is as defined in any of numbered paragraphs (42) to (44) above;

$R^e$ and $R^f$ are as defined in either of numbered paragraphs (47) or (48) above;

$R^k$ and $R^l$ are as defined in any of numbered paragraphs (61) to (67) above; and X, $R_x$, $R_3$, $R^m$, $R^n$, $R^p$ and $R^q$ have any of the definitions appearing in numbered paragraphs (2) to (84) above.

In another embodiment, the compound has a structure according to formula (I), wherein Q is $NR_a$, wherein $R_a$ is H or (1-4C)alkyl;

$R_4$ and $R_5$ are as defined in any of numbered paragraphs (75) to (79) above;

$R_1$ is as defined in any of numbered paragraphs (8) to (14) above;

$R_2$ is as defined in numbered paragraph (17) to (18) above;

$R^k$ and $R^l$ are as defined in any of numbered paragraphs (61) to (67) above; and $R_3$, $R^m$, $R^n$, $R^p$ and $R^q$ have any of the definitions appearing in numbered paragraphs (2) to (84) above.

In another embodiment, the compound has a structure according to formula (I), wherein Q is $NR_a$, wherein $R_e$ is H or (1-4C)alkyl;

$R_4$ and $R_5$ are as defined in any of numbered paragraphs (75) to (79) above;

$R_1$ is as defined in any of numbered paragraphs (8) to (14) above;

$R_2$ is as defined in any one of numbered paragraphs (17) to (18) above;

$R^k$ and $R^l$ are as defined in any of numbered paragraphs (61) to (67) above;

$R_3$ is as defined in any one of numbered paragraph (54) to (58) above;

$R^m$, $R^n$ are as defined in any one of numbered paragraphs (80) to (81) above; and $R^p$ is as defined in numbered paragraph (71) above.

In another embodiment, the compound has a structure according to formula (Ia) shown below:

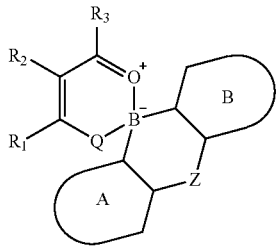

(Ia)

wherein
Q is $NR_a$, wherein $R_a$ is H or (1-4C)alkyl;
Rings A and B are as defined for $R_4$ and $R_5$ in any of numbered paragraphs (73) to (78) above;
$R^m$ and $R^n$ are as defined in either of numbered paragraphs (80) or (81) above;
Z is absent, a bond, a group —$(CH_2)_n$— where n is 1 or 2, a group —$(CH)_m$— wherein m is 1 or 2, or a linking group comprising 1 or 2 heteroatoms selected from N and O; and
$R_a$, $R_1$, $R_2$, $L^1$, $X^1$, X, $R_x$, $R_b$, $R_c$, $R_d$, $R^e$, $R^f$, $R^g$, $R^h$, $R^i$, $R^j$, $R_3$, $R^k$, $R^l$, $R^p$, $R^q$ and $R^o$ have any of the definitions appearing in numbered paragraphs (2) to (84) above.

In another embodiment, the compound has a structure according to formula (Ia), wherein
Q is $NR_a$, wherein $R_a$ is H;
Rings A and B are as defined for $R_4$ and $R_5$ in any of numbered paragraphs (73) to (78) above;
$R^m$ and $R^n$ are as defined in either of numbered paragraphs (80) or (81) above;
Z is absent, a bond, a group —$(CH_2)_n$— where n is 1 or 2, a group —$(CH)_m$— wherein m is 1 or 2, or a linking group comprising 1 or 2 heteroatoms selected from N and O;
$R_1$ is as defined in any of numbered paragraphs (8) to (14) above; and
$R_2$, $L^1$, $X^1$, X, $R_x$, $R_b$, $R_c$, $R_d$, $R^e$, $R^f$, $R^g$, $R^h$, $R^i$, $R^j$, $R_3$, $R^k$, $R^l$, $R^p$, $R^q$ and $R^o$ have any of the definitions appearing in numbered paragraphs (2) to (84) above.

In another embodiment, the compound has a structure according to formula (Ia), wherein
Q is $NR_a$, wherein $R_a$ is H;
Rings A and B are as defined for $R_4$ and $R_5$ in any of numbered paragraphs (73) to (78) above;
$R^m$ and $R^n$ are as defined in either of numbered paragraphs (80) or (81) above;
Z is absent, a bond, a group —$(CH_2)_n$— where n is 1 or 2, a group —$(CH)_m$— wherein m is 1 or 2, or a linking group comprising 1 or 2 heteroatoms selected from N and O;
$R_1$ is as defined in any of numbered paragraphs (8) to (14) above;
$R_2$ is as defined in numbered paragraph (16) above;
$L^1$ is as defined in either of numbered paragraphs (19) or (20) above;
$X^1$ is as defined in either of numbered paragraphs (23) or (24) above; and
X, $R_x$, $R_b$, $R_c$, $R^e$, $R^f$, $R^g$, $R^h$, $R^i$, $R^j$, $R_3$, $R^k$, $R^l$, $R^p$, $R^q$ and $R^o$ have any of the definitions appearing in numbered paragraphs (2) to (84) above.

In another embodiment, the compound has a structure according to formula (Ia), wherein
Q is $NR_a$, wherein $R_a$ is H;
Rings A and B are as defined for $R_4$ and $R_5$ in any of numbered paragraphs (73) to (78) above;
$R^m$ and $R^n$ are as defined in either of numbered paragraphs (80) or (81) above;
Z is absent, a bond, a group —$(CH_2)_n$— where n is 1 or 2, a group —$(CH)_m$— wherein m is 1 or 2, or a linking group comprising 1 or 2 heteroatoms selected from N and O;
$R_1$ is as defined in any of numbered paragraphs (7) to (14) above;
$R_2$ is as defined in numbered paragraph (16) above;
$L^1$ is as defined in either of numbered paragraphs (19) or (20) above;
$X^1$ is as defined in either of numbered paragraphs (23) or (24) above;
$R_b$ is as defined in any of numbered paragraphs (34) to (41) above;
$R_c$ is as defined in any of numbered paragraphs (42) to (44) above;
or $R_b$ and $R_e$ are as defined in numbered paragraph (46) above; and
X, $R_x$, $R^e$, $R^f$, $R^g$, $R^h$, $R_3$, $R^k$, $R^l$, $R^p$, $R^q$ and $R^o$ have any of the definitions appearing in numbered paragraphs (2) to (84) above.

In another embodiment, the compound has a structure according to formula (Ia), wherein
Q is $NR_a$, wherein $R_a$ is H;
Rings A and B are as defined for $R_4$ and $R_5$ in any of numbered paragraphs (73) to (78) above;
$R^m$ and $R^n$ are as defined in either of numbered paragraphs (80) or (81) above;
Z is absent, a bond, a group —$(CH_2)_n$— where n is 1 or 2, a group —$(CH)_m$— wherein m is 1 or 2, or a linking group comprising 1 or 2 heteroatoms selected from N and O;
$R_1$ is as defined in any of numbered paragraphs (8) to (14) above;
$R_2$ is as defined in numbered paragraph (16) above;
$L^1$ is as defined in either of numbered paragraphs (19) or (20) above;
$X^1$ is as defined in either of numbered paragraphs (21) or (24) above;
$R_b$ is as defined in any of numbered paragraphs (34) to (41) above;
$R_c$ is as defined in any of numbered paragraphs (42) to (44) above;
or $R_b$ and $R_c$ are as defined in numbered paragraph (46) above;
$R^e$ and $R^f$ are as defined in either of numbered paragraphs (47) or (48) above;
$R^k$ and $R^l$ are as defined in either of numbered paragraphs (61) or (67) above;
$R^i$ and $R^j$ are as defined in numbered paragraph (54) above;
$R^o$ is as defined in any of numbered paragraphs (82) to (84) above; and
X, $R_x$, $R^p$, $R^q$ and $R_3$ have any of the definitions appearing in numbered paragraphs (2) to (84) above.

In another embodiment, the compound has a structure according to formula (Ia), wherein
Q is $NR_a$, wherein $R_a$ is H;
Rings A and B are as defined for $R_4$ and $R_5$ in any of numbered paragraphs (77) to (78) above;

$R^m$ and $R^n$ are as defined in either of numbered paragraphs (80) or (81) above;

Z is absent, a bond, a group —$(CH_2)_n$— where n is 1 or 2, a group —$(CH)_m$— wherein m is 1 or 2, or a linking group comprising 1 or 2 heteroatoms selected from N and O;

$R_1$ is as defined in any of numbered paragraphs (7) to (14) above;

$R_2$ is as defined in numbered paragraph (16) above;

$L^1$ is as defined in either of numbered paragraphs (19) or (20) above;

$X^1$ is as defined in either of numbered paragraphs (23) or (24) above;

$R_b$ is as defined in any of numbered paragraphs (34) to (41) above;

$R_c$ is as defined in any of numbered paragraphs (42) to (44) above;

or $R_b$ and $R_c$ are as defined in numbered paragraph (46) above;

$R^e$ and $R^f$ are as defined in either of numbered paragraphs (47) or (48) above;

$R^k$ and $R^l$ are as defined in either of numbered paragraphs (61) or (67) above;

$R^i$ and $R^j$ are as defined in numbered paragraph (54) above;

$R^o$ is as defined in any of numbered paragraphs (82) to (84) above; and

X, $R_x$, $R^p$, $R^q$ and $R_3$ have any of the definitions appearing in numbered paragraphs (2) to (84) above.

In another embodiment, the compound has a structure according to formula (Ia), wherein Q is $NR_a$, wherein $R_a$ is H;

Rings A and B are as defined for $R_4$ and $R_5$ in any of numbered paragraphs (77) to (78) above;

$R^m$ and $R^n$ are as defined in either of numbered paragraphs (80) or (81) above;

Z is absent, a bond, a group —$(CH_2)_n$— where n is 1 or 2, a group —$(CH)_m$— wherein m is 1 or 2, or a linking group comprising 1 or 2 heteroatoms selected from N and O;

$R_1$ is as defined in any of numbered paragraphs (10) to (14) above;

$R_2$ is as defined in any one of numbered paragraphs (17) to (18) above;

$R^k$ and $R^l$ are as defined in any of numbered paragraphs (61) to (67) above;

$R_3$ is as defined in any one of numbered paragraph (54) to (58) above;

$R^m$, $R^n$ are as defined in any one of numbered paragraphs (80) to (81) above; and $R^p$ is as defined in numbered paragraph (71) above.

In another embodiment, the compound has a structure according to formula (Ib) shown below:

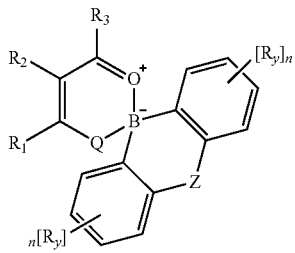

(Ib)

wherein

Q is $NR_a$, wherein $R_a$ is H or (1-4C)alkyl;

each $R_y$ is independently halo, (1-4C)alkyl, (1-4C)haloalkyl, phenyl or (1-2C)alkoxy;

n is 0, 1 or 2;

Z is absent, a bond, a group —$(CH_2)_n$— where n is 1 or 2, a group —$(CH)_m$— wherein m is 1 or 2, or a linking group comprising 1 or 2 heteroatoms selected from N and O; and $R_a$, $R_1$, $R_2$, $L^1$, $X^1$, X, $R_x$, $R_b$, $R_c$, $R_d$, $R^e$, $R^f$, $R^g$, $R^h$, $R^i$, $R^j$, $R_3$, $R^k$, $R^l$, $R^p$, $R^q$ and $R^o$ have any of the definitions appearing in numbered paragraphs (2) to (84) above.

In another embodiment, the compound has a structure according to formula (Ib), wherein Q is $NR_a$, wherein $R_a$ is H;

each $R_y$ is independently halo, (1-4C)alkyl, (1-4C)haloalkyl, phenyl or (1-2C)alkoxy;

n is 0, 1 or 2;

Z is absent, a bond, a group —$(CH_2)_n$— where n is 1 or 2, a group —$(CH)_m$— wherein m is 1 or 2, or a linking group comprising 1 or 2 heteroatoms selected from N and O;

$R_1$ is as defined in any of numbered paragraphs (7) to (13) above; and $R_2$, $L^1$, $X^1$, X, $R_x$, $R_b$, $R_c$, $R_d$, $R^e$, $R^f$, $R^g$, $R^h$, $R^i$, $R^j$, $R_3$, $R^k$, $R^l$, $R^p$, $R^q$ and $R^o$ have any of the definitions appearing in numbered paragraphs (2) to (84) above.

In another embodiment, the compound has a structure according to formula (Ib), wherein Q is $NR_a$, wherein $R_a$ is H;

each $R_y$ is independently halo, (1-4C)alkyl, (1-4C)haloalkyl, phenyl or (1-2C)alkoxy;

n is 0, 1 or 2;

Z is absent, a bond, a group —$(CH_2)_n$— where n is 1 or 2, a group —$(CH)_m$— wherein m is 1 or 2, or a linking group comprising 1 or 2 heteroatoms selected from N and O;

$R_1$ is as defined in any of numbered paragraphs (7) to (14) above;

$R_2$ is as defined in numbered paragraph (16) above;

$L^1$ is as defined in either of numbered paragraphs (19) or (20) above;

$X^1$ is as defined in either of numbered paragraphs (23) or (24) above; and

X, $R_x$, $R_b$, $R_c$, $R^e$, $R^f$, $R^g$, $R^h$, $R^i$, $R^j$, $R_3$, $R^k$, $R^l$, $R^p$, $R^q$ and $R^o$ have any of the definitions appearing in numbered paragraphs (2) to (84) above.

In another embodiment, the compound has a structure according to formula (Ib), wherein Q is $NR_a$, wherein $R_a$ is H;

each $R_y$ is independently halo, (1-4C)alkyl, (1-4C)haloalkyl, phenyl or (1-2C)alkoxy;

n is 0, 1 or 2;

Z is absent, a bond, a group —$(CH_2)_n$— where n is 1 or 2, a group —$(CH)_m$— wherein m is 1 or 2, or a linking group comprising 1 or 2 heteroatoms selected from N and O;

$R_1$ is as defined in any of numbered paragraphs (8) to (14) above;

$R_2$ is as defined in numbered paragraph (16) above;

$L^1$ is as defined in either of numbered paragraphs (19) or (20) above;

$X^1$ is as defined in either of numbered paragraphs (23) or (24) above;

$R_b$ is as defined in any of numbered paragraphs (34) to (41) above;

$R_c$ is as defined in any of numbered paragraphs (42) to (44) above;

or $R_b$ and $R_c$ are as defined in numbered paragraph (46) above; and

X, $R_x$, $R^e$, $R^f$, $R^g$, $R^h$, $R_3$, $R^k$, $R^l$, $R^p$, $R^q$ and $R^o$ have any of the definitions appearing in numbered paragraphs (2) to (84) above.

In another embodiment, the compound has a structure according to formula (Ib), wherein Q is $NR_a$, wherein $R_a$ is H;

each $R_y$ is independently halo, (1-4C)alkyl, (1-4C)haloalkyl, phenyl or (1-2C)alkoxy;

n is 0, 1 or 2;

Z is absent, a bond, a group —$(CH_2)_n$— where n is 1 or 2, a group —$(CH)_m$— wherein m is 1 or 2, or a linking group comprising 1 or 2 heteroatoms selected from N and O;

$R_1$ is as defined in any of numbered paragraphs (8) to (14) above;

$R_2$ is as defined in numbered paragraph (16) above;

$L^1$ is as defined in either of numbered paragraphs (19) or (20) above;

$X^1$ is as defined in either of numbered paragraphs (23) or (24) above;

$R_b$ is as defined in any of numbered paragraphs (34) to (41) above;

$R_c$ is as defined in any of numbered paragraphs (42) to (44) above;

or $R_b$ and $R_c$ are as defined in numbered paragraph (46) above;

$R^e$ and $R^f$ are as defined in either of numbered paragraphs (47) or (48) above;

$R^k$ and $R^l$ are as defined in either of numbered paragraphs (61) or (67) above;

$R^i$ and $R^j$ are as defined in numbered paragraph (54) above;

$R^o$ is as defined in any of numbered paragraphs (82) to (84) above; and

X, $R_x$, $R^p$, $R^q$ and $R_3$ have any of the definitions appearing in numbered paragraphs (2) to (84) above.

In another embodiment, the compound has a structure according to formula (Ib), wherein Q is $NR_a$, wherein $R_a$ is H;

each $R_y$ is independently halo, (1-4C)alkyl, (1-4C)haloalkyl, phenyl or (1-2C)alkoxy;

n is 0, 1 or 2;

Z is absent, a bond, a group —$(CH_2)_n$— where n is 1 or 2, a group —$(CH)_m$— wherein m is 1 or 2, or a linking group comprising 1 or 2 heteroatoms selected from N and O;

$R_1$ is as defined in any of numbered paragraphs (6) to (14) above;

$R_2$ is as defined in numbered paragraphs (14) above;

$L^1$ is as defined in either of numbered paragraphs (19) or (20) above;

$X^1$ is as defined in either of numbered paragraphs (23) or (24) above;

$R_b$ is as defined in any of numbered paragraphs (34) to (41) above;

$R_c$ is as defined in any of numbered paragraphs (42) to (44) above;

or $R_b$ and $R_c$ are as defined in numbered paragraph (44) above;

$R^e$ and $R^f$ are as defined in either of numbered paragraphs (47) or (48) above;

$R^k$ and $R^l$ are as defined in either of numbered paragraphs (61) or (67) above;

$R^i$ and $R^j$ are as defined in numbered paragraph (54) above;

$R^o$ is as defined in any of numbered paragraphs (82) to (84) above; and

X, $R_x$, $R^p$, $R^q$ and $R_3$ have any of the definitions appearing in numbered paragraphs (2) to (84) above.

In another embodiment, the compound has a structure according to formula (Ib), wherein Q is $NR_a$, wherein $R_a$ is H;

each $R_y$ is independently halo, (1-4C)alkyl, (1-4C)haloalkyl, phenyl or (1-2C)alkoxy;

n is 0, 1 or 2;

Z is absent, a bond, a group —$(CH_2)_n$— where n is 1 or 2, a group —$(CH)_m$— wherein m is 1 or 2, or a linking group comprising 1 or 2 heteroatoms selected from N and O;

$R_1$ is as defined in any of numbered paragraphs (8) to (14) above;

$R_2$ is as defined in numbered paragraphs (16) above;

$L^1$ is as defined in either of numbered paragraphs (19) or (20) above;

$X^1$ is as defined in either of numbered paragraphs (23) or (24) above;

$R_b$ is as defined in any of numbered paragraphs (34) to (41) above;

$R_c$ is as defined in any of numbered paragraphs (42) to (44) above;

or $R_b$ and $R_c$ are as defined in numbered paragraph (46) above;

$R^e$ and $R^f$ are as defined in either of numbered paragraphs (47) or (48) above;

$R^k$ and $R^l$ are as defined in either of numbered paragraphs (61) or (67) above;

$R^i$ and $R^j$ are as defined in numbered paragraph (54) above;

$R^o$ is as defined in paragraph (84) above; and

X, $R_x$, $R^p$, $R^q$ and $R_3$ have any of the definitions appearing in numbered paragraphs (2) to (84) above.

In another embodiment, the compound has a structure according to formula (Ib), wherein Q is $NR_a$, wherein $R_a$ is H;

each $R_y$ is independently halo, (1-4C)alkyl, (1-4C)haloalkyl, phenyl or (1-2C)alkoxy;

n is 0, 1 or 2;

Z is absent, a bond, a group —$(CH_2)_n$— where n is 1 or 2, a group —$(CH)_m$— wherein m is 1 or 2, or a linking group comprising 1 or 2 heteroatoms selected from N and O;

$R_1$ is as defined in any of numbered paragraphs (10) to (14) above;

$R_2$ is as defined in any one of numbered paragraphs (17) to (18) above;

$R^k$ and $R^l$ are as defined in any of numbered paragraphs (61) to (67) above;

$R_3$ is as defined in any of numbered paragraph (54) to (58) above;

$R^m$, $R^n$ are as defined in any one of numbered paragraphs (80) to (81) above; and $R^p$ is as defined in numbered paragraph (71) above.

In another embodiment, the compound has a structure according to formula (Ic) shown below:

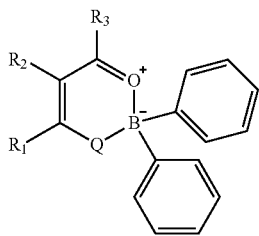

(Ic)

wherein

Q is $NR_a$, wherein $R_a$ is H or (1-4C)alkyl; and $R_a$, $R_1$, $R_2$, $L^1$, $X^1$, X, $R_x$, $R_b$, $R_c$, $R_d$, $R^e$, $R^f$, $R^g$, $R^h$, $R^i$, $R^j$, $R_3$, $R^k$, $R^l$ and $R^o$ have any of the definitions appearing in numbered paragraphs (2) to (84) above.

In another embodiment, the compound has a structure according to formula (Ic), wherein Q is $NR_a$, wherein $R_a$ is H or (1-4C)alkyl;

$R_1$ is as defined in any of numbered paragraphs (8) to (14) above; and

Q, $R_a$, $R_2$, $L^1$, $X^1$, X, $R_x$, $R_b$, $R_c$, $R_d$, $R^e$, $R^f$, $R^g$, $R^h$, $R^i$, $R^j$, $R_3$, $R^k$, $R^l$, $R^p$, $R^q$ and $R^o$ have any of the definitions appearing in numbered paragraphs (2) to (84) above.

In another embodiment, the compound has a structure according to formula (Ic), wherein Q is $NR_a$, wherein $R_a$ is H;

$R_1$ is as defined in any of numbered paragraphs (8) to (14) above; and $R_2$, $L^1$, $X^1$, X, $R_x$, $R_b$, $R_c$, $R_d$, $R^e$, $R^f$, $R^g$, $R^h$, $R^i$, $R^j$, $R_3$, $R^k$, $R^l$, $R^p$, $R^q$ and $R^o$ have any of the definitions appearing in numbered paragraphs (2) to (84) above.

In another embodiment, the compound has a structure according to formula (Ic), wherein Q is $NR_a$, wherein $R_a$ is H;

$R_1$ is as defined in any of numbered paragraphs (8) to (14) above;

$R_2$ is as defined in numbered paragraph (16) above; and $L^1$, $X^1$, X, $R_x$, $R_b$, $R_c$, $R_d$, $R^e$, $R^f$, $R^g$, $R^h$, $R^i$, $R^j$, $R_3$, $R^k$, $R^l$, $R^p$, $R^q$ and $R^o$ have any of the definitions appearing in numbered paragraphs (2) to (84) above.

In another embodiment, the compound has a structure according to formula (Ic), wherein Q is $NR_a$, wherein $R_a$ is H;

$R_1$ is as defined in any of numbered paragraphs (8) to (14) above;

$R_2$ is as defined in numbered paragraph (16) above;

$L^1$ is as defined in either of numbered paragraphs (19) or (20) above;

$X^1$ is as defined in either of numbered paragraphs (23) or (24) above; and

X, $R_x$, $R_b$, $R_c$, $R^e$, $R^f$, $R^g$, $R^h$, $R^i$, $R^j$, $R_3$, $R^k$, $R^l$, $R^p$, $R^q$ and $R^o$ have any of the definitions appearing in numbered paragraphs (2) to (84) above.

In another embodiment, the compound has a structure according to formula (Ic), wherein Q is $NR_a$, wherein $R_a$ is H;

$R_1$ is as defined in any of numbered paragraphs (8) to (14) above;

$R_2$ is as defined in numbered paragraphs (16) above;

$L^1$ is as defined in either of numbered paragraphs (19) or (20) above;

$X^1$ is as defined in either of numbered paragraphs (23) or (24) above;

$R_b$ is as defined in any of numbered paragraphs (34) to (41) above;

$R_c$ is as defined in any of numbered paragraphs (42) to (44) above;

or $R_b$ and $R_c$ are as defined in numbered paragraph (46) above; and

X, $R_x$, $R^e$, $R^f$, $R^g$, $R^h$, $R_3$, $R^k$, $R^l$, $R^p$, $R^q$ and $R^o$ have any of the definitions appearing in numbered paragraphs (2) to (84) above.

In another embodiment, the compound has a structure according to formula (Ic), wherein Q is $NR_a$, wherein $R_a$ is H;

$R_1$ is as defined in any of numbered paragraphs (8) to (14) above $R_2$ is as defined in numbered paragraph (16) above;

$L^1$ is as defined in either of numbered paragraphs (19) or (20) above;

$X^1$ is as defined in either of numbered paragraphs (23) or (24) above;

$R_b$ is as defined in any of numbered paragraphs (34) to (41) above;

$R_c$ is as defined in any of numbered paragraphs (42) to (44) above;

or $R_b$ and $R_c$ are as defined in numbered paragraph (46) above;

$R^e$ and $R^f$ are as defined in either of numbered paragraphs (47) or (48) above;

$R^k$ and $R^l$ are as defined in either of numbered paragraphs (61) or (67) above;

$R^o$ is as defined in any of numbered paragraphs (82) to (84) above; and

X, $R_x$, $R^p$, $R^q$ and $R_3$, have any of the definitions appearing in numbered paragraphs (2) to (84) above.

In another embodiment, the compound has a structure according to formula (Ic), wherein Q is $NR_a$, wherein $R_a$ is H;

$R_1$ is as defined in any of numbered paragraphs (8) to (14) above $R_2$ is as defined in numbered paragraph (16) above;

$L^1$ is as defined in either of numbered paragraphs (19) or (20) above;

$X^1$ is as defined in either of numbered paragraphs (23) or (24) above;

$R_b$ is as defined in any of numbered paragraphs (34) to (41) above;

$R_c$ is as defined in any of numbered paragraphs (42) to (44) above;

or $R_b$ and $R_c$ are as defined in numbered paragraph (46) above;

$R^e$ and $R^f$ are as defined in either of numbered paragraphs (47) or (48) above;

$R^k$ and $R^l$ are as defined in either of numbered paragraphs (61) or (67) above;

$R^o$ is as defined in paragraph (84) above; and

X, $R_x$, $R^p$, $R^q$ and $R_3$ have any of the definitions appearing in numbered paragraphs (2) to (84) above.

In another embodiment, the compound has a structure according to formula (Ic), wherein Q is $NR_a$, wherein $R_a$ is H;

$R_1$ is as defined in any of numbered paragraphs (7) to (14) above $R_2$ is as defined in numbered paragraph (16) above;

$L^1$ is as defined in numbered paragraph (20) above;

$X^1$ is as defined in either of numbered paragraph (24) above;

$R_b$ is as defined in any of numbered paragraphs (36) to (41) above;

$R_c$ is as defined in any of numbered paragraphs (43) to (44) above;

or $R_b$ and $R_c$ are as defined in numbered paragraph (45) above;

$R^e$ and $R^f$ are as defined in either of numbered paragraphs (47) or (48) above;

$R^k$ and $R^l$ are as defined in either of numbered paragraphs (65) or (67) above;

$R^o$ is as defined in paragraph (84) above; and $X$, $R_x$, $R^p$, $R^q$ and $R_3$ have any of the definitions appearing in numbered paragraphs (2) to (84) above.

In a particularly suitable embodiment, the compound has a structure according to formula (Ic), wherein Q is $NR_a$, wherein $R_a$ is H;

$R_1$ is as defined in numbered paragraph (14) above $R_2$ is as defined in numbered paragraph (15) above;

$L^1$ is as defined in numbered paragraph (20) above;

$X^1$ is as defined in numbered paragraph (24) above;

$R_b$ is as defined in numbered paragraph (41) above;

$R_c$ is as defined in numbered paragraph (44) above;

or $R_b$ and $R_c$ are as defined in numbered paragraph (46) above;

$R^e$ and $R^f$ are as defined in numbered paragraph (48) above;

$R^k$ and $R^l$ are as defined in numbered paragraph (67) above;

$X$, $R_x$, $R^p$, $R^q$ and $R_3$ have any of the definitions appearing in numbered paragraphs (2) to (84) above.

In a particularly suitable embodiment, the compound has a structure according to formula (Ic), wherein Q is $NR_a$, wherein $R_a$ is H;

$R_1$ is as defined in numbered paragraph (14) above;

$R_2$ is as defined in numbered paragraph (18) above;

$R^k$ and $R^l$ are as defined in numbered paragraph (67) above;

$R_3$ is as defined in numbered paragraph (58) above;

$R^m$, $R^n$ are as defined in numbered paragraph (81) above; and $R^p$ is as defined in numbered paragraph (71) above.

In another embodiment, the compound has a structure according to formula (Id) shown below:

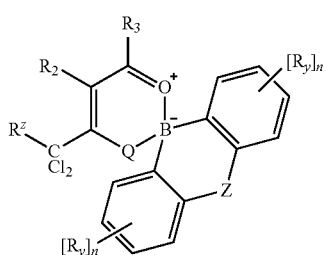

(Id)

wherein Q, Z, $R_y$, n, $R_2$ or $R_3$ as defined hereinbefore and $R^z$ is H or Cl.

In an embodiment, the compound has a structure according to formula (Id) wherein $R_2$ is H, C(O)OMe, C(O)OEt, C(O)Me, $C(O)NH_2$ or $C(O)NMe_2$.

In another embodiment, the compound has a structure according to formula (Ie) shown below:

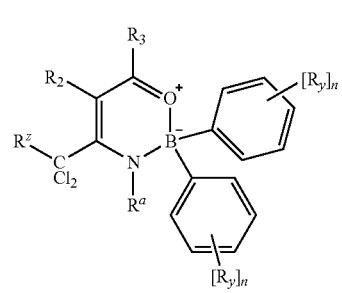

(Ie)

wherein $R^a$, $R^z$, $R_y$, n, $R_2$ or $R_3$ as as defined hereinbefore.

In an embodiment, the compound has a structure according to formula (Ie) wherein $R_2$ is H, C(O)OMe, C(O)OEt, C(O)Me, $C(O)NH_2$ or $C(O)NMe_2$.

In another embodiment, the compound has a structure according to formula (If) shown below:

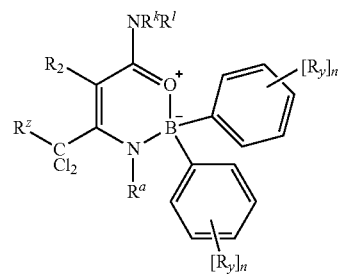

(If)

wherein $R^z$, $R^a$, $R_y$, n, $R_2$, $L^1$, $X^1$, X, $R^k$ and $R^l$ each have any one for the definitions set out hereinbefore.

In an embodiment, the compound has a structure according to formula (If) wherein $R_2$ is H, C(O)OMe, C(O)OEt, C(O)Me, $C(O)NH_2$ or $C(O)NMe_2$.

Particular compounds of the present invention include any one of the compounds exemplified in the present application, or a pharmaceutically acceptable salt or solvate thereof, and, in particular, any one of the following:

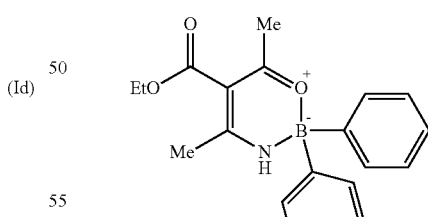

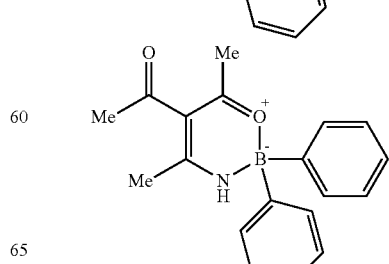

27
-continued
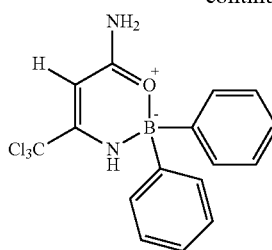
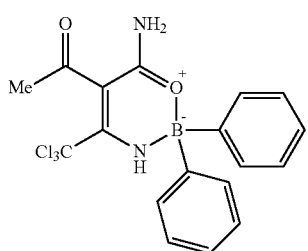
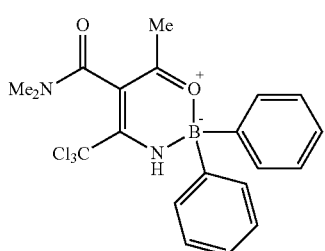
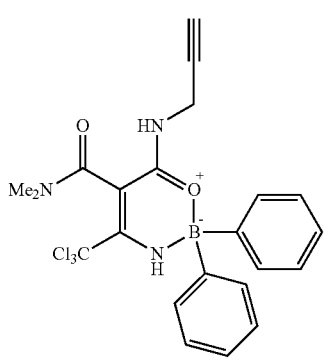
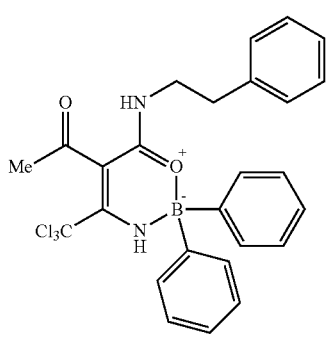
28
-continued
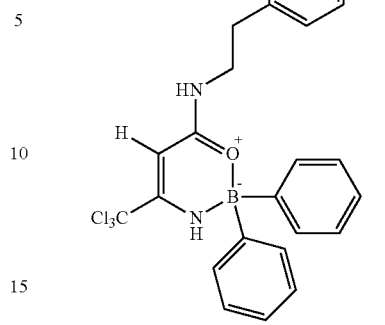
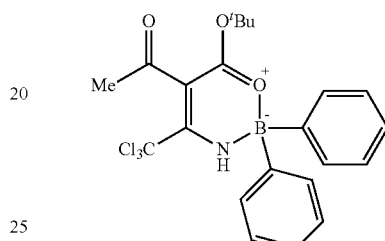
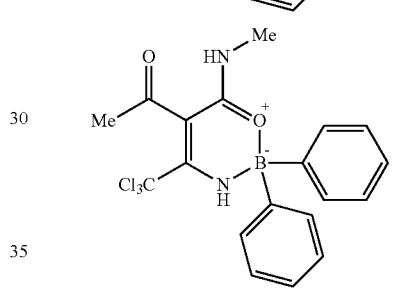
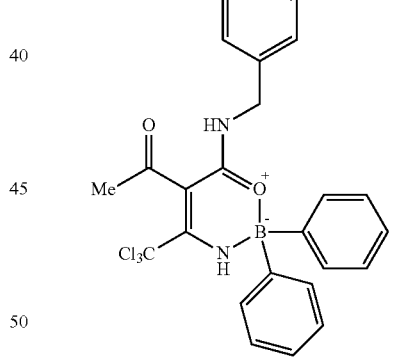
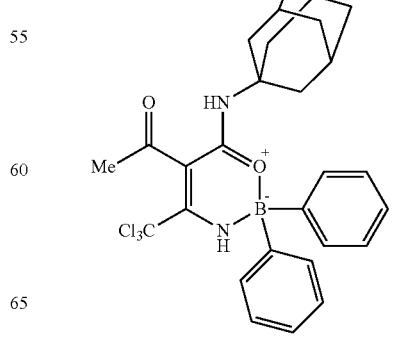

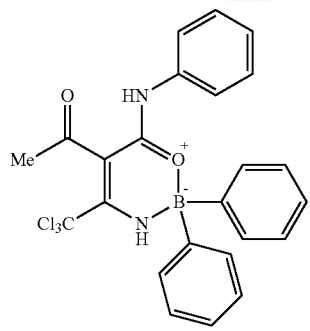
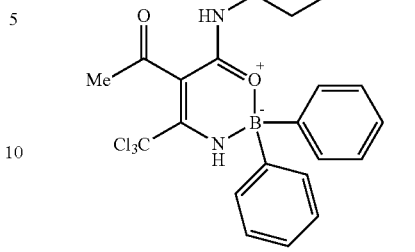
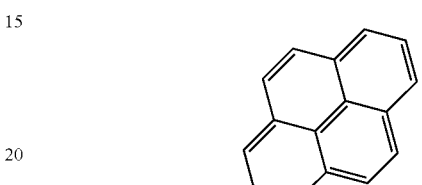
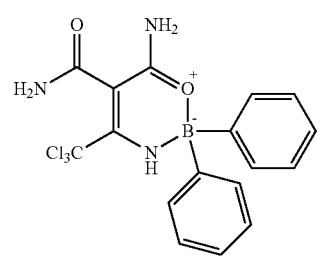
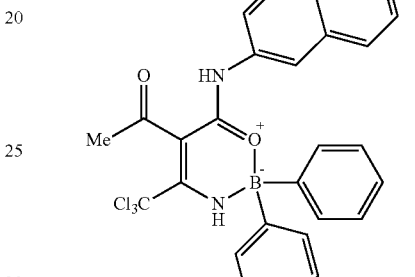
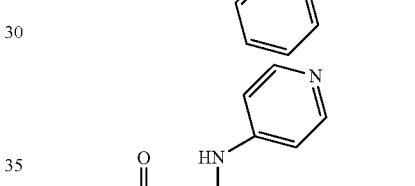
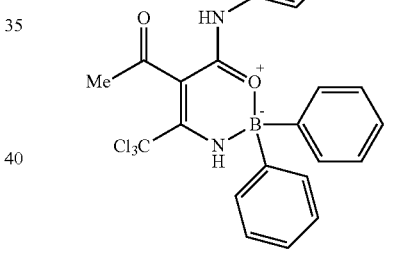
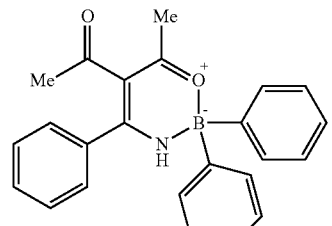
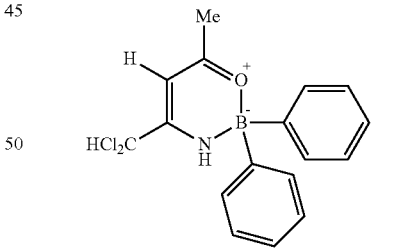
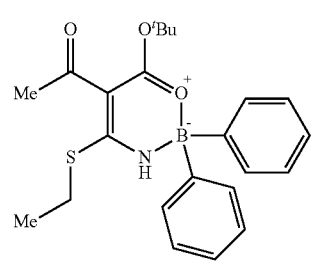
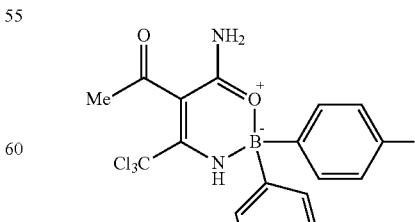
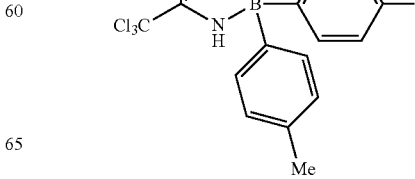
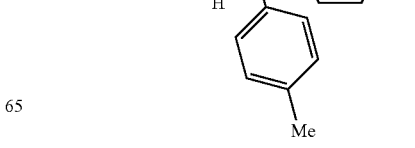

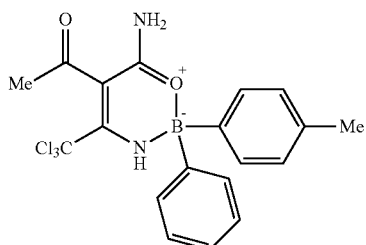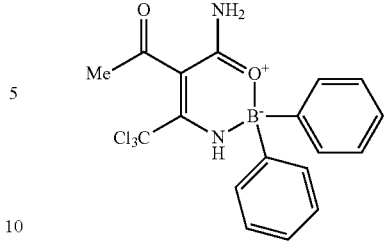

More particular compounds of the present invention include any one of the compounds exemplified in the present application, or a pharmaceutically acceptable salt or solvate thereof, and, in particular, any one of the following:

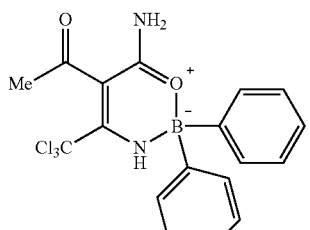

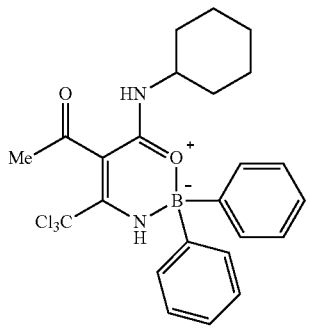

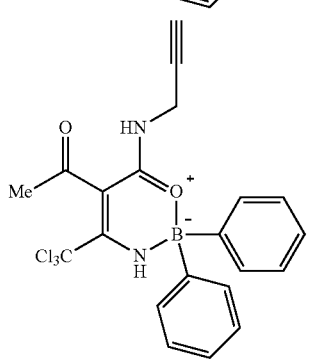

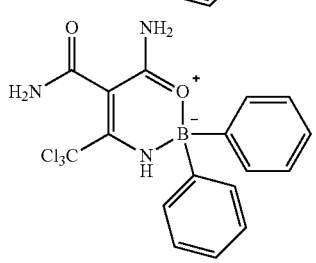

A particular compound is the following, or a pharmaceutically acceptable salt or solvate thereof:

The various functional groups and substituents making up the compounds of the present invention are typically chosen such that the molecular weight of the compound does not exceed 1000. More usually, the molecular weight of the compound will be less than 750, for example less than 700, or less than 650, or less than 600, or less than 550. More preferably, the molecular weight is less than 525 and, for example, is 500 or less.

Suitable or preferred features of any compounds of the present invention may also be suitable features of any other aspect.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess inflammasome inhibitory activity.

The present invention also encompasses compounds of the invention as defined herein which comprise one or more isotopic substitutions. For example, H may be in any isotopic form, including $^1$H, $^2$H(D), and $^3$H (T); C may be in any isotopic form, including $^{12}$C, $^{13}$C, and $^{14}$C; and O may be in any isotopic form, including $^{16}$O and $^{18}$O; and the like.

It is also to be understood that certain compounds of the invention may exist in solvated as well as unsolvated forms such as, for example, hydrated forms. It is to be understood that the invention encompasses all such solvated forms that possess inflammasome inhibitory activity.

It is also to be understood that certain compounds of the invention may exhibit polymorphism, and that the invention encompasses all such forms that possess inflammasome inhibitory activity.

Compounds of the invention may exist in a number of different tautomeric forms and references to compounds of the invention include all such forms. For the avoidance of doubt, where a compound can exist in one of several tautomeric forms, and only one is specifically described or shown, all others are nevertheless embraced by compounds of the invention. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

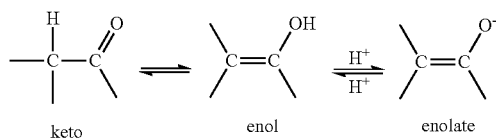

keto      enol      enolate

Compounds of the invention containing an amine function may also form N-oxides. A reference herein to a compound of the formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

The compounds of the invention may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the invention and in-vivo cleavable amide derivatives that may be formed at a carboxy group or an amino group in a compound of the invention.

Accordingly, the present invention includes those compounds of the formula I as defined hereinbefore when made available by organic synthesis and when made available within the human or animal body by way of cleavage of a pro-drug thereof. Accordingly, the present invention includes those compounds of the formula I that are produced by organic synthetic means and also such compounds that are produced in the human or animal body by way of metabolism of a precursor compound, that is a compound of the formula I may be a synthetically-produced compound or a metabolically-produced compound.

A suitable pharmaceutically acceptable pro-drug of a compound of the formula I is one that is based on reasonable medical judgement as being suitable for administration to the human or animal body without undesirable pharmacological activities and without undue toxicity.

Various forms of pro-drug have been described, for example in the following documents:—
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the formula I that possesses a carboxy group is, for example, an in vivo cleavable ester thereof. An in vivo cleavable ester of a compound of the formula I containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_{3-8}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethyl esters.

The in vivo effects of a compound of the formula I may be exerted in part by one or more metabolites that are formed within the human or animal body after administration of a compound of the formula I. As stated hereinbefore, the in vivo effects of a compound of the formula I may also be exerted by way of metabolism of a precursor compound (a pro-drug).

It shall also be appreciated that compounds of formula I may also be covalently linked (at any suitable position) to other groups such as, for example, solubilising moieties (for example, PEG polymers), moieties that enable them to be bound to a solid support (such as, for example, biotin-containing moieties), and targeting ligands (such as antibodies or antibody fragments).

Synthesis

In the description of the synthetic methods described below and in the referenced synthetic methods that are used to prepare the staring materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

It will be appreciated that during the synthesis of the compounds of the invention in the processes defined below, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example $BF_3.OEt_2$. A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia.

Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group

In a particular aspect, the present invention provides a method of synthesising a compound of the formula I, or a pharmaceutically acceptable salt or solvate thereof, the method comprising:

a) reacting a compound of formula A:

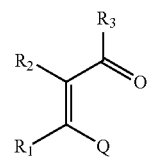

(A)

wherein,

Q, $R_1$, $R_2$ and $R_3$ have any of the definitions listed hereinbefore, with a compound of formula B:

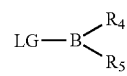

(B)

wherein

LG is a suitable leaving group; and $R_4$ and $R_5$ have any of the definitions listed hereinbefore; and b) optionally thereafter, and if necessary:
i) removing any protecting groups present;
ii) converting the compound formula I into another compound of formula I; and/or
iii) forming a pharmaceutically acceptable salt or solvate thereof.

Suitably the reaction between compound A and compound B takes place in the presence of a suitable solvent. Any suitable solvent or solvent mixture may be used for this reaction. A person skilled in the art will know how to select suitable solvents or solvent mixtures for use in these reactions. Examples of suitable solvents include THF, diethyl ether, DCM, DCE (1,2-dichloroethane), $CHCl_3$, toluene and MeCN.

A person skilled in the art will be able to select appropriate reaction conditions to use in order to facilitate this reaction. Suitably, the reaction is carried out in anhydrous conditions and in the presence of an inert atmosphere, such as argon or nitrogen. The reaction may also be carried out an elevated temperature, such as, for example, within the range of 20 to 160° C. or, more suitably 40 to 100° C. (depending on the solvent utilised), for a suitable time period of, for example, 30 minutes to 7 days, or more suitably 2 to 20 hours. Reflux conditions may be used. Microwave conditions may also be used.

The compound of formula A can be prepared by processes known in the art, and suitably by the processes described herein with reference to the examples.

The compound of formula B can be prepared by processes known in the art, and suitably by the processes described herein with reference to the examples.

Suitable leaving groups will be apparent to one of ordinary skill in the art, including —OBu, —OPr and —OMe. In an embodiment, LG is selected from:
i) OH; and
ii) O—$B(R_4)(R_5)$.

In a particular embodiment, the compound B is diphenylborinic anhydride (DPBA).

In a further aspect of the invention, there is provided a compound of formula I obtainable, obtained, or directly obtained by any one of the processes defined herein.

By way of example, particular synthetic schemes by which compounds of the invention can be prepared are shown below in Schemes 1 to 6:

Scheme 1

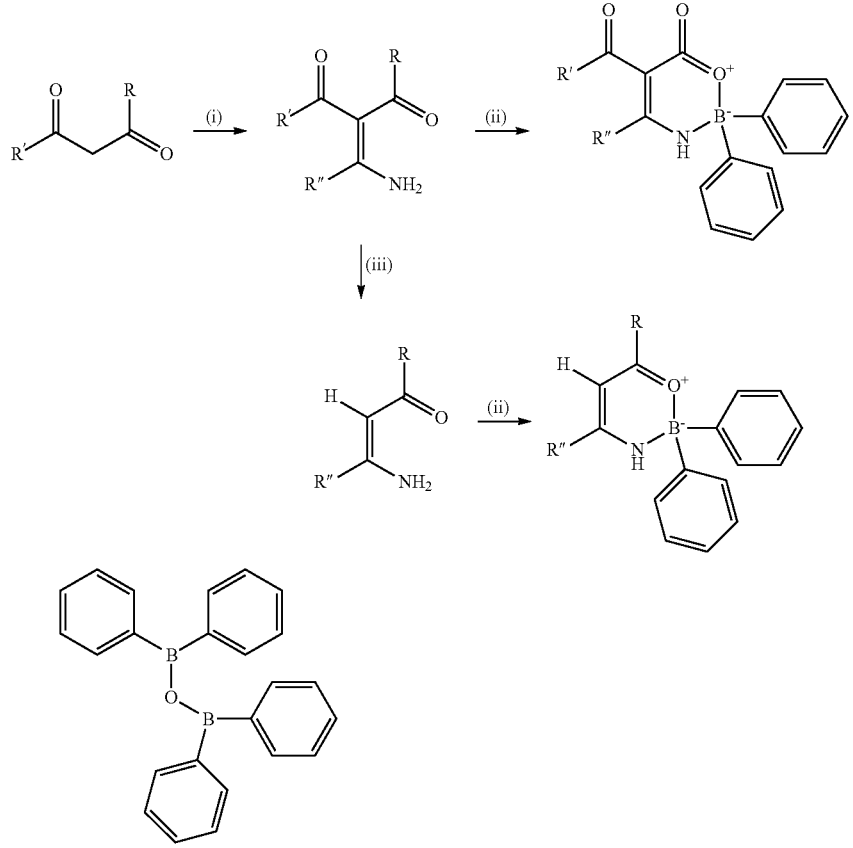

DPBA (diphenylborinic anhydride)

R = Me, $NH_2$; R' = Me, OEt; R" = $CCl_3$, Me (i) $Cl_3CCN$, $Zn(acac)_2$, DCM/DCE, r.t. - 70° C., 3 h or MeCN, $SnCl_4$, toluene, 80-110° C., 4 h; (ii) DPBA, THF, 50° C., 16 h; (iii) $K_2CO_{3(sat)}$, EtOH, r.t., 24 h.

Scheme 2
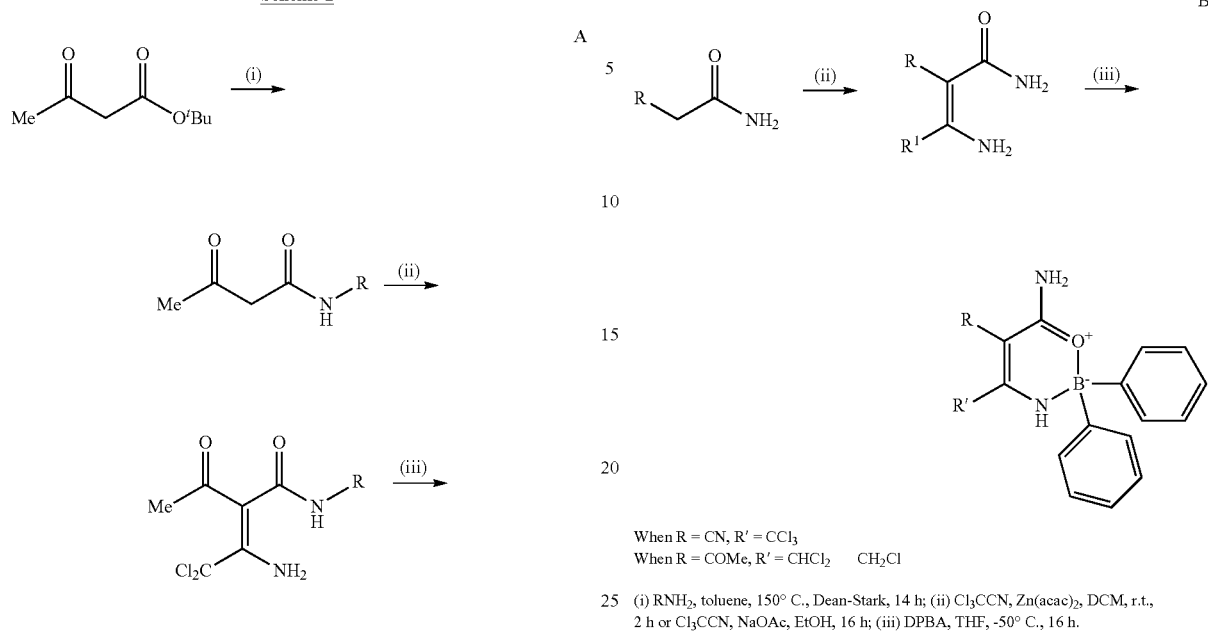
When R = CN, R' = CCl₃
When R = COMe, R' = CHCl₂  CH₂Cl
(i) RNH₂, toluene, 150° C., Dean-Stark, 14 h; (ii) Cl₃CCN, Zn(acac)₂, DCM, r.t., 2 h or Cl₃CCN, NaOAc, EtOH, 16 h; (iii) DPBA, THF, -50° C., 16 h.
Scheme 3
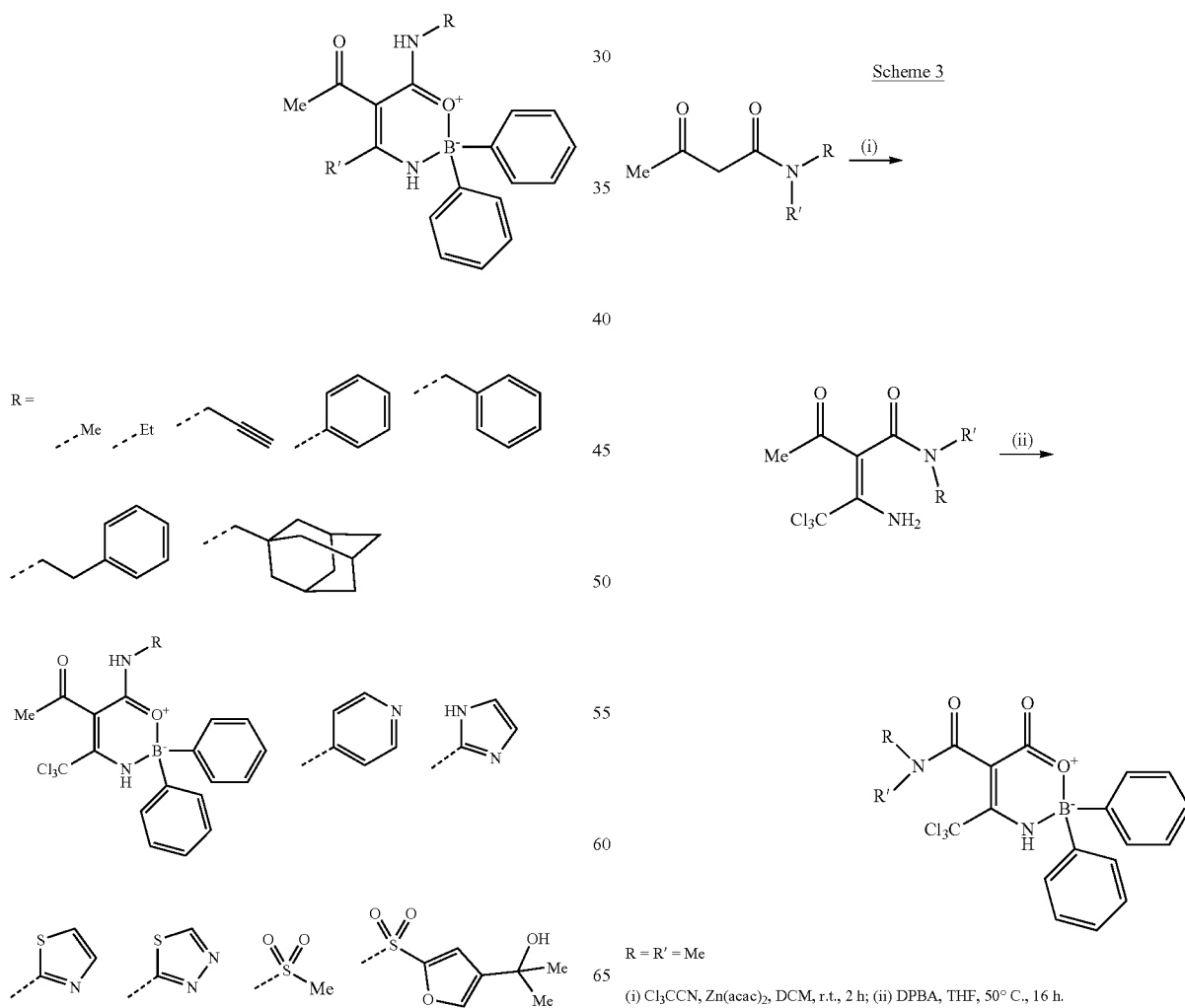
R = R' = Me
(i) Cl₃CCN, Zn(acac)₂, DCM, r.t., 2 h; (ii) DPBA, THF, 50° C., 16 h.

Scheme 4
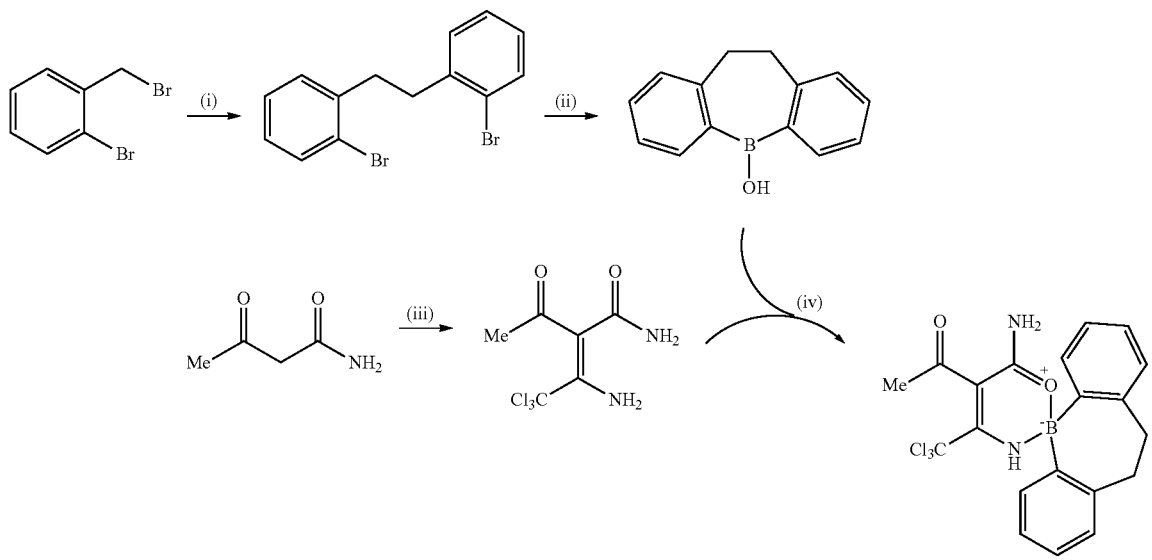
(i) n-BuLi or s-BuLi, THF, -78° C.; 2 h; (ii) s-BuLi, (i-PrO)₃B, Et₂O, -78° C. → r.t. 16 h; 1 M HCL, r.t., 2h; (iii) Cl₃CCCN, Zn(acac)₂, DCM, r.t., 2 h; (iv) THF, 50° C., 16 h.
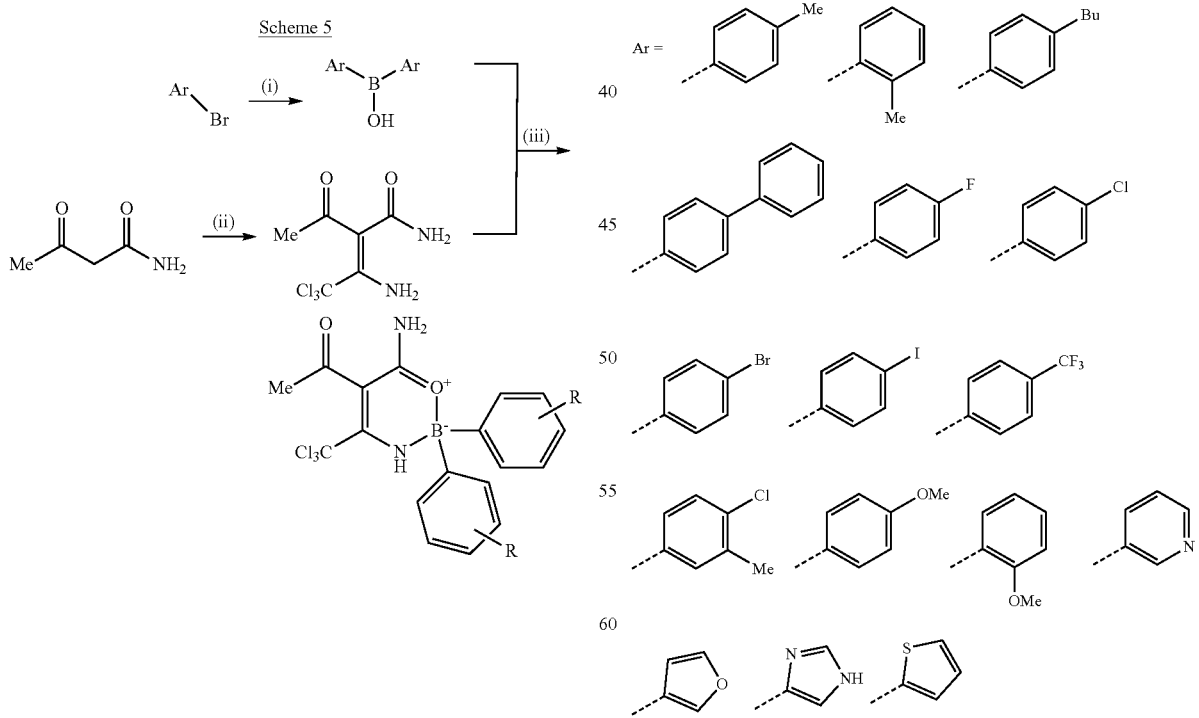
(i) n-BuLi or s-BuLi, Et₂O, -78° C., 2 h; (i-Pro)₃B, Et₂O, -78° C. → r.t., 16 h; 1M HCl, r.t., 2 h; (ii) Cl₃CCN, Zn(acac)₂, DCM, r.t., 2 h; (iii) THF, 50° C., 16 h.

43

Scheme 6

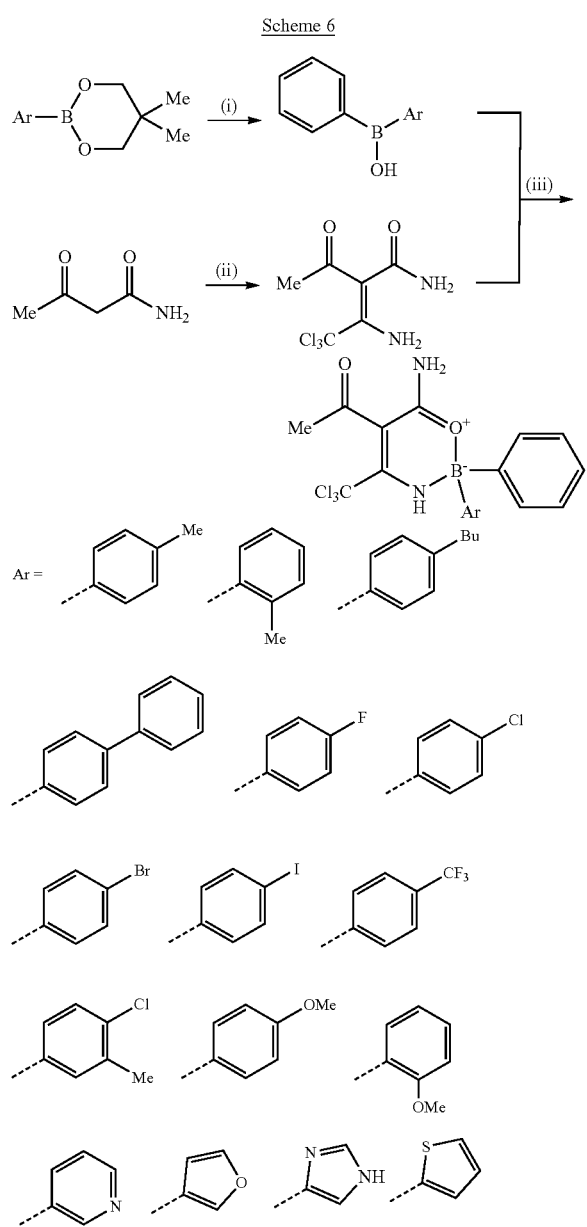

(i) PhLi, (i-Pro)₃B, Et₂O, -78° C. → r.t., 1 h; 1M HCl, r.t., 30 min; 2,2-dimethylpropane-1,3-diol, THF, r.t., 4 h; (ii) Cl₃CCN, Zn(acac)₂, DCM, r.t., 2 h; (iii) THF, 50° C., 16 h Pharmaceutical Compositions According to a further aspect of the invention there is provided a pharmaceutical composition which comprises a compound of the invention as defined hereinbefore, or a pharmaceutically acceptable salt or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy of proliferative disease is an amount sufficient to symptomatically relieve in a warm-blooded animal, particularly a human the symptoms of infection, to slow the progression of infection, or to reduce in patients with symptoms of infection the risk of getting worse.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the conditions, the age and sex of the animal or patient and the route of administration, according to well known principles of medicine.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

In one aspect, the present invention provides a compound of Formula I, or a pharmaceutically acceptable salt or solvate thereof, or a pharmaceutical composition as defined herein for use as a medicament, wherein the compound is optionally not one of the following:

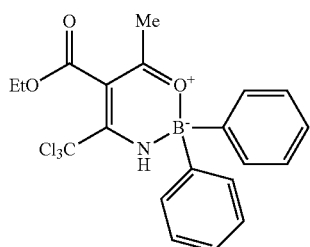

-continued

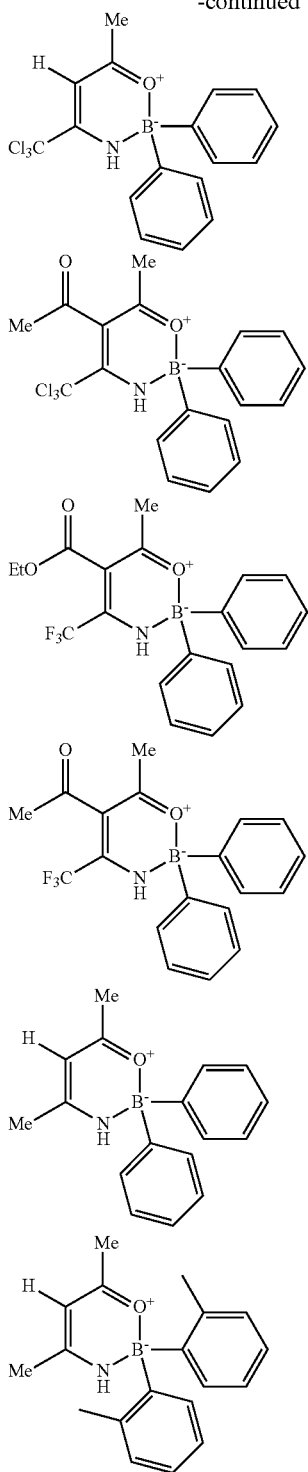

In other aspects, the present invention provides a compound
(i) for use in the treatment of diseases or conditions in which interleukin 11 activity is implicated,
(ii) for use in the production of an inflammasome inhibitory effect,
(iii) for use in the production of an anti-inflammatory effect, and/or
(iv) for use in the treatment of inflammation, said compound, or a pharmaceutically acceptable salt or solvate thereof, having the structural formula I shown below:

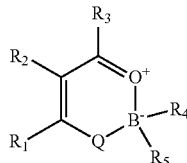

(I)

wherein
Q is O or $NR_a$, wherein $R_a$ is H or (1-4C)alkyl;
$R_1$ is halo, (1-4C)alkyl, (1-4C)haloalkyl, S-(1-4C)alkyl, aryl, heteroaryl or a (1-6C)α,β-unsaturated aldehyde or ketone;
$R_2$ is selected from hydrogen, halo, amino, cyano, nitro, hydroxyl, or a group $-L^1-X^1-R_b$ wherein
$L^1$ is absent or (1-2C)alkylene
$X^1$ is absent or selected from —O—, —C(O)—, —C(X)O—, —OC(X)—, —CH(OR$_c$)—, —N(R$_c$)—, —N(R$_c$)—C(X)—, —N(R$_c$)—C(X)O—, —C(X)—N(R$_c$)—, —N(R$_d$)C(X)N(R$_c$)—, —S—, —SO—, —SO$_2$—, —S(O)$_2$N(R$_c$)—, or —N(R$_c$)SO$_2$— wherein X is O or NR$_x$; R$_x$ is hydrogen or (1-3C)alkyl; and R$_c$ and R$_d$ are each independently selected from hydrogen or (1-6C)alkyl; and
$R_b$ is hydrogen, (1-6C)alkyl, (2-6C)alkenyl, (2-6C)alkynyl, cyano, aryl, aryl(1-2C)alkyl, (3-6C)cycloalkyl, heteroaryl, heterocyclyl or a sugar or amino acid, each of which is optionally substituted by one or more substituent groups independently selected from oxo, halo, cyano, nitro, hydroxy, carboxy, phosphate, NR$^e$R$^f$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, aryl, aryloxy, heterocyclyl, heterocyclyloxy, heterocyclyl-(1-2C)alkyl, heteroaryl, heteroaryloxy, heteroaryl-(1-2C)alkyl, C(O)NR$^e$R$^f$, NR$^e$C(O)R$^f$, NR$^e$S(O)$_2$R$^f$ and S(O)$_2$NR$^e$R$^f$;
wherein R$^e$ and R$^f$ are each independently selected from hydrogen, (1-4C)alkyl or (3-6C)cycloalkyl or (3-6C)cycloalkyl(1-2C)alkyl;
or R$^e$ and R$^f$ can be linked such that, together with the nitrogen atom to which they are attached, they form a heterocyclic ring which is optionally substituted by oxo, halo, cyano, nitro, hydroxy, carboxy, NR$^g$R$^h$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, C(O)NR$^g$R$^h$, NR$^g$C(O)R$^h$, NR$^g$S(O)$_2$R$^h$ and S(O)$_2$NR$^g$R$^h$, wherein R$^g$ and R$^h$ are each independently selected from hydrogen, (1-4C)alkyl, (3-6C)cycloalkyl or (3-6C)cycloalkyl(1-2C)alkyl;
or R$_b$ and R$_c$ are linked such that, together with the nitrogen atom to which they are attached, they form a heterocyclic ring which is optionally substituted by oxo, halo, cyano, nitro, hydroxy, carboxy, NR$^i$R$^j$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, C(O)NR$^i$R$^j$, NR$^i$C(O)R$^j$, NR$^i$S(O)$_2$ R$^j$ and S(O)$_2$NR$^i$R$^j$, wherein R$^i$ and R$^j$ are each independently selected from hydrogen, (1-4C)alkyl, (3-6C)cycloalkyl or (3-6C)cycloalkyl(1-2C)alkyl;

R$_3$ is selected from methyl, OR$^p$, C(O)OR$^p$, C(O)NR$^p$R$^q$ or NR$^k$R$^l$, wherein R$^k$ and R$^l$ are each independently selected from hydrogen, (1-6C)alkyl, (3-10C)cycloalkyl, (3-10C)cycloalkyl(1-2C)alkyl, (2-6C)alkenyl, (2-6C)alkynyl, aryl, aryl(1-2C)alkyl, heteroaryl, heteroaryl(1-2C)alkyl, S(O)R$^o$, S(O)$_2$R$^o$ or a sugar or amino acid residue;

R$^o$ is selected from (1-4C)alkyl, (2-4C)alkenyl, (2-4C)alkynyl or an aryl or heteroaryl group, each of which may be optionally substituted with one or more substituents selected from halo, OH, (1-4C)alkyl, (1-4C)hydroxyalkyl, (2-4C)alkenyl and (2-4C)alkynyl;

R$^p$ and R$^q$ are independently selected from hydrogen, (1-6C)alkyl, (3-10C)cycloalkyl, (3-10C)cycloalkyl(1-2C)alkyl, (2-6C)alkenyl, (2-6C)alkynyl, aryl, aryl(1-2C)alkyl, heteroaryl or heteroaryl(1-2C)alkyl R$_4$ and R$_5$ are each independently aryl or heteroaryl ring, each of which is optionally substituted by halo, cyano, nitro, hydroxy, carboxy, NR'''R'', (1-2C)alkoxy, (1-4C)alkyl, (1-4C)haloalkyl, (3-4C)cycloalkyl, (3-4C)cycloalkyl-(1-2C)alkyl, aryl, aryl(1-2C)alkyl, (1-2C)alkanoyl, (1-2C)alkylsulphonyl, SR''', SOR''', C(O)NR'''R'', NR'''C(O)R'', NR'''S(O)R'' and S(O)$_2$NR'''R'', wherein R''' and R'' are each independently selected from hydrogen, (1-2C)alkyl;

or R$_4$ and R$_5$ are linked to one another by a bond, an alkylene linker optionally comprising one or more heteroatoms, or a fused cycloalkyl, aryl, heteroaryl or heterocyclic ring;

or a pharmaceutically acceptable salt thereof.

In an embodiment, the disease or condition in which interleukin 1β activity is implicated is selected from diabetes and metabolic disease, atherosclerosis and vascular disease, myocardial infarction, acute cerebrovascular disease (e.g. stroke), inflammatory lung disease, inflammatory skin disease (e.g. psoriasis, eczema, contact dermatitis), Alzheimer's disease and other neurological diseases (e.g. MS and Parkinson's), inflammatory joint disease (e.g. arthritis, gout), autoinflammatory diseases (e.g. Muckle Wells and other CAPS) and certain cancers.

In another aspect, the present invention provides a method of inhibiting inflammasome activity in vitro or in vivo, said method comprising contacting a cell with an effective amount of a compound of formula I defined herein, or a pharmaceutically acceptable salt or solvate thereof.

In another aspect, the present invention provides provided a method of treating a disease or condition in which interleukin 1β activity is implicated, said method comprising administering to a patient in need of such treatment a therapeutically effective amount of a compound of formula I defined herein, or a pharmaceutically acceptable salt or solvate thereof, or a pharmaceutical composition as defined herein.

For the avoidance of doubt, for those medical uses and methods of treatment discussed above, unless otherwise stated, it will be understood that the following compounds are comprised within the scope of the invention:

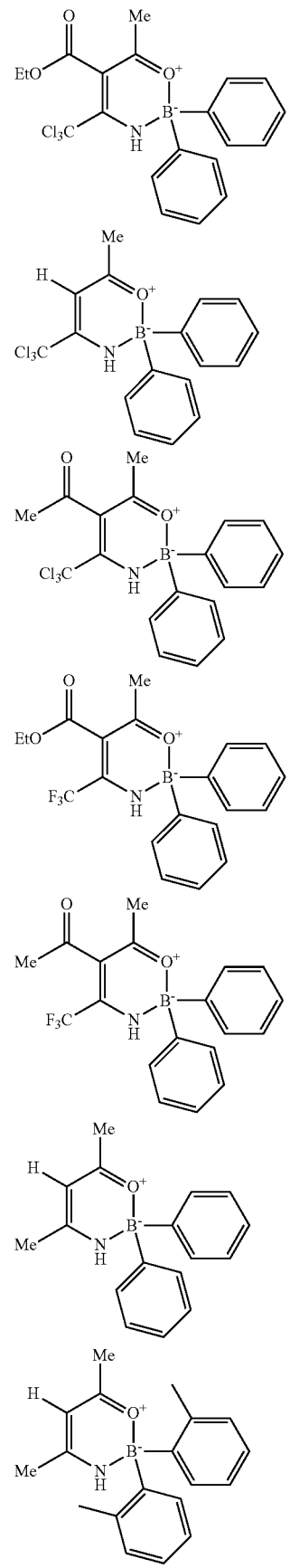

It will be understood that any and all of the definitions for Q, $R_a$, $R_1$, $R_2$, $L^1$, $X^1$, X, $R_x$, $R_b$, $R_c$, $R_d$, $R^e$, $R^f$, $R^g$, $R^h$, $R^i$, $R^j$, $R_3$, $R^k$, $R^l$, $R_4$, $R_5$, $R^m$, $R^n$, $R^p$, $R^q$ and $R^o$, as well as any and all of the sub-formulae of formula (I), outlined above under the heading "compounds of the invention" are equally applicable to the therapeutic uses and methods of treatment outlined above.

Routes of Administration

The compounds of the invention or pharmaceutical composition comprising the active compound may be administered to a subject by any convenient route of administration, whether systemically/peripherally or topically (ie. at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

In another aspect, the present invention provides a compound of formula I defined herein in combination with one or more other therapeutic agents
(i) for use in the treatment of diseases or conditions in which interleukin 1β activity is implicated,
(ii) for use in the production of an inflammasome inhibitory effect,
(iii) for use in the production of an anti-inflammatory effect, and/or
(iv) for use in the treatment of inflammation.

In an embodiment, the one or more other therapeutic agents is a compound or pharmaceutical composition that is effective in the treatment of inflammation.

EXAMPLES

One or more embodiments of the invention will now be exemplified, for the purpose of illustration only, with reference to the accompanying figures, in which FIG. 1 shows the effects of compounds 3 (BC7), 4 (NBC1), 6 (BC23), 8 (NBC2), 9 (NBC3), 11 (NBC4), 13 (NBC5) and 14 (NBC6) on IL-1β release quantified by ELISA. Data are the mean±SD of at least 4 separate experiments.

FIG. 2 shows the effects of compounds 14 (NBC6), 19 (NBC21), 22 (NBC15), 24 (NBC16), 27 (NBC12), 30 (NBC14), 33 (NBC17), 36 (NBC13), 38 (NBC18), 41 (NBC25), 42 (NBC24), 43 (NBC28), 44 (NBC23), 45 (NBC26), 48 (NBC19), 51 (NBC20), 54 (NBC22), 55 (NBC29) and 57 (NBC32) on IL-1 release quantified by ELISA. Data are the mean±SD of at least 4 separate experiments.

CHEMICALS AND METHODS

Figure 1:
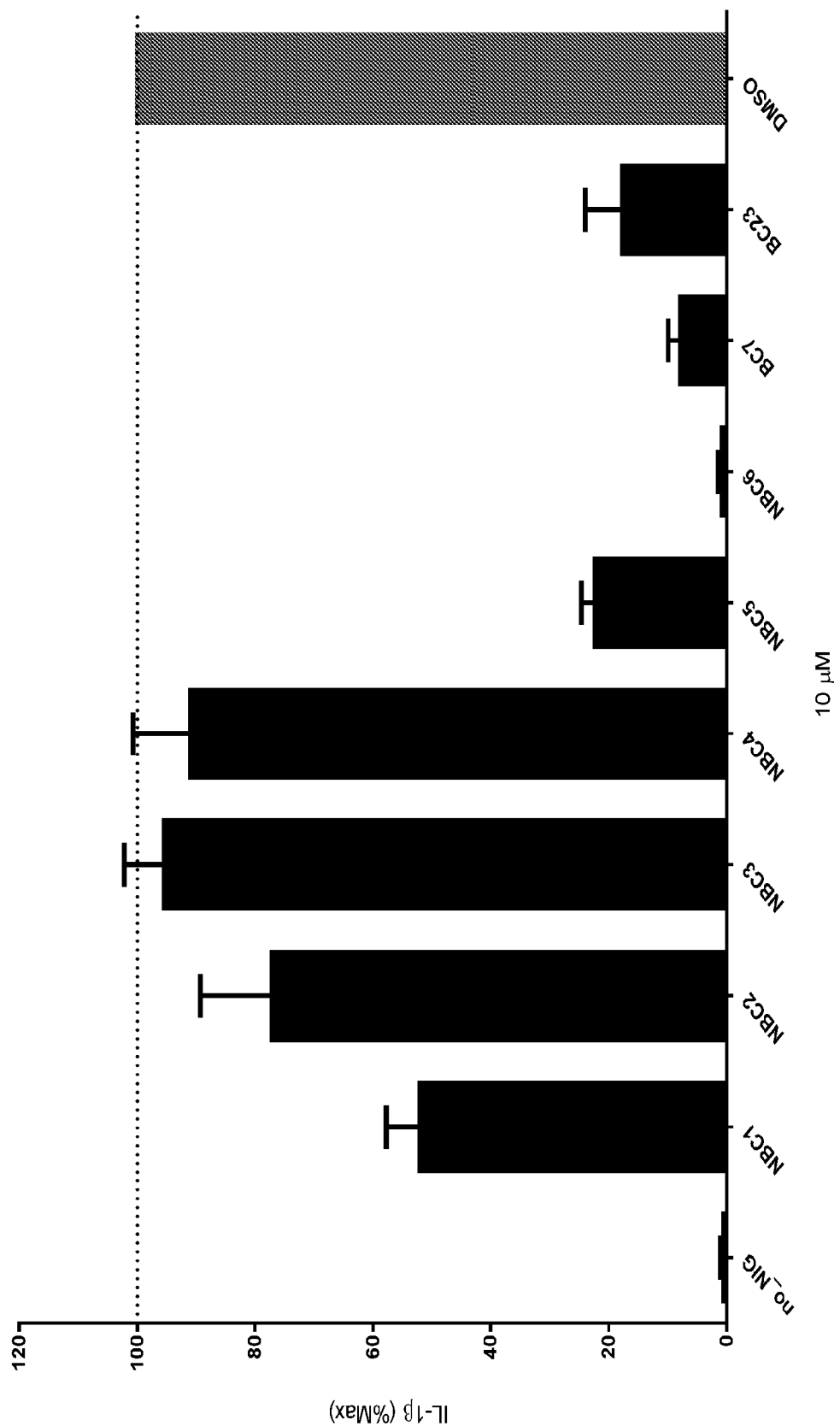

All chemicals, solvents and deuterated solvents were purchased from Sigma-Aldrich, Alfa-Aesar and Fisher Scientific. A Bruker Avance 400 spectrometer was used to record $^1$H and $^{13}$C NMR spectra. Infrared spectroscopy was conducted on a JASCO FT/IR-4100 spectrophotometer using the Spectra Manager II (JASCO) software package. Chemical shifts are defined in parts per million (ppm) and referenced against tetramethylsilane (δ=0). Evaporation of solvents was conducted on a Buchi rotavapor R-200 equipped with Buchi heating bath B-490. TLC was performed using silica gel 60 on aluminium sheets with $F_{254}$. All spots were visualised using a MV Mineralight lamp (254/365) UVGL-58. A silica gel with particle size 40-63 microns was used for column chromatography. All purified products using the column chromatography method were evaporated in vacuo to completeness. Microwave irradiation was carried out on a Biotage® Initiator Classic microwave using 2-5 mL Biotage® glass vials.

Example 1—Synthesis of Compounds

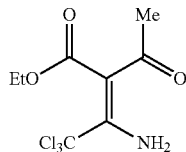

1

Ethyl (E)-2-acetyl-3-amino-4,4,4-trichloro-2-butenoate (1) was prepared by a revised method to that described by Veronese et al, 1986[21]. To a suspension of zinc(II) acetylacetonate hydrate (56 mg, 0.2 mmol) in anhydrous 1,2-dichloroethane (5 mL), ethyl acetoacetate (1.26 mL, 10 mmol) and trichloroacetonitrile (1.50 mL, 15 mmol) were added. The mixture was heated at 70° C. under $N_2$ for 3 h. The reaction mixture was extracted with DCM and extract dried over $MgSO_4$. The solution was concentrated and purified by flash column chromatography (ethyl acetate/n-hexane, 1:8) to give 0.56 g (21%) of (1) as a brown oil. $^1$H NMR (400.1 MHz, $CDCl_3$): δ 4.19 (q, J=7.2 Hz, 2H, $CH_3C\underline{H}_2O$), 2.23 (3H, s, 3H, $C\underline{H}_3CO$), 1.29 (t, J=7.0 Hz, 3H, $C\underline{H}_3CH_2O$), $NH_2$ signal was not observed; $MS(ES^+)$ (m/z): 274.0 [M+H, $^{35}$Cl, $^{35}$Cl, $^{35}$Cl, 38%]$^+$, 276.0 [M+H, $^{35}$Cl, $^{35}$Cl, $^{37}$Cl, 48%]$^+$, 278.0 [M+H, $^{35}$Cl, $^{37}$Cl, $^{37}$Cl, 23%]$^+$, 280.0 [M+H, $^{37}$Cl, $^{37}$Cl, $^{37}$Cl, 6%]$^+$, 338.0 [M−H+$Zn^{2+}$, $^{35}$Cl, $^{35}$Cl, $^{35}$Cl, 100%]$^+$, 340.0 [M−H+$Zn^{2+}$, $^{35}$Cl, $^{35}$Cl, $^{37}$Cl, 50%]$^+$, 342.0 [M−H+$Zn^{2+}$, $^{35}$Cl, $^{37}$Cl, $^{37}$Cl, 25%]$^+$.

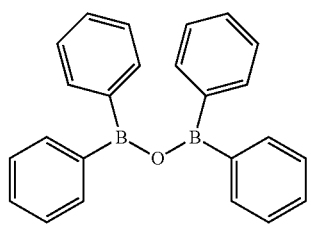

2

Diphenylborinic anhydride (2) was prepared according to that described by Hosoya et al, 2006[22]. $^1$H NMR (400.1

MHz, CDCl$_3$): δ 7.80 (d, J=7.2 Hz, 2H, B-Ph(o)), 7.71 (d, J=7.2 Hz, 2H, B-Ph(o)), 7.25-7.47 (m, 6H, B-Ph(m/p)); IR: 1596 (C—C, in-ring stretch), 1435 (C—C, in-ring stretch), 1273 (B—C, stretch), 1055 (B—C, stretch), 1026 (C—C, in-plane deformation), 852 (B—O, symmetric stretch), 749 (C—H, out-of-plane deformation), 695 (C—C, out-of-plane ring deformation), 645 (B—O, out-of-plane deformation) cm$^{-1}$. A small broad singlet at δ 5.72 is attributed to some hydrolysed diphenylborinic acid (B—O$\underline{H}$).

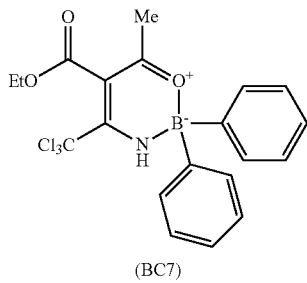

(BC7)

Ethyl (E)-2-acetyl-3-amino-4,4,4-trichloro-2-butenoate Diphenylboron (3; BC7)

To a suspension of DPBA (0.25 g, 0.73 mmol) in anhydrous THF (4 mL), ethyl (E)-2-acetyl-3-amino-4,4,4-trichloro-2-butenoate (0.4 g, 1.46 mmol) was added. The mixture was heated under microwave irradiation at 150° C. under N$_2$ for 30 mins. The reaction mixture was cooled and dissolved in DCM. The solution was concentrated and purified by flash column chromatography (ethyl acetate/n-hexane, 1:49) to give 26.1 mg (8%) of (3) as a yellow solid. mp: 109-110° C.; $^1$H NMR (400.1 MHz, CDCl$_3$): δ 7.29 (dd, J=8.0 Hz & 1.6 Hz, 4H, B-Ph(o)), 7.12-7.27 (m, 6H, B-Ph(m/p)), 4.11 (q, J=7.2 Hz, 2H, CH$_3$C$\underline{H}_2$O), 2.42 (s, 3H, C$\underline{H}_3$CO), 1.23 (t, J=7.2 Hz, 3H, C$\underline{H}_3$CH$_2$O), N$\underline{H}$ signal not observed; $^{13}$C NMR (100.6 MHz, CDCl$_3$): δ 188.9 (CH$_3$$\underline{C}$O), 165.4 (Cl$_3$C(NH)$\underline{C}$=C), 164.3 (EtO$_2$$\underline{C}$), 131.8 (B-Ph(o)), 127.6 (B-Ph(m)), 127.0 (B-Ph(p)), 102.3 (Cl$_3$C(NH)C=$\underline{C}$), 93.4 (CCl$_3$), 61.7 (CH$_3$$\underline{C}$H$_2$O), 24.4 ($\underline{C}$H$_3$CO), 13.7 (CH$_3$$\underline{C}$H$_2$O), B-Ph quaternary signal not observed; IR: 3306 (N—H), 1709 (C=O), 1592 (C=C, conjugated) cm$^{-1}$; MS(ES$^-$) (m/z): 435.2 [M–H, $^{10}$B, $^{35}$Cl, $^{35}$Cl, $^{35}$Cl, 10%]$^-$, 436.2 [M–H, $^{11}$B, $^{35}$Cl, $^{35}$Cl, $^{35}$Cl, 58%]$^-$, 437.2 [M–H, $^{10}$B, $^{35}$Cl, $^{35}$Cl, $^{37}$Cl, 29%]$^-$, 438.2 [M–H, $^{11}$B, $^{35}$Cl, $^{35}$Cl, $^{37}$Cl, 58%]$^-$, 439.2 [M–H, $^{10}$B, $^{35}$Cl, $^{37}$Cl, $^{37}$Cl, 17%]$^-$, 440.2 [M–H, $^{11}$B, $^{35}$Cl, $^{37}$Cl, $^{37}$Cl, 26%]$^-$, 441.3 [M–H, $^{10}$B, $^{37}$Cl, $^{37}$Cl, $^{37}$Cl, 8%]$^-$, 442.2 [M–H, $^{11}$B, $^{37}$Cl, $^{37}$Cl, $^{37}$Cl, 3%]$^-$; HRMS (m/z): [M–H]$^-$ calcd. for C$_{20}$H$_{18}$$^{11}$B$^{35}$Cl$_3$NO$_3$, 436.0449; found, 436.0431.

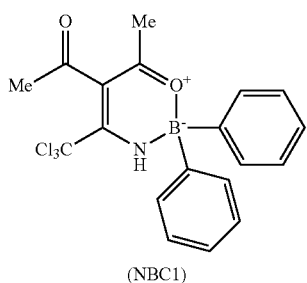

(NBC1)

3-(1-Amino-2,2,2-trichloroethylidene)pentane-2,4-dione diphenylboron (4; NBC1) was prepared by a revised method to that described by Veronese et al, 1986[21] and Vasil'ev et al, 1994[23]. To a suspension of zinc acetylacetonate hydrate (56 mg, 0.2 mmol) in anhydrous DCM (4 mL), acetylacetone (1.03 mL, 10 mmol) and trichloroacetonitrile (5.00 mL, 50 mmol) were added. The reaction mixture was stirred at room temperature under N$_2$ for 16 h. The mixture was extracted with DCM and extract dried over MgSO$_4$. The solution was concentrated by evaporation in vacuo to give crude 3-(1-amino-2,2,2-trichloroethylidene)pentane-2,4-dione as a yellow oil. The crude product (0.42 g, 2.95 mmol) was added to DPBA (0.40 g, 1.16 mmol) suspended in anhydrous THF (4 mL). The reaction mixture was heated at 50° C. under N$_2$ for 16 h. Residual solid was removed by filtration. The filtrate was concentrated and purified by flash column chromatography (ethyl acetate/n-hexane, 1:4) to give 59.1 mg (13%) of (4) as a yellow oil. $^1$H NMR (400.1 MHz, CDCl$_3$): δ 7.30 (dd, J=7.8 Hz &1.8 Hz, 4H, B-Ph(o)), 7.16-7.27 (m, 6H, B-Ph(m/p)), 2.26 (s, 3H, CH$_3$), 2.24 (s, 3H, CH$_3$), N$\underline{H}$ signal not observed; $^{13}$C NMR (100.6 MHz, CDCl$_3$): δ 198.9 (CH$_3$$\underline{C}$O), 185.4 (CH$_3$$\underline{C}$O), 163.3 (Cl$_3$C(NH)$\underline{C}$=C), 131.8 (B-Ph(o)), 127.6 (B-Ph(m)), 127.1 (B-Ph(p)), 111.6 (Cl$_3$C(NH)C=$\underline{C}$), 93.0 (CCl$_3$), 34.5 ($\underline{C}$H$_3$CO), 23.6 ($\underline{C}$H$_3$CO), B-Ph quaternary signal not observed; IR: 3343 (N—H), 1690 (C=O), 1578 (C=C, conjugated) cm$^{-1}$; MS(ES$^-$) (m/z): 405.1 [M–H, $^{10}$B, $^{35}$Cl, $^{35}$Cl, $^{35}$Cl, 13%]$^-$, 406.2 [M–H, $^{11}$B, $^{35}$Cl, $^{35}$Cl, $^{35}$Cl, 78%]$^-$, 407.2 [M–H, $^{10}$B, $^{35}$Cl, $^{35}$Cl, $^{37}$Cl, 21%]$^-$, 408.1 [M–H, $^{11}$B, $^{35}$Cl, $^{35}$Cl, $^{37}$Cl, 100%]$^-$, 409.1 [M–H, $^{10}$B, $^{35}$Cl, $^{37}$Cl, $^{37}$Cl, 22%]$^-$, 410.0 [M–H, $^{11}$B, $^{35}$Cl, $^{37}$Cl, $^{37}$Cl, 54%]$^-$, 411.2 [M–H, $^{10}$B, $^{37}$Cl, $^{37}$Cl, $^{37}$Cl, 7%]$^-$, 412.1 [M–H, $^{11}$B, $^{37}$Cl, $^{37}$Cl, $^{37}$Cl, 4%]$^-$; HRMS (m/z): [M–H]$^-$ calcd. for C$_{19}$H$_{16}$$^{11}$B$^{35}$Cl$_3$NO$_2$, 406.0343; found, 406.0353.

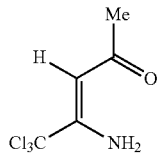

(Z)-4-Amino-5,5,5-trichloropent-3-en-2-one (5) was prepared by a revised method to that described by Coenon et al, 1965[24]. To a suspension of zinc acetylacetonate hydrate (56 mg, 0.1 mmol) in anhydrous DCM (5 mL), acetylacetone (1.03 mL, 10 mmol) and trichloroacetonitrile (5.00 mL, 50 mmol) were added. The reaction mixture was stirred at room temperature under N$_2$ for 16 h. The mixture was washed with water and extracted with DCM and extract dried over MgSO$_4$. The solution was concentrated by evaporation in vacuo to give crude 3-(1-amino-2,2,2-trichloroethylidene) pentane-2,4-dione as a yellow oil. The crude product was dissolved in ethanol (5 mL). A saturated aqueous solution of potassium carbonate (10 mL) was added. The reaction mixture was stirred at room temperature for 24 h. The mixture was extracted with EtOAc. The extracted organic layer was dried over MgSO$_4$. The solution was concentrated and purified by flash column chromatography (ethyl acetate/n-hexane, 1:9) to give 1.04 g (52%) of (5) as a pale orange solid. mp: 66-68° C. (lit.[4] 67-68° C.); $^1$H NMR (400.1 MHz, CDCl$_3$): δ 5.85 (t, J=1.2 Hz, 1H, Cl$_3$C(NH$_2$)C=C$\underline{H}$), 2.16 (s, 3H, C$\underline{H}_3$CO), N$\underline{H}_2$ signal was not observed; IR: 3299 (N—H), 3159 (N—H), 1621 (C=O), 1600 (C=C, conjugated), 1505 (C=C—NH$_2$) cm$^{-1}$; TOF MS(ES$^+$) (m/z):

201.9 [M+H, $^{35}$Cl, $^{35}$Cl, $^{35}$Cl, 96%]$^+$, 203.9 [M+H, $^{35}$Cl, $^{35}$Cl, $^{37}$Cl, 83%]$^+$, 205.9 [M+H, $^{35}$Cl, $^{37}$Cl, $^{37}$Cl, 32%]$^+$, 207.9 [M+H, $^{37}$Cl, $^{37}$Cl, $^{37}$Cl, 6%]$^+$, 402.1 [2×M, $^{35}$Cl, $^{35}$Cl, $^{35}$Cl, 100%]$^+$.

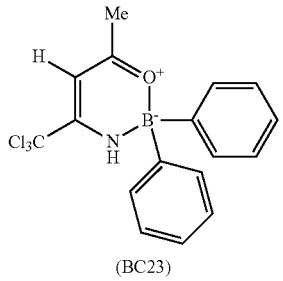

(BC23)

(Z)-4-Amino-5,5,5-trichloropent-3-en-2-one diphenylboron (6; BC23) was prepared by a revised method to that described by Vasil'ev et al, 1992[25]. (Z)-4-Amino-5,5,5-trichloropent-3-en-2-one (1.04 g, 5.15 mmol) was added to a suspension of DPBA (0.89 g, 2.57 mmol) in anhydrous THF (4 mL). The mixture was heated at 50° C. under N$_2$ for 16 h. The reaction mixture was extracted with DCM and the extract dried over MgSO$_4$. The solution was concentrated and purified by flash column chromatography (ethyl acetate/hexane, 1:19) to give 0.53 g (56%) of (6) as a yellow solid. mp: 113-114° C. (lit.[5] 112.5-113.5° C.); $^1$H NMR (400.1 MHz, CDCl$_3$): δ 7.31 (dd, J=8.0 Hz & 1.6 Hz, B-Ph(o)), 7.15-7.26 (m, 6H, B-Ph(m/p)), 5.72 (d, J=2.8 Hz, 2H, Cl$_3$C(NH)C=C$\underline{H}$), 2.18 (s, 3H, C$\underline{H}_3$CO), N$\underline{H}$ signal not observed; $^{13}$C NMR (100.6 MHz, CDCl$_3$): δ 186.2 (CH$_3$$\underline{C}$O), 165.8 (Cl$_3$C(NH)$\underline{C}$=CH), 131.7 (B-Ph(o)), 127.5 (B-Ph(m)), 126.8 (B-Ph(p)), 92.8 (CCl$_3$), 91.6 (Cl$_3$C(NH)C=$\underline{C}$H), 24.7 ($\underline{C}$H$_3$CO), B-Ph quaternary signal not observed; IR: 3321 (N—H), 1600 (C=C, conjugated), 1523 (C=C—NH) cm$^{-1}$; MS(ES$^-$) (m/z): 363.0 [M–H, $^{10}$B, $^{35}$Cl, $^{35}$Cl, $^{35}$Cl, 19%]$^-$, 364.0 [M–H, $^{11}$B, $^{35}$Cl, $^{35}$Cl, $^{35}$Cl, 100%]$^-$, 365.0 [M–H, $^{10}$B, $^{35}$Cl, $^{35}$Cl, $^{37}$Cl, 32%]$^-$, 366.0 [M–H, $^{11}$B, $^{35}$Cl, $^{35}$Cl, $^{37}$Cl, 95%]$^-$, 367.0 [M–H, $^{10}$B, $^{35}$Cl, $^{37}$Cl, $^{37}$Cl, 19%]$^-$, 368.0 [M–H, $^{11}$B, $^{35}$Cl, $^{37}$Cl, $^{37}$Cl, 28%]$^-$, 369.1 [M–H, $^{10}$B, $^{37}$Cl, $^{37}$Cl, $^{37}$Cl, 8%]$^-$, 370.1 [M–H, $^{11}$B, $^{37}$Cl, $^{37}$Cl, $^{37}$Cl, 3%]$^-$; MS(ES$^+$) (m/z): 286.9 [M–Ph, $^{10}$B, $^{35}$Cl, $^{35}$Cl, $^{35}$Cl, 18%]$^+$, 288.0 [M–Ph, $^{11}$B, $^{35}$Cl, $^{35}$Cl, $^{35}$Cl, 100%]$^+$, 289.0 [M–Ph, $^{10}$B, $^{35}$Cl, $^{35}$Cl, $^{37}$Cl, 30%]$^+$, 289.9 [M–Ph, $^{11}$B, $^{35}$Cl, $^{35}$Cl, $^{37}$Cl, 94%]$^+$, 290.9 [M–Ph, $^{10}$B, $^{35}$Cl, $^{37}$Cl, $^{37}$Cl, 13%]$^+$, 291.9 [M–Ph, $^{11}$B, $^{35}$Cl, $^{37}$Cl, $^{37}$Cl, 29%]$^+$, 293.0 [M–Ph, $^{10}$B, $^{37}$Cl, $^{37}$Cl, $^{37}$Cl, 3%]$^+$, 294.0 [M–Ph, $^{11}$B, $^{37}$Cl, $^{37}$Cl, $^{37}$Cl, 5%]$^+$, 365.0 [M+H, $^{10}$B, $^{35}$Cl, $^{35}$Cl, $^{35}$Cl, 3%]$^+$, 366.0 [M+H, $^{11}$B, $^{35}$Cl, $^{35}$Cl, $^{35}$Cl, 12%]$^+$, 387.0 [M+Na, $^{10}$B, $^{35}$Cl, $^{35}$Cl, $^{35}$Cl, 16%]$^+$ 388.0 [M+Na, $^{11}$B, $^{35}$Cl, $^{35}$Cl, $^{35}$Cl, 46%]$^+$, 389.0 [M+Na, $^{10}$B, $^{35}$Cl, $^{35}$Cl, $^{37}$Cl, 16%]$^+$, 390.0 [M+Na, $^{11}$B, $^{35}$Cl, $^{35}$Cl, $^{37}$Cl, 42%]$^+$, 391.0 [M+Na, $^{10}$B, $^{35}$Cl, $^{37}$Cl, $^{37}$Cl, 10%]$^+$, 392.0 [M+Na, $^{11}$B, $^{35}$Cl, $^{37}$Cl, $^{37}$Cl, 13%]$^+$, 393.0 [M+Na, $^{10}$B, $^{37}$Cl, $^{37}$Cl, $^{37}$Cl, 4%]$^+$, 394.0 [M+Na, $^{11}$B, $^{37}$Cl, $^{37}$Cl, $^{37}$Cl, 2%]$^+$, 403.0 [M+K, $^{10}$B, $^{35}$Cl, $^{35}$Cl, $^{35}$Cl, 4%]$^+$, 404.0 [M+K, $^{11}$B, $^{35}$Cl, $^{35}$Cl, $^{35}$Cl, 20%]$^+$; 405.0 [M+K, $^{10}$B, $^{35}$Cl, $^{35}$Cl, $^{37}$Cl, 6%]$^+$, 406.0 [M+K, $^{11}$B, $^{35}$Cl, $^{35}$Cl, $^{37}$Cl, 19%]$^+$, 407.0 [M+K, $^{10}$B, $^{35}$Cl, $^{37}$Cl, $^{37}$Cl, 5%]$^+$, 408.0 [M+K, $^{11}$B, $^{35}$Cl, $^{37}$Cl, $^{37}$Cl, 7%]$^+$, 409.0 [M+K, $^{10}$B, $^{37}$Cl, $^{37}$Cl, $^{37}$Cl, 2%]$^+$, 410.0 [M+K, $^{37}$Cl, $^{37}$Cl, $^{37}$Cl, 2%]$^+$; HRMS (m/z): [M–H]$^-$ calcd. for C$_{17}$H$_{14}$$^{11}$B$^{35}$Cl$_3$NO, 364.0237; found, 364.0243.

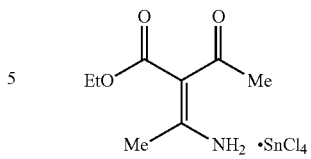

Ethyl (E)-2-acetyl-3-amino-2-butenoate (7)

Tin(IV) chloride (1.17 mL, 10 mmol) was slowly added to a stirring solution of ethyl acetoacetate (1.26 mL, 10 mmol) and acetonitrile (0.52 mL, 10 mmol) suspended in anhydrous toluene (5 mL). A white solid appeared and the reaction mixture was stirred at room temperature under N$_2$ for 30 mins. The mixture was then heated at reflux at 80° C. under N$_2$ for 4 h. An orange solid precipitated from the reaction mixture. The mixture was cooled to room temperature, n-hexane (20 mL) was added to the reaction mixture and was stirred under N$_2$ for 16 h. The solid was filtered and dried in vacuo to give 2.90 g (67%) of tin chelate (7) as an orange solid. mp: 136-138° C.; $^1$H NMR (400.1 MHz, d$_6$-DMSO): δ 10.77 (br s, 1H, CH$_3$(N$\underline{H}_2$)C=CH), 8.37 (br s, 1H, CH$_3$(N$\underline{H}_2$)C=C), 4.11 (q, J=7.1 Hz, 2H, CH$_3$C$\underline{H}_2$O), 2.13 (s, 3H, C$\underline{H}_3$), 2.11 (s, 3H, C$\underline{H}_3$), 1.23 (t, J=7.2 Hz, 3H, C$\underline{H}_3$CH$_2$O); $^{13}$C NMR (100.6 MHz, d$_6$-DMSO): δ 195.3 ($\underline{C}$H$_3$CO), 169.5 (CH$_3$(NH$_2$)$\underline{C}$=C), 168.1 (EtO$_2$$\underline{C}$), 102.1 (CH$_3$(NH$_2$)C=$\underline{C}$), 59.7 (CH$_3$$\underline{C}$H$_2$O), 30.4 ($\underline{C}$H$_3$CO), 22.4 ($\underline{C}$H$_3$(NH$_2$)C=C), 14.5 ($\underline{C}$H$_3$CH$_2$O); IR: 3263 (N—H), 3145 (N—H), 1651 (C=O), 1600 (C=C, conjugated) cm$^{-1}$; MS(ES$^-$) (m/z): 168.8 [M–H, 100%]$^-$; MS(ES$^+$) (m/z): 130.9 [M–Ac, 53%]$^+$, 171.0 [M+H, 18%]$^+$, 194.1 [M+Na, 25%]$^+$.

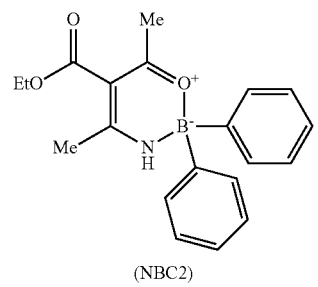

(NBC2)

Ethyl (E)-2-acetyl-3-amino-2-butenoate Diphenylboron (8; NBC2)

Ethyl (E)-2-acetyl-3-amino-2-butenoate (0.98 g, 5.76 mmol) was added to a suspension of DPBA (0.38 g, 1.09 mmol) in anhydrous THF (4 mL). The mixture was heated at 50° C. under N$_2$ for 16 h. The reaction mixture was extracted with DCM and the extract dried over MgSO$_4$. The solution was concentrated and purified by flash column chromatography (ethyl acetate/n-hexane, 1:11) to give 0.30 g (82%) of (8) as a colourless oil. $^1$H NMR (400.1 MHz, CDCl$_3$): δ 7.26 (dd, J=7.8 Hz & 1.4 Hz, 4H, B-Ph(o)), 7.11-7.23 (m, 6H, B-Ph(m/p)), 4.11 (q, J=7.2 Hz, 2H, CH$_3$C$\underline{H}_2$O), 2.42 (s, 3H, C$\underline{H}_3$CO), 2.38 (d, J=0.8 Hz, 3H, C$\underline{H}_3$(NH$_2$)C=C), 1.22 (t, J=7.2 Hz, 3H, C$\underline{H}_3$CH$_2$O), N$\underline{H}$ signal not observed; $^{13}$C NMR (100.6 MHz, CDCl$_3$): δ

186.9 (CH$_3$CO), 170.9 (CH$_3$(NH)C=C), 166.3 (EtO$_2$C), 131.7 (B-Ph(o)), 127.4 (B-Ph(m)), 126.6 (B-Ph(p)), 103.7 (CH$_3$(NH)C=C), 60.4 (CH$_3$CH-$_2$O), 26.4 (CH$_3$CO), 25.7 (CH$_3$(NH)C=C), 14.3 (CH$_3$CH$_2$O), B-Ph quaternary signal not observed; IR: 3316 (N—H), 1701 (C=O), 1603 (C=C, conjugated), 1489 (C=C—NH) cm$^{-1}$; MS(ES$^-$) (m/z): 333.2 [M–H, $^{10}$B, 7%]$^-$, 334.2 [M–H, $^{11}$B, 76%]$^-$, 370.3 [M+$^{35}$Cl, 6%]$^-$, 372.3 [M+$^{37}$Cl, 2%]$^-$; MS(ES$^+$) (m/z): 257.2 [M–Ph, $^{10}$B, 21%]$^+$, 258.2 [M–Ph, $^{11}$B, 100%]$^+$, 335.4 [M+H, $^{10}$B, 5%]$^+$, 336.3 [M+H, $^{11}$B, 22%]$^+$, 358.3 [M+Na, $^{11}$B, 28%]$^+$, 374.3 [M+K, $^1$B, 18%]$^+$; HRMS (m/z): [M+Na]$^+$ calcd. for C$_{20}$H$_{22}$$^{11}$BNO$_3$Na, 358.1590; found, 358.1594.

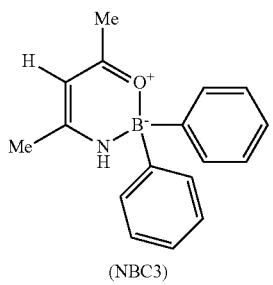

(Z)-4-Aminopent-3-en-2-one Diphenylboron (9; NBC3)

Tin(IV) chloride (1.17 mL, 10 mmol) was slowly added to a stirring solution of acetylacetone (1.03 mL, 10 mmol) and acetonitrile (0.52 mL, 10 mmol) suspended in anhydrous toluene (5 mL). A yellow solid appeared and the reaction mixture was stirred at room temperature under N$_2$ for 30 mins. The mixture was then refluxed at 80° C. under N$_2$ for 4 h. The red viscous oil obtained was cooled to room temperature, washed with n-hexane (20 mL), decanted and then dried in vacuo overnight. The crude product (0.87 g, 8.76 mmol) was added to DPBA (0.38 g, 1.10 mmol) suspended in anhydrous THF (4 mL). The reaction mixture was heated at 50° C. under N$_2$ for 16 h. The reaction mixture was extracted with DCM and the extract dried over MgSO$_4$. The solution was concentrated and purified by flash column chromatography (ethyl acetate/n-hexane, 1:9) to give 51.6 mg (10%) of (9) as a yellow oil. $^1$H NMR (400.1 MHz, CDCl$_3$): δ 7.31 (dd, J=7.8 Hz & 1.4 Hz, 4H, B-Ph(o)), 7.11-7.23 (m, 6H, B-Ph(m/p)), 6.63 (br s, 1H, CH=C(NH)CH$_3$), 5.07 (d, J=2.0 Hz, 1H, CH$_3$(NH)C=CH), 2.28 (d, J=0.8 Hz, 3H, CH$_3$(NH)C=C), 2.02 (s, 3H, CH$_3$CO); $^{13}$C NMR (100.6 MHz, CDCl$_3$): δ 179.7 (CH$_3$CO), 169.4 (CH$_3$(NH)C=C), 131.7 (B-Ph(o)), 127.3 (B-Ph(m)), 126.3 (B-Ph(p)), 96.7 (CH$_3$(NH)C=C), 23.8 (CH$_3$(NH)C=C), 23.7 (CH$_3$CO), B-Ph quaternary signal not observed; IR: 3339 (N—H), 1621 (C=O), 1537 (C=C—NH) cm$^{-1}$; TOF MS(ES$^+$) (m/z): 185.1 [M–Ph, $^{10}$B, $^{12}$C, 26%]$^+$, 186.1 [M–Ph, $^{11}$B, $^{12}$C, 100%]$^+$, 187.1 [M–Ph, $^{11}$B, $^{13}$C, 13%]$^+$, 263.1 [M+H, $^{10}$B, $^{12}$C, 9%]$^+$, 264.1 [M+H, $^{11}$B, $^{12}$C, 30%]$^+$, 265.1 [M+H, $^{11}$B, $^{13}$C, 6%]$^+$, 285.1 [M+Na, $^{10}$B, $^{12}$C, 7%]$^+$, 286.1 [M+Na, $^{11}$B, $^{12}$C, 32%]$^+$, 287.1 [M+Na, $^{11}$B, $^{13}$C, 9%]$^+$, 301.1 [M+K, $^{39}$K, $^{10}$B, $^{12}$C, 14%]$^+$, 302.1 [M+K, $^{39}$K, $^{11}$B, $^{12}$C, 62%]$^+$, 303.1 [M+K, $^{39}$K, $^{11}$B, $^{13}$C, 13%]$^+$, 304.0 [M+K, $^{41}$K, $^{11}$B, $^{12}$C, 7%]$^+$; HRMS (m/z): [M+Na$^+$] calcd. for C$_{17}$H$_{18}$$^{11}$BNONa, 286.1379; found, 286.1382.

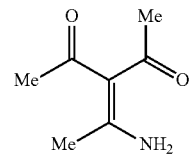

3-(1-Aminoethylidene)pentane-2,4-dione (10)

Tin(IV) chloride (1.17 mL, 10 mmol) was slowly added to a stirring solution of acetylacetone (1.03 mL, 10 mmol), acetonitrile (0.52 mL, 10 mmol) and sodium carbonate (1.08 g, 10.2 mmol) suspended in anhydrous toluene (5 mL). A yellow solid appeared and the reaction mixture was stirred at room temperature under N$_2$ for 30 mins. The mixture was then heated to reflux at 80° C. under N$_2$ for 4 h. An orange solid precipitated from the reaction mixture. The mixture was cooled to room temperature and n-hexane (20 mL) was added. The liquid was decanted and the solid dried in vacuo overnight. The resultant solid was triturated and washed thoroughly with boiling chloroform (25 mL). The mixture was cooled to room temperature, filtered and dried in vacuo to give 0.85 g (61%) of (10) as a cream solid. mp: 129-132° C.; exists as a mixture of tautomers in a 9:1 ratio. $^1$H NMR (400.1 MHz, d$_6$-DMSO): δ 10.65 (br s, 1H, CH$_3$(NH$_2$)C=C), 8.30 (br s, 1H, CH$_3$(NH$_2$)C=C), 5.67 (s, C=CH$_2$ of enol form), 4.88 (d, J=1.4 Hz, C=CH$_2$ of enol form), 2.17 (s, 6H, CH$_3$CO×2), 2.04 (s, 3H, CH$_3$(NH$_2$)C=C); 1.99 (s, 3H, CH$_3$C(OH)C of enol form), 1.91 (s, 3H, CH$_3$(OH)C of enol form); $^{13}$C NMR (100.6 MHz, d$_6$-DMSO): δ 197.9 (CH$_3$CO), 193.0 (CH$_3$CO), 165.2 (CH$_3$(NH$_2$)C=C), 113.1 (CH$_3$(NH$_2$)C=C), 100.6 (H$_2$C=C(OH)C of enol form), 94.1 (H$_2$C=C(OH)C of enol form), 31.2 (CH$_3$CO), 27.5 (CH$_3$CO), 21.3 (CH$_3$(NH$_2$)C=C); MS(ES$^+$) (m/z): 142.1 [M+H, 100%]$^+$, 164.1 [M+Na, 29%]$^+$; HRMS (m/z): [M+H]$^+$ calcd. for C$_7$H$_{12}$NO$_2$, 142.0868; found, 142.0853.

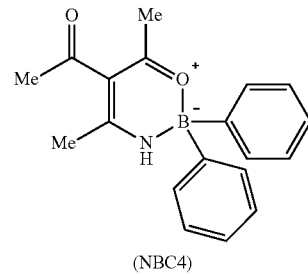

3-(1-Aminoethylidene)pentane-2,4-dione Diphenylboron (11; NBC4)

3-(1-Aminoethylidene)pentane-2,4-dione (0.44 g, 3.14 mmol) was added to a suspension of DPBA (0.36 g, 1.05 mmol) in anhydrous THF (4 mL). The mixture was heated at 50° C. under N$_2$ for 16 h. The reaction mixture was extracted with DCM and extract dried over MgSO$_4$. The solution was concentrated and purified by flash column chromatography (ethyl acetate/n-hexane, 1:4) to give 0.13 g (40%) of (11) as a colourless oil. $^1$H NMR (400.1 MHz, CDCl$_3$): δ 7.26 (dd, J=8.2 Hz & 1.4 Hz, 4H, B-Ph(o)), 7.11-7.23 (m, 6H, B-Ph(m/p)), 2.32 (s, 3H, C$\underline{H}_3$CO), 2.28 (d, J=0.8 Hz, 3H, C$\underline{H}_3$(NH)C=C), 2.20 (s, 3H, C$\underline{H}_3$CO), N$\underline{H}$ signal not observed; $^{13}$C NMR (100.6 MHz, CDCl$_3$): δ 198.2 (CH$_3$CO), 183.5 (CH$_3$$\underline{C}$O), 169.9 (CH$_3$(NH)$\underline{C}$=C), 131.7 (B-Ph(o)), 127.4 (B-Ph(m)), 126.6 (B-Ph(p)), 114.9 (CH$_3$(NH)C=$\underline{C}$), 32.8 ($\underline{C}$H$_3$CO), 25.4 ($\underline{C}$H$_3$(NH)C=C), 25.0 ($\underline{C}$H$_3$CO), B-Ph quaternary signal not observed; IR: 3283 (N—H), 1654 (C=O), 1604 (C=C, conjugated) cm$^{-1}$; MS(ES$^-$) (m/z): 303.3 [M−H, $^{10}$B, $^{12}$C, 15%]$^-$, 304.2 [M−H, $^{11}$B, $^{12}$C, 100%]$^-$, 305.2 [M−H, $^{11}$B, $^{13}$C, 15%]$^-$; MS(ES$^+$) (m/z): 227.3 [M−Ph, $^{10}$B, $^{12}$C, 10%]$^+$, 228.2 [M−Ph, $^{11}$B, $^{12}$C, 40%]$^+$, 229.2 [M−Ph, $^{11}$B, $^{13}$C, 9%]$^+$, 305.2 [M+H, $^{10}$B, $^{12}$C, 3%]$^+$, 306.4 [M+H, $^{11}$B, $^{12}$C, 45%]$^+$, 307.4 [M+H, $^{11}$B, $^{13}$C, 6%]$^+$, 328.3 [M+Na, $^{11}$B, $^{12}$C, 30%]$^+$, 344.4 [M+K, $^{11}$B, $^{12}$C, 9%]$^+$; HRMS (m/z): [M+H]$^+$ calcd. for C$_{19}$H$_{21}$$^{11}$BNO$_2$, 306.1669; found, 306.1654.

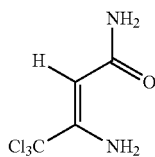

(Z)-3-Amino-4,4-trichlorobut-2-enamide (12)

Acetoacetamide (1.01 g, 10 mmol) and trichloroacetonitrile (1 mL, 10 mmol) were added to a suspension of zinc acetylacetonate hydrate (56 mg, 0.2 mmol) in anhydrous DCM (10 mL). The reaction mixture was stirred at room temperature under N$_2$ for 16 h. The white solid that precipitated was extracted with EtOAc and the extract dried over MgSO$_4$. The solution was concentrated and purified by flash column chromatography (ethyl acetate/n-hexane, 1:1) to give 0.78 g (39%) of (12) as a cream solid. mp: 95-97° C.; $^1$H NMR (400.1 MHz, CDCl$_3$): δ 6.72 (br s, 1H, CON$\underline{H}_2$), 5.33 (s, 1H, CCl$_3$(NH$_2$)C=C$\underline{H}$), 5.30 (br s, 1H, CON$\underline{H}_2$), N$\underline{H}_2$ signal not observed; $^{13}$C NMR (100.6 MHz, CDCl$_3$): δ 170.6 (CONH$_2$), 156.8 (CCl$_3$(NH$_2$)$\underline{C}$=C), 94.3 (CCl$_3$), 86.1 (CCl$_3$(NH$_2$)C=$\underline{C}$); MS(ES$^-$) (m/z): 201.9 [M−H, $^{35}$Cl, $^{35}$Cl, $^{35}$Cl, 79%]$^-$, 203.9 [M−H, $^{35}$Cl, $^{35}$Cl, $^{37}$Cl, 46%]$^-$, 205.9 [M−H, $^{35}$Cl, $^{37}$Cl, $^{37}$Cl, 30%]$^-$, 207.9 [M−H, $^{37}$Cl, $^{37}$Cl, $^{37}$Cl, 11%]$^-$; IR: 3479 (N—H, amide), 3412 (N—H, amide), 3277 (N—H, amine), 3154 (N—H, amine), 1649 (C=O, amide band I), 1623 (C=O, amide band II), 1589 (C=C, conjugated), 1539 (C=C—NH$_2$) cm$^{-1}$; MS(ES$^+$) (m/z): 203.0 [M+H, $^{35}$Cl, $^{35}$Cl, $^{35}$Cl, 7%]$^+$, 204.9 [M+H, $^{35}$Cl, $^{35}$Cl, $^{37}$Cl, 57%]$^+$, 206.9 [M+H, $^{35}$Cl, $^{37}$Cl, $^{37}$Cl, 9%]$^+$, 208.9 [M+H, $^{37}$Cl, $^{37}$Cl, $^{37}$Cl, 2%]$^+$; HRMS (m/z): [M+H]$^+$ calcd. for C$_4$H$_6$$^{35}$Cl$_3$N$_2$O, 202.9546; found, 202.9545.

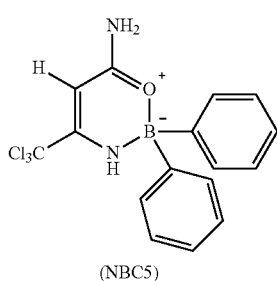

(Z)-3-Amino-4,4-trichlorobut-2-enamide Diphenylboron (13; NBC5)

(Z)-3-Amino-4,4-trichlorobut-2-enamide (0.51 g, 2.50 mmol) was added to a suspension of DPBA (0.41 g, 1.19 mmol) in anhydrous THF (4 mL). The reaction mixture was heated at 50° C. under N$_2$ for 16 h. The reaction mixture was extracted with EtOAc and extract dried over MgSO$_4$. The solution was concentrated and purified by flash column chromatography (ethyl acetate/n-hexane, 1:4) to give 57.2 mg (13%) of (13) as a cream solid. mp: 148-149° C.; $^1$H NMR (400.1 MHz, CDCl$_3$): δ 7.34 (dd, J=8.0 Hz &1.2 Hz, 4H, B-Ph(o)), 7.13-7.25 (m, 6H, B-Ph(m/p)), 6.29 (br s, 1H, Cl$_3$C(N$\underline{H}$)C=CH), 5.34 (br s, 2H, CON$\underline{H}_2$), 5.15 (d, J=2.4 Hz, 1H, Cl$_3$C(NH)C=C$\underline{H}$); $^{13}$C NMR (100.6 MHz, CDCl$_3$): δ 170.8 (CONH$_2$), 164.6 (Cl$_3$C(NH)$\underline{C}$=CH), 132.0 (B-Ph(o)), 127.3 (B-Ph(m)), 126.6 (B-Ph(p)), 93.6 (CCl$_3$), 76.3 (Cl$_3$C(NH)C=$\underline{C}$H), B-Ph quaternary signal not observed; IR: 3485 (N—H), 3363 (N—H), 1619 (C=O), 1577 (C=C, conjugated), 1542 (C=C—NH) cm$^{-1}$; MS(ES$^-$) (m/z): 364.1 [M−H, $^{10}$B, $^{35}$Cl, $^{35}$Cl, $^{35}$Cl, 8%]$^-$, 365.1 [M−H, $^{11}$B, $^{35}$Cl, $^{35}$Cl, $^{35}$Cl, 100%]$^-$, 366.0 [M−H, $^{10}$B, $^{35}$Cl, $^{35}$Cl, $^{37}$Cl, 16%]$^-$, 367.0 [M−H, $^{11}$B, $^{35}$Cl, $^{35}$Cl, $^{37}$Cl, 28%]$^-$, 368.0 [M−H, $^{10}$B, $^{35}$Cl, $^{37}$Cl, $^{37}$Cl, 8%]$^-$, 369.0 [M−H, $^{11}$B, $^{35}$Cl, $^{37}$Cl, $^{37}$Cl, 27%]$^-$, 370.1 [M−H, $^{10}$B, $^{37}$Cl, $^{37}$Cl, $^{37}$Cl, 6%]$^-$, 371.3 [M−H, $^{11}$B, $^{37}$Cl, $^{37}$Cl, $^{37}$Cl, 2%]$^-$; MS(ES)$^+$ (m/z): 389.1 [M+Na, $^{11}$B, $^{35}$Cl, $^{35}$Cl, $^{35}$Cl, 5%]$^+$, 391.1 [M+Na, $^{11}$B, $^{35}$Cl, $^{35}$Cl, $^{37}$Cl, 8%]$^+$, 393.1 [M+Na, $^{35}$Cl, $^{37}$Cl, $^{37}$Cl, 3%]$^+$; HRMS (m/z): [M−H]$^-$ calcd. for C$_{16}$H$_{13}$$^{10}$B$^{35}$Cl$_3$N$_2$O, 364.0223; found, 364.0231.

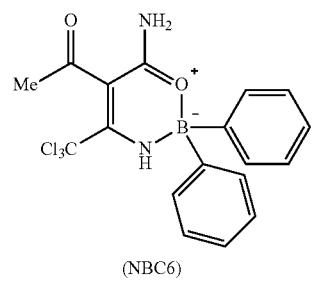

(Z)-2-Acetyl-3-amino-4,4-trichlorobut-2-enamide diphenylboron (14; NBC6)

To a suspension of zinc acetylacetonate hydrate (56 mg, 0.2 mmol) and sodium carbonate (1.08 g, 1.02 mmol) in anhydrous DCM (5 mL), acetoacetamide (1.01 g, 10 mmol) and trichloroacetonitrile (1 mL, 10 mmol) were added. The reaction mixture was stirred at room temperature under N$_2$ for 3 h. The white solid that precipitated was extracted with EtOAc, dried over MgSO$_4$ and concentrated by evaporation in vacuo to give crude (Z)-2-acetyl-3-amino-4,4-trichlorobut-2-enamide as a yellow oil. The crude product (1.34 g, 5.47 mmol) was added to DPBA (0.38 g, 1.09 mmol) suspended in anhydrous THF (4 mL). The reaction mixture was heated at 50° C. under N$_2$ for 16 h. The reaction mixture was extracted with DCM. The solution was concentrated and purified by flash column chromatography (ethyl acetate/n-hexane, 1:9). The collected fractions were combined, evaporated and stirred in cold n-hexane (15 mL) for 30 mins. The precipitate was filtered to give 0.15 g (34%) of (14) as a yellow solid. mp: 134-135° C.; $^1$H NMR (300.1 MHz, CDCl$_3$): δ 9.25 (br s, 1H, CON$\underline{H}_2$), 7.61 (br s, 1H, Cl$_3$C(N$\underline{H}$)C=C), 7.40 (d, J=5.7 Hz, 4H, B-Ph(o)), 7.20-7.35 (m, 6H, B-Ph(m/p)), 6.00 (br s, 1H, CON$\underline{H}_2$), 2.30 (s, 3H, C$\underline{H}_3$CO); $^{13}$C NMR (100.6 MHz, CDCl$_3$): δ 197.1 (CH$_3\underline{C}$O), 168.2 (CONH$_2$), 164.5 (Cl$_3$C(NH)$\underline{C}$=C), 130.9 (B-Ph(o)), 126.4 (B-Ph(m)), 125.8 (B-Ph(p)), 97.1 (Cl$_3$C(NH)C=$\underline{C}$), 94.0 (CCl$_3$), 32.9 ($\underline{C}H_3$CO), B-Ph quaternary signal not observed; $^{11}$B NMR (160.5 MHz, CDCl$_3$) δ 2.37; IR: 3390 (N—H), 3329 (N—H), 1647 (C=O), 1606 (C=C, conjugated), 1552 (C=C—NH) cm$^{-1}$; MS(ES$^-$) (m/z): 202.0 [M–C$_{14}$H$_{11}$BO, $^{35}$Cl, $^{35}$Cl, $^{35}$Cl, 91%]$^-$, 204.0 [M–C$_{14}$H$_{11}$BO, $^{35}$Cl, $^{35}$Cl, $^{37}$Cl, 100%]$^-$, 206.0 [M–C$_{14}$H$_{11}$BO, $^{35}$Cl, $^{37}$Cl, $^{37}$Cl, 15%]$^-$, 208.0 [M–C$_{14}$H$_{11}$BO, $^{37}$Cl, $^{37}$Cl, $^{37}$Cl, 3%]; 406.1 [M–H, $^{10}$B, $^{35}$Cl, $^{35}$Cl, $^{35}$Cl, 20%]$^-$, 407.1 [M–H, $^{11}$B, $^{35}$Cl, $^{35}$Cl, $^{35}$Cl, 61%]$^-$, 408.0 [M–H, $^{10}$B, $^{35}$Cl, $^{35}$Cl, $^{37}$Cl, 31%]$^-$, 409.0 [M–H, $^{11}$B, $^{35}$Cl, $^{35}$Cl, $^{37}$Cl, 100%]$^-$, 410.2 [M–H, $^{10}$B, $^{35}$Cl, $^{37}$Cl, $^{37}$Cl, 24%]$^-$, 411.2 [M–H, $^{11}$B, $^{35}$Cl, $^{37}$Cl, $^{37}$Cl, 21%]$^-$, 412.5 [M–H, $^{10}$B, $^{37}$Cl, $^{37}$Cl, $^{37}$Cl, 4%]$^-$, 413.2 [M–H, $^{11}$B, $^{37}$Cl, $^{37}$Cl, $^{37}$Cl, 3%]$^-$; MS(ES$^+$) (m/z): 330.1 [M–Ph, $^{10}$B, $^{35}$Cl, $^{35}$Cl, $^{35}$Cl, 12%]$^+$, 331.2 [M–Ph, $^{11}$B, $^{35}$Cl, $^{35}$Cl, $^{35}$Cl, 65%]$^+$, 332.2 [M–Ph, $^{10}$B, $^{35}$Cl, $^{35}$Cl, $^{37}$Cl, 8%]$^+$, 333.2 [M–Ph, $^{11}$B, $^{35}$Cl, $^{35}$Cl, $^{37}$Cl, 63%]$^+$, 334.2 [M–Ph, $^{10}$B, $^{35}$Cl, $^{37}$Cl, $^{37}$Cl, 16%]$^+$, 335.3 [M–Ph, $^{11}$B, $^{35}$Cl, $^{37}$Cl, $^{37}$Cl, 33%]$^+$, 336.3 [M–Ph, $^{10}$B, $^{37}$Cl, $^{37}$Cl, $^{37}$Cl, 5%]$^+$, 337.3 [M–Ph, $^{11}$B, $^{37}$Cl, $^{37}$Cl, $^{37}$Cl, 3%]$^+$, 408.4 [M+H, $^{10}$B, $^{35}$Cl, $^{35}$Cl, $^{35}$Cl, 11%]$^+$, 409.2 [M+H, $^{11}$B, $^{35}$Cl, $^{35}$Cl, $^{35}$Cl, 73%]$^+$, 410.2 [M+H, $^{10}$B, $^{35}$Cl, $^{35}$Cl, $^{37}$Cl, 16%]$^-$, 411.2 [M+H, $^{11}$B, $^{35}$Cl, $^{35}$Cl, $^{37}$Cl, 84%]$^+$, 412.2 [M+H, $^{10}$B, $^{35}$Cl, $^{37}$Cl, $^{37}$Cl, 8%]$^+$, 413.2 [M+H, $^{11}$B, $^{35}$Cl, $^{37}$Cl, $^{37}$Cl, 17%]$^+$, 414.2 [M+H, $^{10}$B, $^{37}$Cl, $^{37}$Cl, $^{37}$Cl, 4%]$^+$, 415.2 [M+H, $^{11}$B, $^{37}$Cl, $^{37}$Cl, $^{37}$Cl, 3%]$^+$, 430.2 [M+Na, $^{10}$B, $^{35}$Cl, $^{35}$Cl, $^{35}$Cl, 4%]$^+$, 431.2 [M+Na, $^{11}$B, $^{35}$Cl, $^{35}$Cl, $^{35}$Cl, 46%]$^+$, 432.1 [M+Na, $^{10}$B, $^{35}$Cl, $^{35}$Cl, $^{37}$Cl, 13%]$^+$, 433.2 [M+Na, $^{11}$B, $^{35}$Cl, $^{35}$Cl, $^{37}$Cl, 17%]$^+$, 434.2 [M+Na, $^{10}$B, $^{35}$Cl, $^{37}$Cl, $^{37}$Cl, 9%]$^+$, 435.2 [M+Na, $^{11}$B, $^{35}$Cl, $^{37}$Cl, $^{37}$Cl, 10%]$^+$, 436.2 [M+Na, $^{10}$B, $^{37}$Cl, $^{37}$Cl, $^{37}$Cl, 3%]$^+$, 437.2 [M+Na, $^{11}$B, $^{37}$Cl, $^{37}$Cl, $^{37}$Cl, 5%]$^+$, 447.2 [M+K, $^{11}$B, $^{35}$Cl, $^{35}$Cl, $^{35}$Cl, 18%]$^+$, 449.5 [M+K, $^{11}$B, $^{35}$Cl, $^{35}$Cl, $^{37}$Cl, 8%]$^+$; HRMS (m/z): [M+H]$^+$ calcd. for C$_{18}$H$_{15}$$^{11}$B$^{35}$Cl$_2$$^{37}$ClN$_2$O$_2$, 411.0419; found, 411.0451.

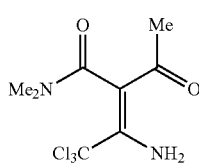

(Z)-2-Acetyl-3-amino-4,4,4-trichloro-N,N-dimethyl-but-2-enamide (15)

Zinc acetylacetonate hydrate (28 mg, 0.1 mmol) and sodium carbonate (1.08 g, 1.02 mmol) was suspended in anhydrous DCM (10 mL). N,N-Dimethylacetoacetamide (1.21 mL, 10 mmol) and trichloroacetonitrile (1 mL, 10 mmol) were added. The reaction mixture was stirred at room temperature under N$_2$ for 16 h. The reaction mixture was extracted in EtOAc, washed with brine and concentrated by evaporation in vacuo to give 2.41 g (88%) of (15) as a cream solid. mp: 102-104° C.; $^1$H NMR (400.1 MHz, CDCl$_3$): δ 8.56 (br s, 1H, Cl$_3$C(N$\underline{H}$)C=C), 2.97 (d, J=3.3 Hz, 6H, CON(C$\underline{H}_3$)$_2$), 2.14 (s, 3H, C$\underline{H}_3$CO); $^{13}$C NMR (100.6 MHz, CDCl$_3$): δ 196.7 (CH$_3\underline{C}$O), 168.6 (Cl$_3$C(NH$_2$)$\underline{C}$=C), 155.6 ($\underline{C}$ON(CH$_3$)$_2$), 103.2 (Cl$_3$C(NH$_2$)C=$\underline{C}$), 93.3 (CCl$_3$), 38.8 (CON($\underline{C}H_3$)$_2$), 35.1 (CON($\underline{C}H_3$)$_2$), 27.9 ($\underline{C}H_3$CO); IR: 3282 (N—H), 1602 (C=C, conjugated), 1497 (C=C—NH$_2$) cm$^{-1}$; MS(ES$^-$) (m/z): 270.9 [M–H, $^{35}$Cl, $^{35}$Cl, $^{35}$Cl, 18%]$^-$, 273.0 [M–H, $^{35}$Cl, $^{37}$Cl, $^{37}$Cl, 22%]$^-$, 275.0 [M–H, $^{35}$Cl, $^{37}$Cl, $^{37}$Cl, 5%]$^-$, 277.0 [M–H, $^{37}$Cl, $^{37}$Cl, $^{37}$Cl, 3%]$^-$; MS(ES$^+$) (m/z): 273.0 [M+H, $^{35}$Cl, $^{35}$Cl, $^{35}$Cl, 100%]$^+$, 275.0 [M+H, $^{35}$Cl, $^{35}$Cl, $^{37}$Cl, 54%]$^+$, 277.0 [M+H, $^{35}$Cl, $^{37}$Cl, $^{37}$Cl, 83%]$^+$, 279.0 [M+H, $^{37}$Cl, $^{37}$Cl, $^{37}$Cl, 12%]$^+$, 295.0 [M+Na, $^{35}$Cl, $^{35}$Cl, $^{35}$Cl, 49%]$^+$, 297.0 [M+Na, $^{35}$Cl, $^{35}$Cl, $^{37}$Cl, 52%]$^+$, 299.0 [M+Na, $^{35}$Cl, $^{37}$Cl, $^{37}$Cl, 12%]$^+$, 301.0 [M+Na, $^{37}$Cl, $^{37}$Cl, $^{37}$Cl, 2%]$^+$, 311.0 [M+K, $^{35}$Cl, $^{35}$Cl, $^{35}$Cl, 23%]$^+$, 313.0 [M+K, $^{35}$Cl, $^{35}$Cl, $^{37}$Cl, 20%]$^+$, 315.0 [M+K, $^{35}$Cl, $^{37}$Cl, $^{37}$Cl, 8%]$^+$, 317.0 [M+K, $^{37}$Cl, $^{37}$Cl, 1%]$^+$; HRMS (m/z): [M+H]$^+$ calcd. for C$_8$H$_{11}$$^{135}$Cl$_3$N$_2$O$_2$Na, 294.9784; found, 294.9789.

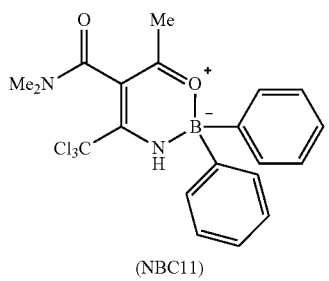

(Z)-2-Acetyl-3-amino-4,4,4-trichloro-N,N-dimethyl-but-2-enamide Diphenylboron (16; NBC11)

Zinc acetylacetonate hydrate (28 mg, 0.1 mmol) and sodium carbonate (1.08 g, 1.02 mmol) was suspended in anhydrous DCM (10 mL). N,N-Dimethylacetoacetamide (1.29 g, 10 mmol) and trichloroacetonitrile (1 mL, 10 mmol) were added. The reaction mixture was stirred at room temperature under N$_2$ for 16 h. The reaction mixture was extracted in EtOAc, washed with brine and concentrated by evaporation in vacuo to give crude (Z)-2-acetyl-3-amino-4, 4,4-trichloro-N,N-dimethylbut-2-enamide as a cream solid. The crude product (1.86 g, 8.02 mmol) was added to DPBA (0.69 g, 2.01 mmol) and suspended in anhydrous THF (8 mL). The reaction mixture was heated at 50° C. under N$_2$ for 16 h. The reaction mixture was extracted in DCM. The solution was concentrated and purified by flash column chromatography (ethyl acetate/n-hexane, 1:2). n-Hexane (15 mL) was added and stirred for 30 min to induce precipitation. The resulting residue was recrystallized in toluene/n-hexane (1:1) to give 0.48 g (54%) of (16) as a yellow solid. mp: 112-113° C.; $^1$H NMR (400.1 MHz, CDCl$_3$): δ 7.94 (br s, 1H, Cl$_3$C(N$\underline{H}$)C=C), 7.42 (d, J=10.0 Hz, 2H, B-Ph(o)), 7.37 (d, J=10.8 Hz, 2H, B-Ph(o)), 7.17-7.35 (m, 6H, B-Ph (m/p)), 2.93 (s, 3H, CON(C$\underline{H}_3$)$_2$), 2.34 (s, 3H, C$\underline{H}_3$), 2.28 (s, 3H, C$\underline{H}_3$); $^{13}$C NMR (100.6 MHz, CDCl$_3$): δ 184.6 (CH$_3$$\underline{C}$O), 164.9 (Cl$_3$C(NH)$\underline{C}$=C), 160.7 ($\underline{C}$ON(CH$_3$)$_2$), 131.5 (B-Ph(o)), 130.0 (B-Ph(o)), 126.7 (B-Ph(m)), 126.3 (B-Ph (p)), 126.3 (B-Ph(m)), 125.7 (B-Ph(p)), 103.8 (Cl$_3$C(NH) C=$\underline{C}$), 91.5 (CCl$_3$), 36.8 (CON($\underline{C}H_3$)$_2$), 34.3 (CON($\underline{C}H_3$)$_2$), 21.8 ($\underline{C}H_3$CO), B-Ph quaternary signal not observed; IR: 3301 (N—H), 1626 (C=O), 1585 (C=C, conjugated), 1460 (C=C—NH) cm$^{-1}$; MS(ES$^-$) (m/z): 434.1 [M–H, $^{10}$B, $^{35}$Cl, $^{35}$Cl, $^{35}$Cl, 24%]$^-$, 435.0 [M–H, $^{11}$B, $^{35}$Cl, $^{35}$Cl, $^{35}$Cl, 51%]$^-$, 436.0 [M–H, $^{10}$B, $^{35}$Cl, $^{35}$Cl, $^{37}$Cl, 21%]$^-$, 437.1 [M–H, $^{11}$B, $^{35}$Cl, $^{35}$Cl, $^{37}$Cl, 100%]$^-$, 438.0 [M–H, $^{10}$B, $^{35}$Cl, $^{37}$Cl, $^{37}$Cl, 11%]$^-$, 439.0 [M–H, $^{11}$B, $^{35}$Cl, $^{37}$Cl, $^{37}$Cl, 22%]$^-$, 440.0 [M–H, $^{10}$B, $^{37}$Cl, $^{37}$Cl, $^{37}$Cl, 6%]$^-$, 441.0 [M–H, $^{11}$B, $^{37}$Cl, $^{37}$Cl, $^{37}$Cl, 3%]$^-$; MS(ES$^+$) (m/z): 358.0 [M–Ph, $^{10}$B, $^{35}$Cl, $^{35}$Cl, $^{35}$Cl, 3%]$^+$, 359.0 [M–Ph, $^{11}$B, $^{35}$Cl, $^{35}$Cl, $^{35}$Cl, 10%]$^+$, 362.0 [M–Ph, $^{10}$B, $^{35}$Cl, $^{35}$Cl, $^{37}$Cl, 4%]$^+$, 361.0 [M–Ph, $^{11}$B, $^{35}$Cl, $^{35}$Cl, $^{37}$Cl, 13%]$^+$, 362.0 [M–Ph, $^{10}$B, $^{35}$Cl, $^{37}$Cl, $^{37}$Cl, 5%]$^+$, 363.0 [M–Ph, $^{11}$B, $^{35}$Cl, $^{37}$Cl, $^{37}$Cl, 6%]$^+$, 436.1 [M+H, $^{10}$B, $^{35}$Cl, $^{35}$Cl, $^{35}$Cl, 10%]$^-$, 437.1 [M+H, $^{11}$B, $^{35}$Cl, $^{35}$Cl, $^{35}$Cl, 70%]$^+$, 438.0 [M+H, $^{10}$B, $^{35}$Cl, $^{35}$Cl, $^{37}$Cl, 27%]$^+$, 439.0 [M+H, $^{11}$B, $^{35}$Cl, $^{35}$Cl, $^{37}$Cl, 45%]$^+$, 440.1 [M+H, $^{10}$B, $^{35}$Cl, $^{37}$Cl, $^{37}$Cl, 19%]$^+$, 441.1 [M+H, $^{11}$B, $^{35}$Cl, $^{37}$Cl, $^{37}$Cl, 26%]$^+$, 442.1 [M+H, $^{10}$B, $^{37}$Cl, $^{37}$Cl, $^{37}$Cl, 5%]$^+$, 443.1 [M+H, $^{11}$B, $^{37}$Cl, $^{37}$Cl, $^{37}$Cl, 2%]$^+$; HRMS (m/z): [M–H]$^-$ calcd. for $C_{20}H_{19}{}^{11}B^{35}Cl_3N_2O_2$, 435.0605; found, 435.0616.

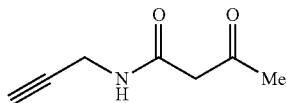

17

N-Propargylacetoacetamide (17) was prepared by a revised method to that described by Álvarez-Pérez & Marco-Contelles, 2011[26]. tert-Butyl acetoacetate (0.75 mL, 4.50 mmol) was suspended in toluene (5 mL). Propargylamine (0.26 mL, 4.10 mmol) was added. The mixture was heated at 110° C. under $N_2$ for 14 h. The reaction mixture was dissolved in $Et_2O$ and washed with 1N HCl (2×10 mL). The aqueous layers were combined and basified using NaOH 50% (w/v). Once neutralised (pH=7-8), the aqueous layer was extracted with EtOAc and the extract dried over $MgSO_4$. The solution was concentrated in vacuo to give 0.40 g (65%) of (17) as a dark orange oil. $^1$H NMR (300.1 MHz, CDCl$_3$): δ 7.37 (br s, 1H, CONH), 4.08 (dd, J=5.4 & 2.4 Hz, 2H, HC≡CCH$_2$), 3.46 (s, 2H, CH$_3$COCH$_2$), 2.28 (s, 3H, CH$_3$CO), 2.25 (t, J=2.6 Hz, 1H, HC≡CCH$_2$); $^{13}$C NMR (100.1 MHz, CDCl$_3$): 204.5 (CH$_3$CO), 165.3 (CONH), 79.2 (HC≡CCH$_2$), 71.6 (HC≡CCH$_2$), 49.0 (CH$_3$COCH$_2$), 31.1 (CH$_3$CO), 29.1 (HC≡CCH$_2$); MS(ES$^-$) (m/z): 138.0 [M–H, 100%]$^-$; IR: 3281 (N—H), 3271 (C≡C), 1712 (C=O, ketone), 1650 (C=O, amide band I), 1550 (C=O, amide band II) cm$^{-1}$; MS(ES$^+$) (m/z): 140.0 [M+H, 92%]$^+$, 162.0 [M+Na, 88%]$^+$; HRMS (m/z): [M+H]$^+$ calcd. for $C_7H_{10}NO_2$, 140.0712; found, 140.0713.

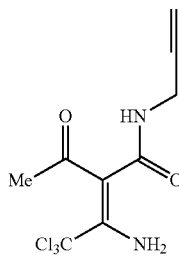

18

(Z)-2-Acetyl-3-amino-4,4,4-trichloro-N-(prop-2-yn-1-yl)but-2-enamide (18)

To a suspension of zinc acetylacetonate hydrate (6.3 mg, 0.02 mmol) and sodium carbonate (0.24 g, 2.28 mmol) in anhydrous DCM (5 mL), N-propargylacetoacetamide (0.31 g, 2.23 mmol) and trichloroacetonitrile (0.22 mL, 2.23 mmol) were added. The reaction mixture was stirred at room temperature under $N_2$ for 2 h. The reaction mixture was extracted with DCM, dried over $MgSO_4$ and concentrated by evaporation in vacuo to give 0.51 g (81%) of (18) as a brown solid. mp: 77-79° C.; $^1$H NMR (300.1 MHz, CDCl$_3$): 8.66 (br s, 1H, NH$_2$), 6.07 (br s, 1H, CONH), 4.10 (dd, J=5.3 & 2.6 Hz, 2H, HC≡CCH$_2$), 2.25 (s, 3H, CH$_3$CO), 2.21 (t, J=2.6 Hz, 1H, HC≡CCH$_2$), 1×NH signal not observed; $^{13}$C NMR (100.1 MHz, CDCl$_3$): 197.4 (CH$_3$CO), 167.2 (C=C(NH$_2$)CCl$_3$), 157.0 (CONH), 104.0 (C=C(NH$_2$)CCl$_3$), 93.2 (CCl$_3$), 78.4 (HC≡CCH$_2$), 72.2 (HC≡CCH$_2$), 30.1 (CH$_3$CO), 28.4 (HC≡CCH$_2$); IR: 3247 (C≡C), 1650 (C=O), 1609 (C=C, conjugated), 1524 (C=C—NH$_2$); MS(ES$^+$) (m/z): 282.9 [M+H, 19%]$^+$, 304.9 [M+Na, $^{35}$Cl, $^{35}$Cl, 130%]$^+$, 306.9 [M+Na, $^{35}$Cl, $^{35}$Cl, $^{37}$Cl, 15%]$^+$, 308.9 [M+Na, $^{35}$Cl, $^{37}$Cl, $^{37}$Cl, 4%]$^+$, 310.9 [M+Na, $^{37}$Cl, $^{37}$Cl, $^{37}$Cl, 2%]$^+$.

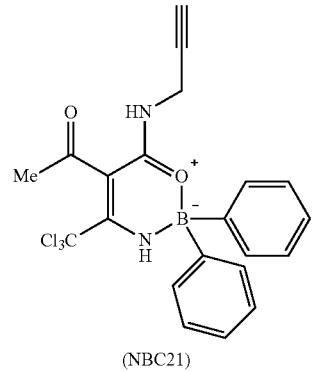

19

(NBC21)

(Z)-2-Acetyl-3-amino-4,4,4-trichloro-N-(prop-2-yn-1-yl)but-2-enamide Diphenylboron (19; NBC21)

(Z)-2-Acetyl-3-amino-4,4,4-trichloro-N-(prop-2-yn-1-yl) but-2-enamide (0.37 g, 1.31 mmol) was added to DPBA (0.23 g, 0.66 mmol) suspended in anhydrous THF (4 mL). The reaction mixture was heated at 50° C. under $N_2$ for 16 h. The reaction mixture was extracted in DCM. The solution was concentrated and purified by flash column chromatography (ethyl acetate/n-hexane, 1:7). The collected fractions were combined, evaporated and stirred in cold n-hexane (15 mL) for 30 mins. The precipitate was filtered to give 63.1 mg (22%) of (19) as a yellow solid. mp: 147-148° C.; $^1$H NMR (300.1 MHz, CDCl$_3$): δ 7.82 (br s, 1H, Cl$_3$C(NH)C=C), 7.16-7.34 (m, 10H, B-Ph), 5.70 (t, J=5.4 Hz, 1H, CONH), 3.99 (dd, J=5.3 & 2.6 Hz, 2H, HC≡CCH$_2$), 2.29 (s, 3H, CH$_3$CO), 2.16 (t, J=2.7 Hz, 1H, HC≡CCH$_2$); $^{13}$C NMR (100.6 MHz, CDCl$_3$): δ 187.2 (CH$_3$CO), 164.4 (Cl$_3$C(NH)C=C), 162.3 (CONH), 131.6 (B-Ph(o)), 127.6 (B-Ph(m)), 127.1 (B-Ph(p)), 104.5 (Cl$_3$C(NH)C=C), 92.7 (CCl$_3$), 78.2 (HC≡CCH$_2$), 72.2 (HC≡CCH$_2$), 29.9 (HC≡CCH$_2$), 23.3 (CH$_3$CO), B-Ph quaternary signal not observed; IR: 3309 (N—H), 3277 (C≡C), 1644 (C=O, amide band I), 1597 (C=C, conjugated), 1541 (C=O, amide band II) 1523 (C=C—NH) cm$^{-1}$; MS(ES$^-$) (m/z): 444.1 [M–H, $^{10}$B, $^{35}$Cl, $^{35}$Cl, $^{35}$Cl, 15%]$^-$, 445.0 [M–H, $^{11}$B, $^{35}$Cl, $^{35}$Cl, $^{35}$Cl, 85%]$^-$, 446.1 [M–H, $^{10}$B, $^{35}$Cl, $^{35}$Cl, $^{37}$Cl, 17%]$^-$, 447.2 [M–H, $^{11}$B, $^{35}$Cl, $^{35}$Cl, $^{37}$Cl, 28%]$^-$, 447.9 [M–H, $^{10}$B, $^{35}$Cl, $^{37}$Cl, $^{37}$Cl, 12%]$^-$, 449.2 [M–H, $^{11}$B, $^{35}$Cl, $^{37}$Cl, $^{37}$Cl, 11%]$^-$, 450.0 [M–H, $^{10}$B, $^{37}$Cl, $^{37}$Cl, $^{37}$Cl, 4%]$^-$, 451.2 [M–H, $^{11}$B, $^{37}$Cl, $^{37}$Cl, $^{37}$Cl, 3%]$^-$; MS(ES$^+$) (m/z): 447.0 [M+H, $^{35}$Cl, $^{35}$Cl, $^{35}$Cl, 8%]$^+$; HRMS (m/z): [M+H]$^+$ calcd. for C$_{21}$H$_{17}$BCl$_3$N$_2$O$_2$, 445.0453; found, 445.0439.

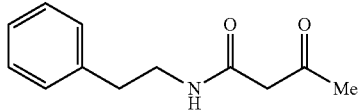

N-Phenethylacetoacetamide (20)

tert-Butyl acetoacetate (1.49 mL, 9.00 mmol) was suspended in toluene (150 mL). Phenethylamine (1.03 mL, 8.20 mmol) was added. The mixture was heated at 150° C. for 14 h using Dean Stark apparatus. The reaction mixture was dissolved in Et$_2$O and washed with 1N HCl (2×10 mL). A yellow solid formed in the organic phase and was discarded by Buchner filtration. The aqueous layers were combined and basified aqueous NaOH 50% (w/v). Once neutralised (pH=7-8), the aqueous layer was extracted with EtOAc and combined with the filtrate from the organic phase. The extract was dried over MgSO$_4$ and concentrated in vacuo to give 1.19 g (71%) of (20) as a dark orange oil. $^1$H NMR (300.1 MHz, CDCl$_3$): δ 7.08-7.27 (m, 5H, Aryl-$\underline{H}$, 6.94 (br s, 1H, N$\underline{H}$), 3.45 (q, J=6.6 Hz, 2H, NHC$\underline{H}_2$CH$_2$), 3.27 (s, 2H, CH$_3$COC$\underline{H}_2$), 2.74 (t, J=7.1 Hz, 2H, NHCH$_2$C$\underline{H}_2$), 2.14 (s, 3H, CH$_3$CO); $^{13}$C NMR (100.1 MHz, CDCl$_3$): 204.4 (CH$_3$$\underline{C}$O), 165.4 (CONH), 138.7 (Ph(ipso)), 128.7 (Ph(o)), 128.6 (Ph(m)), 126.5 (Ph(p)), 49.8 (CH$_3$$\underline{C}$OCH$_2$), 40.7 (NH$\underline{C}$H$_2$CH$_2$), 35.6 (NHCH$_2$$\underline{C}$H$_2$), 30.9 ($\underline{C}$H$_3$CO); IR: 3303 (N—H), 1716 (C=O, ketone), 1644 (C=O, amide band I), 1542 (C=O, amide band II) cm$^{-1}$; MS(ES$^-$) (m/z): 204.0 [M–H, 100%]$^-$; MS(ES$^+$) (m/z): 164.1 [M–C$_2$H$_3$O, 47%]$^+$ 206.1 [M+H, 100%]$^+$, 228.0 [M+Na, 68%]$^+$, 244.0 [M+K, 62%]$^+$.

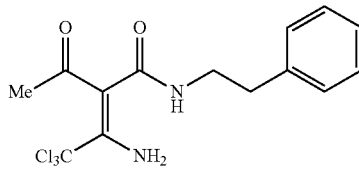

(Z)-2-Acetyl-3-amino-4,4,4-trichloro-N-phenethyl-but-2-enamide (21)

N-Phenethylacetoacetamide (1.19 g, 5.80 mmol) and trichloroacetonitrile (0.58 mL, 5.80 mmol) were added to a suspension of zinc acetylacetonate hydrate (16.3 mg, 0.06 mmol) and sodium carbonate (0.63 g, 5.92 mmol) in anhydrous DCM (10 mL). The reaction mixture was stirred at room temperature under N$_2$ for 2 h. The reaction mixture was extracted with DCM, dried over MgSO$_4$ and concentrated by evaporation in vacuo to give 1.82 g (90%) of (21) as a brown solid. mp: 89-91° C.; $^1$H NMR (300.1 MHz, CDCl$_3$): 8.58 (br s, 2H, N$\underline{H}_2$), 7.05-7.31 (m, 5H, Aryl-$\underline{H}$), 3.61 (q, J=6.5 Hz, 2H, NHC$\underline{H}_2$CH$_2$), 2.85 (t, J=6.9 Hz, 2H, NHCH$_2$C$\underline{H}_2$), 2.16 (s, 3H, CH$_3$CO); $^{13}$C NMR (100.1 MHz, CDCl$_3$): 197.7 (CH$_3$$\underline{C}$O), 167.7 (C=$\underline{C}$(NH$_2$)CCl$_3$), 156.5 (CONH), 138.4 (Ph(ipso)), 128.8 (Ph(o)), 128.7 (Ph(m)), 126.8 (Ph(p)), 104.8 ($\underline{C}$=C(NH$_2$)CCl$_3$), 93.3 (CCl$_3$), 41.4 (NH$\underline{C}$H$_2$CH$_2$), 34.7 (NHCH$_2$$\underline{C}$H$_2$), 28.3 ($\underline{C}$H$_3$CO); IR: 3293 (N—H), 1621 (C=O), 1536 (C=O), 1496 (C=C—NH$_2$) cm$^{-1}$.

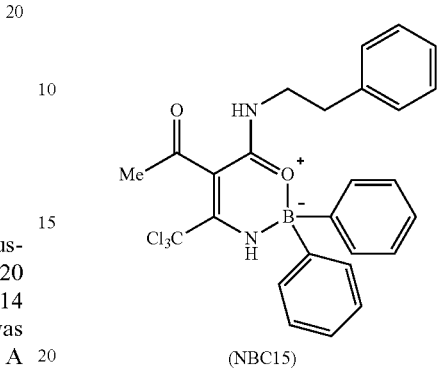

(NBC15)

(Z)-2-Acetyl-3-amino-4,4,4-trichloro-N-phenethyl-but-2-enamide Diphenylboron (22; NBC15)

(Z)-2-Acetyl-3-amino-4,4,4-trichloro-N-(phenethyl)but-2-enamide (0.81 g, 2.31 mmol) was added to DPBA (0.27 g, 0.77 mmol) suspended in anhydrous THF (10 mL). The reaction mixture was heated at 50° C. under N$_2$ for 16 h. The reaction mixture was extracted in DCM. The solution was concentrated and purified by flash column chromatography (ethyl acetate/n-hexane, 1:4) to give 70.4 mg (18%) of (22) as a yellow oil and exists as a mixture of rotamers in ~7:3 ratio. $^1$H NMR (300.1 MHz, CDCl$_3$): 7.71 (br s, 1H, C=C(N$\underline{H}$)CCl$_3$), 7.01-7.31 (m, 15H, 3×Aryl-$\underline{H}$ of major and minor rotamers), 5.38 (br s, 1H, CON$\underline{H}$ of major rotamer), 5.31 (br s, 1H, CON$\underline{H}$ of minor rotamer), 3.70 (q, 2H, NHC$\underline{H}_2$CH$_2$ of minor rotamer), 3.47 (q, J=6.5 Hz, 2H, NHCH$_2$C$\underline{H}_2$ of major rotamer), 2.86 (t, 2H, NHCH$_2$CH$_2$ of minor rotamer), 2.72 (t, J=6.9 Hz, 2H, NHCH$_2$C$\underline{H}_2$ of major rotamer), 2.17 (s, 3H, CH$_3$CO), 1.99 (s, 3H, CH$_3$C(OH) of enol form); $^{13}$C NMR (100.1 MHz, CDCl$_3$): 187.2 (CH$_3$$\underline{C}$O), 164.8 (C=$\underline{C}$(NH$_2$)CCl$_3$), 162.1 (CONH), 138.2 (Ph (ipso)), 131.7 (B-Ph(o)), 128.8 (Ph(m)), 128.6 (Ph(o)), 127.6 (B-Ph(m)), 127.2 (Ph(m)), 127.0 (B-Ph(p)), 105.6 ($\underline{C}$=C(NH$_2$)CCl$_3$), 92.7 (CCl$_3$), 41.3 (NH$\underline{C}$H$_2$CH$_2$), 34.7 (NHCH$_2$$\underline{C}$H$_2$), 23.2 ($\underline{C}$H$_3$CO), B-Ph quaternary signal not observed; IR: 3341 (N—H), 1649 (C=O), 1594 (C=C, conjugated), 1519 (C=C—NH) cm$^{-1}$; MS(ES$^-$) (m/z): 510.1 [M–H, $^{10}$B, $^{35}$Cl, $^{35}$Cl, $^{35}$Cl, 6%]$^-$, 511.1 [M–H, $^{11}$B, $^{35}$Cl, $^{35}$Cl, $^{35}$Cl, 33%]$^-$, 512.2 [M–H, $^{10}$B, $^{35}$Cl, $^{35}$Cl, $^{37}$Cl, 13%]$^-$, 513.2 [M–H, $^{11}$B, $^{35}$Cl, $^{35}$Cl, $^{37}$Cl, 32%]$^-$, 514.1 [M–H, $^{10}$B, $^{35}$Cl, $^{37}$Cl, $^{37}$Cl, 7%]$^-$, 515.1 [M–H, $^{11}$B, $^{37}$Cl, $^{37}$Cl, 11%]$^-$, 516.1 [M–H, $^{10}$B, $^{37}$Cl, $^{37}$Cl, $^{37}$Cl, 2%]$^-$, 517.1 [M–H, $^{11}$B, $^{37}$Cl, $^{37}$Cl, $^{37}$Cl, 1%]$^-$; MS(ES$^+$) (m/z): 512.2 [M+H, $^{10}$B, $^{35}$Cl, $^{35}$Cl, $^{35}$Cl, 14%]$^+$, 513.1 [M+H, $^{11}$B, $^{35}$Cl, $^{35}$Cl, $^{35}$Cl, 68%]$^+$, 514.1 [M+H, $^{10}$B, $^{35}$Cl, $^{35}$Cl, $^{37}$Cl, 31%]$^+$, 515.1 [M+H, $^{11}$B, $^{35}$Cl, $^{35}$Cl, $^{37}$Cl, 74%]$^+$, 516.1 [M+H, $^{10}$B, $^{37}$Cl, $^{37}$C, $^{35}$Cl, 30%]$^+$, 517.1 [M+H, $^{11}$B, $^{35}$Cl, $^{37}$Cl, $^{37}$Cl, 22%]$^+$, 518.1 [M+H, $^{10}$B, $^{37}$Cl, $^{37}$Cl, $^{37}$Cl, 13%]$^+$, 519.1 [M+H, $^{11}$B, $^{37}$Cl, $^{37}$Cl, $^{37}$Cl, 11%]$^+$, 534.1 [M+Na, $^{10}$B, $^{35}$Cl, $^{35}$Cl, $^{35}$Cl, 15%]$^+$, 535.1 [M+Na, $^{11}$B, $^{35}$Cl, $^{35}$Cl, $^{35}$Cl, 41%]$^+$, 536.1 [M+Na, $^{10}$B, $^{35}$Cl, $^{35}$Cl, $^{37}$Cl, 10%]$^+$, 537.1 [M+Na, $^{11}$B, $^{35}$Cl, $^{35}$Cl, $^{37}$Cl, 33%]$^+$, 538.1 [M+Na, $^{10}$B, $^{35}$Cl, $^{37}$Cl, $^{37}$Cl, 14%]$^4$, 539.1 [M+Na, $^{11}$B, $^{35}$Cl, $^{37}$Cl, $^{37}$Cl, 26%]$^+$, 540.1 [M+Na, $^{10}$B, $^{37}$Cl, $^{37}$Cl, $^{37}$Cl, 3%]+, 540.1 [M+Na, $^{11}$B, $^{37}$Cl, $^{37}$Cl, $^{37}$Cl, 2%]+; HRMS (m/z): [M+H]+ calcd. for $C_{26}H_{25}{}^{35}Cl_3N_2O_2$, 513.1075; found, 513.1073.

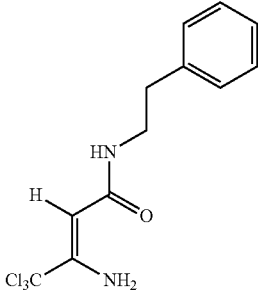

(Z)-3-Amino-4,4,4-trichloro-N-phenethylbut-2-enamide (23)

N-Phenethylacetoacetamide (0.55 g, 2.67 mmol) and trichloroacetonitrile (0.27 mL, 2.67 mmol) were added to a suspension of zinc acetylacetonate hydrate (7.5 mg, 0.03 mmol) and sodium carbonate (0.29 g, 2.73 mmol) in anhydrous DCM (10 mL). The reaction mixture was stirred at room temperature under $N_2$ for 2 h. The reaction mixture was extracted with DCM, dried over $MgSO_4$ and purified by flash column chromatography (ethyl acetate/n-hexane, 1:3) to give 0.40 g (49%) of (23) as a brown oil. $^1$H NMR (300.1 MHz, CDCl$_3$): 7.08-7.33 (m, 5H, Aryl-H), 6.61 (br s, 2H, NH$_2$), 5.41 (br s, 1H, NHCH$_2$CH$_2$), 5.21 (s, 1H, C=CH), 3.50 (q, J=6.6 Hz, 2H, NHCH$_2$CH$_2$), 2.77 (t, J=6.9 Hz, 2H, NHCH$_2$CH$_2$); $^{13}$C NMR (100.1 MHz, CDCl$_3$): 168.4 (C=C(NH$_2$)CCl$_3$), 155.4 (CONH), 138.9 (Ph(ipso)), 128.8 (Ph(m)), 128.7 (Ph(o)), 126.5 (Ph(p)), 94.5 (CCl$_3$), 87.8 (C=C(NH$_2$)CCl$_3$), 40.4 (NHCH$_2$CH$_2$), 35.9 (NHCH$_2$CH$_2$); MS(ES$^-$) (m/z): 306.0 [M−H, $^{35}$Cl, $^{35}$Cl, $^{35}$Cl, 100%]$^-$, 308.0 [M−H, $^{35}$Cl, $^{35}$Cl, $^{37}$Cl, 92%]$^-$, 310.0 [M−H, $^{35}$Cl, $^{37}$Cl, $^{37}$Cl, 30%]$^-$, 312.0 [M−H, $^{37}$Cl, $^{37}$Cl, $^{37}$Cl, 5%]$^-$; MS(ES$^+$) (m/z): 307.0 [M+H, $^{35}$Cl, $^{35}$Cl, $^{35}$Cl, 100%]$^+$, 309.0 [M+H, $^{35}$Cl, $^{35}$Cl, $^{37}$Cl, 95%]$^+$, 311.0 [M+H, $^{35}$Cl, $^{37}$Cl, $^{37}$Cl, 26%]$^+$, 313.0 [M+H, $^{37}$Cl, $^{37}$Cl, $^{37}$Cl, 2%]$^+$, 329.0 [M+Na, $^{35}$Cl, $^{35}$Cl, $^{35}$Cl, 84%]$^+$, 331.0 [M+Na, $^{35}$Cl, $^{35}$Cl, $^{37}$Cl, 69%]$^+$, 333.0 [M+Na, $^{35}$Cl, $^{37}$Cl, $^{37}$Cl, 25%]$^+$, 335.0 [M+Na, $^{37}$Cl, $^{37}$Cl, $^{37}$Cl, 4%]$^+$, 345.0 [M+K, $^{35}$Cl, $^{35}$Cl, $^{35}$Cl, 11%]$^-$, 347.0 [M+K, $^{35}$Cl, $^{35}$Cl, $^{37}$Cl, 13%]$^+$, 349.0 [M+K, $^{35}$Cl, $^{37}$Cl, $^{37}$Cl, 10%]$^+$, 351.0 [M+K, $^{37}$Cl, $^{37}$Cl, $^{37}$Cl, 3%]$^+$.

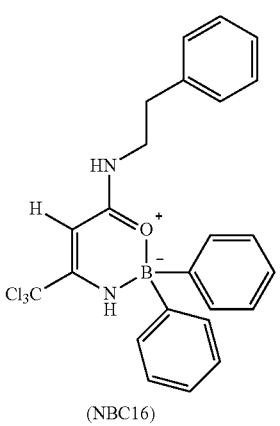

(Z)-3-Amino-4,4,4-trichloro-N-phenethylbut-2-enamide Diphenyl Boron (24; NBC16)

(Z)-3-Amino-4,4,4-trichloro-N-(phenethyl)but-2-enamide (0.36 g, 1.15 mmol) was added to DPBA (0.13 g, 0.38 mmol) suspended in anhydrous THF (4 mL). The reaction mixture was heated at 50° C. under $N_2$ for 16 h. The reaction mixture was extracted in DCM. The solution was concentrated and purified by flash column chromatography (ethyl acetate/n-hexane, 1:4) to give 32.1 mg (18%) of (24) as a yellow solid. mp: 106-108° C., exists as a mixture of rotamers in ~3:1 ratio. $^1$H NMR (300.1 MHz, CDCl$_3$): 7.05-7.41 (m, 15H, 3×Aryl-H of major and minor rotamers), 6.36 (br s, 1H, C=C(NH)CCl$_3$ of minor rotamer), 5.95 (br s, 1H, C=C(NH)CCl$_3$ of major rotamer), 5.47 (br s, 1H, CONH of minor rotamer), 5.32 (br s, 1H, CONH of major rotamer), 5.14 (s, 1H, CH=C(NH)CCl$_3$ of minor rotamer), 5.06 (d, J=1.8 Hz, 1H, CH=C(NH)CCl$_3$ of major rotamer), 3.67 (q, J=6.6 Hz, 2H, NHCH$_2$CH$_2$ of major rotamer), 3.42 (q, 2H, NHCH$_2$CH$_2$ of minor rotamer), 2.83 (t, J=6.8 Hz, 2H, NHCH$_2$CH$_2$); $^{13}$C NMR (100.1 MHz, CDCl$_3$): 169.3 (CONH), 162.9 (C=C(NH$_2$)CCl$_3$), 137.8 (Ph(ipso)), 131.8 (B-Ph(o)), 128.9 (Ph(m)), 128.8 (Ph(o)), 127.3 (B-Ph(m)), 126.5 (Ph(p)), 126.3 (B-Ph(p)), 94.5 (CCl$_3$), 42.2 (NHCH$_2$CH$_2$), 35.8 (NHCH$_2$CH$_2$), B-Ph quaternary signal and C=C(NH$_2$)CCl$_3$ signal not observed; IR: 3367 (N—H), 1580 (C=C, conjugated), 1509 (C=C—NH) cm$^{-1}$; MS(ES$^-$) (m/z): 468.1 [M−H, $^{10}$B, $^{35}$Cl, $^{35}$Cl, $^{35}$C, 14%]$^-$, 469.1 [M−H, $^{11}$B, $^{35}$Cl, $^{35}$Cl, $^{35}$Cl, 100%]$^-$, 470.1 [M−H, $^{10}$B, $^{35}$Cl, $^{35}$Cl, $^{37}$Cl, 48%]$^-$, 471.2 [M−H, $^{11}$B, $^{35}$Cl, $^{35}$Cl, $^{37}$Cl, 77%], 472.1 [M−H, $^{10}$B, $^{35}$Cl, $^{37}$Cl, $^{37}$Cl, 31%]$^-$, 473.2 [M−H, $^{11}$B, $^{35}$Cl, $^{37}$Cl, $^{37}$Cl, 24%]$^-$, 474.0 [M−H, $^{10}$B, $^{37}$Cl, $^{37}$Cl, $^{37}$Cl, 5%]$^-$, 475.2 [M−H, $^{11}$B, $^{37}$Cl, $^{37}$Cl, $^{37}$Cl, 3%]$^-$; MS(ES$^+$) (m/z): 392.1 [M−Ph, $^{10}$B, $^{35}$Cl, $^{35}$Cl, $^{35}$Cl, 13%]$^+$, 393.1 [M−Ph, $^{11}$B, $^{35}$Cl, $^{35}$Cl, $^{35}$Cl, 40%]$^+$, 394.1 [M−Ph, $^{10}$B, $^{35}$Cl, $^{35}$Cl, $^{37}$Cl, 30%]$^+$, 395.0 [M−Ph, $^{11}$B, $^{35}$Cl, $^{35}$Cl, $^{37}$Cl, 59%]$^+$, 396.1 [M−Ph, $^{10}$B, $^{35}$Cl, $^{37}$Cl, $^{37}$Cl, 12%]$^+$, 397.1 [M−Ph, $^{11}$B, $^{35}$Cl, $^{37}$Cl, $^{37}$Cl, 15%]$^+$, 398.1 [M−Ph, $^{10}$B, $^{37}$Cl, $^{37}$Cl, $^{37}$Cl, 5%]$^+$, 399.1 [M−Ph, $^{11}$B, $^{37}$Cl, $^{37}$Cl, $^{37}$Cl, 11%]$^+$, 470.1 [M+H, $^{10}$B, $^{35}$Cl, $^{35}$Cl, $^{35}$Cl, 22%]$^+$, 471.1 [M+H, $^{11}$B, $^{35}$Cl, $^{35}$Cl, $^{35}$Cl, 100%]$^+$, 472.1 [M+H, $^{10}$B, $^{35}$Cl, $^{35}$Cl, $^{37}$Cl, 36%]$^+$, 473.1 [M+H, $^{11}$B, $^{35}$Cl, $^{35}$Cl, $^{37}$Cl, 98%]$^+$, 474.1 [M+H, $^{10}$B, $^{35}$Cl, $^{37}$Cl, $^{35}$Cl, 37%]$^+$, 475.2 [M+H, $^{11}$B, $^{35}$Cl, $^{37}$Cl, $^{37}$Cl, 28%]$^+$, 476.2 [M+H, $^{10}$B, $^{37}$Cl, $^{37}$Cl, $^{37}$Cl, 12%]$^+$, 477.2 [M+H, $^{11}$B, $^{37}$Cl, $^{37}$Cl, $^{37}$Cl, 4%]$^+$, 492.1 [M+Na, $^{10}$B, $^{35}$Cl, $^{35}$Cl, $^{35}$Cl, 3%]$^+$, 493.1 [M+Na, $^{11}$B, $^{35}$Cl, $^{35}$Cl, $^{35}$Cl, 22%]$^+$, 494.1 [M+Na, $^{10}$B, $^{35}$Cl, $^{35}$Cl, $^{37}$Cl, 4%]$^+$, 495.2 [M+Na, $^{11}$B, $^{35}$Cl, $^{35}$Cl, $^{37}$Cl, 10%]$^+$, 496.2 [M+Na, $^{10}$B, $^{35}$Cl, $^{37}$Cl, $^{37}$Cl, 7%]$^+$, 497.2 [M+Na, $^{11}$B, $^{35}$Cl, $^{37}$Cl, $^{37}$Cl, 5%]$^+$, 498.2 [M+Na, $^{10}$B, $^{37}$Cl, $^{37}$Cl, $^{37}$Cl, 3%]$^+$, 499.2 [M+Na, $^{11}$B, $^{37}$Cl, $^{37}$Cl, $^{37}$Cl, 2%]$^+$, 508.1 [M+K, $^{10}$B, $^{35}$Cl, $^{35}$Cl, $^{35}$Cl, 3%]$^+$, 509.1 [M+K, $^{11}$B, $^{35}$Cl, $^{35}$Cl, $^{35}$Cl, 20%]$^+$, 510.1 [M+K, $^{10}$B, $^{35}$Cl, $^{35}$Cl, $^{37}$Cl, 4%]$^+$, 511.2 [M+K, $^{11}$B, $^{35}$Cl, $^{35}$Cl, $^{37}$Cl, 13%]$^+$, 512.2 [M+K, $^{10}$B, $^{35}$Cl, $^{37}$Cl, $^{37}$Cl, 5%]$^+$, 513.2 [M+K, $^{11}$B, $^{35}$Cl, $^{37}$Cl, $^{37}$Cl, 8%]$^+$, 514.2 [M+K, $^{10}$B, $^{37}$Cl, $^{37}$Cl, $^{37}$Cl, 3%]$^-$, 515.2 [M+K, $^{11}$B, $^{37}$Cl, $^{37}$Cl, $^{37}$Cl, 4%]$^+$. HRMS (m/z): [M−H]$^-$ calcd. for $C_{24}H_{21}{}^{11}B^{35}Cl_3N_2O$, 469.0817; found, 469.0830.

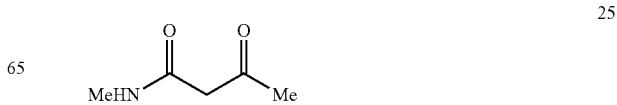

N-Methylacetoacetamide (25)

tert-Butyl acetoacetate (1.49 mL, 9.00 mmol) was suspended in toluene (150 mL). Methylamine (0.78 mL, 22.50 mmol) was added. The mixture was heated at 150° C. for 14 h using Dean Stark apparatus. The reaction mixture was dissolved in Et$_2$O and washed with 1N HCl (2×10 mL). The aqueous layer was basified with aqueous NaOH 50% (w/v). Once neutralised (pH=7-8), the aqueous layer was extracted with EtOAc and combined with the filtrate from the organic phase. The extract was dried over MgSO$_4$ and concentrated in vacuo to give 0.90 g (88%) of (25) as a dark orange oil. $^1$H NMR (300.1 MHz, CDCl$_3$): 7.09 (br s, 1H, N$\underline{H}$), 3.40 (s, 2H, CH$_3$COC$\underline{H}_2$), 2.80 (d, J=4.5 Hz, 3H, C$\underline{H}_3$NH), 2.24 (s, 3H, CH$_3$CO); $^{13}$C NMR (100.1 MHz, CDCl$_3$): 204.6 (CH$_3$$\underline{C}$O), 166.2 (CONH), 49.6 (CH$_3$CO$\underline{C}$H$_2$), 30.9 ($\underline{C}$H$_3$CO), 27.9 (CH$_3$NH, minor rotamer), 26.2 (CH$_3$NH, major rotamer); IR: 3305 (N—H), 1715 (C=O, ketone), 1641 (C=O, amide band I), 1556 (C=O, amide band II) cm$^{-1}$; MS(ES$^+$) (m/z): 116.0 [M+H, 59%]$^+$, 138.0 [M+Na, 81%]$^+$.

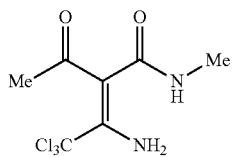

26

(Z)-2-Acetyl-3-amino-4,4,4-trichloro-N-methylbut-2-enamide (26)

N-Methylacetoacetamide (0.29 g, 2.50 mmol) and trichloroacetonitrile (0.25 mL, 2.50 mmol) were added to a suspension of zinc acetylacetonate hydrate (7.1 mg, 0.03 mmol) and sodium carbonate (0.27 g, 2.55 mmol) in anhydrous DCM (10 mL). The reaction mixture was stirred at room temperature under N$_2$ for 3 h. The reaction mixture was extracted with DCM, dried over MgSO$_4$ and concentrated by evaporation in vacuo to give 0.40 g (62%) of (26) as a brown solid. mp: 92-94° C.; $^1$H NMR (300.1 MHz, CDCl$_3$): 8.65 (br s, 2H, N$\underline{H}_2$), 6.06 (br s, 1H, CONH), 2.85 (d, J=4.8 Hz, CH$_3$NH), 2.23 (s, 3H, CH$_3$CO); $^{13}$C NMR (100.1 MHz, CDCl$_3$): 196.7 ($\underline{C}$H$_3$CO), 167.4 (C=$\underline{C}$(NH$_2$)CCl$_3$), 155.7 (CONH), 103.7 ($\underline{C}$=C(NH$_2$)CCl$_3$), 92.4 (CCl$_3$), 27.4 ($\underline{C}$H$_3$CO), 26.3 (CH$_3$NH); IR: 3276 (N—H), 1646 (C=O), 1637 (C=O), 1558 (C=O) cm$^{-1}$; MS(ES$^-$) (m/z): 257.0 [M-H, $^{35}$Cl, $^{35}$Cl, $^{35}$Cl, 78%]$^-$, 258.9 [M-H, $^{35}$Cl, $^{35}$Cl, $^{37}$Cl, 100%]$^-$, 261.0 [M-H, $^{35}$Cl, $^{37}$Cl, $^{37}$Cl, 28%]$^-$, 263.0 [M-H, $^{37}$Cl, $^{37}$Cl, $^{37}$Cl, 3%]$^-$, 292.9 [M+$^{35}$Cl, $^{35}$Cl, $^{35}$Cl, $^{35}$Cl, 24%]$^-$, 295.0 [M+$^{35}$Cl, $^{35}$Cl, $^{35}$Cl, $^{37}$Cl, 22%]$^-$, 297.0 [M+$^{35}$Cl, $^{35}$Cl, $^{37}$Cl, $^{37}$Cl, 11%]$^-$, 209.0 [M+$^{35}$Cl, $^{37}$Cl, $^{37}$Cl, $^{37}$Cl, 3%]$^-$; MS(ES$^+$) (m/z): 217.0 [M-C$_2$H$_3$O, 33%]$^+$, 259.0 [M+H, $^{35}$Cl, $^{35}$Cl, $^{35}$Cl, 51%]$^+$, 261.0 [M+H, $^{35}$Cl, $^{35}$Cl, $^{37}$Cl, 38%]$^+$, 263.0 [M+H, $^{35}$Cl, $^{37}$Cl, $^{37}$Cl, 17%]$^+$, 265.0 [M+H, $^{37}$Cl, $^{37}$Cl, $^{37}$Cl, 2%]$^+$, 281.0 [M+Na, $^{35}$Cl, $^{35}$Cl, $^{35}$Cl, 70%]$^+$, 283.0 [M+Na, $^{35}$Cl, $^{35}$Cl, $^{37}$Cl, 80%]$^+$, 285.0 [M+Na, $^{35}$Cl, $^{37}$Cl, $^{37}$Cl, 34%]$^+$, 287.0 [M+Na, $^{37}$Cl, $^{37}$Cl, $^{37}$Cl, 4%]$^+$.

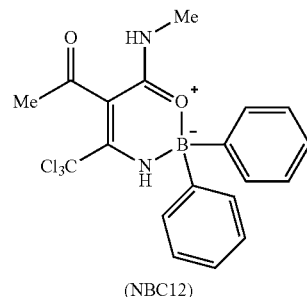

27

(Z)-2-Acetyl-3-amino-4,4,4-trichloro-N-methylbut-2-enamide Diphenylboron (27; NBC12)

(Z)-2-Acetyl-3-amino-4,4,4-trichloro-N-(methyl)but-2-enamide (0.40 g, 1.54 mmol) was added to DPBA (0.18 g, 0.51 mmol) suspended in anhydrous THF (4 mL). The reaction mixture was heated at 50° C. under N$_2$ for 16 h. The reaction mixture was extracted in DCM. The solution was concentrated and purified by flash column chromatography (ethyl acetate/n-hexane, 3:7). n-Hexane (15 mL) was added and stirred for 30 min to induce precipitation and filtered to give 8.0 mg (4%) of (27) as a yellow solid. $^1$H NMR (300.1 MHz, CDCl$_3$): δ 7.85 (br s, 1H, Cl$_3$C(N$\underline{H}$)C=C), 7.24-7.44 (m, 10H, B-Ph), 2.84 (d, J=5.1 Hz, 3H, CH$_3$NH), 2.39 (s, 3H, C$\underline{H}_3$CO); $^{13}$C NMR (100.6 MHz, CDCl$_3$): δ 187.4 (CH$_3$$\underline{C}$O), 165.3 (Cl$_3$C(NH)$\underline{C}$=C), 162.2 (CONH), 131.7 (B-Ph (o)), 127.5 (B-Ph(m)), 127.0 (B-Ph(p)), 105.4 (Cl$_3$C(NH)C=$\underline{C}$), 92.9 (CCl$_3$), 27.1 (CH$_3$NH), 23.3 ($\underline{C}$H$_3$CO), B-Ph quaternary signal not observed; IR: 3313 (N—H), 1638 (C=O), 1593 (C=C, conjugated), 1524 (C=C—NH) cm$^{-1}$; MS(ES$^-$) (m/z): 420.0 [M-H, $^{10}$B, $^{35}$Cl, $^{35}$Cl, $^{35}$Cl, 23%]$^-$, 421.0 [M-H, $^{11}$B, $^{35}$Cl, $^{35}$Cl, $^{35}$Cl, 100%]$^-$, 422.0 [M-H, $^{10}$B, $^{35}$Cl, $^{35}$Cl, $^{37}$Cl, 38%]$^-$, 423.0 [M-H, $^{11}$B, $^{35}$Cl, $^{35}$Cl, $^{37}$Cl, 93%]$^-$, 424.0 [M-H, $^{10}$B, $^{35}$Cl, $^{37}$Cl, $^{37}$Cl, 25%]$^-$, 425.0 [M-H, $^{11}$B, $^{35}$Cl, $^{37}$Cl, $^{37}$Cl, 27%]$^-$, 426.0 [M-H, $^{10}$B, $^{37}$Cl, $^{37}$Cl, $^{37}$Cl, 4%]$^-$, 427.0 [M-H, $^{11}$B, $^{37}$Cl, $^{37}$Cl, 2%]$^-$; MS(ES$^+$) (m/z): 344.0 [M-Ph, $^{10}$B, $^{35}$Cl, $^{35}$Cl, $^{35}$Cl, 5%]$^+$, 345.0 [M-Ph, $^{11}$B, $^{35}$Cl, $^{35}$Cl, $^{35}$Cl, 43%]$^+$, 346.0 [M-Ph, $^{10}$B, $^{35}$Cl, $^{35}$Cl, $^{37}$Cl, 11%]$^+$, 347.0 [M-Ph, $^{11}$B, $^{35}$Cl, $^{35}$Cl, $^{37}$Cl, 40%]$^+$, 348.0 [M-Ph, $^{10}$B, $^{35}$Cl, $^{37}$Cl, $^{37}$Cl, 8%]$^+$, 349.0 [M-Ph, $^{11}$B, $^{35}$Cl, $^{37}$Cl, $^{37}$Cl, 7%]$^+$, 350.0 [M-Ph, $^{10}$B, $^{37}$Cl, $^{37}$Cl, $^{37}$Cl, 3%]$^+$, 351.0 [M-Ph, $^{11}$B, $^{37}$Cl, $^{37}$Cl, $^{37}$Cl, 6%]$^+$, 422.1 [M+H, $^{10}$B, $^{35}$Cl, $^{35}$Cl, $^{35}$Cl, 35%]$^+$, 423.1 [M+H, $^{11}$B, $^{35}$Cl, $^{35}$Cl, $^{35}$Cl, 77%]$^+$, 424.0 [M+H, $^{10}$B, $^{35}$Cl, $^{35}$Cl, $^{37}$Cl, 60%]$^+$, 425.0 [M+H, $^{11}$B, $^{35}$Cl, $^{35}$Cl, $^{37}$Cl, 100%]$^+$, 426.0 [M+H, $^{10}$B, $^{35}$Cl, $^{37}$Cl, $^{35}$Cl, 39%]$^+$, 427.0 [M+H, $^{11}$B, $^{35}$Cl, $^{37}$Cl, $^{37}$Cl, 48%]$^+$, 428.0 [M+H, $^{10}$B, $^{37}$Cl, $^{37}$Cl, $^{37}$Cl, 8%]$^+$, 429.0 [M+H, $^{11}$B, $^{37}$Cl, $^{37}$Cl, $^{37}$Cl, 7%]$^+$, 444.0 [M+Na, $^{10}$B, $^{35}$Cl, $^{35}$Cl, $^{35}$Cl, 20%]$^+$, 445.0 [M+Na, $^{11}$B, $^{35}$Cl, $^{35}$Cl, $^{35}$Cl, 53%]$^+$, 446.0 [M+Na, $^{10}$B, $^{35}$Cl, $^{35}$Cl, $^{37}$Cl, 12%]$^+$, 447.0 [M+Na, $^{11}$B, $^{35}$Cl, $^{35}$Cl, $^{37}$Cl, 49%]$^+$, 448.0 [M+Na, $^{10}$B, $^{35}$Cl, $^{37}$Cl, $^{37}$Cl, 12%]$^+$, 449.0 [M+Na, $^{11}$B, $^{35}$Cl, $^{37}$Cl, $^{37}$Cl, 14%]$^+$, 450.0 [M+Na, $^{10}$B, $^{37}$Cl, $^{37}$Cl, $^{37}$Cl, 2%]$^+$, 451.0 [M+Na, $^{11}$B, $^{37}$Cl, $^{37}$Cl, $^{37}$Cl, 3%]$^+$.

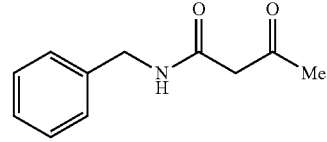

28

N-Benzylacetoacetamide (28)

tert-Butyl acetoacetate (1.49 mL, 9.00 mmol) was suspended in toluene (150 mL). Benzylamine (0.89 mL, 8.20 mmol) was added. The mixture was heated at 150° C. for 14 h using Dean Stark apparatus. The reaction mixture was dissolved in Et$_2$O and washed with 1N HCl (2×10 mL). The aqueous layers were combined and basified aqueous NaOH 50% (w/v). Once neutralised (pH=7-8), the aqueous layer was extracted with EtOAc. The extract was dried over MgSO$_4$ and concentrated in vacuo to give 1.52 g (97%) of (28) as a cream solid. mp: 85-87° C.; $^1$H NMR (300.1 MHz, CDCl$_3$): δ 7.24-7.40 (m, 5H, Aryl-H), 7.36 (br s, 1H, NH), 4.46 (d, J=5.7 Hz, 2H, NHCH$_2$) 3.45 (s, 2H, CH$_3$COCH$_2$), 2.27 (s, 3H, CH$_3$CO); $^{13}$C NMR (100.1 MHz, CDCl$_3$): 204.5 (CH$_3$CO), 165.5 (CONH), 137.9 (Ph(ipso)), 128.7 (Ph(m)), 127.7 (Ph(o)), 127.5 (Ph(p)), 49.6 (CH$_3$COCH$_2$), 43.5 (NH CH$_2$Ph), 31.0 (CH$_3$CO); IR: 3245 (N—H), 1712 (C=O, ketone), 1638 (C=O, amide band I), 1577 (C=O, amide band II) cm$^{-1}$; MS(ES$^-$) (m/z): 190.1 [M−H, 5%]$^-$; 226.1 [M+$^{35}$Cl, 100%]$^-$, 228.1 [M+$^{37}$Cl, 33%]$^-$; MS(ES$^+$) (m/z): 192.1 [M+H, 100%]$^+$214.1 [M+Na, 63%]$^+$, 228.0 [M+Na, 68%]$^+$, 244.0 [M+K, 62%]$^+$.

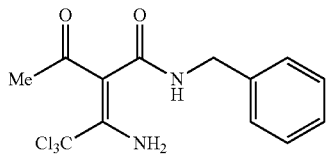

(Z)-2-Acetyl-3-amino-4,4,4-trichloro-N-benzyl but-2-enamide (29)

N-Benzylacetoacetamide (1.51 g, 7.91 mmol) and trichloroacetonitrile (0.79 mL, 7.91 mmol) were added to a suspension of zinc acetylacetonate hydrate (22.3 mg, 0.08 mmol) and sodium carbonate (0.85 g, 8.06 mmol) in anhydrous DCM (10 mL). The reaction mixture was stirred at room temperature under N$_2$ for 3 h. The reaction mixture was extracted with DCM, dried over MgSO$_4$ and concentrated by evaporation in vacuo to give 1.99 g (75%) of (29) as a cream solid. mp: 92-93° C.; $^1$H NMR (300.1 MHz, CDCl$_3$): 8.61 (br s, 2H, NH$_2$), 7.22-7.31 (m, 5H, Aryl-H), 6.12 (br s, 1H, CONH) 4.45 (d, J=5.4 Hz, 2H, NHCH$_2$), 2.24 (s, 3H, CH$_3$CO); $^{13}$C NMR (100.1 MHz, CDCl$_3$): 197.6 (CH$_3$CO), 167.3 (C=C(NH$_2$)CCl$_3$), 156.7 (CONH), 136.9 (Ph(ipso)), 128.8 (Ph(m)), 128.5 (Ph(o)), 127.9 (Ph(p)), 104.6 (C=C(NH$_2$)CCl$_3$), 93.4 (CCl$_3$), 45.1 (NHCH$_2$Ph), 28.5 (CH$_3$CO); IR: 3297 (N—H), 1619 (C=O), 1541 (C=O), 1495 (C=C—NH$_2$) cm$^{-1}$; MS(ES$^-$) (m/z): 333.1 [M−H, $^{35}$Cl, $^{35}$Cl, $^{35}$Cl, 43%]$^-$, 335.1 [M−H, $^{35}$Cl, 36Cl, $^{37}$Cl, 38%]$^-$, 337.1 [M−H, $^{35}$Cl, $^{37}$Cl, $^{37}$Cl, 11%]$^-$, 339.1 [M−H, $^{37}$Cl, $^{37}$Cl, $^{37}$Cl, 2%]$^-$, 369.1 [M+$^{35}$Cl, $^{35}$Cl, $^{35}$Cl, 351C, 89%]$^-$, 370.1 [M+$^{37}$Cl, $^{35}$Cl, $^{35}$Cl, $^{35}$Cl, 5%]$^-$, 371.1 [M+$^{35}$Cl, $^{35}$Cl, $^{35}$Cl, $^{37}$Cl, 100%]$^-$, 372.1 [M+$^{37}$Cl, $^{35}$Cl, $^{35}$Cl, $^{37}$Cl, 15%]$^-$, 373.1 [M+$^{35}$Cl, $^{35}$Cl, $^{37}$Cl, $^{37}$Cl, 47%]$^-$, 374.1 [M+$^{37}$Cl, $^{35}$Cl, $^{37}$Cl, $^{37}$Cl, 3%]$^-$, 375.1 [M+$^{35}$Cl, $^{37}$Cl, $^{37}$Cl, $^{37}$Cl, 6%]$^-$, 376.1 [M+$^{37}$Cl, $^{37}$Cl, $^{37}$Cl, $^{37}$Cl, 1%]$^-$; MS(ES$^+$) (m/z): 335.1 [M+H, $^{35}$Cl, $^{35}$Cl, $^{35}$Cl, 70%]$^+$, 337.1 [M+H, $^{35}$Cl, $^{35}$Cl, $^{37}$Cl, 98%]$^+$, 339.1 [M+H, $^{35}$Cl, $^{37}$Cl, $^{37}$Cl, 29%]$^+$, 341.1 [M+H, $^{37}$Cl, $^{37}$Cl, $^{37}$Cl, 3%]$^+$, 357.1 [M+Na, $^{35}$Cl, $^{35}$Cl, $^{35}$Cl, 30%]$^+$, 359.1 [M+Na, $^{35}$Cl, $^{35}$Cl, $^{37}$Cl, 18%]$^+$, 361.1 [M+Na, $^{35}$Cl, $^{37}$Cl, $^{37}$Cl, 4%]$^+$, 363.1 [M+Na, $^{37}$Cl, $^{37}$Cl, $^{37}$Cl, 1%]$^+$.

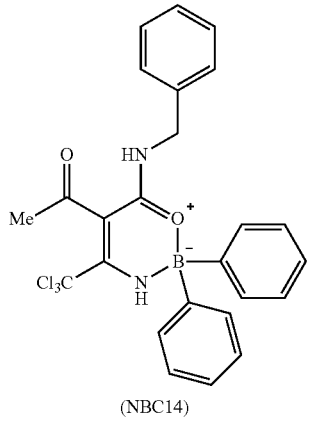

(Z)-2-Acetyl-3-amino-4,4,4-trichloro-N-benzylbut-2-enamide Diphenylboron (30; NBC14)

(Z)-2-Acetyl-3-amino-4,4,4-trichloro-N-benzylbut-2-enamide (1.13 g, 3.38 mmol) was added to DPBA (0.39 g, 1.13 mmol) suspended in anhydrous THF (4 mL). The reaction mixture was heated at 50° C. under N$_2$ for 16 h. The reaction mixture was extracted in DCM. The solution was concentrated and purified by flash column chromatography (ethyl acetate/n-hexane, 1:7). The collected fractions were combined, evaporated and stirred in cold n-hexane (15 mL) for 30 mins. The precipitate was filtered to give 68.7 mg (12%) of (30) as a yellow solid and exists as a mixture of rotamers in ~4:1 ratio. mp: 131-132° C.; $^1$H NMR (300.1 MHz, CDCl$_3$): $^1$H NMR (300.1 MHz, CDCl$_3$): 7.85 (br s, 1H, C=C(NH)CCl$_3$), 7.00-7.45 (m, 15H, 3×Aryl-H of major and minor rotamers), 5.87 (br s, 1H, CONH of minor rotamer), 5.86 (br s, 1H, CONH of major rotamer), 4.77 (d, 2H, NHCH$_2$Ph of minor rotamer), 4.43 (d, J=5.7 Hz, 2H, NHCH$_2$Ph of major rotamer), 2.36 (s, 3H, CH$_3$CO); $^{13}$C NMR (100.1 MHz, CDCl$_3$): 187.2 (CH$_3$CO), 164.5 (C=C(NH$_2$)CCl$_3$), 162.2 (CONH), 136.7 (Ph(ipso)), 131.7 (B-Ph(o)), 128.8 (Ph(m)), 128.4 (Ph(o)), 127.9 (Ph(p)), 127.5 (B-Ph(m)), 127.0 (B-Ph(p)), 105.2 (C=C(NH$_2$)CCl$_3$), 92.8 (CCl$_3$), 44.8 (NHCH$_2$Ph), 23.4 (CH$_3$CO), B-Ph quaternary signal not observed; IR: 3303 (N—H), 1631 (C=O), 1596 (C=C, conjugated), 1526 (C=C—NH) cm$^{-1}$; MS(ES$^-$) (m/z): 455.1 [M−Ac, $^{10}$B, $^{35}$Cl, $^{35}$Cl, $^{35}$Cl, 9%]$^-$, 456.2 [M−Ac, $^{11}$B, $^{35}$Cl, $^{35}$Cl, $^{35}$Cl, 74%]$^-$, 457.2 [M−Ac, $^{10}$B, $^{35}$Cl, $^{35}$Cl, $^{37}$Cl, 40%]$^-$, 458.2 [M−Ac, $^{11}$B, $^{35}$Cl, $^{35}$Cl, $^{37}$Cl, 100%]$^-$, 459.2 [M−Ac, $^{10}$B, $^{35}$Cl, $^{37}$Cl, $^{37}$Cl, 17%]$^-$, 460.2 [M−Ac, $^{11}$B, $^{35}$Cl, $^{37}$Cl, $^{37}$Cl, 18%]$^-$, 461.1 [M−Ac, $^{10}$B, $^{37}$Cl, $^{37}$Cl, $^{37}$Cl, 4%]$^-$, 462.1 [M−Ac, $^{11}$B, $^{37}$Cl, $^{37}$Cl, $^{37}$Cl, 3%]$^-$, 496.2 [M−H, $^{10}$B, $^{35}$Cl, $^{35}$Cl, $^{35}$Cl, 50%]$^-$, 497.2 [M−H, $^{11}$B, $^{35}$Cl, $^{35}$Cl, $^{35}$Cl, 73%]$^-$, 498.2 [M−H, $^{10}$B, $^{35}$Cl, $^{35}$Cl, $^{37}$Cl, 60%]$^-$, 499.2 [M−H, $^{11}$B, $^{35}$Cl, $^{35}$Cl, $^{37}$Cl, 73%]$^-$, 500.2 [M−H, $^{10}$B, $^{35}$Cl, $^{37}$Cl, $^{37}$Cl, 37%], 501.2 [M−H, $^{11}$B, $^{35}$Cl, $^{37}$, $^{37}$Cl, 18%]$^-$, 502.2 [M−H, $^{10}$B, $^{37}$Cl, $^{37}$Cl, $^{37}$Cl, 3%]$^-$, 503.2 [M−H, $^{11}$B, $^{37}$Cl, $^{37}$Cl, $^{37}$Cl, 2%]$^-$; MS(ES$^+$) (m/z): 498.1 [M+H, $^{10}$B, $^{35}$Cl, $^{35}$Cl, $^{35}$Cl, 13%]$^+$, 499.2 [M+H, $^{11}$B, $^{35}$Cl, $^{35}$Cl, $^{35}$Cl, 80%]$^+$, 500.2 [M+H, $^{10}$B, $^{35}$Cl, $^{35}$Cl, $^{37}$Cl, 35%]$^+$, 501.2 [M+H, $^{11}$B, $^{35}$Cl, $^{35}$Cl, $^{37}$Cl, 100%]$^+$, 502.2 [M+H, $^{10}$B, $^{35}$Cl, $^{37}$Cl, $^{35}$Cl, 26%]$^+$, 503.1 [M+H, $^{11}$B, $^{35}$Cl, $^{37}$Cl, $^{37}$Cl, 32%]⁺, 504.1 [M+H, $^{10}$B, $^{37}$Cl, $^{37}$Cl, $^{37}$Cl, 5%]⁺, 505.1 [M+H, $^{11}$B, $^{37}$Cl, $^{37}$Cl, $^{37}$Cl, 3%]⁺, 520.2 [M+Na, $^{10}$B, $^{35}$Cl, $^{35}$Cl, $^{35}$Cl, 18%]⁺, 521.2 [M+Na, $^{11}$B, $^{35}$Cl, $^{35}$Cl, $^{35}$Cl, 24%]⁺, 522.2 [M+Na, $^{10}$B, $^{35}$Cl, $^{35}$Cl, $^{37}$Cl, 11%]⁺, 523.1 [M+Na, $^{11}$B, $^{35}$Cl, $^{35}$Cl, $^{37}$Cl, 19%]⁺, 524.1 [M+Na, $^{10}$B, $^{35}$Cl, $^{37}$Cl, $^{37}$Cl, 6%]⁺, 525.1 [M+Na, $^{11}$B, $^{35}$Cl, $^{37}$Cl, $^{37}$Cl, 4%]⁺, 526.1 [M+Na, $^{10}$B, $^{37}$Cl, $^{37}$Cl, $^{37}$Cl, 2%]⁺, 527.1 [M+Na, $^{11}$B, $^{37}$Cl, $^{37}$Cl, $^{37}$Cl, 1%].

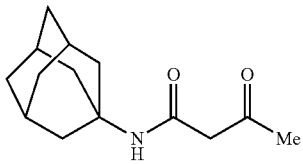

31

N-Adamantylacetoacetamide (31)

tert-Butyl acetoacetate (1.49 mL, 9.00 mmol) was suspended in toluene (150 mL). 1-Adamantylamine (1.23 g, 8.20 mmol) was added. The mixture was heated at 150° C. for 14 h using Dean Stark apparatus. The reaction mixture was dissolved in Et$_2$O (10 mL) and washed with 1N HCl (2×10 mL). The organic layer was dried over MgSO$_4$ and concentrated in vacuo. The solid obtained was filtered and washed with cold Et$_2$O to give 1.05 g (55%) of (31) as an orange solid. mp: 81-82° C.; $^1$H NMR (300.1 MHz, CDCl$_3$): δ 6.50 (br s, 1H, NH), 3.32 (s, 2H, CH$_3$COCH$_2$), 2.26 (s, 3H, CH$_3$CO), 2.07 (m, 3H, Adamantyl-H$_2$), 2.01 (m, 6H, Adamantyl-H$_3$ and Adamantyl-H$_2$), 1.68 (m, 6H, Adamantyl-H$_1$); $^{13}$C NMR (100.1 MHz, CDCl$_3$): 204.9 (CH$_3$CO), 164.2 (CONH), 52.1 (Adamantyl-C$_4$), 51.2 (CH$_3$COCH$_2$), 41.5 (Adamantyl-C$_3$), 36.3 (Adamantyl-C$_2$), 30.9 (CH$_3$CO), 29.4 (Adamantyl-C$_1$); IR: 3310 (N—H), 2903 (Adamantyl CH$_2$ stretch), 2849 (Adamantyl CH$_2$ stretch), 1721 (C═O, ketone), 1639 (C═O, amide band I), 1545 (C═O, amide band II) cm$^{-1}$; MS(ES⁻) (m/z): 270.1 [M+Cl, $^{35}$Cl, 100%]⁻, 272.2 [M+Cl, $^{37}$Cl, 48%]⁻; MS(ES⁺) (m/z): 236.1 [M+H, 100%]⁺, 471.4 [2M+H, 93%]⁺, 493.4 [2M+Na, 49%]⁺.

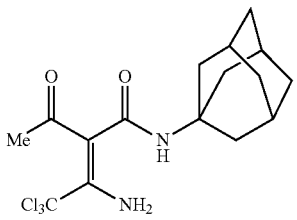

32

(Z)-2-Acetyl-3-amino-4,4,4-trichloro-N-adamantyl-but-2-enamide (32)

N-Adamantylacetoacetamide (1.05 g, 4.47 mmol) and trichloroacetonitrile (0.45 mL, 4.47 mmol) were added to a suspension of zinc acetylacetonate hydrate (12.6 mg, 0.05 mmol) and sodium carbonate (0.48 g, 4.56 mmol) in anhydrous DCM (10 mL). The reaction mixture was stirred at room temperature under N$_2$ for 3 h. The precipitate was filtered, washed with EtOAc to remove sodium carbonate and concentrated by evaporation in vacuo to give 0.69 g (41%) of (32) as a white solid. mp: 105-106° C.; $^1$H NMR (300.1 MHz, CDCl$_3$): 8.55 (br s, 2H, NH$_2$), 5.54 (br s, 1H, CONH) 2.29 (s, 3H, CH$_3$CO), 2.02 (m, 10H, Adamantyl-H), 1.91 (d, J=2.4 Hz, 1H, Adamantyl-H), 1.64 (m, 7H, Adamantyl-H); IR: 3309 (N—H), 2903 (Adamantyl CH$_2$ stretch), 2849 (Adamantyl CH$_2$ stretch), 1633 (C═O), 1617 (C═C, conjugated), 1517 (C═C—NH$_2$) cm$^{-1}$; MS(ES⁻) (m/z): 377.1 [M–H, $^{35}$Cl, $^{35}$Cl, $^{35}$Cl, 12%]⁻, 379.1 [M–H, $^{35}$Cl, $^{35}$Cl, $^{37}$Cl, 9%]⁻, 381.1 [M–H, $^{35}$Cl, $^{37}$Cl, $^{37}$Cl, 4%]⁻, 383.1 [M–H, $^{37}$Cl, $^{37}$Cl, $^{37}$Cl, 1%]⁻, 413.1 [M+$^{35}$Cl, $^{35}$Cl, $^{35}$Cl, $^{35}$Cl, 91%]⁻, 414.1 [M+$^{37}$Cl, $^{35}$Cl, $^{35}$Cl, $^{35}$Cl, 8%]⁻, 415.1 [M+$^{35}$Cl, $^{35}$Cl, $^{35}$Cl, $^{37}$Cl, 100%]⁻, 416.1 [M+$^{37}$Cl, $^{35}$Cl, $^{35}$Cl, $^{37}$Cl, 15%]⁻, 417.1 [M+$^{35}$Cl, $^{35}$Cl, $^{37}$Cl, $^{37}$Cl, 44%]⁻, 418.1 [M+$^{37}$Cl, $^{35}$Cl, $^{37}$Cl, $^{37}$Cl, 13%]⁻, 419.1 [M+$^{35}$Cl, $^{37}$Cl, $^{37}$Cl, $^{37}$Cl, 7%]⁻, 420.2 [M+$^{37}$Cl, $^{37}$Cl, $^{37}$Cl, $^{37}$Cl, 3%]⁻; MS(ES⁺) (m/z): 379.1 [M+H, $^{35}$Cl, $^{35}$Cl, $^{35}$Cl, 100%]⁺, 381.1 [M+H, $^{35}$Cl, $^{35}$Cl, $^{37}$Cl, 45%]⁺, 383.1 [M+H, $^{35}$Cl, $^{37}$Cl, $^{37}$Cl, 13%]⁺, 385.1 [M+H, $^{37}$Cl, $^{37}$Cl, $^{37}$Cl, 3%]⁺, 401.1 [M+Na, $^{35}$Cl, $^{35}$Cl, $^{35}$Cl, 81%]⁺, 403.1 [M+Na, $^{35}$Cl, $^{35}$Cl, $^{37}$Cl, 84%]⁺, 405.1 [M+Na, $^{35}$Cl, $^{37}$Cl, $^{37}$Cl, 19%]⁺, 407.1 [M+Na, $^{37}$Cl, $^{37}$Cl, $^{37}$Cl, 4%]⁺.

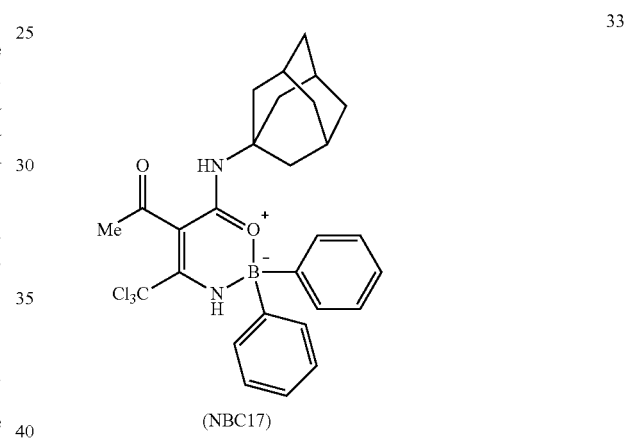

33

(NBC17)

(Z)-2-Acetyl-3-amino-4,4,4-trichloro-N-adamantyl but-2-enamide Diphenylboron (33; NBC17)

(Z)-2-Acetyl-3-amino-4,4,4-trichloro-N-adamantylbut-2-enamide (0.44 g, 1.15 mmol) was added to DPBA (0.26 g, 0.77 mmol) suspended in anhydrous THF (5 mL). The reaction mixture was heated at 50° C. under N$_2$ for 16 h. The reaction mixture was extracted in DCM. The solution was concentrated and purified by flash column chromatography (ethyl acetate/n-hexane, 1:19). The collected fractions were combined, evaporated and stirred in cold n-hexane (15 mL) for 30 mins. The precipitate was filtered to give to 0.14 g (33%) of (33) as a yellow solid. mp: 115-116° C.; $^1$H NMR (300.1 MHz, CDCl$_3$): 7.73 (br s, 1H, C═C(NH)CCl$_3$), 7.12-7.33 (m, 10H, Aryl-H), 5.08 (br s, 1H, CONH), 2.29 (s, 3H, CH$_3$CO), 1.99 (m, 3H, Adamantyl-H), 1.87 (m, 6H, Adamantyl-H), 1.59 (m, 6H, Adamantyl-H); IR: 3318 (N—H), 2909 (Adamantyl CH$_2$ stretch), 2851 (Adamantyl CH$_2$ stretch), 1638 (C═O), 1603 (C═C, conjugated), 1526 (C═C—NH) cm$^{-1}$; MS(ES⁻) (m/z): 540.2 [M–H, $^{10}$B, $^{35}$Cl, $^{35}$Cl, $^{35}$Cl, 10%]⁻, 541.2 [M–H, $^{11}$B, $^{35}$Cl, $^{35}$Cl, $^{35}$Cl, 100%]⁻, 542.2 [M–H, $^{10}$B, $^{35}$Cl, $^{35}$Cl, $^{37}$Cl, 45%]⁻, 543.2 [M–H, $^{11}$B, $^{35}$Cl, $^{35}$Cl, $^{37}$Cl, 64%]⁻, 544.2 [M–H, $^{10}$B, $^{35}$Cl, $^{37}$Cl, $^{37}$Cl, 23%]⁻, 545.2 [M–H, $^{11}$B, $^{35}$Cl, $^{37}$Cl, $^{37}$Cl, 33%]⁻, 546.2 [M–H, $^{10}$B, $^{37}$Cl, $^{37}$Cl, $^{37}$Cl, 3%]⁻, 547.2

[M−H, $^{11}$B, $^{37}$Cl, $^{37}$Cl, $^{37}$Cl, 2%]$^−$; MS(ES$^+$) (m/z): 542.2 [M+H, $^{10}$B, $^{35}$Cl, $^{35}$Cl, $^{35}$Cl, 22%]$^+$, 543.2 [M+H, $^{11}$B, $^{35}$Cl, $^{35}$Cl, $^{35}$Cl, 100%]$^+$, 544.2 [M+H, $^{10}$B, $^{35}$Cl, $^{35}$Cl, $^{37}$Cl, 39%]$^+$, 545.2 [M+H, $^{11}$B, $^{35}$Cl, $^{35}$Cl, $^{37}$Cl, 70%]$^+$, 546.2 [M+H, $^{10}$B, $^{35}$Cl, $^{37}$Cl, $^{37}$Cl, 35%]$^+$, 547.2 [M+H, $^{11}$B, $^{35}$Cl, $^{37}$Cl, $^{37}$Cl, 24%]$^+$, 548.2 [M+H, $^{10}$B, $^{37}$Cl, $^{37}$Cl, $^{37}$Cl, 11%]$^+$, 549.2 [M+H, $^{11}$B, $^{37}$Cl, $^{37}$Cl, $^{37}$Cl, 2%]$^+$, 534.1 [M+Na, $^{10}$B, $^{35}$Cl, $^{35}$Cl, $^{35}$Cl, 15%]$^+$, 535.1 [M+Na, $^{11}$B, $^{35}$Cl, $^{35}$Cl, $^{35}$Cl, 41%]$^+$, 536.1 [M+Na, $^{10}$B, $^{35}$Cl, $^{35}$Cl, $^{37}$Cl, 10%]$^+$, 537.1 [M+Na, $^{11}$B, $^{35}$Cl, $^{35}$Cl, $^{37}$Cl, 33%]$^+$, 538.1 [M+Na, $^{10}$B, $^{35}$Cl, $^{37}$Cl, $^{37}$Cl, 14%]$^+$, 539.1 [M+Na, $^{11}$B, $^{35}$Cl, $^{37}$Cl, $^{37}$Cl, 26%]$^+$, 540.1 [M+Na, $^{10}$B, $^{37}$Cl, $^{37}$Cl, $^{37}$Cl, 3%]$^+$, 540.1 [M+Na, $^{11}$B, $^{37}$Cl, $^{37}$Cl, $^{37}$Cl, 2%]$^+$.

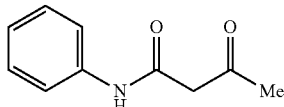

N-Phenylacetoacetamide (34)

tert-Butyl acetoacetate (1.49 mL, 9.00 mmol) was suspended in toluene (150 mL). Aniline (0.74 mL, 8.20 mmol) was added. The mixture was heated at 150° C. for 14 h using Dean Stark apparatus. The reaction mixture was dissolved in Et$_2$O (20 mL) and washed with 1N HCl (2×10 mL). The aqueous layers were combined and basified aqueous NaOH 50% (w/v). Once neutralised (pH=7-8), the aqueous layer was extracted with EtOAc. The extract was dried over MgSO$_4$ and concentrated in vacuo affording a pure solid. The organic layer was also dried over MgSO$_4$ and concentrated in vacuo to recover product. The solid obtained from the organic phase was filtered, washed with cold Et$_2$O and combined with the solid obtained from the water phase to give 0.82 g (56%) of (34) as an orange solid. mp: 81-83° C.; $^1$H NMR (300.1 MHz, CDCl$_3$): δ 9.13 (br s, 1H, NH), 7.56 (d, J=8.1 Hz, 2H, Ph(o)), 7.34 (t, J=7.8 Hz, 2H, Ph(m)), 7.14 (t, J=7.4 Hz, 1H, Ph(p)), 3.61 (s, 2H, CH$_3$COCH$_2$), 2.34 (s, 3H, CH$_3$CO); $^{13}$C NMR (100.1 MHz, CDCl$_3$): 205.2 (CH$_3$CO), 163.3 (CONH), 137.5 (Ph(ipso)), 129.0 (Ph(m)), 124.6 (Ph(p)), 120.2 (Ph(o)), 49.7 (CH$_3$COCH$_2$), 31.3 (CH$_3$CO); IR: 3253 (N—H), 1710 (C=O, ketone), 1659 (C=O, amide band I), 1598 (C=O, amide band II) cm$^{−1}$; MS(ES$^−$) (m/z): 204.0 [M−H, 100%]$^−$; MS(ES$^+$) (m/z): 164.1 [M−C$_2$H$_3$O, 47%]$^+$ 206.1 [M+H, 100%]$^+$, 228.0 [M+Na, 68%]$^+$, 244.0 [M+K, 62%]$^+$.

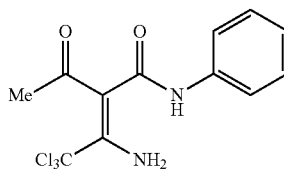

(Z)-2-Acetyl-3-amino-4,4,4-trichloro-N-phenylbut-2-enamide (35)

N-Phenylacetoacetamide (0.82 g, 4.61 mmol) and trichloroacetonitrile (0.46 mL, 4.61 mmol) were added to a suspension of zinc acetylacetonate hydrate (13.0 mg, 0.05 mmol) and sodium carbonate (0.50 g, 4.71 mmol) in anhydrous DCM (10 mL). The reaction mixture was stirred at room temperature under N$_2$ for 3 h. The precipitate was filtered, washed with EtOAc to remove sodium carbonate and concentrated by evaporation in vacuo to give 0.62 g (42%) of (35) as a cream solid. mp: 105-107° C.; $^1$H NMR (300.1 MHz, CDCl$_3$): 8.73 (br s, 2H, NH$_2$), 7.72 (br s, 1H, CONH), 7.50 (d, J=8.1 Hz, 2H, Ph(o)), 7.30 (t, J=7.8 Hz, 2H, Ph(m)), 7.10 (t, J=7.4 Hz, 1H, Ph(p)), 2.32 (s, 3H, CH$_3$CO); $^{13}$C NMR (100.1 MHz, CDCl$_3$): 197.6 (CH$_3$CO), 165.5 (C=C(NH$_2$)CCl$_3$), 157.0 (CONH), 137.8 (Ph(ipso)), 129.2 (Ph(m)), 125.0 (Ph(p)), 119.9 (Ph(o)), 105.4 (C=C(NH$_2$)CCl$_3$), 93.4 (CCl$_3$), 28.6 (CH$_3$CO); IR: 3267 (N—H), 1647 (C=O), 1617 (C=O), 1595 (C=C, conjugated), 1528 (C=C—NH$_2$) cm$^{−1}$; MS(ES$^−$) (m/z): 319.0 [M−H, $^{35}$Cl, $^{35}$Cl, $^{35}$Cl, 100%]$^−$, 321.0 [M−H, $^{35}$Cl, $^{35}$Cl, $^{37}$Cl, 65%]$^−$, 323.0 [M−H, $^{35}$Cl, $^{37}$Cl, $^{37}$Cl, 30%]$^−$, 325.0 [M−H, $^{37}$Cl, $^{37}$Cl, $^{37}$Cl, 3%]$^−$; MS(ES$^+$) (m/z): 227.9 [M−C$_6$H$_6$N, $^{35}$Cl, $^{35}$Cl, $^{35}$Cl, 61%]$^+$, 229.9 [M−C$_6$H$_6$N, $^{35}$Cl, $^{35}$Cl, $^{37}$Cl, 47%]$^+$, 231.9 [M−C$_6$H$_6$N, $^{35}$Cl, $^{37}$Cl, $^{37}$Cl, 12%]$^+$, 233.0 [M−C$_6$H$_6$N, $^{37}$Cl, $^{37}$Cl, $^{37}$Cl, 5%]$^+$, 279.1 [M−C$_2$H$_3$O, $^{35}$Cl, $^{35}$Cl, $^{35}$Cl, 34%]$^+$, 281.0 [M−C$_2$H$_3$O, $^{35}$Cl, $^{35}$Cl, $^{37}$Cl, 4%]$^+$, 283.0 [M−C$_2$H$_3$O, $^{35}$Cl, $^{37}$Cl, $^{37}$Cl, 3%]$^+$, 285.0 [M−C$_2$H$_3$O, $^{37}$Cl, $^{37}$Cl, $^{37}$Cl, 2%]$^+$, 321.0 [M+H, $^{35}$Cl, $^{35}$Cl, $^{35}$Cl, 100%]$^+$, 323.0 [M+H, $^{35}$Cl, $^{35}$Cl, $^{37}$Cl, 72%]$^+$, 325.0 [M+H, $^{35}$Cl, $^{37}$Cl, $^{37}$Cl, 18%]$^+$, 327.0 [M+H, $^{37}$Cl, $^{37}$Cl, $^{37}$Cl, 2%]$^+$, 343.0 [M+Na, $^{35}$Cl, $^{35}$Cl, $^{35}$Cl, 24%]$^+$, 345.0 [M+Na, $^{35}$Cl, $^{35}$Cl, $^{37}$Cl, 15%]$^+$, 347.0 [M+Na, $^{35}$Cl, $^{37}$Cl, $^{37}$Cl, 4%]$^+$, 349.0 [M+Na, $^{37}$Cl, $^{37}$Cl, $^{37}$Cl, 2%]$^+$.

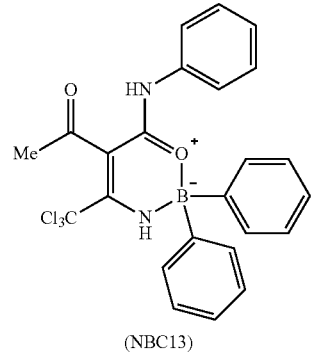

(NBC13)

(Z)-2-Acetyl-3-amino-4,4,4-trichloro-N-phenylbut-2-enamide Diphenylboron (36; NBC13)

(Z)-2-Acetyl-3-amino-4,4,4-trichloro-N-phenylbut-2-enamide (0.62 g, 1.94 mmol) was added to DPBA (0.37 g, 1.06 mmol) suspended in anhydrous THF (4 mL). The reaction mixture was heated at 50° C. under N$_2$ for 16 h. The reaction mixture was extracted in DCM. The solution was concentrated and purified by flash column chromatography (ethyl acetate/n-hexane, 1:7). The collected fractions were combined, evaporated and stirred in cold n-hexane (15 mL) for 30 mins. The precipitate was filtered to give to 0.21 g (41%) of (36) as a yellow solid. mp: 131-133° C.; $^1$H NMR (300.1 MHz, CDCl$_3$): 7.96 (br s, 1H, C=C(NH)CCl$_3$), 7.12-7.48 (m, 16H, 3×Aryl-H and CONH), 2.46 (s, 3H, CH$_3$CO); $^{13}$C NMR (100.1 MHz, CDCl$_3$): 187.6 (CH$_3$CO), 162.5 (C=C(NH$_2$)CCl$_3$), 162.4 (CONH), 137.4 (Ph(ipso)), 131.7 (B-Ph(o)), 129.2 (Ph(m)), 127.6 (B-Ph(m)), 127.2

(Ph(p)), 125.1 (B-Ph(p)), 119.7 (Ph(o)), 106.4 ($\underline{C}$=C(NH$_2$)CCl$_3$), 92.8 (CCl$_3$), 23.4 ($\underline{CH_3}$CO), B-Ph quaternary signal not observed; IR: 3350 (N—H), 1654 (C=O), 1596 (C=C, conjugated), 1520 (C=C—NH) cm$^{-1}$; MS(ES$^-$) (m/z): 482.2 [M−H, $^{10}$B, $^{35}$Cl, $^{35}$Cl, $^{35}$Cl, 13%]$^-$, 483.2 [M−H, $^{11}$B, $^{35}$Cl, $^{35}$Cl, $^{35}$Cl, 63%]$^-$, 484.2 [M−H, $^{10}$B, $^{35}$Cl, $^{35}$Cl, $^{37}$Cl, 29%]$^-$, 485.1 [M−H, $^{11}$B, $^{35}$Cl, $^{35}$Cl, $^{37}$Cl, 100%]$^-$, 486.2 [M−H, $^{10}$B, $^{35}$Cl, $^{37}$Cl, $^{37}$Cl, 15%]$^-$, 487.2 [M−H, $^{11}$B, $^{37}$Cl, $^{37}$Cl, $^{37}$Cl, 23%]$^-$, 488.1 [M−H, $^{10}$B, $^{37}$Cl, $^{37}$Cl, $^{37}$Cl, 3%]$^-$, 489.1 [M−H, $^{11}$B, $^{37}$Cl, $^{37}$Cl, $^{37}$Cl, 1%]$^-$; MS(ES$^+$) (m/z): 484.1 [M+H, $^{10}$B, $^{35}$Cl, $^{35}$Cl, $^{35}$Cl, 5%]$^+$, 485.1 [M+H, $^{11}$B, $^{35}$Cl, $^{35}$Cl, $^{35}$Cl, 37%]$^+$, 486.1 [M+H, $^{10}$B, $^{35}$Cl, $^{35}$Cl, $^{37}$Cl, 12%]$^+$, 487.1 [M+H, $^{11}$B, $^{35}$Cl, $^{35}$Cl, $^{37}$Cl, 28%]$^+$, 488.1 [M+H, $^{10}$B, $^{35}$Cl, $^{37}$Cl, $^{35}$Cl, 4%]$^+$, 489.1 [M+H, $^{11}$B, $^{35}$Cl, $^{37}$Cl, $^{37}$Cl, 11%]$^+$, 490.2 [M+H, $^{10}$B, $^{37}$Cl, $^{37}$Cl, $^{37}$Cl, 3%]$^+$, 491.2 [M+H, $^{11}$B, $^{37}$Cl, $^{37}$Cl, $^{37}$Cl, 1%]$^+$, 506.1 [M+Na, $^{10}$B, $^{35}$Cl, $^{35}$Cl, $^{35}$Cl, 38%]$^+$, 507.1 [M+Na, $^{11}$B, $^{35}$Cl, $^{35}$Cl, $^{35}$Cl, 100%]$^+$, 508.1 [M+Na, $^{10}$B, $^{35}$Cl, $^{35}$Cl, $^{37}$Cl, 43%]$^+$, 509.1 [M+Na, $^{11}$B, $^{35}$Cl, $^{35}$Cl, $^{37}$Cl, 78%]$^+$, 510.1 [M+Na, $^{10}$B, $^{35}$Cl, $^{37}$Cl, $^{37}$Cl, 19%]$^+$, 511.1 [M+Na, $^{11}$B, $^{35}$Cl, $^{37}$Cl, $^{37}$Cl, 26%]$^+$, 512.1 [M+Na, $^{10}$B, $^{37}$Cl, $^{37}$Cl, $^{37}$Cl, 3%]$^+$, 513.1 [M+Na, $^{11}$B, $^{37}$Cl, $^{37}$Cl, $^{37}$Cl, 2%]$^+$.

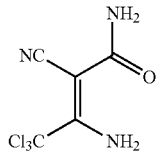

37

(Z)-2-Cyano-3-amino-4,4,4-trichlorobut-2-enamide (37) was prepared by a revised method to that described by Ibrahim et al, 1985[27]. Cyanoacetamide (1.68 g, 20 mmol) and trichloroacetonitrile (2 mL, 20 mmol) were added to a suspension of sodium acetate (1.64 g, 20 mmol) and anhydrous ethanol (100 mL). The reaction mixture was stirred at room temperature under N$_2$ for 16 h. The reaction mixture was dissolved in water, the precipitate was filtered and recrystallized from EtOH to give 0.45 g (10%) of (37) as a cream solid. mp: 124-126° C. (lit.[7] 152 OC); $^1$H NMR (300.1 MHz, d$_4$-MeOH): 11.08 (br s, 1H, N$\underline{H}_2$), 8.79 (br s, 1H, N$\underline{H}_2$), 7.43 (br s, 1H, CON$\underline{H}$), 7.20 (br s, 1H, CON$\underline{H}$); IR: 3323 (N—H), 3198 (N—H), 2197 (C≡N), 1660 (C=O), 1593 (C=C, conjugated) cm$^{-1}$; MS(ES$^-$) (m/z): 225.9 [M−H, $^{35}$Cl, $^{35}$Cl, $^{35}$Cl, 71%]$^-$, 227.9 [M−H, $^{35}$Cl, $^{35}$Cl, $^{37}$Cl, 100%]$^-$, 229.9 [M−H, $^{35}$Cl, $^{37}$Cl, $^{37}$Cl, 22%]$^-$, 231.9 [M−H, $^{37}$Cl, $^{37}$Cl, $^{37}$Cl, 3%]$^-$.

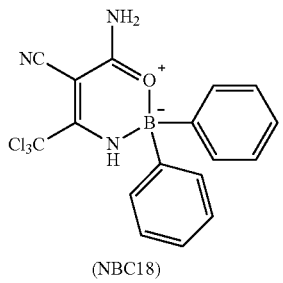

38

(Z)-2-Cyano-3-amino-4,4,4-trichlorobut-2-enamide Diphenylboron (38; NBC18)

(E)-2-Cyano-3-amino-4,4,4-trichlorobut-2-enamide (0.36 g, 1.58 mmol) was added to DPBA (0.36 g, 1.04 mmol) suspended in anhydrous THF (5 mL). The reaction mixture was heated at 50° C. under N$_2$ for 16 h. The reaction mixture was extracted in DCM. The solution was concentrated and purified by flash column chromatography (ethyl acetate/n-hexane, 1:9) to give 0.30 g (74%) of (38) as a grey solid. mp: 153-155° C.; $^1$H NMR (300.1 MHz, CDCl$_3$): 7.66 (br s, 1H, C=C(N$\underline{H}$)CCl$_3$), 7.16-7.30 (m, 10H, Aryl-$\underline{H}$), 6.48 (br s, 1H, CON$\underline{H}_2$), 5.98 (br s, 1H, CON$\underline{H}_2$); $^{13}$C NMR (100.1 MHz, CDCl$_3$): 170.5 (C=$\underline{C}$(NH)CCl$_3$), 163.9 (CONH), 130.6 (B-Ph(o)), 126.7 (B-Ph(m)), 126.3 (B-Ph(p)), 114.4 (CN), 90.8 (CCl$_3$), 63.3 ($\underline{C}$=C(NH$_2$)CCl$_3$); IR: 3385 (N—H), 3353 (N—H), 2227 (C≡N), 1649 (C=O), 1596 (C=C, conjugated), 1524 (C=C—NH) cm$^{-1}$; MS(ES$^-$) (m/z): 389.1 [M−H, $^{10}$B, $^{35}$Cl, $^{35}$Cl, $^{35}$Cl, 19%]$^-$, 390.1 [M−H, $^{11}$B, $^{35}$Cl, $^{35}$Cl, $^{35}$Cl, 100%]$^-$, 391.1 [M−H, $^{10}$B, $^{35}$Cl, $^{35}$Cl, $^{37}$Cl, 22%]$^-$, 392.1 [M−H, $^{11}$B, $^{35}$Cl, $^{35}$Cl, $^{37}$Cl, 63%]$^-$, 393.1 [M−H, $^{10}$B, $^{35}$Cl, $^{37}$Cl, $^{37}$Cl, 21%]$^-$, 394.1 [M−H, $^{11}$B, $^{35}$Cl, $^{37}$Cl, $^{37}$Cl, 27%]$^-$, 395.1 [M−H, $^{10}$B, $^{37}$Cl, $^{37}$Cl, $^{37}$Cl, 2%]$^-$, 396.2 [M−H, $^{11}$B, $^{37}$Cl, $^{37}$Cl, $^{37}$Cl, 3%]$^-$; MS(ES$^+$) (m/z): 413.0 [M+Na, $^{10}$B, $^{35}$Cl, $^{35}$Cl, $^{35}$Cl, 14%]$^+$, 414.0 [M+Na, $^{11}$B, $^{35}$Cl, $^{35}$Cl, $^{35}$Cl, 67%]$^+$, 415.0 [M+Na, $^{10}$B, $^{35}$Cl, $^{35}$Cl, $^{37}$Cl, 24%]$^+$, 416.0 [M+Na, $^{11}$B, $^{35}$Cl, $^{35}$Cl, $^{37}$Cl, 100%]$^+$, 417.0 [M+Na, $^{10}$B, $^{35}$Cl, $^{37}$Cl, $^{37}$Cl, 11%]$^+$, 418.1 [M+Na, $^{11}$B, $^{35}$Cl, $^{37}$Cl, $^{37}$Cl, 18%]$^+$, 419.1 [M+Na, $^{10}$B, $^{37}$Cl, $^{37}$Cl, $^{37}$Cl, 4%]$^+$, 420.1 [M+Na, $^{11}$B, $^{37}$Cl, $^{37}$Cl, $^{37}$Cl, 3%]$^+$.

Further Synthetic Procedures

Scheme 1 - General enaminones synthesis from 1,3-dicarbonyls and nitriles.

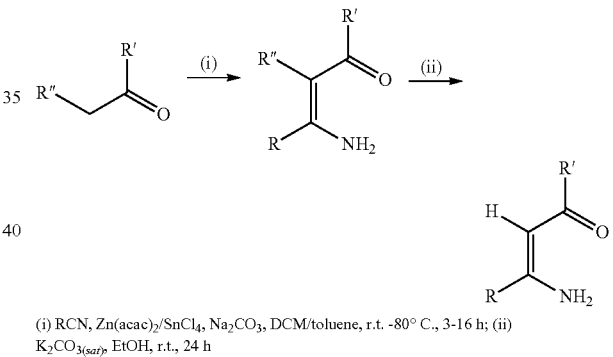

(i) RCN, Zn(acac)$_2$/SnCl$_4$, Na$_2$CO$_3$, DCM/toluene, r.t. -80° C., 3-16 h; (ii) K$_2$CO$_{3(sat)}$, EtOH, r.t., 24 h General Procedure for Enaminone Reaction Using Zn(acac)

An appropriate nitrile (1 eq) was added to a suspension containing 1,3-dicarbonyl (1 eq), Zn(acac)$_2$ (1-2% mol) and Na$_2$CO$_3$ (1.1 eq) in anhydrous DCM (5 mL). The mixture was stirred at room temperature under N$_2$ for 3 h, unless otherwise stated. DCM/EtOAc (15 mL) was added and the mixture washed with H$_2$O, dried over MgSO$_4$ and concentrated in vacuo.

For deacetylated compounds, K$_2$CO$_{3(sat)}$ (10 mL) and EtOH (5 mL) was then added and the mixture was stirred at room temperature for 24 h. The mixture was extracted with EtOAc, dried over MgSO$_4$ and concentrated in vacuo. Alternatively, acetylated enaminones were passed through SiO$_2$ by flash column chromatography to give the corresponding deacetylated products.

General Procedure for Enaminone Reaction Using SnCl$_4$

An appropriate nitrile (1 eq) was added to a suspension containing 1,3-dicarbonyl (1 eq) and Na$_2$CO$_3$ (1.1 eq) in anhydrous toluene (10 mL). For deacetylated products, addition of Na$_2$CO$_3$ was omitted. SnCl$_4$ (1 eq) was slowly added and the mixture was stirred at room temperature under N$_2$ for 30 min. The mixture was then heated to 80° C. and stirred for 4 h, unless otherwise stated. MeCN (20 mL) was added to dissolve the gummy solid, filtered to remove Na$_2$CO$_3$, concentrated in vacuo and dried under vacuum overnight. After 16 h, boiling CHCl$_3$ (20 mL) was added and refluxed for 1 h. The solid was filtered and dried under vacuum.

(Z)-2-Acetyl-3-amino-4,4,4-trichlorobut-2-enamide (39)

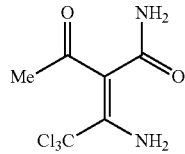

39

Yield: 54%, white solid. mp: 108-110° C.; $^1$H NMR (300.1 MHz, CDCl$_3$): δ 8.75 (br s, 2H, N$\underline{H}_2$), 6.02 (br s, 1H, CON$\underline{H}_2$), 5.95 (br s, 1H, CON$\underline{H}_2$), 2.38 (s, 3H, C$\underline{H}_3$CO); $^{13}$C NMR (100.6 MHz, CDCl$_3$): δ 197.2 (CH$_3$$\underline{C}$O), 169.9 (CONH$_2$), 156.7 (Cl$_3$C(NH$_2$)$\underline{C}$=C), 104.0 (Cl$_3$C(NH$_2$)C=$\underline{C}$), 93.3 ($\underline{C}$Cl$_3$), 28.5 ($\underline{C}$H$_3$CO); IR: 3417 (N—H), 3310 (N—H), 3209 (N—H), 1651 (C=O), 1592 (C=C, conjugated) cm$^{-1}$.

Tert-Butyl (Z)-2-acetyl-3-amino-4,4,4-trichlorobut-2-enoate (40)

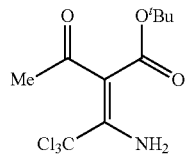

40

Yield: 88%, cream solid. mp: 75-76° C.; $^1$H NMR (300.1 MHz, CDCl$_3$): δ 2.31 (s, 3H, C$\underline{H}_3$CO), 1.55 (s; 9H, (C$\underline{H}_3$)$_3$C); $^{13}$C NMR (100.1 MHz, CDCl$_3$): δ 196.7 (CH$_3$$\underline{C}$O), 167.3 (C=$\underline{C}$(NH$_2$)CCl$_3$), 157.5 (CONHCH$_2$), 104.1 ($\underline{C}$=C(NH$_2$)CCl$_3$), 93.4 ($\underline{C}$Cl$_3$), 82.4 ((CH$_3$)$_3$$\underline{C}$), 29.1 ($\underline{C}$H$_3$CO), 27.7 (($\underline{C}$H$_3$)$_3$C); IR: 3310 (N—H), 2979 (N—H), 1712 (C=O), 1673 (C=O), 1605 (C=C, conjugated) cm$^{-1}$; MS(ES$^-$) (m/z): 300.0 [M–H, $^{35}$Cl, $^{35}$Cl, $^{35}$Cl, 86%]$^-$, 301.9 [M–H, $^{35}$Cl, $^{35}$Cl, $^{37}$Cl, 100%]$^-$, 304.0 [M–H, $^{35}$Cl, $^{37}$Cl, $^{37}$Cl, 39%]$^-$, 306.0 [M–H, $^{37}$Cl, $^{37}$Cl, $^{37}$Cl, 6%]$^-$; MS(ES$^+$) (m/z): 227.8 [M–O$^t$Bu, $^{35}$Cl, $^{35}$Cl, $^{35}$Cl, 72%]$^+$, 229.8 [M–O$^t$Bu, $^{35}$Cl, $^{35}$Cl, $^{37}$Cl, 74%]$^+$, 231.8 [M–O$^t$Bu, $^{35}$Cl, $^{37}$Cl, $^{37}$Cl, 25%]$^+$, 233.8 [M–O$^t$Bu, $^{37}$Cl, $^{37}$Cl, $^{37}$Cl, 2%]$^+$, 323.9 [M+Na, $^{35}$Cl, $^{35}$Cl, $^{35}$Cl, 10%]$^+$, 325.9 [M+Na, $^{35}$Cl, $^{35}$Cl, $^{37}$Cl, 13%]$^+$, 327.9 [M+Na, $^{35}$Cl, $^{37}$Cl, $^{37}$Cl, 3%]$^+$, 329.9 [M+Na, $^{37}$Cl, $^{37}$Cl, $^{37}$Cl, 1%]$^+$; HRMS (m/z): [M+Na]$^+$ calcd. for C$_{10}$H$_{14}$$^{35}$Cl$_3$NO$_3$Na, 323.9931; found, 323.9931, error: 0.0 ppm.

General Reaction Scheme for Oxazaborinine Synthesis

Scheme 2 - Synthesis of oxazaborinines from enaminones.

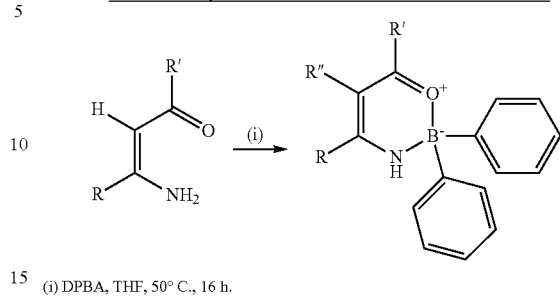

(i) DPBA, THF, 50° C., 16 h.

General Procedure for Oxazaborinine Reaction

An appropriate enaminone (3 eq) was added to a solution of DPBA (1 eq) in anhydrous THF (5 mL). The mixture was stirred at 50° C. under N$_2$ for 16 h. The mixture was concentrated in vacuo and purified by flash column chromatography. The collected fractions were combined, evaporated in vacuo and stirred in cold n-hexane (15 mL) for 30 mins. The precipitate was then filtered and dried under vacuum to give the corresponding oxazaborinine products.

5-(tert-Butoxycarbonyl)-2,2-di phenyl-6-methyl-4-(trichloromethyl)-2,3-dihydro-1,3,2-oxazaborinin-1-ium-2-uide (41; NBC25)

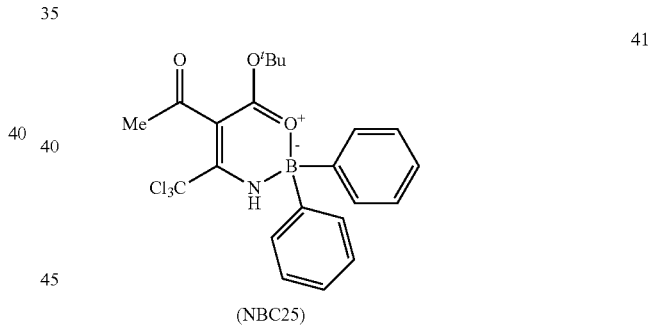

41

(NBC25)

Ethyl acetate/n-hexane, 1:9. Yield: 35%, yellow solid. mp: 147-149° C.; $^1$H NMR (300.1 MHz, CDCl$_3$): δ 7.86 (br s, 1H, C=C(N$\underline{H}$)CCl$_3$), 7.15-7.32 (m, 10H, 2×Ph-$\underline{H}$), 2.34 (s, 3H, C$\underline{H}_3$CO), 1.42 (s, 9H, (C$\underline{H}_3$)$_3$C); $^{13}$C NMR (100.1 MHz, CDCl$_3$): δ 187.2 (CH$_3$$\underline{C}$O), 164.4 (C=$\underline{C}$(NH)CCl$_3$), 163.3 ($\underline{C}$OO), 131.7 (B-Ph(o)), 127.5 (B-Ph(m)), 126.9 (B-Ph(p)), 103.8 ($\underline{C}$=C(NH)CCl$_3$), 93.3 ($\underline{C}$Cl$_3$), 82.8 ((CH$_3$)$_3$$\underline{C}$), 27.8 (($\underline{C}$H$_3$)$_3$C), 24.3 ($\underline{C}$H$_3$CO); B-Ph(i) quaternary signal not observed; IR: 3310 (N—H), 1715 (C=O), 1597 (C=C, conjugated); MS(ES$^-$) (m/z): 463.1 [M–H, $^{10}$B, $^{35}$Cl, $^{35}$Cl, $^{35}$Cl, 8%]$^-$, 464.1 [M–H, $^{11}$B, $^{35}$Cl, $^{35}$Cl, $^{35}$Cl, 64%]$^-$, 465.1 [M–H, $^{10}$B, $^{35}$Cl, $^{35}$Cl, $^{37}$Cl, 32%]$^-$, 466.1 [M–H, $^{11}$B, $^{35}$Cl, $^{35}$Cl, $^{37}$Cl, 100%]$^-$, 467.1 [M–H, $^{10}$B, $^{35}$Cl, $^{37}$Cl, $^{37}$Cl, 32%]$^-$, 468.1 [M–H, $^{11}$B, $^{35}$Cl, $^{37}$Cl, $^{37}$Cl, 20%]$^-$, 469.1 [M–H, $^{10}$B, $^{37}$Cl, $^{37}$Cl, $^{37}$Cl, 5%]$^-$, 470.1 [M–H, $^{11}$B, $^{37}$Cl, $^{37}$Cl, $^{37}$Cl, 3%]$^-$; HRMS (m/z): [M+Na]$^+$ calcd. for C$_{22}$H$_{23}$$^{11}$B$^{35}$Cl$_3$NO$_3$Na, 488.0729; found, 488.0729, error: 0.0 ppm.

6-Amino-5-carbamoyl-2,2-diphenyl-4-(trichloromethyl)-2,3-dihydro-1,3,2-oxazaborinin-1-ium-2-uide (42; NBC24)

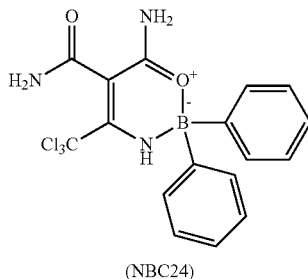

(NBC24)

Crude enaminone product was directly borylated using DPBA due to difficulty in purification. Ethyl acetate/n-hexane, 1:9. Yield: 13%, yellow solid. mp: 155–156° C.; $^1$H NMR (300.1 MHz, DMSO-d$_6$): δ 8.80 (br s, 1H, CONH$_2$), 8.21 (br s, 1H, CONH$_2$), 7.33 (d, J=6.6 Hz, 4H, B-Ph(o) & br s, 1H, CONH$_2$), 7.05-7.24 (m, 7H, B-Ph(m/p) & CONH$_2$); $^{13}$C NMR (100.6 MHz, DMSO-d$_6$): δ 169.0 (CONH$_2$), 167.5 (Cl$_3$C(NH)C=C), 160.2 (CONH$_2$), 131.6 (B-Ph(o)), 126.7 (B-Ph(m)), 125.7 (B-Ph(p)), 93.5 (CCl$_3$), 89.6 (Cl$_3$C(NH)C=C), B-Ph quaternary signal not observed; IR: 3484 (N—H), 3419 (N—H), 3345 (N—H), 3318 (N—H), 1653 (C=O), 1614 (C=C, conjugated), 1559 (C=C—NH) cm$^{-1}$; MS(ES$^-$) (m/z): 407.0 [M–H, $^{10}$B, $^{35}$Cl, $^{35}$Cl, $^{35}$Cl, 12%]$^-$, 408.0 [M–H, $^{11}$B, $^{35}$Cl, $^{35}$Cl, $^{35}$Cl, 100%]$^-$, 409.0 [M–H, $^{10}$B, $^{35}$Cl, $^{35}$Cl, $^{37}$Cl, 19%]$^-$, 410.0 [M–H, $^{11}$B, $^{35}$Cl, $^{35}$Cl, $^{37}$Cl, 68%]$^-$, 411.0 [M–H, $^{10}$B, $^{35}$Cl, $^{37}$Cl, $^{37}$Cl, 5%]$^-$, 412.0 [M–H, $^{11}$B, $^{35}$Cl, $^{37}$Cl, $^{37}$Cl, 21%]$^-$, 413.0 [M–H, $^{10}$B, $^{37}$Cl, $^{37}$Cl, $^{37}$Cl, 3%]$^-$, 414.0 [M–H, $^{11}$B, $^{37}$Cl, $^{37}$Cl, $^{37}$Cl, 3%]$^-$; MS(ES$^+$) (m/z): 330.9 [M–Ph, $^{10}$B, $^{35}$Cl, $^{35}$Cl, $^{35}$Cl, 6%]$^+$, 331.9 [M–Ph, $^{11}$B, $^{35}$Cl, $^{35}$Cl, $^{35}$Cl, 62%]$^+$, 332.9 [M–Ph, $^{10}$B, $^{35}$Cl, $^{35}$Cl, $^{37}$Cl, 10%]$^+$, 333.9 [M–Ph, $^{11}$B, $^{35}$Cl, $^{35}$Cl, $^{37}$Cl, 34%]$^+$, 334.9 [M–Ph, $^{10}$B, $^{35}$Cl, $^{37}$Cl, $^{37}$Cl, 3%]$^+$, 335.9 [M–Ph, $^{11}$B, $^{35}$Cl, $^{37}$Cl, $^{37}$Cl, 8%]$^+$, 337.0 [M–Ph, $^{10}$B, $^{37}$Cl, $^{37}$Cl, $^{37}$Cl, 3%]$^+$, 338.1 [M–Ph, $^{11}$B, $^{37}$Cl, $^{37}$Cl, $^{37}$Cl, 4%]$^+$, 409.0 [M+H, $^{10}$B, $^{35}$Cl, $^{35}$Cl, $^{35}$Cl, 5%]$^+$, 410.0 [M+H, $^{11}$B, $^{35}$Cl, $^{35}$Cl, $^{35}$Cl, 11%]$^+$, 411.0 [M+H, $^{10}$B, $^{35}$Cl, $^{35}$Cl, $^{37}$Cl, 7%]$^+$, 412.0 [M+H, $^{11}$B, $^{35}$Cl, $^{35}$Cl, $^{37}$Cl, 12%]$^+$, 413.0 [M+H, $^{10}$B, $^{35}$Cl, $^{37}$Cl, $^{37}$Cl, 3%]$^+$, 414.1 [M+H, $^{11}$B, $^{35}$Cl, $^{37}$Cl, $^{37}$Cl, 4%]$^+$, 415.1 [M+H, $^{10}$B, $^{37}$Cl, $^{37}$Cl, $^{37}$Cl, 2%]$^+$, 416.1 [M+H, $^{11}$B, $^{37}$Cl, $^{37}$Cl, $^{37}$Cl, 1%]$^+$, 431.0 [M+Na, $^{10}$B, $^{35}$Cl, $^{35}$Cl, $^{35}$Cl, 3%]$^+$, 432.0 [M+Na, $^{11}$B, $^{35}$Cl, $^{35}$Cl, $^{35}$Cl, 40%]$^+$, 433.0 [M+Na, $^{10}$B, $^{35}$Cl, $^{35}$Cl, $^{37}$Cl, 8%]$^+$, 434.0 [M+Na, $^{11}$B, $^{35}$Cl, $^{35}$Cl, $^{37}$Cl, 18%]$^+$, 435.0 [M+Na, $^{10}$B, $^{35}$Cl, $^{37}$Cl, $^{37}$Cl, 5%]$^+$, 436.0 [M+Na, $^{11}$B, $^{35}$Cl, $^{37}$Cl, $^{37}$Cl, 6%]$^+$, 437.0 [M+Na, $^{10}$B, $^{37}$Cl, $^{37}$Cl, $^{37}$Cl, 2%]$^+$, 438.0 [M+Na, $^{11}$B, $^{37}$Cl, $^{37}$Cl, $^{37}$Cl, 1%]$^+$; HRMS (m/z): [M+H]$^+$ calcd. for C$_{17}$H$_{16}$$^{11}$B$^{35}$Cl$_3$N$_3$O$_2$, 410.0396; found, 410.0396, error: 0.0 ppm.

4-(tert-Butyl)-6-methyl-2,2-diphenyl-2,3-dihydro-1,3,2-oxazaborinin-1-ium-2-uide (43; NBC28)

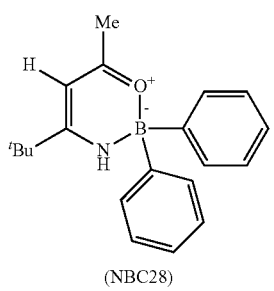

(NBC28)

Crude enaminone product was directly borylated using DPBA due to difficulty in purification. Ethyl acetate/n-hexane, 2:23. Yield: 3%, white solid. mp: 121–122° C.; $^1$H NMR (300.1 MHz, CDCl$_3$): δ 7.08-7.33 (m, 10H, 2×Ph-H), 6.78 (br s, 1H, C=C(NH)C(CH$_3$)$_3$), 5.23 (d, J$_{CH,NH}$=2.1 Hz, 1H, C=CH), 2.02 (s, 3H, CH$_3$CO), 1.16 (s, 9H, (CH$_3$)$_3$C); $^{13}$C NMR (100.1 MHz, CDCl$_3$): δ 178.7, 178.6, 130.6 (B-Ph(o)), 126.2 (B-Ph(m)), 125.1 (B-Ph(p)), 92.5 (C=C(NH)CCl$_3$), 35.9 ((CH$_3$)$_3$C), 26.5 ((CH$_3$)$_3$C), 23.0 (CH$_3$CO); B-Ph(i) quaternary signal not observed; IR: 3381 (N—H), 1610 (C=C, conjugated), 1519 (C=C—NH) cm$^{-1}$; MS(ES$^-$) (m/z): 303.1 [M–H, $^{10}$B, 27%]$^-$, 304.1 [M–H, $^{11}$B, 100%]$^-$; MS(ES$^+$) (m/z): 227.1 [M–Ph, $^{10}$B, 52%]$^+$, 228.1 [M–Ph, $^{11}$B, 100%]$^+$, 305.2 [M+H, $^{10}$B, 19%]$^+$, 306.1 [M+H, $^{11}$B, 77%]$^+$, 327.1 [M+Na, $^{10}$B, 5%]$^+$, 328.1 [M+Na, $^{11}$B, 24%]$^+$; HRMS (m/z): [M+Na]$^+$ calcd. for C$_{20}$H$_{24}$$^{11}$BNONa, 328.1843; found, 328.1841, error: 0.6 ppm.

5-Acetyl-6-methyl-2,2,4-triphenyl-2,3-dihydro-1,3,2-oxazaborinin-1-ium-2-uide (44; NBC23)

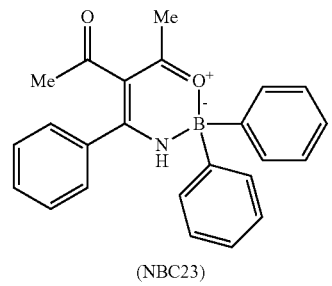

(NBC23)

Crude enaminone product was directly borylated using DPBA due to difficulty in purification. Ethyl acetate/n-hexane, 1:9. Yield: 17%, white solid. mp: 160–163° C.; $^1$H NMR (300.1 MHz, CDCl$_3$): δ 7.47-7.52 (m, 5H, Ph-H), 7.43 (d, J=5.7 Hz, 4H, B-Ph(o)), 7.19-7.37 (m, 6H, B-Ph(m/p)), 7.16 (br s, 1H, C=C(NH)Ph), 2.50 (s, 3H, CH$_3$CO), 1.48 (s, 3H, CH$_3$CO); $^{13}$C NMR (100.1 MHz, CDCl$_3$): δ 196.6 (CH$_3$CO), 186.0 (CH$_3$CO), 169.0 (C=C(NH)Ph), 135.4 (Ph(i)), 131.8 (Ph(p)), 130.8 (B-Ph(o)), 128.7 (Ph(m)), 126.8 (Ph(o)), 126.4 (B-Ph(m)), 125.6 (B-Ph(p)), 113.9 (C=C(NH)Ph), 31.3 (CH$_3$CO), 23.5 (CH$_3$CO); B-Ph(i) quaternary signal not observed; IR: 3208 (N—H), 1638 (C=O), 1628 (C=O) cm$^{-1}$; MS(ES$^-$) (m/z): 366.0 [M–H, $^{11}$B, 100%]$^-$; MS(ES$^+$) (m/z): 368.0 [M+H, $^{11}$B, 100%]$^+$, 390.0 [M+Na, $^{11}$B, 70%]$^+$; HRMS (m/z): [M+Na]$^+$ calcd. for C$_{24}$H$_{22}$$^{11}$BNO$_2$Na, 390.1636; found, 390.1634, error: 0.5 ppm.

5-(tert-Butoxycarbonyl)-4-(ethylthio)-2,2-diphenyl-6-methyl-2,3-dihydro-1,3,2-oxazaborinin-1-ium-2-uide (45; NBC26)

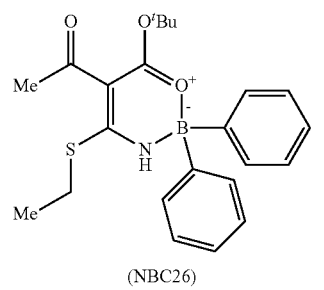

(NBC26)

Crude enaminone product was directly borylated using DPBA due to difficulty in purification. Ethyl acetate/n-hexane, 1:9. Yield: 30%, white solid. mp: 145-148° C.; $^1$H NMR (300.1 MHz, CDCl$_3$): δ 7.30 (d, J=5.7 Hz, 4H, B-Ph(o)), 7.10-7.20 (m, 6H, B-Ph(m/p)), 6.70 (br s, 1H, C=C(N$\underline{H}$)SCH$_2$CH$_3$), 2.70 (q, J=7.5 Hz, 2H, CH$_3$C$\underline{H}$$_2$S), 2.37 (s, 3H, C$\underline{H}$$_3$CO), 1.40 (s, 9H, (C$\underline{H}$$_3$)$_3$C), 1.30 (t, J=7.5 Hz, 3H, C$\underline{H}$$_3$CH$_2$S); $^{13}$C NMR (100.1 MHz, CDCl$_3$): δ 184.0 (CH$_3$$\underline{C}$O), 173.4 ($\underline{C}$OO), 165.5 (C=$\underline{C}$(NH)SCH$_2$CH$_3$), 131.8 (B-Ph(o)), 127.4 (B-Ph(m)), 126.5 (B-Ph(p)), 97.1 ($\underline{C}$=C(NH)CCl$_3$), 82.1 ((CH$_3$)$_3$$\underline{C}$), 28.4 (($\underline{C}$H$_3$)$_3$C), 25.5 (CH$_3$$\underline{C}$H$_2$S), 24.3 ($\underline{C}$H$_3$CO), 11.9 ($\underline{C}$H$_3$ CH$_2$S); B-Ph(i) quaternary signal not observed; IR: 3364 (N—H), 1660 (C=O), 1556 (C=C, conjugated), 1552 (C=C—NH) cm$^{-1}$; MS(ES$^-$) (m/z): 408.2 [M-H, $^{11}$B, 100%]$^-$; HRMS (m/z): [M+Na]$^+$ calcd. for C$_{23}$H$_{28}$$^{11}$BNO$_3$SNa, 432.1775; found, 432.1774, error: 0.2 ppm.

General Reaction Scheme for Oxazaborinine Synthesis

Scheme 4 - Synthesis of oxazaborinines from secondary amides and substituted esters. The synthesis of disubstituted tertiary amides can also be achieved under the same reaction conditions.

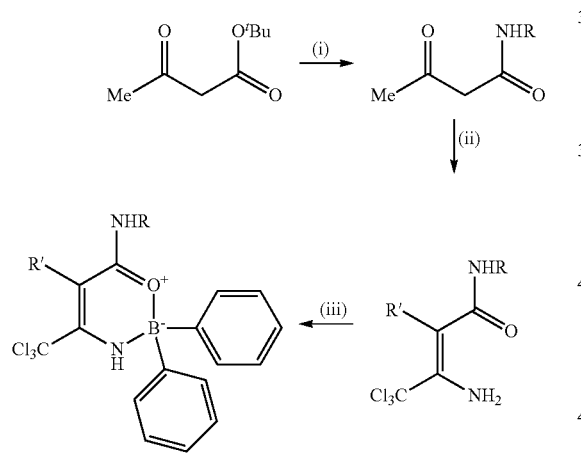

(i) RNH$_2$, toluene, 125° C., 16 h; (ii) Cl$_3$CCN, Zn(acac)$_2$, Na$_2$CO$_3$, DCM, r.t., 3 h; (iii) DPBA, THF, 50° C., 16 h. Cy = cyclohexyl, Ad = adamantyl, Pyr = pyrene, Py = pyridyl.

General Procedure for Acetoacetamide-Based Oxazaborinine Derivative

Unless otherwise stated, an appropriate primary amine (1 eq) was added to a solution of tert-butyl acetoacetate (1.1 eq) in toluene (150 mL) or DMF (5 mL). The mixture was stirred at 50° C. under N$_2$ for 16 h. Solvent was evaporated in vacuo and the residue was dissolved in Et$_2$O/DCM (20 mL), washed with 1N HCl$_{(aq)}$ (2×10 mL), dried over MgSO$_4$ and evaporated in vacuo. All further reactions were conducted in the same manner as previously described for the general procedures for the enaminone reaction and oxazaborinine reaction to give the corresponding oxaborinine products.

N-Cyclohexylacetoacetamide (46)

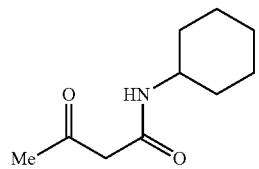

46

Yield: 78%, brown solid. mp: 65-67° C.; $^1$H NMR (300.1 MHz, CDCl$_3$): δ 7.08 (br s, 1H, N$\underline{H}$), 3.70 (p, J=3.6 Hz, 1H, —C$\underline{H}$CH$_2$CH$_2$CH$_2$CH$_2$—), 3.36 (s, 2H, CH$_3$COC$\underline{H}$$_2$), 2.20 (s, 3H, CH$_3$CO); 1.82 (d, J=11.7 Hz, 2H, —CHC H$_2$(CH$_2$)$_3$C$\underline{H}$$_2$—), 1.04-1.70 (m, 8H, —CHCH$_2$(C$\underline{H}$$_2$)$_3$C $\underline{H}$$_2$—); $^{13}$C NMR (100.1 MHz, CDCl$_3$): δ 204.8 (CH$_3$$\underline{C}$O), 164.3 (CONH), 49.9 (CH$_3$CO$\underline{C}$H$_2$), 48.2 (—$\underline{C}$H (CH$_2$)$_2$ (CH$_2$)$_2$CH$_2$—), 32.8 (—CH($\underline{C}$H$_2$)$_2$(CH$_2$)$_2$CH$_2$—), 31.0 ($\underline{C}$H$_3$CO), 25.5 (—CH(CH$_2$)$_2$(CH$_2$)$_2$$\underline{C}$H$_2$), 24.7 (—CH (CH$_2$)$_2$($\underline{C}$H$_2$)$_2$CH$_2$—); IR: 3290 (N—H), 2932 (C—H), 2855 (C—H), 1716 (C=O, ketone), 1638 (C=O, amide band I), 1543 (C=O, amide band II) cm$^{-1}$; MS(ES$^+$) (m/z): 184.1 [M+H, 100%]$^+$, 206.1 [M+Na, 82%]$^+$. HRMS (m/z): [M+H]$^+$ calcd. for C$_{10}$H$_{18}$NO$_2$, 184.1332; found, 184.1329, error: 1.6 ppm.

(Z)-2-Acetyl-3-amino-4,4,4-trichloro-N-cyclohexyl-but-2-enamide (47)

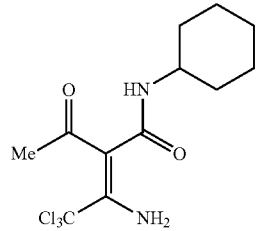

47

Yield: 93%, brown solid. mp: 109-111° C. (dec); $^1$H NMR (300.1 MHz, CDCl$_3$): δ 8.66 (br s, 1H, N$\underline{H}$$_2$), 5.83 (d, J=7.5 Hz, 1H, N$\underline{H}$), 3.81-3.97 (m, J=3.6 Hz, 1H, —C $\underline{H}$CH$_2$CH$_2$CH$_2$CH$_2$—), 2.32 (s, 3H, CH$_3$CO); 1.95-2.08 (m, 2H, —CHC$\underline{H}$$_2$(CH$_2$)$_3$C$\underline{H}$$_2$—), 1.53-1.79 (m, 4H, —CHC$\underline{H}$$_2$(C$\underline{H}$$_2$)$_3$C$\underline{H}$$_2$—), 1.32-1.49 (m, 2H, —CHCH$_2$(C $\underline{H}$$_2$)$_3$CH$_2$—), 1.11-1.27 (m, 3H, —CHCH$_2$(C$\underline{H}$$_2$)$_3$CH$_2$—); $^{13}$C NMR (100.1 MHz, CDCl$_3$): δ 197.8 (CH$_3$$\underline{C}$O), 166.5 (C=$\underline{C}$(NH$_2$)CCl$_3$), 156.3 (CONHCH$_2$), 105.3 ($\underline{C}$= C(NH$_2$)CCl$_3$), 93.5 (CCl$_3$), 49.0 (—$\underline{C}$H(CH$_2$)$_2$ (CH$_2$)$_2$CH$_2$—), 32.4 (—CH($\underline{C}$H$_2$)$_2$(CH$_2$)$_2$CH$_2$—), 28.4 ($\underline{C}$H$_3$CO), 25.5 (—CH(CH$_2$)$_2$($\underline{C}$H$_2$)$_2$CH$_2$—), 24.7 (—CH (CH$_2$)$_2$($\underline{C}$H$_2$)$_2$CH$_2$—); IR: 3271 (N—H), 2929 (N—H), 1721 (C=O, ketone), 1620 (C=O, amide), 1535 (C=C— NH$_2$) cm$^{-1}$; MS(ES$^-$) (m/z): 325.0 [M-H, $^{35}$Cl, $^{35}$Cl, $^{35}$Cl, 100%]$^-$, 327.0 [M-H, $^{35}$Cl, $^{35}$Cl, $^{37}$Cl, 53%]$^-$, 329.0 [M-H, $^{35}$Cl, $^{37}$Cl, $^{37}$Cl, 33%]$^-$, 331.0 [M-H, $^{37}$Cl, $^{37}$Cl, $^{37}$Cl, 3%]$^-$, 361.0 [M+$^{35}$Cl, $^{35}$Cl, $^{35}$Cl, $^{35}$Cl, 87%]$^-$, 363.0 [M+$^{35}$Cl, $^{35}$Cl, $^{37}$Cl, 48%]$^-$, 365.0 [M+$^{35}$Cl, $^{35}$Cl, $^{37}$Cl, $^{37}$Cl, 24%]$^-$, 367.0 [M+$^{35}$Cl, $^{37}$Cl, $^{37}$Cl, $^{37}$Cl, 5%]$^-$; MS(ES$^+$) (m/z): 327.0 [M+H, $^{35}$Cl, $^{35}$Cl, $^{35}$Cl, 62%]$^+$, 329.0 [M+H, $^{35}$Cl, $^{35}$Cl, $^{37}$Cl, 41%]$^+$, 331.0 [M+H, $^{35}$Cl, $^{37}$Cl, $^{37}$Cl, 15%]$^+$, 333.0 [M+H, $^{37}$Cl, $^{37}$Cl, $^{37}$Cl, 2%]$^+$; HRMS (m/z): [M+H]$^+$ calcd. for $C_{12}H_{18}{}^{35}Cl_3N_2O_2$, 327.0428; found, 327.0428, error: 0.0 ppm.

5-Acetyl-6-(cyclohexylamino)-2,2-diphenyl-4-(trichloromethyl)-2,3-dihydro-1,3,2-oxazaborinin-1-ium-2-uide (48; NBC19)

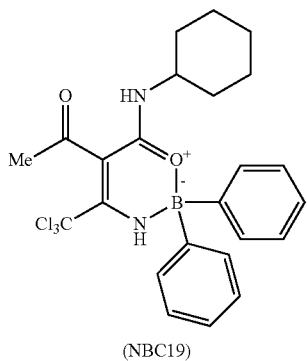

(NBC19)

Ethyl acetate/n-hexane, 1:4. Yield: 9%, yellow solid. mp: 53-54° C.; $^1$H NMR (300.1 MHz, CDCl$_3$): δ 7.82 (br s, 1H, C=C(NH)CCl$_3$), 7.27-7.39 (m, 10H, 2×Ph-H), 5.38 (d, J=7.5 Hz, 1H, CONH), 3.69-3.85 (m, 1H, —CH(CH$_2$)$_2$(CH$_2$)$_2$CH$_2$—), 2.35 (s, 3H, CH$_3$CO); 1.89 (d, J=10.5 Hz, 2H, —CH(CH$_2$)$_2$(CH$_2$)$_2$CH$_2$—), 0.98-1.42 (m, 8H, —CH(CH$_2$)$_2$(CH$_2$)$_2$CH$_2$—); $^{13}$C NMR (100.1 MHz, CDCl$_3$): δ 187.0 (CH$_3$CO), 163.6 (C=C(NH)CCl$_3$), 162.1 (CONH), 156.1 (B-Ph(ipso)), 131.7 (B-Ph(o)), 127.5 (B-Ph(m)), 127.0 (B-Ph(p)), 105.8 (C=C(NH)CCl$_3$), 93.0 (CCl$_3$), 49.1 (—CH(CH$_2$)$_2$(CH$_2$)$_2$CH$_2$—), 32.4 (—CH(CH$_2$)$_2$(CH$_2$)$_2$CH$_2$—), 25.4 (—CH(CH$_2$)$_2$(CH$_2$)$_2$CH$_2$—), 24.7 (—CH(CH$_2$)$_2$(CH$_2$)$_2$CH$_2$—), 23.3 (CH$_3$CO); IR: 3311 (N—H), 2928 (N—H), 1631 (C=O, amide band I), 1594 (C=O, amide band II), 1514 (C=C—NH) cm$^{-1}$; MS(ES$^-$) (m/z): 447.1 [M–C$_2$H$_3$O, $^{10}$B, $^{35}$Cl, $^{35}$Cl, $^{35}$Cl, 20%]$^-$, 448.1 [M–C$_2$H$_3$O, $^{35}$Cl, $^{35}$Cl, $^{35}$Cl, 99%]$^-$, 449.1 [M–C$_2$H$_3$O, $^{10}$B, $^{35}$Cl, $^{35}$Cl, $^{37}$Cl, 33%]$^-$, 450.1 [M–C$_2$H$_3$O, $^{11}$B, $^{35}$Cl, $^{35}$Cl, $^{37}$Cl, 100%]$^-$, 451.1 [M–C$_2$H$_3$O, $^{10}$B, $^{35}$Cl, $^{37}$Cl, $^{37}$Cl, 25%]$^-$, 452.1 [M–C$_2$H$_3$O, $^{11}$B, $^{35}$Cl, $^{37}$Cl, $^{35}$Cl, 23%]$^-$, 453.1 [M–C$_2$H$_3$O, $^{10}$B, $^{37}$Cl, $^{37}$Cl, $^{37}$Cl, 8%]$^-$, 454.1 [M–C$_2$H$_3$O, $^{11}$B, $^{37}$Cl, $^{37}$Cl, $^{37}$Cl, 3%]$^-$, 488.1 [M–H, $^{10}$B, $^{35}$Cl, $^{35}$Cl, $^{35}$Cl, 32%]$^-$, 489.1 [M–H, $^{11}$B, $^{35}$Cl, $^{35}$Cl, $^{35}$Cl, 100%]$^-$, 490.1 [M–H, $^{10}$B, $^{35}$Cl, $^{35}$Cl, $^{37}$Cl, 48%]$^-$, 491.2 [M–H, $^{11}$B, $^{35}$Cl, $^{35}$Cl, $^{37}$Cl, 94%]$^-$, 492.2 [M–H, $^{10}$B, $^{35}$Cl, $^{37}$Cl, $^{35}$Cl, 22%]$^-$, 493.2 [M–H, $^{11}$B, $^{35}$Cl, $^{37}$Cl, $^{37}$Cl, 32%]$^-$, 494.2 [M–H, $^{10}$B, $^{37}$Cl, $^{37}$Cl, $^{37}$Cl, 5%]$^-$, 495.2 [M–H, $^{11}$B, $^{37}$Cl, $^{37}$Cl, $^{37}$Cl, 4%]$^-$. MS(ES$^+$) (m/z): 490.2 [M+H, $^{10}$B, $^{35}$Cl, $^{35}$Cl, $^{35}$Cl, 13%]$^+$, 491.2 [M+H, $^{11}$B, $^{35}$Cl, $^{35}$Cl, $^{35}$Cl, 100%]$^+$, 492.2 [M+H, $^{10}$B, $^{35}$Cl, $^{35}$Cl, $^{37}$Cl, 45%]$^+$, 493.2 [M+H, $^{11}$B, $^{35}$Cl, $^{35}$Cl, $^{37}$Cl, 46%]$^+$, 494.2 [M+H, $^{10}$B, $^{35}$Cl, $^{37}$Cl, $^{37}$Cl, 18%]$^+$, 495.2 [M+H, $^{11}$B, $^{35}$Cl, $^{37}$Cl, $^{37}$Cl, 24%]$^+$, 496.2 [M+H, $^{10}$B, $^{37}$Cl, $^{37}$Cl, $^{37}$Cl, 6%]$^+$, 497.2 [M+H, $^{11}$B, $^{37}$Cl, $^{37}$Cl, $^{37}$Cl, 3%]$^+$. HRMS (m/z): [M+H]$^+$ calcd. for $C_{24}H_{27}{}^{11}B^{35}Cl_3N_2O_2$, 491.1226; found, 491.1226, error: 0.0 ppm.

N-(Pyren-1-ylmethyl)acetoacetamide (49)

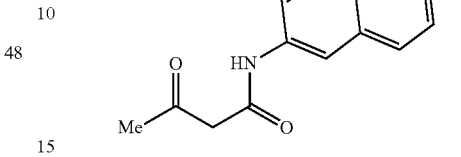

tert-Butyl acetoacetate (0.14 mL, 0.82 mmol) was added to a solution of 1-pyrenemethylamine hydrochloride (0.20 g, 0.75 mmol) and triethylamine (0.21 mL, 1.49 mmol) in toluene (50 mL). The procedure was carried out as described previously. Yield: 0.23 g (98%), orange solid. mp: 130-132° C.; $^1$H NMR (300.1 MHz, CDCl$_3$): δ 7.88-8.21 (m, 9H, pyrene-H), 7.27 (br s, 1H, NH), 5.12 (d, J=5.4 Hz, 2H, CH$_2$NH) 3.41 (s, 2H, CH$_3$COCH$_2$), 2.17 (s, 3H, CH$_3$CO); $^{13}$C NMR (100.1 MHz, CDCl$_3$): δ 204.4 (CH$_3$CO), 165.1 (CONH), 131.3, 130.8, 129.03, 128.96, 128.3, 128.2, 127.5, 127.4, 127.0, 126.1, 125.4, 125.3, 125.0, 124.8, 124.7, 122.7, 49.5 (CH$_3$COCH$_2$), 41.9 (CH$_2$NH) 31.0 (CH$_3$CO); IR: 3284 (N—H), 1714 (C=O, ketone), 1622 (C=O, amide band I), 1536 (C=O, amide band II) cm$^{-1}$; MS(ES$^-$) (m/z): 314.3 [M–H, 15%]$^-$, 350.1 [M+Cl, $^{35}$Cl, 30%]$^-$, 352.1 [M+Cl, $^{37}$Cl, 12%]$^-$; MS(ES$^+$) (m/z): 316.1 [M+H, 84%]$^+$, 338.3 [M+Na, 23%]$^+$. HRMS (m/z): [M–H]$^-$ calcd. for $C_{21}H_{16}NO_2$, 314.1187; found, 314.1185, error: 0.6 ppm.

(Z)-2-Acetyl-3-amino-4,4,4-trichloro-N-(pyren-1-ylmethyl)but-2-enamide (50)

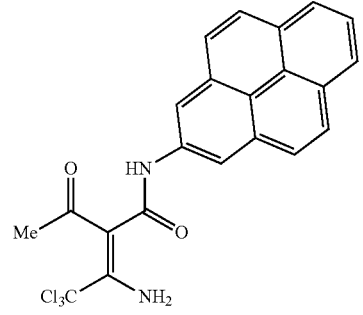

Yield: 76%, orange solid. mp: 124-126° C. (dec); $^1$H NMR (300.1 MHz, CDCl$_3$): δ 8.29 (d, J=9.0 Hz, 1H, pyrene-C8-H), 7.92-8.19 (m, 8H, pyrene-H), 6.21 (br s, 1H, CONHCH$_2$), 5.18 (d, J=5.1 Hz, 2H, CONHCH$_2$), 2.28 (s, 3H, CH$_3$CO); $^{13}$C NMR (100.1 MHz, CDCl$_3$): δ 197.6 (CH$_3$CO), 167.2 (C=C(NH$_2$)CCl$_3$), 156.7 (CONHCH$_2$), 131.5, 131.3, 130.7, 129.9, 128.4, 127.84, 127.77, 127.3, 126.2, 125.6, 125.5, 124.9, 122.9, 104.5 (C=C(NH$_2$)CCl$_3$), 93.4 (CCl$_3$), 43.2 (CH$_3$COCH$_2$), 28.6 (CH$_3$CO), CONHCH$_2$C quaternary signal not observed; IR: 3248 (N—H), 1717

(C=O, ketone), 1620 (C=O, amide), 1520 (C=C—NH$_2$) cm$^{-1}$; MS(ES$^-$) (m/z): 416.0 [M-C$_2$H$_3$O, $^{35}$Cl, $^{35}$Cl, $^{35}$Cl, 50%]$^-$, 418.1 [M-C$_2$H$_3$O, $^{35}$Cl, $^{35}$Cl, $^{37}$Cl, 23%]$^-$, 420.1 [M-C$_2$H$_3$O, $^{35}$Cl, $^{37}$Cl, $^{37}$Cl, 20%]$^-$, 421.1 [M-C$_2$H$_3$O, $^{37}$Cl, $^{37}$Cl, $^{37}$Cl, 8%]$^-$, 457.1 [M-H, $^{35}$Cl, $^{35}$Cl, $^{35}$Cl, 65%]$^-$, 459.0 [M-H, $^{35}$Cl, $^{35}$Cl, $^{37}$Cl, 100%]$^-$, 461.1 [M-H, $^{37}$Cl, $^{37}$Cl, $^{37}$Cl, 12%]$^-$, 463.1 [M-H, $^{37}$Cl, $^{37}$Cl, $^{37}$Cl, 3%]$^-$, 493.0 [M+$^{35}$Cl, $^{35}$Cl, $^{35}$Cl, $^{35}$Cl, 34%]$^-$, 495.0 [M+$^{35}$Cl, $^{35}$Cl, $^{35}$Cl, $^{37}$Cl, 35%]$^-$, 497.0 [M+$^{35}$Cl, $^{35}$Cl, $^{37}$Cl, $^{37}$Cl, 26%]$^-$, 499.0 [M+$^{35}$Cl, $^{37}$Cl, $^{37}$Cl, $^{37}$Cl, 4%]$^-$. HRMS (m/z): [M-H]$^-$ calcd. for C$_{23}$H$_{16}$$^{35}$Cl$_3$N$_2$O$_2$, 457.0283; found, 457.0277, error: 1.3 ppm.

5-Acetyl-2,2-diphenyl-6-((pyren-1-yl methyl)amino)-4-(trichloromethyl)-2,3-dihydro-1,3,2-oxaza-borinin-1-ium-2-uide (51; NBC20)

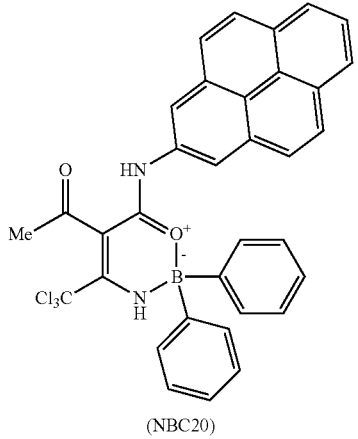

(NBC20)

Ethyl acetate/n-hexane, 1:4. Yield: 12%, yellow solid. mp: 167-169° C. (dec); $^1$H NMR (300.1 MHz, CDCl$_3$): δ 8.03-8.32 (m, 8H, pyrene-H), 7.95 (d, J=7.8 Hz, 1H, pyrene-C3-H), 7.82 (br s, 1H, C=C(NH)CCl$_3$), 7.14-7.33 (m, 10H, 2×Ph-H), 5.90 (t, J=5.1 Hz, 1H, CONHCH$_2$), 5.18 (d, J=5.4 Hz, 2H, CONHCH$_2$), 2.35 (s, 3H, CH$_3$CO); $^{13}$C NMR (100.1 MHz, CDCl$_3$): δ 187.1 (CH$_3$CO), 164.3 (C=C(NH)CCl$_3$), 162.2 (CONHCH$_2$), 131.6 (B-Ph(o)), 131.5, 131.3, 130.7, 129.8, 129.0, 128.4, 127.8, 127.7, 127.5 (B-Ph(m)), 127.3, 126.9 (B-Ph(o)), 126.2, 125.6, 125.5, 125.0, 124.8, 124.7, 122.8, 105.1 (C=C(NH)CCl$_3$), 92.8 (CCl$_3$), 42.7 (CH$_3$COCH$_2$), 23.4 (CH$_3$CO), B-Ph quaternary signal not observed; IR: 3320 (N—H), 3288 (N—H), 1630 (C=O), 1597 (C=C, conjugated), 1521 (C=C—NH) cm$^{-1}$; MS(ES$^-$) (m/z): 620.2 [M-H, $^{10}$B, $^{35}$Cl, $^{35}$Cl, $^{35}$Cl, 20%]$^-$, 621.2 [M-H, $^{11}$B, $^{35}$Cl, $^{35}$Cl, $^{35}$Cl, 98%]$^-$, 622.2 [M-H, $^{10}$B, $^{35}$Cl, $^{35}$Cl, $^{37}$Cl, 47%]$^-$, 623.2 [M-H, $^{11}$B, $^{35}$Cl, $^{35}$Cl, $^{37}$Cl, 100%]$^-$, 624.2 [M-H, $^{10}$B, $^{35}$Cl, $^{37}$Cl, $^{37}$Cl, 33%]$^-$, 625.2 [M-H, $^{11}$B, $^{35}$Cl, $^{37}$Cl, $^{37}$Cl, 19%]$^-$, 626.2 [M-H, $^{10}$B, $^{37}$Cl, $^{37}$Cl, $^{37}$Cl, 9%]$^-$, 627.3 [M-H, $^{11}$B, $^{37}$Cl, $^{37}$Cl, $^{37}$Cl, 4%]$^-$; MS(ES$^+$) (m/z): 622.2 [M+H, $^{10}$B, $^{35}$Cl, $^{35}$Cl, $^{35}$Cl, 11%]$^+$, 623.2 [M+H, $^{11}$B, $^{35}$Cl, $^{35}$Cl, $^{35}$Cl, 69%]$^+$, 624.2 [M+H, $^{10}$B, $^{35}$Cl, $^{35}$Cl, $^{37}$Cl, 30%]$^+$, 625.2 [M+H, $^{11}$B, $^{35}$Cl, $^{35}$Cl, $^{37}$Cl, 100%]$^+$, 626.2 [M+H, $^{10}$B, $^{35}$Cl, $^{37}$Cl, $^{37}$Cl, 36%]$^+$, 627.2 [M+H, $^{11}$B, $^{35}$Cl, $^{37}$Cl, $^{37}$Cl, 28%]$^+$, 628.2 [M+H, $^{10}$B, $^{37}$Cl, $^{37}$Cl, $^{37}$Cl, 5%]$^+$, 629.2 [M+H, $^{11}$B, $^{37}$Cl, $^{37}$Cl, $^{37}$Cl, 3%]$^+$. HRMS (m/z): [M-H]$^-$ calcd. for C$_{35}$H$_{25}$$^{11}$B$^{35}$Cl$_3$N$_2$O$_2$, 621.1080; found, 621.1072, error: 1.3 ppm.

N-Pyridin-4-ylacetoacetamide (52)

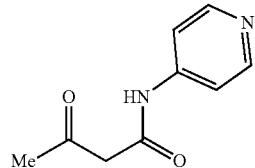

Yield: 57%, cream solid. mp: 92-93° C.; $^1$H NMR (300.1 MHz, CDCl$_3$): δ 9.61 (br s, 1H, NH), 8.53 (d, J=6.0 Hz, 2H, Py-meta), 7.52 (d, J=6.0 Hz, 2H, Py-ortho), 3.64 (s, 2H, CH$_3$COCH$_2$), 2.36 (s, 3H, CH$_3$CO); $^{13}$C NMR (100.1 MHz, CDCl$_3$): δ 204.7 (CH$_3$CO), 164.4 (CONH), 150.6 (Py(m)), 144.7 (Py(ipso)), 114.0 (Py(o)), 49.8 (CH$_3$COCH$_2$), 31.2 (CH$_3$CO); IR: 3245 (N—H), 1721 (C=O, ketone), 1690 (C=O, amide band I), 1595 (C=O, amide band II) cm$^{-1}$; MS(ES$^-$) (m/z): 176.9 [M-H, 100%]$^-$; MS(ES$^+$) (m/z): 178.9 [M+H, 100%]$^+$, 200.9 [M+Na, 11%]$^+$. HRMS (m/z): [M+H]$^+$ calcd. for C$_9$H$_{11}$N$_2$O$_2$, 179.0815; found, 179.0814, error: 0.6 ppm.

(Z)-2-Acetyl-3-amino-4,4,4-trichloro-N-(pyridine-4-yl)but-2-enamide (53)

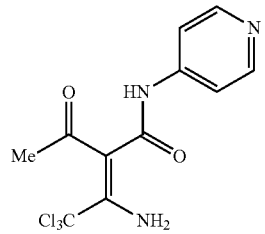

Yield: 51%, cream solid. mp: 105-107° C. (dec); $^1$H NMR (300.1 MHz, CDCl$_3$): δ 8.55 (d, J=6.0 Hz, 2H, Py-meta), 7.92 (br s, 1H, NH), 7.51 (d, J=6.0 Hz, 2H, Py-ortho), 2.37 (s, 3H, CH$_3$CO); IR: 3230 (N—H), 1654 (C=O), 1585 (C=C, conjugated), 1506 (C=C—NH$_2$) cm$^{-1}$; MS(ES$^-$) (m/z): 319.9 [M-H, $^{35}$Cl, $^{35}$Cl, $^{35}$Cl, 72%]$^-$, 321.9 [M-H, $^{35}$Cl, $^{35}$Cl, $^{37}$Cl, 100%]$^-$, 323.9 [M-H, $^{35}$Cl, $^{37}$Cl, $^{37}$Cl, 25%]$^-$, 326.0 [M-H, $^{37}$Cl, $^{37}$Cl, $^{37}$Cl, 3%]$^-$; MS(ES$^+$) (m/z): 322.0 [M+H, $^{35}$Cl, $^{35}$Cl, $^{35}$Cl, 84%]$^+$, 324.0 [M+H, $^{35}$Cl, $^{35}$Cl, $^{37}$Cl, 100%]$^+$, 326.0 [M+H, $^{35}$Cl, $^{37}$Cl, $^{37}$Cl, 70%]$^+$, 328.0 [M+H, $^{37}$Cl, $^{37}$Cl, $^{37}$Cl, 5%]$^+$. HRMS (m/z): [M+H]$^+$ calcd. for C$_{11}$H$_{11}$$^{35}$Cl$_3$N$_3$O$_2$, 321.9911; found, 321.9910, error: 0.3 ppm.

5-Acetyl-2,2-diphenyl-6-(pyridine-4-ylamino)-4-(trichloromethyl)-2,3-dihydro-1,3,2-oxazaborinin-1-ium-2-uide (54; NBC22)

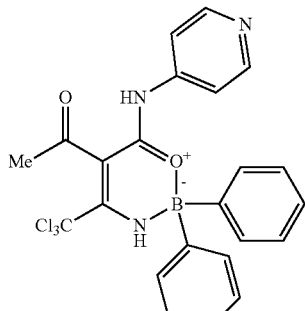

(NBC22)

Ethyl acetate/n-hexane, 3:5. The combined collected fractions were stirred in Et$_2$O (15 mL) instead of n-hexane for 30 mins. Yield: 6%, yellow solid. mp: 124-126° C. (dec); $^1$H NMR (300.1 MHz, CDCl$_3$): δ 8.51 (br s, 2H, C=C(N H)CCl$_3$), 8.01 (br s, 1H, NH), 7.21-7.47 (m, 14H, Py-ortho/meta & Ph-H), 2.43 (s, 3H, CH$_3$CO); IR: 3337 (N—H), 3247 (N—H), 1684 (C=O), 1586 (C=C, conjugated), 1508 (C=C—NH) cm$^{-1}$; MS(ES$^-$) (m/z): 482.9 [M–H, $^{10}$B, $^{35}$Cl, $^{35}$Cl, $^{35}$Cl, 5%]$^-$, 483.9 [M–H, $^{11}$B, $^{35}$Cl, $^{35}$Cl, $^{35}$Cl, 21%]$^-$, 485.0 [M–H, $^{10}$B, $^{35}$Cl, $^{35}$Cl, $^{37}$Cl, 7%]$^-$, 486.1 [M–H, $^{11}$B, $^{35}$Cl, $^{35}$Cl, $^{37}$Cl, 22%]$^-$, 487.2 [M–H, $^{10}$B, $^{35}$Cl, $^{37}$Cl, $^{37}$Cl, 6%]$^-$, 488.2 [M–H, $^{11}$B, $^{35}$Cl, $^{37}$Cl, $^{37}$Cl, 5%], 489.2 [M–H, $^{10}$B, $^{37}$Cl, $^{37}$Cl, $^{37}$Cl, 3%]$^-$, 490.2 [M–H, $^{11}$B, $^{37}$Cl, $^{37}$Cl, $^{37}$Cl, 1%]; MS(ES$^+$) (m/z): 485.1 [M+H, $^{10}$B, $^{35}$Cl, $^{35}$Cl, $^{35}$Cl, 4%]$^+$, 486.1 [M+H, $^{11}$B, $^{35}$Cl, $^{35}$Cl, $^{35}$Cl, 26%]$^+$, 487.1 [M+H, $^{10}$B, $^{35}$Cl, $^{35}$Cl, 371 11%]$^+$, 488.1 [M+H, $^{11}$B, $^{35}$Cl, $^{35}$Cl, $^{37}$Cl, 22%]$^+$, 489.1 [M+H, $^{10}$B, $^{35}$Cl, $^{37}$Cl, $^{37}$Cl, 3%]$^+$, 490.1 [M+H, $^{11}$B, $^{35}$Cl, $^{37}$Cl, $^{37}$Cl, 7%]$^+$, 491.1 [M+H, $^{10}$B, $^{37}$Cl, $^{37}$Cl, $^{37}$Cl, 2%]$^+$, 492.1 [M+H, $^{11}$B, $^{37}$Cl, $^{37}$Cl, $^{37}$Cl, 1%]$^+$. HRMS (m/z): [M+H]$^+$ calcd. for C$_{23}$H$_{20}$$^{11}$B$^{35}$Cl$_3$N$_3$O$_2$, 486.0709; found, 486.0709, error: 0.0 ppm.

Reaction scheme for 4-(Dichloromethyl)-6-Methyl-2,2-diphenyl-2,3-dihydro-1,3,2-oxazaborinin-1-ium-2-uide Scheme 6. Synthesis of oxazaborinine 55 from 6.

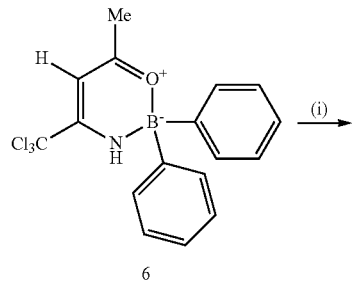

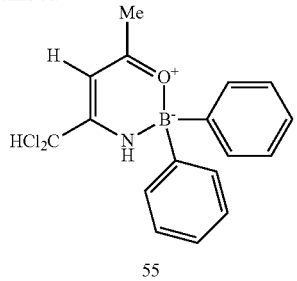

(i) NH$_3$, THF, MW, 150° C., 1 h.

4-(Dichloromethyl)-6-Methyl-2,2-diphenyl-2,3-dihydro-1,3,2-oxazaborinin-1-ium-2-uide (55; NBC29)

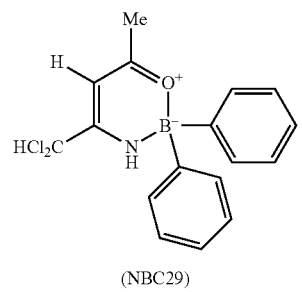

(NBC29)

Ammonia (20.9 mg, 1.23 mmol) was added to 6 (150 mg, 0.41 mmol) in anhydrous THF (total reaction volume of 3 mL). The mixture was subjected to microwave irradiation at 150° C. for 1 h in a 5 mL sealed vial. The reaction mixture was concentrated and purified by flash column chromatography (ethyl acetate/n-hexane, 2:23). Yield: 92.2 mg (68%), yellow oil. $^1$H NMR (300.1 MHz, CDCl$_3$): δ 7.13-7.34 (m, 10H, Aryl-H), 6.06 (s, 1H, CCl$_2$H), 5.30 (d, J$_{CH,NH}$=2.1 Hz, 1H, C=CH), 2.12 (s, 3H, CH$_3$CO); $^{13}$C NMR (100.6 MHz, CDCl$_3$): δ 184.0 (CH$_3$CO), 163.6 (Cl$_3$C(NH)C=C), 130.7 (B-Ph(o)), 126.4 (B-Ph(m)), 125.6 (B-Ph(p)), 92.1 (Cl$_3$C(NH)C=C), 66.4 (CCl$_2$H), 23.3 (CH$_3$CO), B-Ph quaternary signal not observed; IR: 3354 (N—H), 1616 (C=C, conjugated), 1539 (C=C—NH) cm$^{-1}$; MS(ES$^-$) (m/z): 329.0 [M–H, $^{10}$B, $^{35}$Cl, $^{35}$Cl, 15%]$^-$, 330.0 [M–H, $^{11}$B, $^{35}$Cl, $^{35}$Cl, 100%]$^-$, 331.0 [M–H, $^{10}$B, $^{35}$Cl, $^{37}$Cl, 29%]$^-$, 332.0 [M–H, $^{11}$B, $^{35}$Cl, $^{37}$Cl, 40%]$^-$, 333.0 [M–H, $^{10}$B, $^{37}$Cl, $^{37}$Cl, 15%]$^-$, 334.0 [M–H, $^{11}$B, $^{37}$Cl, $^{37}$Cl, 11%]$^-$; MS(ES$^+$) (m/z): 253.0 [M–Ph, $^{10}$B, $^{35}$Cl, $^{35}$Cl, 17%]$^+$, 253.9 [M–Ph, $^{11}$B, $^{35}$Cl, $^{35}$Cl, 100%]$^+$, 255.0 [M–Ph, $^{10}$B, $^{35}$Cl, $^{37}$Cl, 35%]$^+$, 256.0 [M–Ph, $^{11}$B, $^{35}$Cl, $^{37}$Cl, 69%]$^+$, 257.0 [M–Ph, $^{10}$B, $^{37}$Cl, $^{37}$Cl, 17%]$^+$, 257.9 [M–Ph, $^{11}$B, $^{37}$Cl, $^{37}$Cl, 11%]$^+$, 330.0 [M+H, $^{10}$B, $^{35}$Cl, $^{35}$Cl, 3%]$^+$, 331.0 [M+H, $^{11}$B, $^{35}$Cl, $^{35}$Cl, 12%]$^+$, 332.0 [M+H, $^{10}$B, $^{35}$Cl, $^{37}$Cl, 10%]$^+$, 333.0 [M+H, $^{11}$B, $^{35}$Cl, $^{37}$Cl, 6%]$^+$, 334.0 [M+H, $^{10}$B, $^{37}$Cl, $^{37}$Cl, 7%]$^+$, 335.0 [M+H, $^{11}$B, $^{37}$Cl, $^{37}$Cl, 1%]$^+$; HRMS (m/z): [M–H]$^-$ calcd. for C$_{17}$H$_{15}$$^{11}$B$^{35}$Cl$_2$NO, 330.0629; found, 330.0640, error: 3.3 ppm.

General Reaction Scheme for di(aryl)oxazaborinine Synthesis

Scheme 7. Synthesis of bis(aryl)oxazaborinines.

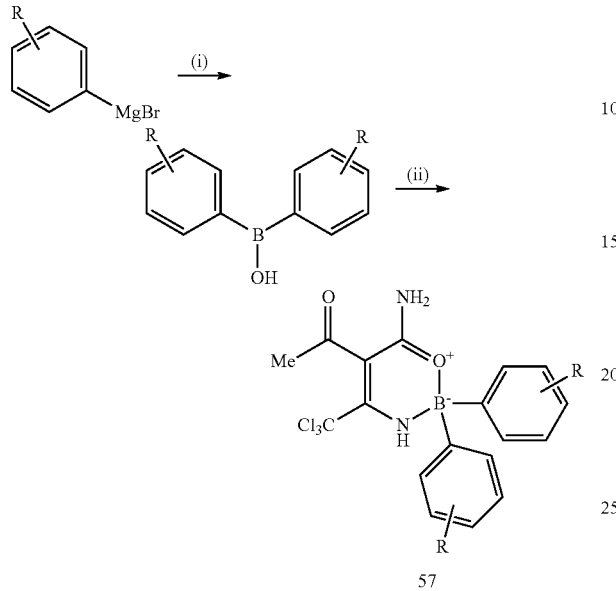

57

R = p-Me
(i) B(OMe)₃, THF, r.t., 3 h, 5% HCl; (ii) 39, THF, r.t., 16 h.

General Procedure for di(aryl)oxazaborinine Synthesis

B(OMe)₃ (5 mmol) was added to an appropriate arylmagnesium bromide (10 mmol) in anhydrous THF (total reaction volume of 15 mL). The mixture was stirred at room temperature under $N_2$ for 2.5 h and then hydrolysed with 5% $HCl_{(aq)}$ (15 mL). EtOAc (30 mL) was added and the mixture washed with $H_2O$, concentrated in vacuo and purified by flash column chromatography to give the corresponding bis(aryl)borinic acid.

(Z)-2-Acetyl-3-amino-4,4,4-trichlorobut-2-enamide (39, 3 eq), as an example, was added to an appropriate bis(aryl) borinic acid (1 eq) in anhydrous THF (5 mL). The mixture was stirred at room temperature under Ar for 16 h. The mixture was concentrated in vacuo and purified by flash column chromatography. The collected fractions were combined, evaporated in vacuo and stirred in cold n-hexane (15 mL) for 30 mins. The precipitate was then filtered and dried under vacuum to give the corresponding bis(aryl)oxazaborinine products.

Di-p-tolylborinic Acid (56)

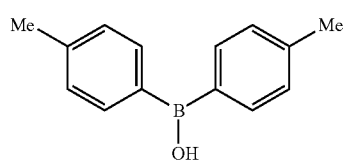

56

Ethyl acetate/n-hexane, 1:19. Yield: 58%, colourless oil. ¹H NMR (300.1 MHz, CDCl₃): δ 7.63 (d, J=7.8 Hz, 2H, B-tolyl(m)-H), 7.18 (d, J=7.5 Hz, 2H, B-tolyl(o)-H), 5.65 (br s, 1H, B—OH), 2.33 (s, 6H, CH₃); ¹³C NMR (100.6 MHz, CDCl₃): δ 141.2 (B-tolyl(p)), 134.8 (B-tolyl(o)), 128.7 (B-tolyl(m)), 21.7 (CH₃), B-tolyl(i) quaternary signal not observed; MS ionisation was not possible with the available instrumentation used.

5-Acetyl-6-amino-2,2-bis(p-tolyl)-4-(trichloromethyl)-2,3-dihydro-1,3,2-oxazaborinin-1-ium-2-uide (57; NBC32)

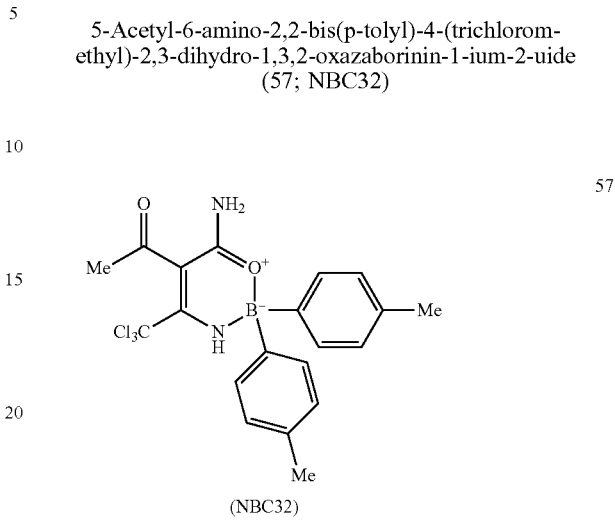

(NBC32)

Ethyl acetate/n-hexane, 2:23. Yield: 14%, yellow solid. mp: 145-148° C. (dec); ¹H NMR (300.1 MHz, CDCl₃): δ 9.23 (br s, 1H, CONH₂), 7.58 (br s, 1H, Cl₃C(NH)C=C), 7.29 (d, J=7.5 Hz, 2H, B-tolyl(o)-H), 7.12 (d, 7.5 Hz, 2H, B-tolyl(m)-H), 5.92 (br s, 1H, CONH₂), 2.34 (s, 6H, CH₃Ar), 2.32 (s, 3H, CH₃CO); ¹³C NMR (100.6 MHz, CDCl₃): δ 198.1 (CH₃CO), 169.2 (CONH₂), 165.5 (Cl₃C(NH)C=C), 156.1 (B-tolyl(i)), 136.2 (B-tolyl(p)), 132.0 (B-tolyl(o)), 128.2 (B-tolyl(m)), 97.9 (Cl₃C(NH)C=C), 94.5 (CCl₃), 34.0 (CH₃CO), 21.3 (CH₃); IR: 3388 (N—H), 3313 (N—H), 1644 (C=O), 1608 (C=C, conjugated), 1561 (C=C—NH) cm⁻¹; MS(ES⁻) (m/z): 434.2 [M–H, ¹⁰B, ³⁵Cl, ³⁵Cl, ³⁵Cl, 12%]⁻, 435.2 [M–H, ¹¹B, ³⁵Cl, ³⁵Cl, ³⁵Cl, 100%]⁻, 436.2 [M–H, ¹⁰B, ³⁵Cl, ³⁵Cl, ³⁷Cl, 24%]⁻, 437.2 [M–H, ¹¹B, ³⁵Cl, ³⁵Cl, ³⁷Cl, 50%]⁻, 438.2 [M–H, ¹⁰B, ³⁷Cl, ³⁷Cl, 11%]⁻, 439.2 [M–H, ¹¹B, ³⁵Cl, ³⁷Cl, ³⁷Cl, 10%]⁻, 440.2 [M–H, ¹⁰B, ³⁷Cl, ³⁷Cl, ³⁷Cl, 3%]⁻, 441.2 [M–H, ¹¹B, ³⁷Cl, ³⁷Cl, ³⁷Cl, 1%]⁻; MS(ES⁺) (m/z): 344.1 [M-Tolyl, ¹⁰B, ³⁵Cl, ³⁵Cl, ³⁵Cl, 10%]⁺, 345.0 [M-Tolyl, ¹¹B, ³⁵Cl, ³⁵Cl, ³⁵Cl, 27%]⁺, 346.0 [M-Tolyl, ¹⁰B, ³⁵Cl, ³⁵Cl, ³⁷Cl, 12%]⁺, 347.0 [M-Tolyl, ¹¹B, ³⁵Cl, ³⁵Cl, ³⁷Cl, 36%]⁺, 348.0 [M-Tolyl, ¹⁰B, ³⁵Cl, ³⁷Cl, ³⁷Cl, 5%]⁺, 349.1 [M-Tolyl, ¹¹B, ³⁵Cl, ³⁷Cl, ³⁷Cl, 21%]⁺, 350.1 [M-Tolyl, ¹⁰B, ³⁷Cl, ³⁷Cl, ³⁷Cl, 5%]⁺, 351.1 [M-Tolyl, ¹¹B, ³⁷Cl, ³⁷Cl, ³⁷Cl, 2%]⁺, 436.1 [M+H, ¹⁰B, ³⁵Cl, ³⁵Cl, ³⁵Cl, 3%]⁺, 437.1 [M+H, ¹¹B, ³⁵Cl, ³⁵Cl, ³⁵Cl, 9%]⁺, 438.1 [M+H, ¹⁰B, ³⁵Cl, ³⁵Cl, ³⁷Cl, 5%]⁻, 439.1 [M+H, ¹¹B, ³⁵Cl, ³⁵Cl, ³⁷Cl, 10%]⁺, 440.1 [M+H, ¹⁰B, ³⁵Cl, ³⁷Cl, ³⁷Cl, 3%]⁺, 441.1 [M+H, ¹¹B, ³⁵Cl, ³⁷Cl, ³⁷Cl, 3%]⁺, 442.1 [M+H, ¹⁰B, ³⁷Cl, ³⁷Cl, ³⁷Cl, 1%]⁺, 443.1 [M+H, ¹¹B, ³⁷Cl, ³⁷Cl, ³⁷Cl, 1%]⁺. HRMS (m/z): [M+H]⁺ calcd. for C₂₀H₂₁¹¹B³⁵Cl₃N₂O₂, 437.0756; found, 437.0738, error: 4.1 ppm.

General Reaction Scheme for aryl(phenyl)oxazaborinine Synthesis

Scheme 8. Synthesis of aryl(phenyl)oxazaborinines.

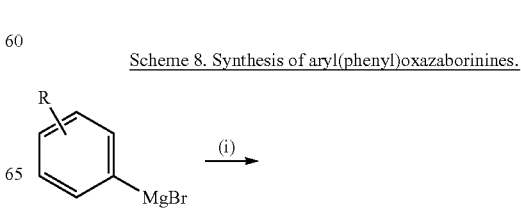

-continued

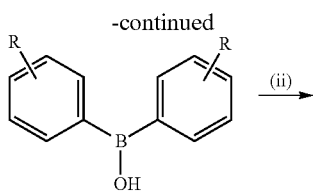

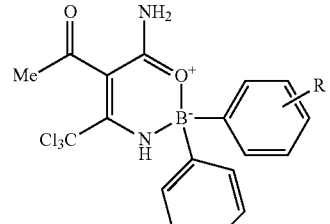

59

R = p-Me
(i) Phenylboronic acid pinacol ester, THF, r.t., 3 h, 6M HCl; (iii) 39, THF, r.t., 16 h.

General Procedure for aryl(phenyl)oxazaborinine Synthesis

An appropriate arylmagnesium bromide (5 mmol) was added phenylboronic acid pinacol ester (5 mmol) in anhydrous THF (total reaction volume of 15 mL). The mixture was stirred at room temperature under $N_2$ for 2.5 h and then hydrolysed with 6M $HCl_{(aq)}$ (15 mL). EtOAc (30 mL) was added and the mixture washed with $H_2O$, concentrated in vacuo and purified by flash column chromatography to give the corresponding aryl(phenyl)borinic acid.

(Z)-2-Acetyl-3-amino-4,4,4-trichlorobut-2-enamide (39, 3 eq), as an example, was added to an appropriate aryl (phenyl)borinic acid (1 eq) in anhydrous THF (5 mL). The mixture was stirred at room temperature under Ar for 16 h. The mixture was concentrated in vacuo and purified by flash column chromatography. The collected fractions were combined, evaporated in vacuo and stirred in cold n-hexane (15 mL) for 30 mins. The precipitate was then filtered and dried under vacuum to give the corresponding aryl(phenyl)oxazaborinine products.

(Phenyl)(p-tolyl)borinic Acid (58)

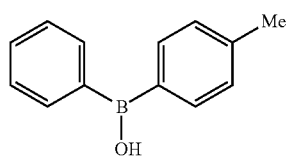

58

Ethyl acetate/n-hexane, 2:23. Yield: 45%, colourless oil. $^1$H NMR (300.1 MHz, CDCl$_3$): δ 7.72 (d, J=7.8 Hz, 2H, B-Ph(o)), 7.64 (d, J=7.8 Hz, 2H, B-tolyl(o)), 7.32-7.47 (m, 3H, B-Ph(m/p)), 7.19 (d, J=7.8 Hz, 2H, B-tolyl(m)), 5.74 (br s, 1H, B—O$\underline{H}$), 2.33 (s, 3H, C$\underline{H}_3$); $^{13}$C NMR (100.6 MHz, CDCl$_3$): δ 141.4 (B-tolyl(p)), 135.0 (B-Ph(o)), 134.6 (B-tolyl(o)), 130.9 (B-Ph(p)), 128.8 (B-tolyl(m)), 127.9 (B-Ph(m)), 21.7 (CH$_3$), B-tolyl(i) and B-Ph(i) quaternary signals not observed; MS(ES$^-$) (m/z): 194.0 [M−H, $^{10}$B, 4%]$^-$, 195.1 [M−H, $^{11}$B, 25%]$^-$. HRMS (m/z): [M−H]$^-$ calcd. for C$_{13}$H$_{12}$$^{11}$BO, 195.0987; found, 195.0973, error: 7.2 ppm.

5-Acetyl-6-amino-2-(phenyl)-2-(p-tolyl)-4-(trichloromethyl)-2,3-dihydro-1,3,2-oxazaborinin-1-ium-2-uide (59; NBC33)

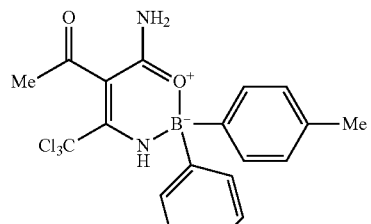

59

(NBC32)

Ethyl acetate/n-hexane, 2:23. Yield: 2%, yellow solid. mp: 141-143° C.; $^1$H NMR (300.1 MHz, CDCl$_3$): δ 9.25 (br s, 1H, CON$\underline{H}_2$), 7.59 (br s, 1H, Cl$_3$C(N$\underline{H}$)C=C), 7.40 (d, J=6.0 Hz, 2H, B-Ph(o)), 7.23-7.34 (m, 5H, B-Ph(m/p), B-tolyl(o)), 7.12 (d, J=7.8 Hz, 2H, B-tolyl(m)), 5.94 (br s, 1H, CON$\underline{H}_2$), 2.34 (s, 3H, C$\underline{H}_3$), 2.31 (s, 3H, C$\underline{H}_3$CO); $^{13}$C NMR (100.6 MHz, CDCl$_3$): δ 192.8 (CH$_3$CO), 163.9 (Cl$_3$C (NH)$\underline{C}$=C), 160.3 (CONH$_2$), 131.1 (B-tolyl(p)), 126.8 (B-Ph(o)), 126.6 (B-tolyl(o)), 123.0 (B-tolyl(m)), 122.1 (B-Ph(m)), 121.5 (B-Ph(p)), 92.7 (Cl$_3$C(NH)C=$\underline{C}$), 89.2 (CCl$_3$), 28.7 (C$\underline{H}_3$CO), 16.0 (C$\underline{H}_3$); MS(ES$^-$) (m/z): 420.2 [M−H, $^{10}$B, $^{35}$Cl, $^{35}$Cl, $^{35}$Cl, 12%]$^-$, 421.1 [M−H, $^{11}$B, $^{35}$Cl, $^{35}$Cl, $^{35}$Cl, 80%]$^-$, 422.2 [M−H, $^{10}$B, $^{35}$Cl, $^{35}$Cl, $^{37}$Cl, 33%]$^-$, 423.2 [M−H, $^{11}$B, $^{35}$Cl, $^{35}$Cl, $^{37}$Cl, 100%]$^-$, 424.1 [M−H, $^{10}$B, $^{35}$Cl, $^{37}$Cl, $^{37}$Cl, 13%]$^-$, 425.1 [M−H, $^{11}$B, $^{35}$Cl, $^{37}$Cl, $^{37}$Cl, 24%]$^-$, 426.2 [M−H, $^{10}$B, $^{37}$Cl, $^{37}$Cl, $^{37}$Cl, 5%]$^-$, 427.2 [M−H, $^{11}$B, $^{37}$Cl, $^{37}$Cl, $^{37}$Cl, 3%]$^-$. HRMS (m/z): [M+H]$^+$ calcd. for C$_{19}$H$_{19}$$^{11}$B$^{35}$Cl$_3$N$_2$O$_2$, 423.0600; found, 423.0605, error: 1.2 ppm.

Example 2—Activity Studies

Figure 2:
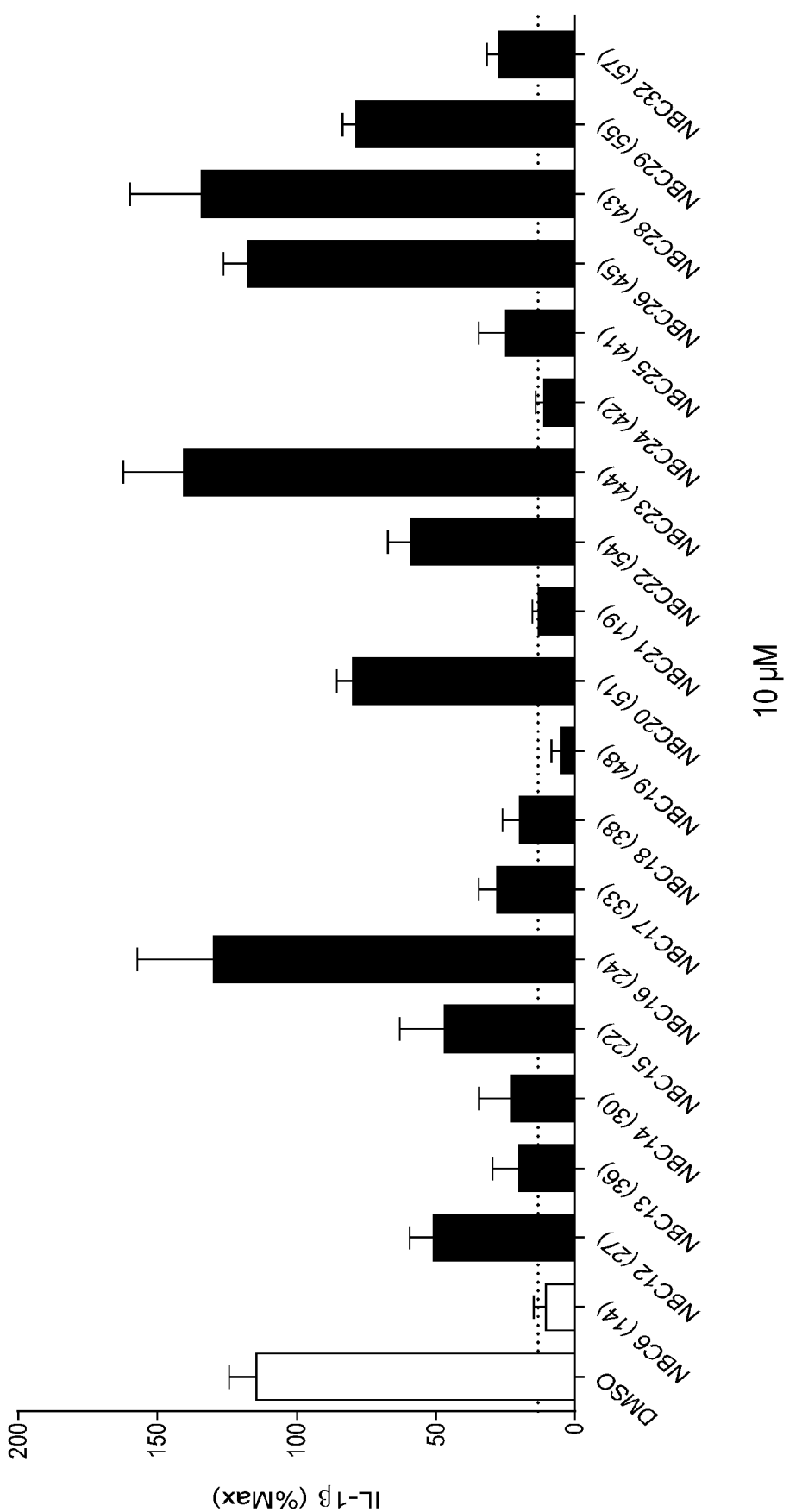
Figure 3:
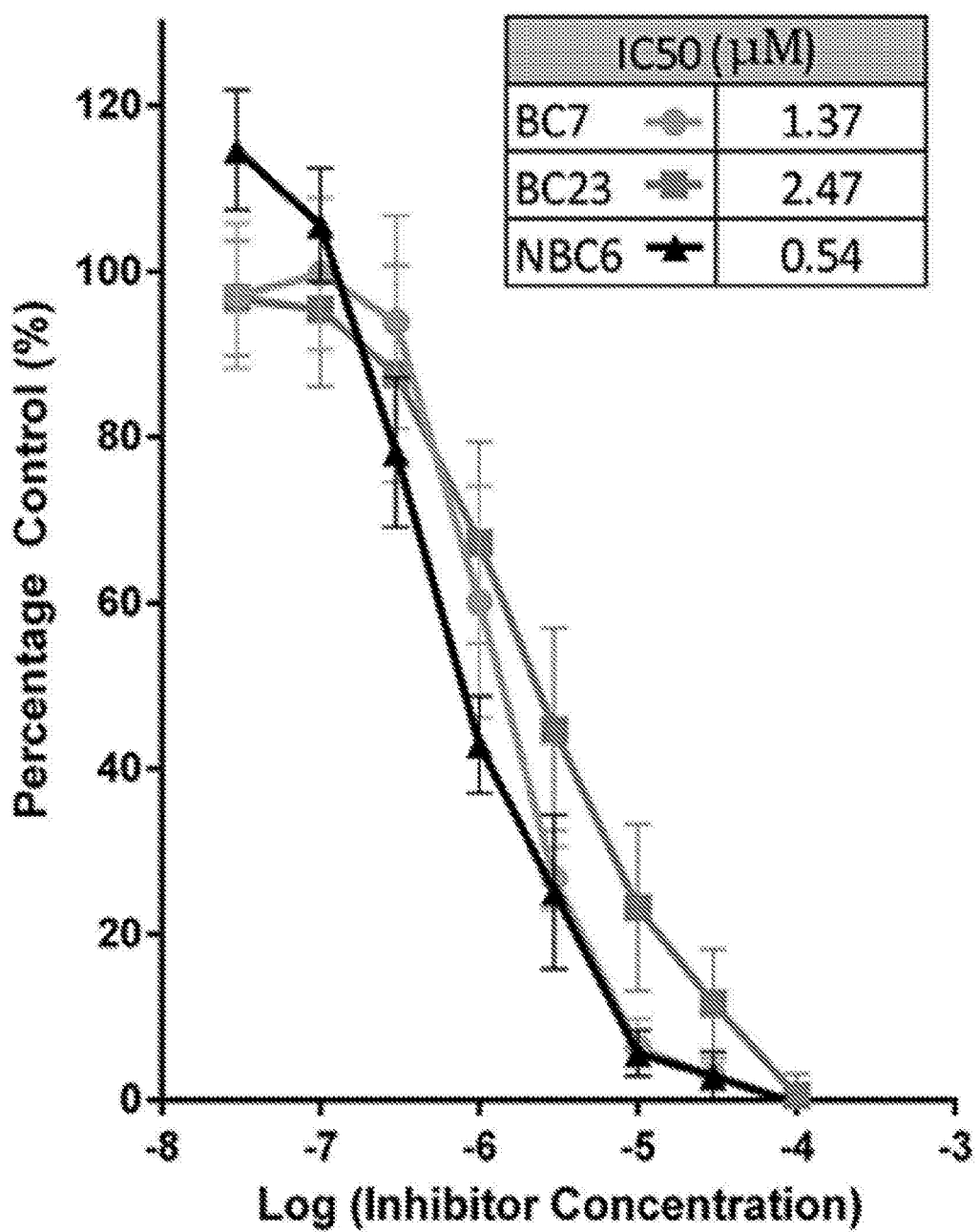
FIG. 3 shows the percentage control against log inhibitor concentration for compounds 3 (BC7), 6 (BC23) and 14 (NBC6).

To screen the compounds of the invention, the human monocytic THP1 cell line was used. Cells were primed with LPS (1 µg/ml, 4 h) and then treated with vehicle (0.5% DMSO) or NBC molecule of the invention (see compounds listed below) at 10 µM for 15 min before activation of the inflammasome and IL-1β release with nigericin (20 µM, 1 h). The NBC molecule was present throughout nigericin stimulation. The effects of the molecules on IL-1β release were normalised to nigericin-induced IL-1β release in the absence of any inhibitor (FIGS. 1-3).

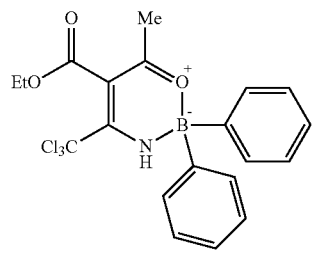

3

4
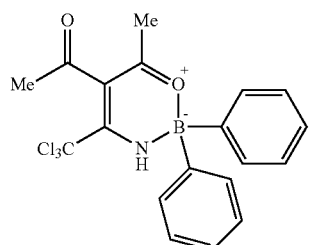
6
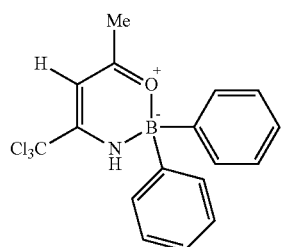
8
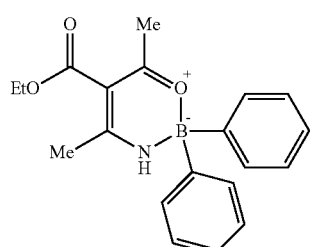
9
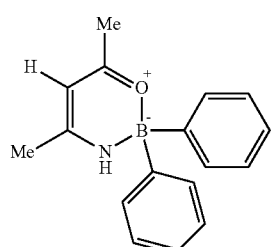
11
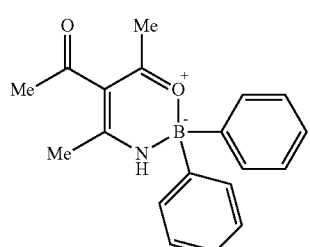
13
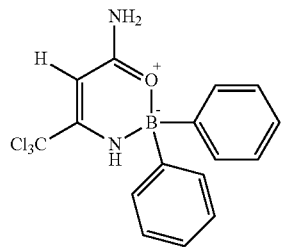
14
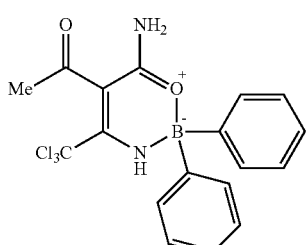
19
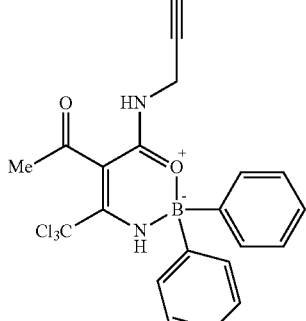
22
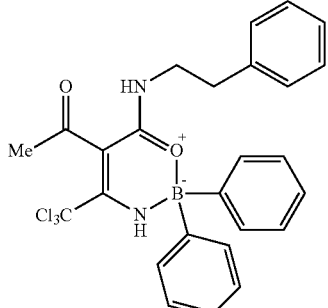
24
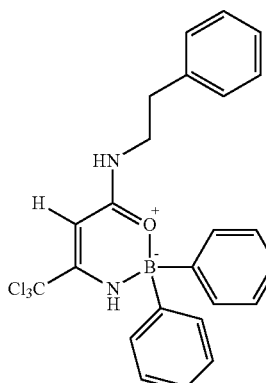
41
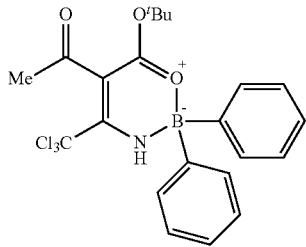

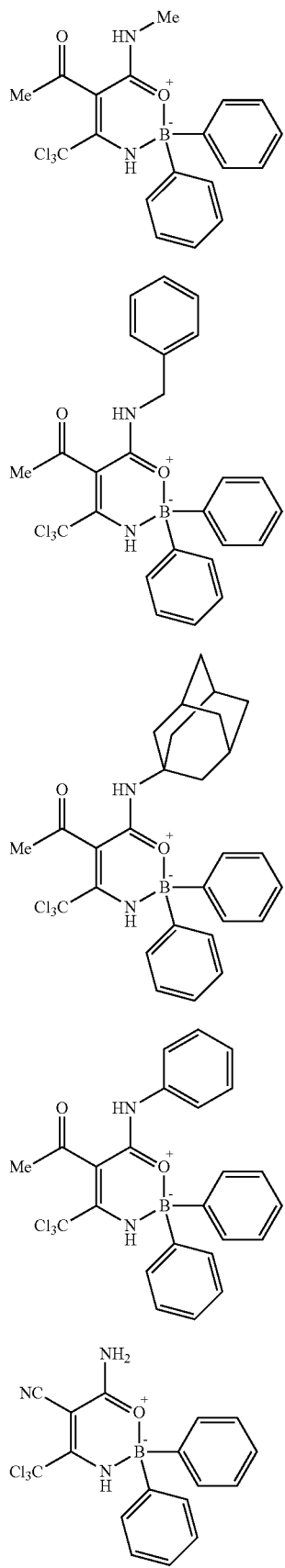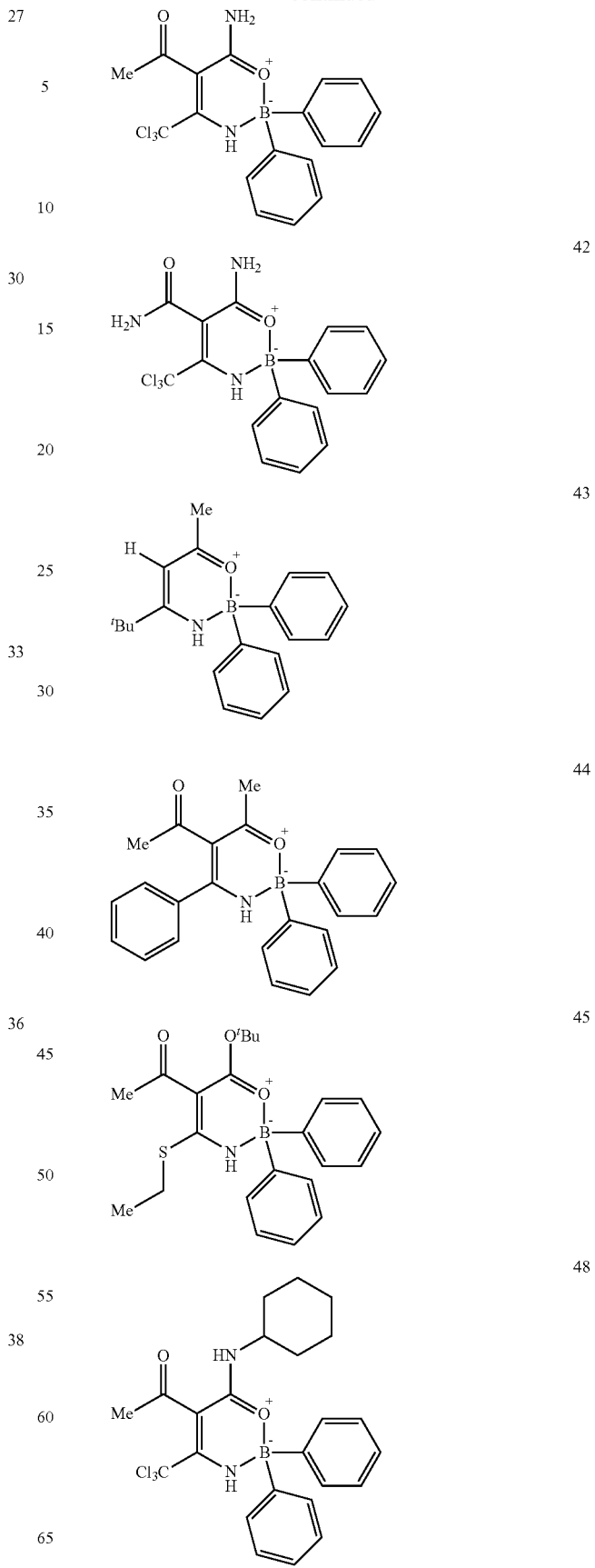

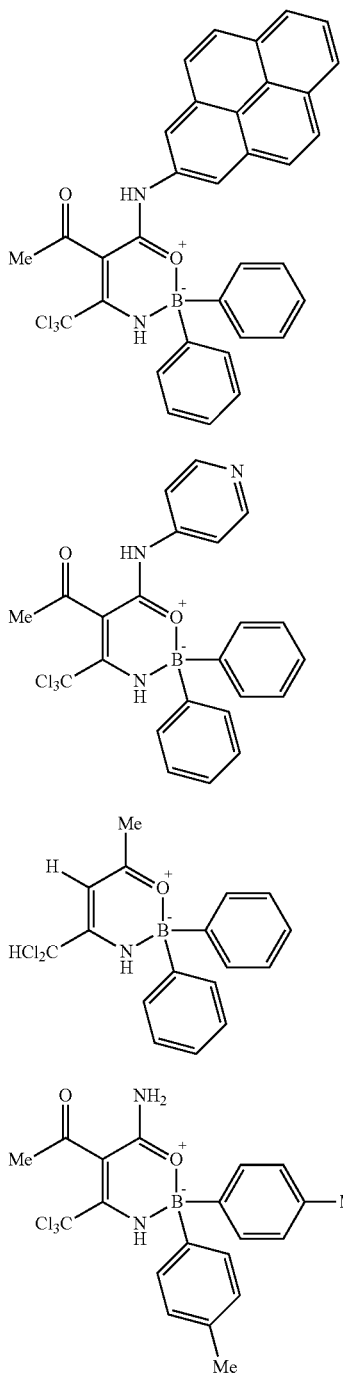

From the screen of NBC molecules, compounds 14 (NBC6), 48 (NBC19) and 42 (NBC24) were observed to be the most potent (FIGS. 1 and 2), and further analysis revealed increased potency of compound 14 (NBC6) with an IC50 of 500 nM (FIG. 3). Due to the presence of the amide group in compound 14 (NBC6) there was also increased solubility with the c log P of 14 (NBC6) now 3.4 compared to 4.99 for 3 (BC7) and 6 (BC23). The solubility of compound 14 (NBC6) is now comparable to drugs of the NSAID class such as Ibuprofen (3.68) and Mefenamic acid (3.36).

Example 3—X-ray Crystalloaraphy

Figure 4A:
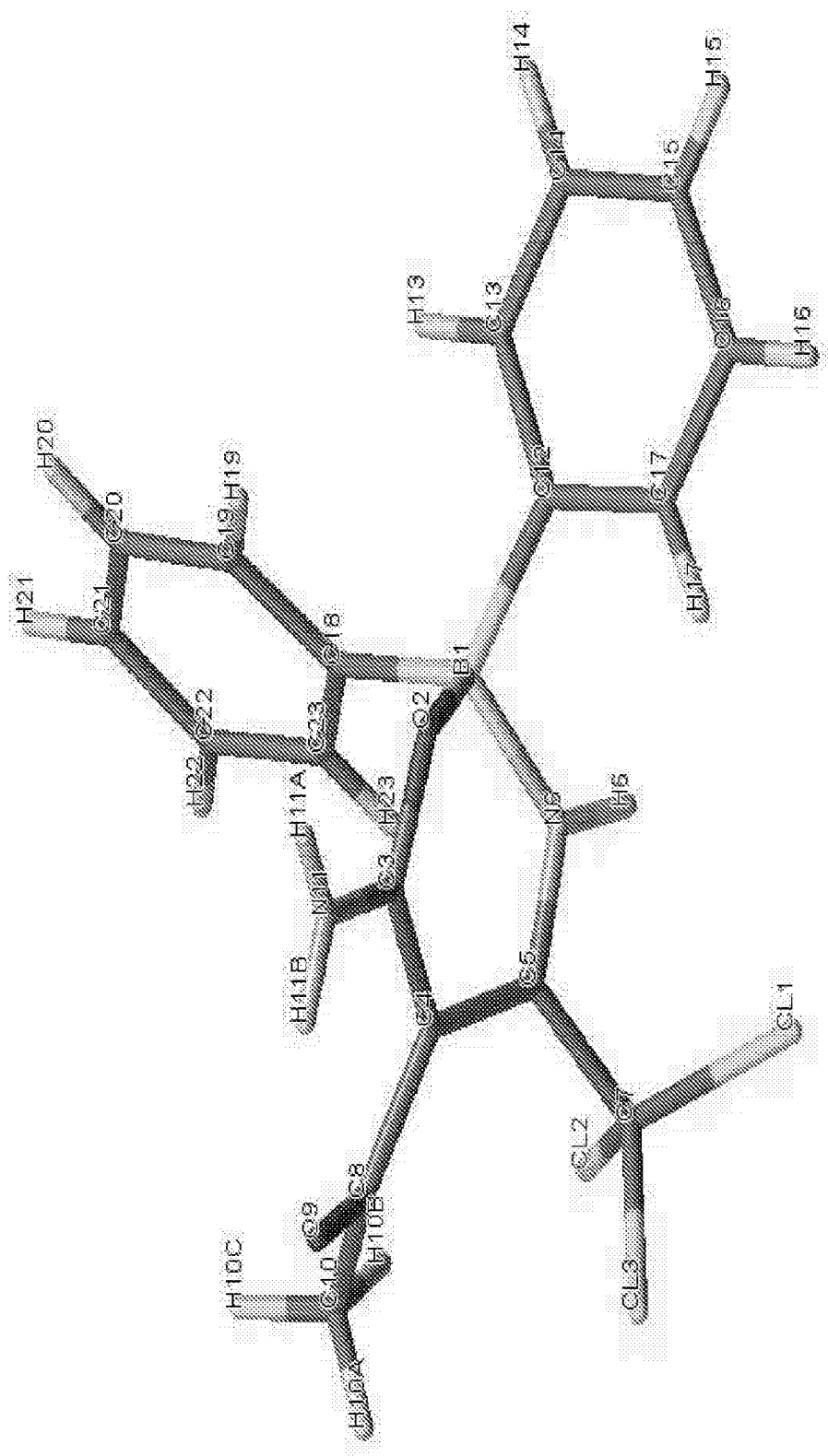
FIG. 4 shows the crystal structures of: a) compound 14 (NBC6) in Example 1; and b) compound 16 (NBC11) in Example 1.
Figure 4B:
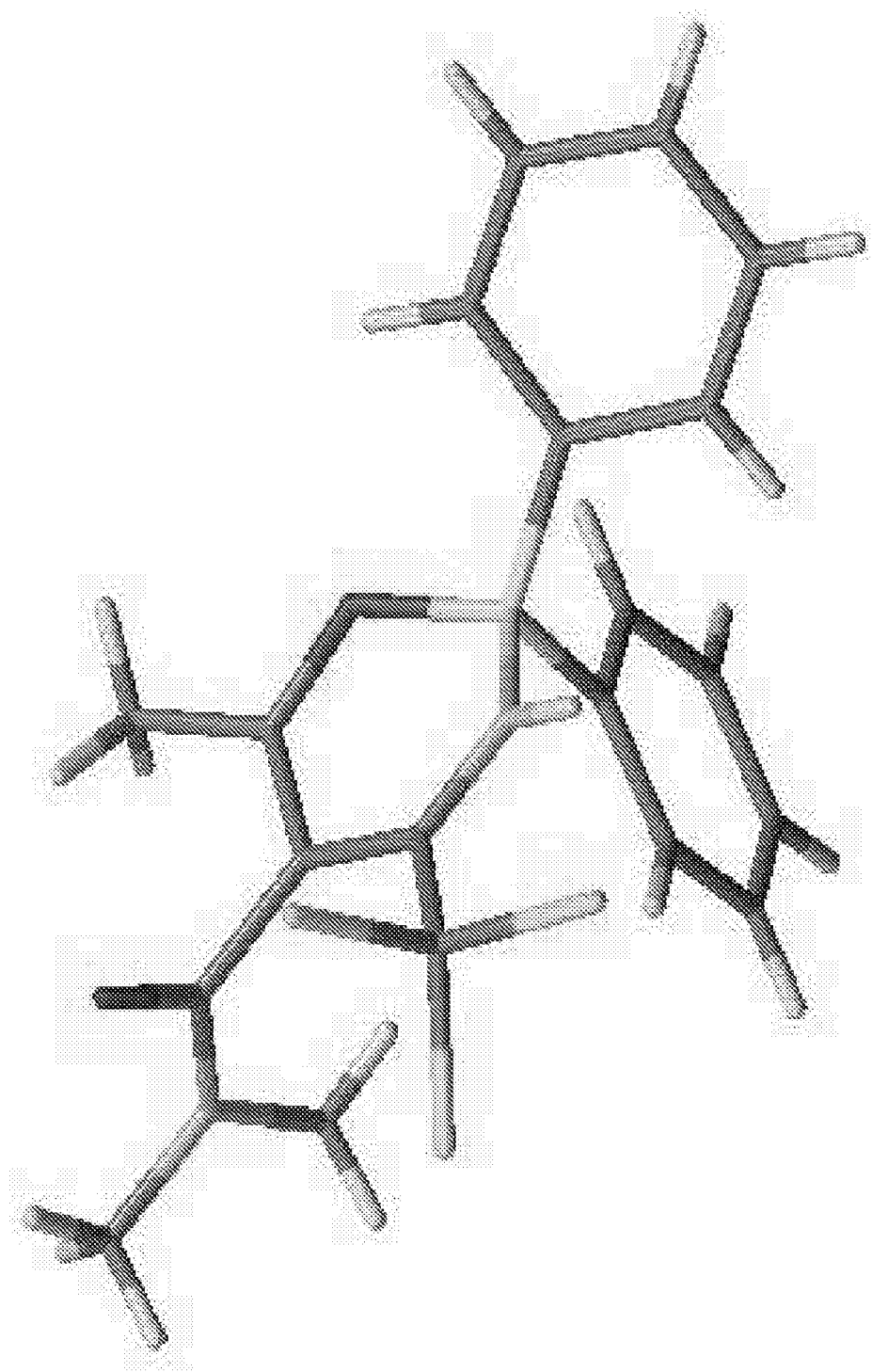

FIG. 4 shows the crystal structures of compound 14 (NBC6) in Example 1 and compound 16 (NBC11) in Example 1.

While specific embodiments of the invention have been described herein for the purpose of reference and illustration, various modifications will be apparent to a person skilled in the art without departing from the scope of the invention as defined by the appended claims.

REFERENCES

1 Rock, K. L., Latz, E., Ontiveros, F. & Kono, H. The sterile inflammatory response. Annual review of immunology 28, 321-342, doi:10.1146/annurev-immunol-030409-101311 (2010).
2 Dinarello, C. A., Simon, A. & van der Meer, J. W. Treating inflammation by blocking interleukin-1 in a broad spectrum of diseases. Nature reviews. Drug discovery 11, 633-652, doi:10.1038/nrd3800 (2012).
3 Chen, G. Y. & Nunez, G. Sterile inflammation: sensing and reacting to damage. Nature reviews. Immunology 10, 826-837, doi:10.1038/nri2873 (2010).
4 Takeuchi, O. & Akira, S. Pattern recognition receptors and inflammation. Cell 140, 805-820, doi:10.1016/j.cell.2010.01.022 (2010).
5 Latz, E., Xiao, T. S. & Stutz, A. Activation and regulation of the inflammasomes. Nature reviews. Immunology 13, 397-411, doi:10.1038/nri3452 (2013).
6 Gross, O. et al. Inflammasome activators induce interleukin-1 alpha secretion via distinct pathways with differential requirement for the protease function of caspase-1. Immunity 36, 388-400, doi:10.1016/j.immuni.2012.01.018 (2012).
7 Denes, A., Lopez-Castejon, G. & Brough, D. Caspase-1: is IL-1 just the tip of the ICEberg? Cell death & disease 3, e338, doi:10.1038/cddis.2012.86 (2012).
8 Mariathasan, S. et al. Cryopyrin activates the inflammasome in response to toxins and ATP. Nature 440, 228-232, doi:10.1038/nature04515 (2006).
9 Luheshi, N. M., Giles, J. A., Lopez-Castejon, G. & Brough, D. Sphingosine regulates the NLRP3-inflammasome and IL-1 beta release from macrophages. European journal of immunology 42, 716-725, doi:10.1002/eji.201142079 (2012).
10 Martinon, F., Petrilli, V., Mayor, A., Tardivel, A. & Tschopp, J. Gout-associated uric acid crystals activate the NALP3 inflammasome. Nature 440, 237-241, doi:10.1038/nature04516 (2006).
11 Duewell, P. et al. NLRP3 inflammasomes are required for atherogenesis and activated by cholesterol crystals. Nature 464, 1357-1361, doi:10.1038/nature08938 (2010).
12 Halle, A. et al. The NALP3 inflammasome is involved in the innate immune response to amyloid-beta. Nature immunology 9, 857-865, doi:10.1038/ni.1636 (2008).
13 Munoz-Planillo, R. et al. K(+) efflux is the common trigger of NLRP3 inflammasome activation by bacterial toxins and particulate matter. Immunity 38, 1142-1153, doi:10.1016/j.immuni.2013.05.016 (2013).
14 Hornung, V. & Latz, E. Critical functions of priming and lysosomal damage for NLRP3 activation. European journal of immunology 40, 620-623, doi:10.1002/eji.200940185 (2010).
15 Shimada, K. et al. Oxidized mitochondrial DNA activates the NLRP3 inflammasome during apoptosis. Immunity 36, 401-414, doi:10.1016/j.immuni.2012.01.009 (2012).

16 Lopez-Castejon, G. et al. Deubiquitinases regulate the activity of caspase-1 and interleukin-1 beta secretion via assembly of the inflammasome. *The Journal of biological chemistry* 288, 2721-2733, doi:10.1074/jbc.M112.422238 (2013).

17 Juliana, C. et al. Non-transcriptional priming and deubiquitination regulate NLRP3 inflammasome activation. *The Journal of biological chemistry* 287, 36617-36622, doi:10.1074/jbc.M112.407130 (2012).

18 Py, B. F., Kim, M. S., Vakifahmetoglu-Norberg, H. & Yuan, J. Deubiquitination of NLRP3 by BRCC3 critically regulates inflammasome activity. *Molecular cell* 49, 331-338, doi:10.1016/j.molcel.2012.11.009 (2013).

19 Dinarello, C. A. & van der Meer, J. W. Treating inflammation by blocking interleukin-1 in humans. *Seminars in immunology* 25, 469-484, doi:10.1016/j.smim.2013.10.008 (2013).

Lopez-Castejon, G. & Pelegrin, P. Current status of inflammasome blockers as anti-inflammatory drugs. *Expert opinion on investigational drugs* 21, 995-1007, doi: 10.1517/13543784.2012.690032 (2012).

21 Veronese, A. C., Talmelli, C. & Gandolfi, V., Metal-catalyzed Reactions of β-Dicarbonyls with Trichloroacetonitrile: Synthesis of β-Trichloromethylenaminodiones. *J. Mol. Catal.* 1986; 34: 195-198.

22 Hosoya, T., Uekusa, H., Ohashi, Y., Ohhara, T & Kuroki, R. A New Photoisomerization Process of the 4-Cyanobutyl Group in a Cobaloxime Complex Crystal Observed by Neutron Diffration. *Bull. Chem. Soc. Jpn.* 2006; 79(5): 692-701.

23 Vasil'ev, L. S., Azarevich, O. G., Bogdanov, V. S., Ugrak, B. I. & Dorokhov, V. A. Chelate synthesis of functionally substituted 2-trichloromethylpyridines. *Russ. Chem. Bull.* 1994; 43(7): 1342-1343.

24 Coenen, M., Faust, J., Ringel, C. & Mayer, R. Synthesen mit Trichloracetonitril. *J. Prakt. Chem.* 1965; 27(5-6): 239-250.

25 Vasil'ev, L. S., Azarevich, O. G., Bogdanov, V. S., Bochkareva, M. N. & Dorokhov, V. A. Boron chelates with 5,5,5-trifluoro- and 5,5,5-trichloro-4-aminopent-3-en-2-ones. *Bull. Russ. Acad. Sci. Ch₊.* 1992; 41(11): 2104-2107.

26 Álvarez-Pérez, M. & Marco-Contelles, J. Modification of conditions for the selective p reparation of 2-amino-3-cyano-4-phenylpyridines. *ARKIVOC.* 2011; ii: 283-296.

27 Ibrahim, N. S., Abdelrazek, F. M., Aziz, S. I. & Elnagdi, M. H. Nitriles in Organic Synthesis: The Reaction of Trichloroacetonitrile with Active Methylene Reagents. *Monatsh Chem.* 1985; 116: 551-556.

The invention claimed is:

1. A compound having the structural formula I shown below:

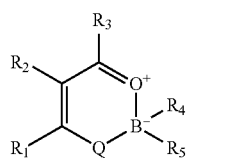

(I)

wherein

Q is $NR_a$, wherein $R_a$ is H or (1-4C)alkyl;

$R_1$ is halo, (1-4C)alkyl, (2-4C)haloalkyl, dihalomethyl, trichloromethyl, S-(2-4C)alkyl, aryl, heteroaryl or a (1-6C)α,β-unsaturated aldehyde or ketone;

$R_2$ is hydrogen, halo, amino, cyano, nitro, hydroxyl, or a group

-L¹-X¹—$R_b$ wherein $L^1$ is absent or (1-2C)alkylene $X^1$ is absent or selected from —O—, —C(O)—, —C(X)O—, —OC(X)—, —CH($OR_c$)—, —N($R_c$)—, —N($R_c$)—C(X)—, —N($R_c$)—C(X)O—, —C(X)—N($R_c$)—, —N($R_d$)C(X)N($R_c$)—, —S—, —SO—, —$SO_2$—, —S(O)$_2$N($R_c$)—, or —N($R_c$)$SO_2$— wherein X is O or $NR_x$; $R_x$ is hydrogen or (1-3C)alkyl; and $R_c$ and $R_d$ are each independently hydrogen or (1-6C)alkyl; and $R_b$ is hydrogen, (1-6C)alkyl, (2-6C)alkenyl, (2-6C)alkynyl, cyano, aryl, aryl(1-2C)alkyl, (3-6C)cycloalkyl, heteroaryl, heterocyclyl or a sugar or amino acid, each of which is optionally substituted by one or more substituent groups independently selected from the group consisting of oxo, halo, cyano, nitro, hydroxy, carboxy, phosphate, $NR^eR^f$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, aryl, aryloxy, heterocyclyl, heterocyclyloxy, heterocyclyl-(1-2C)alkyl, heteroaryl, heteroaryloxy, heteroaryl-(1-2C)alkyl, $C(O)NR^eR^f$, $NR^eC(O)R^f$, $NR^eS(O)_2R^f$ and $S(O)_2NR^eR^f$; wherein $R^e$ and $R^f$ are each independently selected from hydrogen, (1-4C)alkyl or (3-6C)cycloalkyl or (3-6C)cycloalkyl(1-2C)alkyl;

or $R^e$ and $R^f$ can be linked such that, together with the nitrogen atom to which they are attached, they form a heterocyclic ring which is optionally substituted by oxo, halo, cyano, nitro, hydroxy, carboxy, $NR^gR^h$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, $C(O)NR^gR^h$, $NR^gC(O)R^h$, $NR^gS(O)_2R^h$ and $S(O)_2NR^gR^h$, wherein $R^g$ and $R^h$ are each independently hydrogen, (1-4C)alkyl, (3-6C)cycloalkyl or (3-6C)cycloalkyl(1-2C)alkyl;

or $R_b$ and $R_c$ are linked such that, together with the nitrogen atom to which they are attached, they form a heterocyclic ring which is optionally substituted by a substituent selected from the group consisting of oxo, halo, cyano, nitro, hydroxy, carboxy, $NR^iR^j$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, $C(O)NR^iR^j$, $NR^iC(O)R^j$, $NR^iS(O)_2R^j$ and $S(O)_2NR^iR^j$, wherein $R^i$ and $R^j$ are each independently selected from hydrogen, (1-4C)alkyl, (3-6C)cycloalkyl or (3-6C)cycloalkyl(1-2C)alkyl;

$R_3$ is methyl, $OR^p$, $C(O)OR^p$, $C(O)NR^pR^q$ or $NR^kR^l$;

wherein $R^k$ and $R^l$ are each independently hydrogen, (1-6C)alkyl, (3-10C)cycloalkyl, (3-10C)cycloalkyl(1-2C)alkyl, (2-6C)alkenyl, (2-6C)alkynyl, aryl, aryl(1-2C)alkyl, heteroaryl, heteroaryl (1-2C)alkyl, $S(O)R^o$, $S(O)_2R^o$ or a sugar or amino acid residue;

$R^o$ is (1-4C)alkyl, (2-4C)alkenyl, (2-4C)alkynyl, an aryl or heteroaryl group, each of which may be optionally substituted with one or more substituents selected from the group consisting of halo, OH, (1-4C)alkyl, (1-4C)hydroxyalkyl, (2-4C)alkenyl and (2-4C)alkynyl;

$R^p$ and $R^q$ are independently hydrogen, (1-6C)alkyl, (3-10° C.)cycloalkyl, (3-10C)cycloalkyl(1-2C)alkyl, (2-6C)alkenyl, (2-6C)alkynyl, aryl, aryl(1-2C)alkyl, heteroaryl or heteroaryl(1-2C)alkyl;

$R_4$ and $R_5$ are each independently aryl or heteroaryl ring, each of which is optionally substituted by a substituent selected from the group consisting of halo, cyano, nitro, hydroxy, carboxy, NR'''R'', (1-2C)alkoxy, (1-4C)alkyl, (1-4C)haloalkyl, (3-4C)cycloalkyl, (3-4C)cycloalkyl-(1-2C)alkyl, aryl, aryl(1-2C)alkyl, (1-2C)alkanoyl, (1-2C)alkylsulphonyl, SR''', SOR''', C(O)NR'''R'', NR'''C(O)R'', NR'''S(O)R'' and S(O)$_2$NR'''R'', wherein R''' and R'' are each independently selected from hydrogen, (1-2C)alkyl;

or $R_4$ and $R_5$ are linked to one another by a bond, an alkylene linker optionally comprising one or more heteroatoms, or a fused cycloalkyl, aryl, heteroaryl or heterocyclic ring;

or a pharmaceutically acceptable salt thereof, with the proviso that the compound is not one of the following:

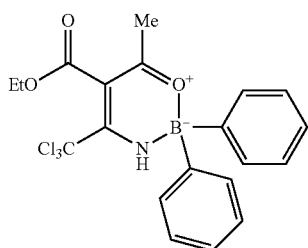

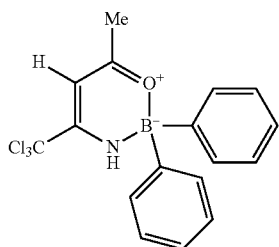

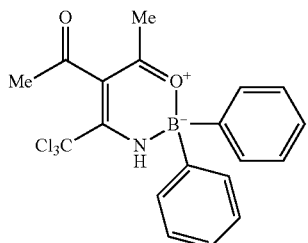

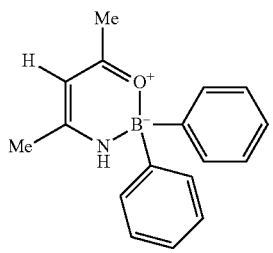

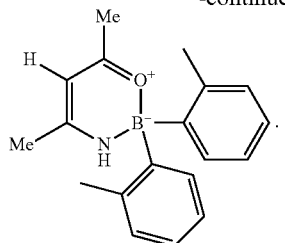

2. The compound of claim 1, wherein $R_1$ is (1-4C)alkyl or (2-4C)haloalkyl, dihalomethyl, trichloromethyl.

3. The compound of claim 1, wherein $R^k$ and $R^l$ are each independently hydrogen, (1-4C)alkyl, (5-10C)cycloalkyl, (5-10C)cycloalkyl(1-2C)alkyl, (2-4C)alkenyl, (2-4C)alkynyl, phenyl, phenyl(1-2C)alkyl, 5-6 membered heteroaryl (e.g. pyridinyl, imidazolyl, thiazolyl, thiadiazolyl or furanyl), 5-6 membered heteroaryl(1-2C)alkyl, S(O)R° or S(O)$_2$R°.

4. The compound of claim 1, wherein $R_2$ is hydrogen or a group -L$^1$-X$^1$—R$_b$.

5. The compound of claim 1, wherein $L_1$ is absent.

6. The compound of claim 1, wherein X$^1$ is absent or X$^1$ is —O—, —C(O)—, —C(X)O—, —OC(X)—, —CH(OR$_c$)—, —N(R$_c$)—C(X)O—, —C(X)—N(R$_c$)—, —S—, —SO—, —SO$_2$—, —S(O)$_2$N(R$_c$)—, or —N(R$_c$)SO$_2$—.

7. The compound of claim 1, wherein $R_b$ is hydrogen, (1-6C)alkyl, (2-4C)alkenyl, (2-4C)alkynyl, cyano, aryl, aryl(1-2C)alkyl, (3-6C)cycloalkyl, heteroaryl or heterocyclyl, each of which is optionally substituted by one or more substituent groups independently selected from the group consisting of oxo, halo, hydroxy, carboxy, NR$^e$R$^f$, (1-4C)alkoxy and (1-4C)alkyl.

8. The compound of claim 1, wherein $R_4$ and $R_5$ are each independently phenyl or 5-6 membered heteroaryl ring, each of which is optionally substituted by a substituent selected from the group consisting of halo, cyano, nitro, hydroxy, carboxy, NR'''R'', (1-2C)alkoxy, (1-4C)alkyl, (1-4C)haloalkyl, (3-4C)cycloalkyl, (3-4C)cycloalkyl-(1-2C)alkyl, aryl, aryl(1-2C)alkyl, (1-2C)alkanoyl, (1-2C)alkylsulphonyl, SR''', SOR''', C(O)NR'''R'', NR'''C(O)R'', NR'''S(O)R'' and S(O)$_2$NR'''R'', or $R_4$ and $R_5$ are linked to one another by a bond, an alkylene linker optionally comprising one or more heteroatoms, a fused cycloalkyl, aryl, heteroaryl or heterocyclic ring.

9. The compound of claim 1, wherein the compound has a structure according to formula (Ia) shown below:

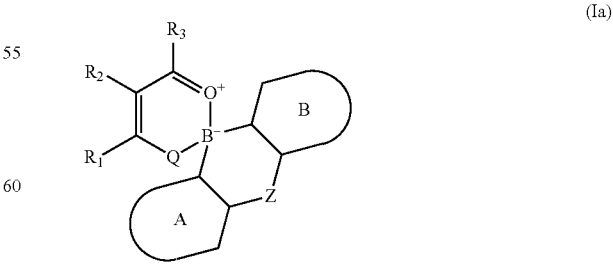

(Ia)

wherein
rings A and B are each independently phenyl or 5-6 membered heteroaryl ring, each of which is optionally substituted by a substituent selected from the group consisting of halo, hydroxy, carboxy, NR'''R'', (1-2C) alkoxy, (1-4C)alkyl, (1-4C)haloalkyl, aryl, aryl(1-2C) alkyl and (1-2C)alkanoyl;

Z is absent, a bond, a group —(CH$_2$)$_n$— where n is 1 or 2, a group —(CH)$_m$— wherein m is 1 or 2, or a linking group comprising 1 or 2 heteroatoms selected from N and O; and R$_1$, R$_2$ and R$_3$ are as defined in claim 1.

10. The compound of claim 9, wherein rings A and B are each independently selected from phenyl, pyridinyl, furanyl, thiophenyl or imidazolyl, each of which may be optionally substituted with one or more substituents selected from the group consisting of halo, hydroxy, carboxy, NR'''R'', (1-2C) alkoxy, phenyl, phenyl(1-2C)alkyl (1-4C)alkyl and (1-4C) haloalkyl.

11. The compound of claim 1, wherein R$^k$ and R$^l$ are each independently hydrogen, (1-4C)alkyl, (6-10C)cycloalkyl, (2-4C)alkynyl, phenyl or aryl(1-2C)alkyl.

12. The compound of claim 1, wherein X$^1$ is absent or X$^1$ is —O—, —C(O)—, —C(X)O—, —OC(X)—, —CH(OR$_c$)—, —N(R$_c$)—C(X)O— or —C(X)—N(R$_c$)—.

13. The compound of claim 1, wherein R$_b$ is (1-4C)alkyl, cyano, phenyl, (3-6C)cycloalkyl, 5-6 membered heteroaryl or 5-6 membered heterocyclyl, each of which is optionally substituted by one or more substituent groups independently selected from the group consisting of oxo, halo, hydroxy, carboxy, NR$^e$R$^f$, (1-4C)alkoxy and (1-4C)alkyl.

14. The compound of claim 1, wherein R$^e$ and R$^f$ are each independently hydrogen, (1-4C)alkyl or (3-6C)cycloalkyl or (3-6C)cycloalkyl(1-2C)alkyl.

15. The compound of claim 1, wherein R$^o$ is (1-4C)alkyl, an aryl or 5-6 membered heteroaryl group optionally substituted with one or more substituents selected from the group consisting of halo, (1-4C)alkyl, (1-4C)hydroxyalkyl, (2-4C)alkenyl and (2-4C)alkynyl.

16. The compound of claim 1, wherein the compound has a structure according to formula (Ib) shown below:

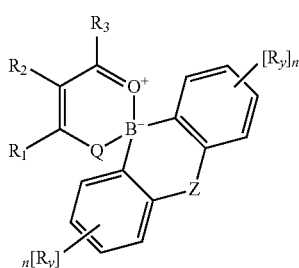

(Ib)

wherein each R$_y$ is independently halo, 1-4C)alkyl, (1-4C)haloalkyl, phenyl or (1-2C)alkoxy;

n is 0, 1 or 2;

Z is absent, a bond, or a group —(CH$_2$)$_n$— where n is 1 or 2; and

R$_1$, R$_2$ and R$_3$ are as defined in claim 1.

17. The compound of claim 1, wherein R$_1$ is methyl, dihalomethyl or trichloromethyl.

18. The compound of claim 1, wherein R$_1$ is methyl or CCl$_3$.

19. The compound of claim 1, wherein R$^e$ and R$^f$ are each independently hydrogen or (1-4C)alkyl.

20. The compound of claim 9, wherein Z is absent.

21. The compound of claim 1, wherein the compound has a structure according to formula (Ic) shown below:

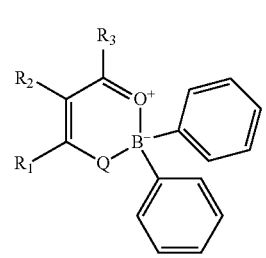

(Ic)

wherein

Q, R$_1$, R$_2$ and R$_3$ are as defined in claim 1.

22. A compound is selected from any of those compounds below:

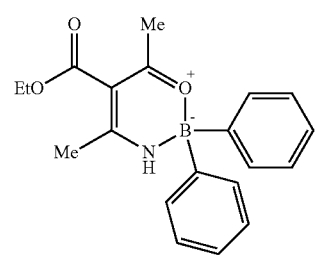

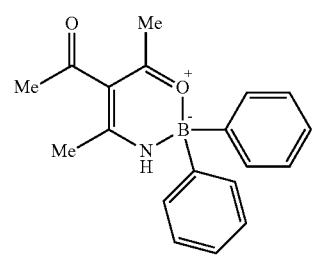

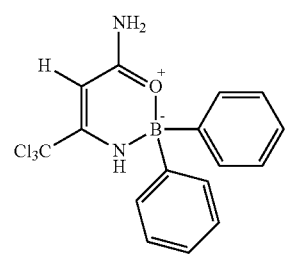

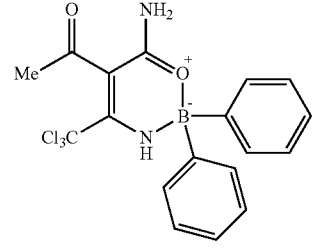

105
-continued
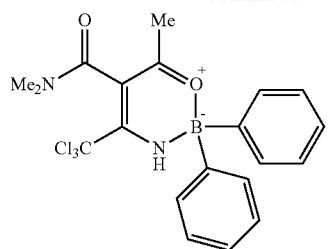
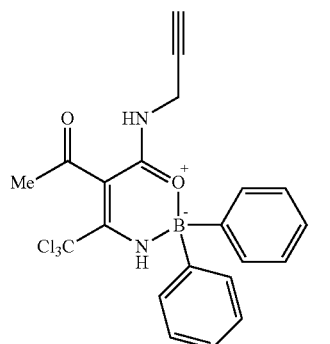
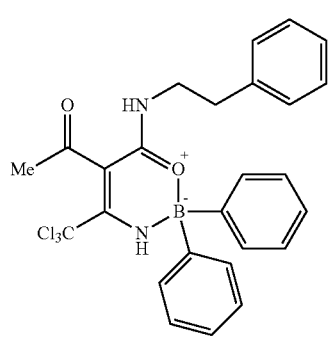
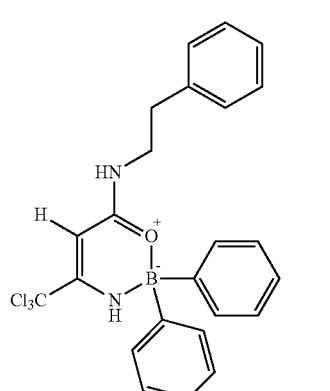
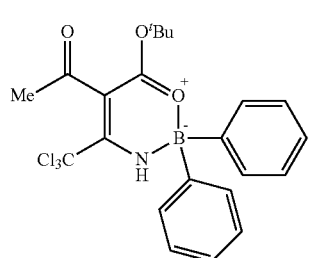
106
-continued
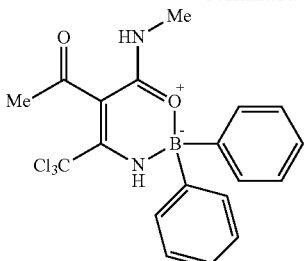
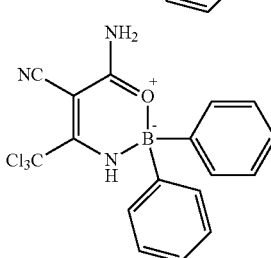

-continued
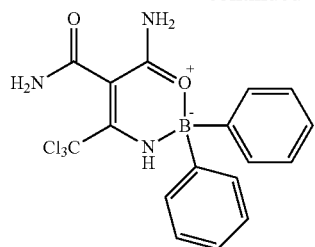
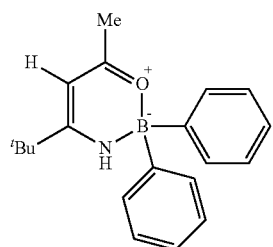
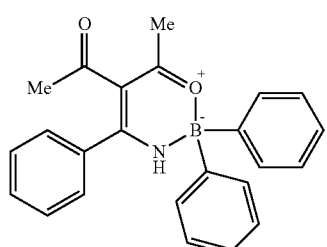
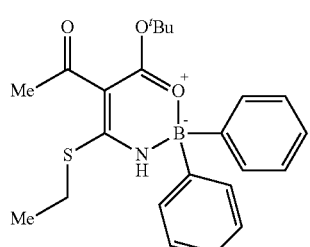
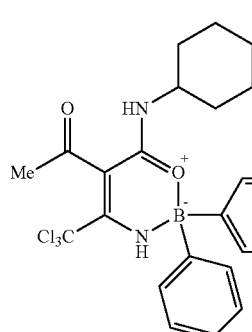
-continued
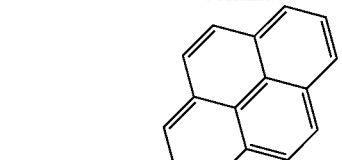
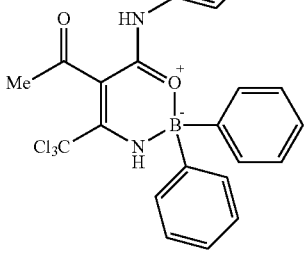
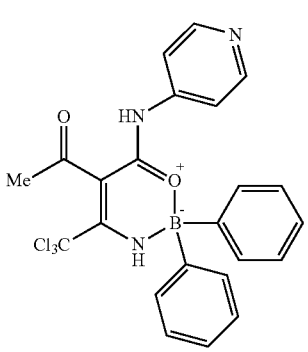
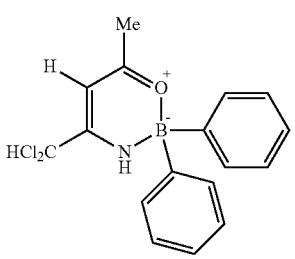
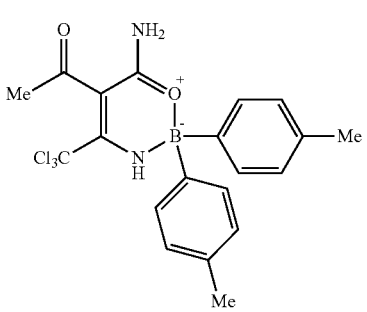
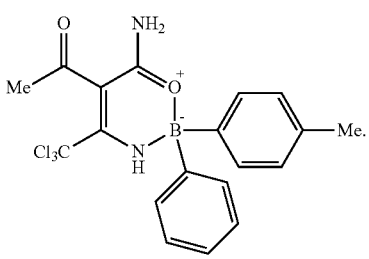

23. A compound is selected from any of those compounds below:
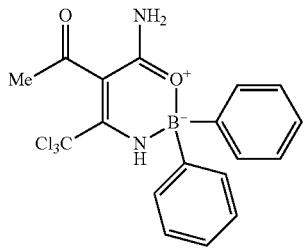
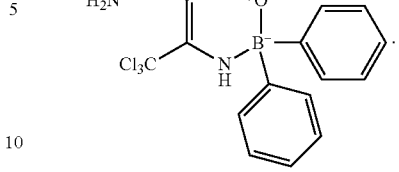
24. The compound of claim 23, wherein the compound is:
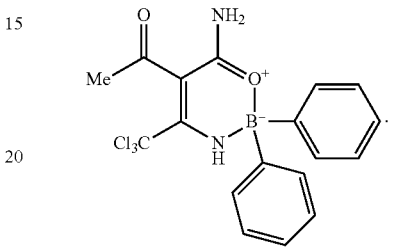
25. A pharmaceutical composition comprising a compound of formula I of claim 1, or a pharmaceutically acceptable salt or solvate thereof, and one or more pharmaceutically acceptable excipients.
* * * * *

UNITED STATES PATENT AND TRADEMARK OFFICE
CERTIFICATE OF CORRECTION

PATENT NO. : 10,570,157 B2
APPLICATION NO. : 15/748557
DATED : February 25, 2020
INVENTOR(S) : Brough et al.

Page 1 of 1

It is certified that error appears in the above-identified patent and that said Letters Patent is hereby corrected as shown below:

In the Claims

Column 101, Line 2, Claim 1:
"(3-10° C.)cycloalkyl, (3-10C)cycloalkyl(1-2C)" should read, --(3-10C)cycloalkyl, (3-10C)cycloalkyl(1-2C)--

Signed and Sealed this
First Day of September, 2020

Andrei Iancu
*Director of the United States Patent and Trademark Office*